US012715873B2

(12) United States Patent
Duan et al.

(10) Patent No.: US 12,715,873 B2
(45) Date of Patent: Aug. 25, 2026

(54) PYRAZOLOPYRIDAZINONE COMPOUND, AND PHARMACEUTICAL COMPOSITION AND USE THEREOF

(71) Applicant: BroadenBio Co., Ltd., Beijing (CN)

(72) Inventors: Gongping Duan, Beijing (CN); Xingmin Zhang, Beijing (CN); Zhihua Wang, Beijing (CN); Xianglong Wei, Beijing (CN); Min Li, Beijing (CN)

(73) Assignee: BroadenBio Co., Ltd., Beijing (CN)

( * ) Notice: Subject to any disclaimer, the term of this patent is extended or adjusted under 35 U.S.C. 154(b) by 582 days.

(21) Appl. No.: 18/044,501

(22) PCT Filed: Nov. 3, 2021

(86) PCT No.: PCT/CN2021/128460

§ 371 (c)(1), (2) Date: Mar. 8, 2023

(87) PCT Pub. No.: WO2022/095904

PCT Pub. Date: May 12, 2022

(65) Prior Publication Data

US 2023/0322789 A1 Oct. 12, 2023

(30) Foreign Application Priority Data

Nov. 3, 2020 (CN) ........................ 202011209391.X

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ................ C07D 487/04; C07D 519/00; C07D 491/107; C07D 498/04; A61P 31/12; A61P 35/02; A61P 31/14; A61P 35/00; A61P 31/16; A61P 31/18; A61P 31/20; A61P 31/22; Y02P 20/55; A61K 31/5025; A61K 31/506; A61K 31/5377; A61K 31/5383

See application file for complete search history.

(56) References Cited

FOREIGN PATENT DOCUMENTS

| | | | |
|---|---|---|---|
| CN | 114437074 | A | 5/2022 |
| JP | H04307542 | A | 10/1992 |
| JP | 2019530670 | A | 10/2019 |
| WO | 2004072029 | A2 | 8/2004 |
| WO | 2018049152 | A1 | 3/2018 |
| WO | 2018049191 | A1 | 3/2018 |
| WO | 2018049200 | A1 | 3/2018 |
| WO | 2019238067 | A1 | 12/2019 |

OTHER PUBLICATIONS

CAS Reg. No. 746647-41-6, which entered STN database on Sep. 17, 2004 (Year: 2004).*
Japanese Office Action for JP2022-560929.
Extended European Search Report mailed on Feb. 7, 2024 in EP Application No. 21888601.8.

* cited by examiner

*Primary Examiner* — Kamal A Saeed
*Assistant Examiner* — Meghan C Heasley
(74) *Attorney, Agent, or Firm* — Fox Rothschild LLP

(57) ABSTRACT

Provided in the present application are a compound represented by formula (I), a pharmaceutical composition containing the compound, and the use thereof. The compound represented by formula (I) of the present application has a good effect in terms of inhibiting the activity of HPK1.

(I)

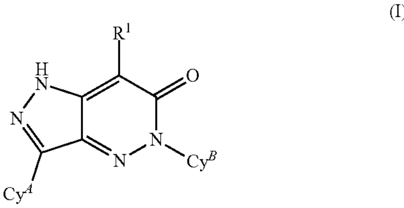

17 Claims, No Drawings

PYRAZOLOPYRIDAZINONE COMPOUND, AND PHARMACEUTICAL COMPOSITION AND USE THEREOF

CROSS REFERENCE TO RELATED APPLICATIONS

This application is the U.S. national phase of International Patent Application No. PCT/CN2021/128460, filed on Nov. 3, 2021, which claims priority to Chinese Patent Application No. 202011209391.X, filed on Nov. 3, 2020, the disclosures of which are incorporated herein by reference in their entirety.

TECHNICAL FIELD

The present application relates to a pyrazolopyridazinone compound, particularly a pyrazolopyridazinone derivative with HPK1 inhibitory activity.

BACKGROUND ART

Hematopoietic progenitor kinase 1 (HPK1), belonging to the mitogen-activated protein kinase kinase kinase kinase-4 (MAP4K) family, is a serine/threonine kinase originally cloned from hematopoietic progenitor cells (Hu, M. C. et al., Genes Dev. 1996; 10:2251-2264; Keifer, F. et al, The EMBO Journal 1996; 15:7013-7025). HPK1 is mainly distributed in lymphoid organs and lymphoid tissues, such as bone marrow, lymph nodes, thymus, etc., and is expressed predominantly in immune cells (T cells, B cells, dendritic cells, macrophages, etc.) (Hu, M. C. et al., Genes Dev. 1996; 10:2251-2264). This has drawn attention to the immunomodulatory role of HPK1.

Studies have shown that HPK1 is a negative regulator of the T cell receptor (TCR) signaling pathway. TCR signaling causes the activation of HPK1, and subsequently binding to SLP-76 protein (Lasserre, R. et al., J Cell Biol. 2011; 195:839-853; Shui, J. et al., Nature Immuno. 2007; 8:84-91). Activated HPK1 phosphorylates the Ser376 residue of SLP-76, promoting the binding of SLP-76 to 14-3-3 protein (Di Bartolo, V. et al., J. Exp. Med. 2007; 204:681-691; Shui, J. et al, Nature Immuno. 2007; 8:84-91). The SLP-76/14-3-3 interaction downregulates ERK signaling and calcium flux, and triggers the ubiquitination of SLP-76. The degradation of the SLP-76 complex blocks the TCR activation pathway consequently, thereby inhibiting T cell function (Lasserre, R. et al, J. Cell Biol. 2011; 195:839-853).

In in vivo experiments, HPK1 knockout mice showed enhanced T cell function under antigen stimulation and produced more cytokines, such as IL-2 and IFN-γ (Shui, J. et al., Nature Immuno. 2007; 8:84-91; Alzabin, S. et al, J. Immunol. 2009; 182:6187-6194; Alzabin, S. et al, Cancer Immunol. Immunother. 2010; 59:419-429). Further studies demonstrated that the kinase activity of HPK1 plays a key role in the negative regulation of immune cells. Compared with wild-type mice, mice with blockade of the kinase activity of HPK1 showed enhanced CD8+ T cell function, faster clearance of chronic lymphocytic meningitis virus, and better inhibition of tumor growth (Hernandez, S. et al., Cell Reports 2018; 25:80-94). In Lewis lung cancer (LLC) model, mice transfected with $HPK1^{-/-}$ T cells exhibited stronger antitumor immune responses than wild-type (Sawasdikosol, S. et al., Immunol. Res. 2012; 54:262-265). Similar studies revealed that the immunosuppressive effects of HPK1 on B cells (Sauer, K. et al., J. Biol. Chem. 2001; 276:45207-45216; Tsuji, S. et al., J. Exp. Med. 2001; 194:529-539; Wang, X. et al, J. Biol. Chem. 2012; 287: 34091-34100; Königsberger, S. et al, PLos One, 2010; 5: e12468), dendritic cells (Alzabin, S. et al, J. Immunol. 2009; 182:6187-6194), NK cells and Treg cells are also derived from its kinase activity (Liu, J. et al., PLos One, 2019; 14: e0212670).

Clinical studies have found that, comparing with health controls, the HPK1 levels were significantly downregulated in tissues from patients of systemic lupus erythematosus (Zhang, Q. et al, J. Autoimmun., 2011; 37:180-189) and psoriatic arthritis (Stoeckman, A. K. et al, Genes Immun 2006; 7:583-591; Baltiwalla, F. M. et al., Mol. Med. 2005; 11:21-29), suggesting that HPK1 downregulation contributes to the enhancement of autoimmune responses. On the other hand, upregulation of HPK1 levels has been observed in various cancers, such as acute myeloid leukemia (Chen-Deutsch, X. et al., Leuk. Res. 2012; 36:884-888; Chen-Deutsch, X. et al., Cell Cycle 2012; 11:1364-1373), bladder urothelial carcinoma (Wang. Y et al, Mol. Med. Rep. 2012; 5:260-265), extramammary Paget's disease (Qian, Y et al, Am J. Dermatopathol. 2011; 33:681-686) and colon cancer (Yang, H. S. et al., Mol. Cell Biol. 2006; 26:1297-1306).

Therefore, HPK1 is a potential target for the treatment of tumors and viral diseases. The development of small-molecule inhibitors of HPK1 kinase holds important clinical promise. Although some patent applications for small molecule HPK1 inhibitors have been published, such as WO2018049191, WO2018049200, WO2018102366, WO2018183964, WO2019090198, WO2019206049, WO2019238067 and WO2020092528, no drug targeting HPK1 has been approved yet. Therefore, the development of novel small-molecule HPK1 inhibitors with good activity is still an urgent need.

SUMMARY

A main purpose of this application is to provide a compound of formula (I), or a pharmaceutically acceptable salt, hydrate, solvate, active metabolite, polymorph, isotope labeled compound, isomer or prodrug thereof, (I)

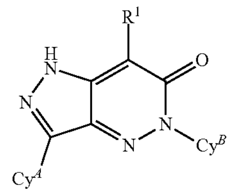

wherein, $R^1$ is selected from:

1) hydrogen, halogen, cyano, —C(═O)$NR^aR^b$, —$OR^a$ and —$NR^aR^b$;
2) $C_{1-6}$ alkyl, $C_{2-4}$ alkenyl, $C_{2-4}$ alkynyl, $C_{3-8}$ cycloalkyl and 3- to 8-membered aliphatic heterocyclyl, unsubstituted or optionally substituted with 1, 2, 3 or 4 substituents independently selected from $R^{11}$;

$R^a$ and $R^b$ are each independently selected from:

1) hydrogen;
2) $C_{1-6}$ alkyl, $C_{2-4}$ alkenyl, $C_{2-4}$ alkynyl, $C_{3-6}$ monocyclic cycloalkyl, and 3- to 6-membered aliphatic monocyclic heterocyclyl, unsubstituted or optionally substituted with 1, 2, or 3 substituents independently selected from $R^{11}$; or $R^a$ and $R^b$ attached to the same nitrogen atom, together with the nitrogen atom, form a 3-6 membered aliphatic monocyclic heterocyclyl unsubstituted or optionally substituted with 1, 2 or 3 substituents independently selected from $R^{11}$;

$R^{11}$ is selected from fluorine, chlorine, $C_{1-3}$ alkyl and hydroxyl;

$Cy^A$ is selected from 6- to 10-membered aryl or 5- to 10-membered heteroaryl, unsubstituted or optionally substituted with 1, 2, 3, 4 or 5 substituents independently selected from $R^{12}$;

$R^{12}$ is selected from:

1) oxo, halogen, cyano, $—C(═O)R^{a2}$, $—C(═O)OR^{a2}$, $—C(═O)NR^{a2}R^{b2}$, $—C(═NR^{d2})NR^{a2}R^{b2}$, $—OR^{a2}$, $—OC(═O)R^{a2}$, $—OC(═O)OR^{c2}$, $—OC(═O)NR^{a2}R^{b2}$, $—SR^{a2}$, $—S(═O)R^{c2}$, $—S(═O)_2R^{c2}$, sulfonic acid group, $—S(═O)NR^{a2}R^{b2}$, $—S(═O)_2NR^{a2}R^{b2}$, $—S(═O)(═NR^{d2})R^{c2}$, $—NR^{a2}R^{b2}$, $—NR^{a2}C(═O)R^{b2}$, $—NR^{a2}C(═O)OR^{c2}$, $—NR^{c2}C(═O)NR^{a2}R^{b2}$, $—NR^{c2}C(═NR^{d2})NR^{a2}R^{b2}$, $—NR^{a2}S(═O)_2R^{c2}$, $—NR^{c2}S(═O)_2NR^{a2}R^{b2}$, nitro, $—PR^{c2}R^{f2}$, $—P(═O)R^{c2}R^{f2}$ and phosphonic acid group;

2) $C_{1-6}$ alkyl, $C_{2-6}$ alkenyl, $C_{2-6}$ alkynyl, 6- to 10-membered aryl, 5- to 10-membered heteroaryl, $C_{3-12}$ cycloalkyl and 3- to 12-membered aliphatic heterocyclyl, unsubstituted or optionally substituted with 1, 2, 3, 4, 5 or 6 substituents independently selected from $R^{22}$;

3) the two $R^{12}$ substituents attached to two adjacent ring-forming atoms on the aryl or heteroaryl group of $Cy^A$ respectively, together with the two said ring-forming atoms, form a $C_{5-12}$ alicyclic or a 5- to 12-membered aliphatic heterocyclyl, unsubstituted or optionally substituted by 1, 2, 3, 4, 5 or 6 substituents independently selected from $R^{22}$;

$R^{a2}$, $R^{b2}$ and $R^{e2}$ are each independently selected from:

1) hydrogen;

2) $C_{1-4}$ alkyl, $C_{2-4}$ alkenyl, $C_{2-4}$ alkynyl, phenyl, 5-6 membered heteroaryl, $C_{3-12}$ cycloalkyl and 3-12 membered aliphatic heterocyclyl, unsubstituted or optionally substituted with 1, 2, 3, 4, 5 or 6 substituents independently selected from $R^{22}$;

or, $R^{a2}$ and $R^{b2}$ attached to the same nitrogen atom, together with the nitrogen, form a 3-12 membered aliphatic heterocyclyl, unsubstituted or optionally substituted with 1, 2, 3, 4 or 5 substituents independently selected from $R^{22}$;

$R^{c2}$ and $R^{f2}$ are each independently selected from the group consisting of $C_{1-4}$ alkyl, $C_{2-4}$ alkenyl, $C_{2-4}$ alkynyl, phenyl, 5-6 membered heteroaryl, $C_{3-12}$ cycloalkyl and 3-12 membered aliphatic heterocyclyl, unsubstituted or optionally substituted with 1, 2, 3, 4 or 5 substituents independently selected from $R^{22}$.

or, $R^{c2}$ and $R^{f2}$ attached to the same phosphorous atom, together with the phosphorous, form a 3-12 membered aliphatic heterocyclyl, unsubstituted or optionally substituted with 1, 2, 3, 4 or 5 substituents independently selected from $R^{22}$;

$R^{d2}$ is selected from:

1) hydrogen, cyano, nitro and $—S(═O)_2R^G$;

2) $C_{1-4}$ alkyl, $C_{2-4}$ alkenyl, $C_{2-4}$ alkynyl, phenyl, 5-6 membered heteroaryl, $C_{3-12}$ cycloalkyl and 3-12 membered aliphatic heterocyclyl, unsubstituted or optionally selected from 1, 2, 3, 4 or 5 substituents independently selected from $R^{22}$;

$R^{22}$ is selected from:

1) oxo, halogen, cyano, $—C(═O)R^{a4}$, $—C(═O)OR^{a4}$, $—C(═O)NR^{a4}R^{b4}$, $—C(═NR^{d4})NR^{a4}R^{b4}$, $—OR^{a4}$, $—OC(═O)R^{a4}$, $—OC(═O)OR^{c4}$, $—OC(═O)NR^{a4}R^{b4}$, $—SR^{a4}$, $—S(═O)R^{c4}$, $—S(═O)_2R^{c4}$, sulphonic acid group, $—S(═O)NR^{a4}R^{b4}$, $—S(═O)_2NR^{a4}R^{b4}$, $—S(═O)(═NR^{d4})R^{c4}$, $—NR^{a4}R^{b4}$, $—NR^{a4}C(═O)R^{b4}$, $—NR^{a4}C(═O)OR^{c4}$, $—NR^{e4}C(═O)NR^{a4}R^{b4}$, $—NR^{e4}C(═NR^{d4})NR^{a4}R^{b4}$, $—NR^{a4}S(═O)_2R^{c4}$, $—NR^{e4}S(═O)_2NR^{a4}R^{b4}$, nitro, $—PR^{c4}R^{f4}$, $—P(═O)R^{c4}R^{f4}$, phosphonic acid group and imino group ($═N—R^{d4}$);

2) $C_{1-6}$ alkyl, $C_{1-6}$ alkylene, $C_{2-6}$ alkenyl, $C_{2-6}$ alkynyl, phenyl, 5-6 membered heteroaryl, $C_{3-10}$ cycloalkyl and 3-10 membered aliphatic heterocyclyl, unsubstituted or optionally substituted with 1, 2, 3, 4 or 5 substituents independently selected from $R^{32}$;

$R^{a4}$, $R^{b4}$ and $R^{c4}$ are each independently selected from:

1) hydrogen;

2) $C_{1-4}$ alkyl, $C_{2-4}$ alkenyl, $C_{2-4}$ alkynyl, phenyl, 5-6 membered heteroaryl, $C_{3-10}$ cycloalkyl and 3-10 membered aliphatic heterocyclyl, unsubstituted or optionally substituted with 1, 2, 3, 4 or 5 substituents independently selected from $R^{32}$;

or, $R^{a4}$ and $R^{b4}$ attached to the same nitrogen atom, together with the nitrogen, form a 3-10 membered aliphatic heterocyclyl, unsubstituted or optionally substituted with 1, 2, 3, 4 or 5 substituents independently selected from $R^{32}$;

$R^{c4}$ and $R^{f4}$ are each independently selected from $C_{1-4}$ alkyl, $C_{2-4}$ alkenyl, $C_{2-4}$ alkynyl, phenyl, 5-6 membered heteroaryl, $C_{3-10}$ cycloalkyl and 3-10 membered aliphatic heterocyclyl, unsubstituted or optionally substituted with 1, 2, 3, 4 or 5 substituents independently selected from $R^{32}$;

or, $R^{c4}$ and $R^{f4}$ attached to the same phosphorous atom, together with the phosphorous, form a 3-10 membered aliphatic heterocyclyl, unsubstituted or optionally substituted with 1, 2, 3, 4 or 5 substituents independently selected from $R^{32}$, $R^{d4}$ is selected from:

1) hydrogen, cyano, nitro and $—S(═O)_2R^G$;

2) $C_{1-4}$ alkyl, $C_{2-4}$ alkenyl, $C_{2-4}$ alkynyl, phenyl, 5-6 membered heteroaryl, $C_{3-10}$ cycloalkyl and 3-10 membered aliphatic heterocyclyl, unsubstituted or optionally substituted with 1, 2, 3, 4 or 5 substituents independently selected from $R^{32}$, $R^{32}$ is selected from:

1) oxo, halogen, cyano, $—C(═O)R^{a6}$, $—C(═O)OR^{a6}$, $—C(═O)NR^{a6}R^{b6}$, $—C(═NR^{d6})NR^{a6}R^{b6}$, $—OR^{a6}$, $—OC(═O)R^{a6}$, $—OC(═O)OR^{c6}$, $—OC(═O)NR^{a6}R^{b6}$, $—SR^{a6}$, $—S(═O)R^{c6}$, $—S(═O)_2R^{c6}$, sulphonic acid group, $—S(═O)NR^{a6}R^{b6}$, $—S(═O)_2NR^{a6}R^{b6}$, $—S(═O)(═NR^{d6})R^{c6}$, $—NR^{a6}R^{b6}$, $—NR^{a6}C(═O)R^{b6}$, $—NR^{a6}C(═O)OR^{c6}$, $—NR^{c6}C(═O)NR^{a6}R^{b6}$, $—NR^{e6}C(═NR^{d6})NR^{a6}R^{b6}$, $—NR^{a6}S(═O)_2R^{c6}$, $—NR^{e6}S(═O)_2NR^{a6}R^{b6}$, nitro, $—PR^{c6}R^{f6}$, $—P(═O)R^{c6}R^{f6}$, phosphonic acid group and imino group ($═N—R^{d6}$);

2) $C_{1-4}$ alkyl, $C_{1-4}$ alkylene, $C_{2-4}$ alkenyl, $C_{2-4}$ alkynyl, phenyl, 5-6 membered heteroaryl, $C_{3-8}$ cycloalkyl and 3-8 membered aliphatic heterocyclyl, unsubstituted or optionally substituted with 1, 2, 3 or 4 substituents independently selected from $R^G$;

$R^{a6}$, $R^{b6}$ and $R^{e6}$ are each independently selected from:

1) hydrogen;

2) $C_{1-4}$ alkyl, $C_{2-4}$ alkenyl, $C_{2-4}$ alkynyl, phenyl, 5-6 membered heteroaryl, $C_{3-8}$ cycloalkyl and 3-8 membered aliphatic heterocyclyl, unsubstituted or optionally substituted with 1, 2, 3 or 4 substituents independently selected from $R^G$;

or, $R^{a6}$ and $R^{b6}$ attached to the same nitrogen atom, together with the nitrogen, form a 3-8 membered aliphatic heterocyclyl, unsubstituted or optionally substituted with 1, 2, 3 or 4 substituents independently selected from $R^G$;

$R^{c6}$ and $R^{f6}$ are each independently selected from $C_{1-4}$ alkyl, $C_{2-4}$ alkenyl, $C_{2-4}$ alkynyl, phenyl, 5-6 membered heteroaryl, $C_{3-8}$ cycloalkyl and 3-8 membered aliphatic heterocyclyl, unsubstituted or optionally substituted with 1, 2, 3 or 4 substituents independently selected from $R^G$;

or, $R^{e6}$ and $R^{f6}$ attached to the same phosphorous atom, together with the phosphorous, form a 3-8 membered aliphatic heterocyclyl, unsubstituted or optionally substituted with 1, 2, 3 or 4 substituents independently selected from $R^G$;

$R^{d6}$ is selected from:

1) hydrogen, cyano, nitro and —S(═O)$_2R^G$;

2) $C_{1-4}$ alkyl, $C_{2-4}$ alkenyl, $C_{2-4}$ alkynyl, phenyl, 5-6 membered heteroaryl, $C_{3-8}$ cycloalkyl, 3-8 membered aliphatic heterocyclyl, unsubstituted or optionally substituted with 1, 2, 3 or 4 substituents independently selected from $R^G$;

$Cy^B$ is selected from 6-10 membered aryl or 5-10 membered heteroaryl, unsubstituted or optionally substituted with 1, 2, 3, 4 or 5 substituents independently selected from $R^{13}$;

$R^{13}$ is selected from:

1) oxo, halogen, cyano, —C(═O)$R^{a3}$, —C(═O)O$R^{a3}$, —C(═O)N$R^{a3}R^{b3}$, —C(═N$R^{d3}$)N$R^{a3}R^{b3}$, —O$R^{a3}$, —OC(═O)$R^{a3}$, —OC(═O)O$R^{c3}$, —OC(═O)N$R^{a3}R^{b3}$, —S$R^{a3}$, —S(═O)$R^{c3}$, —S(═O)$_2R^{c3}$, sulphonic acid group, —S(═O)N$R^{a3}R^{b3}$, —S(═O)$_2$N$R^{a3}R^{b3}$, —S(═O)(═N$R^{d3}$)$R^{c3}$, —N$R^{a3}R^{b3}$, —N$R^{a3}$C(═O)$R^{b3}$, —N$R^{a3}$C(═O)O$R^{c3}$, —N$R^{c3}$C(═O)N$R^{a3}R^{b3}$, —N$R^{c3}$C(═N$R^{a3}$)N$R^{a3}R^{b3}$, —N$R^{a3}$S(═O)$_2R^{c3}$, —N$R^{c3}$S(═O)$_2$N$R^{a3}R^{b3}$, nitro, —P$R^{c3}R^{f3}$, —P(═O)$R^{e3}R^{f3}$ and phosphonic acid group;

2) $C_{1-6}$ alkyl, $C_{2-6}$ alkenyl, $C_{2-6}$ alkynyl, 6-10 membered aryl, 5-10 membered heteroaryl, $C_{3-12}$ cycloalkyl and 3-12 membered aliphatic heterocyclyl, unsubstituted or optionally substituted with 1, 2, 3, 4, 5 or 6 substituents independently selected from $R^{23}$;

3) two $R^{13}$ attached to two adjacent ring-forming atoms on the aryl or heteroaryl group of $Cy^B$ respectively, together with the two said ring-forming atoms form a $C_{5-12}$ alicyclic ring or a 5-12 membered aliphatic heterocyclyl, unsubstituted or optionally substituted with 1, 2, 3, 4 or 5 substituents independently selected from $R^{23}$;

$R^{a3}$, $R^{b3}$ and $R^{e3}$ are each independently selected from:

1) hydrogen;

2) $C_{1-4}$ alkyl, $C_{2-4}$ alkenyl, $C_{2-4}$ alkynyl, phenyl, 5-6 membered heteroaryl, $C_{3-12}$ cycloalkyl and 3-12 membered aliphatic heterocyclyl, unsubstituted or optionally substituted with 1, 2, 3, 4, 5 or 6 substituents independently selected from $R^{23}$;

or, $R^{a3}$ and $R^{b3}$ attached to the same nitrogen atom, together with the nitrogen, form a 3-12 membered aliphatic heterocyclyl, unsubstituted or optionally substituted with 1, 2, 3, 4 or 5 substituents independently selected from $R^{23}$;

$R^{c3}$ and $R^{f3}$ are each independently selected from $C_{1-4}$ alkyl, $C_{2-4}$ alkenyl, $C_{2-4}$ alkynyl, phenyl, 5-6 membered heteroaryl, $C_{3-12}$ cycloalkyl and 3-12 membered aliphatic heterocyclyl, unsubstituted or optionally substituted with 1, 2, 3, 4 or 5 substituents independently selected from $R^{23}$;

or, $R^{c3}$ and $R^{f3}$ attached to the same phosphorous atom, together with the phosphorous atom, form a 3-12 membered aliphatic heterocyclyl, unsubstituted or optionally substituted with 1, 2, 3, 4 or 5 substituents independently selected from $R^{23}$;

$R^{d3}$ selected from:

1) hydrogen, cyano, nitro and S(═O)$_2R^G$;

2) $C_{1-4}$ alkyl, $C_{2-4}$ alkenyl, $C_{2-4}$ alkynyl, phenyl, 5-6 membered heteroaryl, $C_{3-12}$ cycloalkyl and 3-12 membered aliphatic heterocyclyl, unsubstituted or optionally substituted with 1, 2, 3, 4 or 5 substituents independently selected from $R^{23}$;

$R^{23}$ is selected from:

1) oxo, halogen, cyano, —C(═O)$R^{a5}$, —C(═O)O$R^{a5}$, —C(═O)N$R^{a5}R^{b5}$, —C(═N$R^{d5}$)N$R^{a5}R^{b5}$, —O$R^{a5}$, —OC(═O)$R^{a5}$, —OC(═O)O$R^{e5}$, —OC(═O)N$R^{a5}R^{b5}$, —S$R^{a5}$, —S(═O)$R^{e5}$, —S(═O)$_2R^{c5}$, sulphonic acid group, —S(═O)N$R^{a5}R^{b5}$, —S(═O)$_2$N$R^{a5}R^{b5}$, —S(═O)(═N$R^{d5}$)$R^{c5}$, —N$R^{a5}R^{b5}$, —N$R^{a5}$C(═O)$R^{b5}$, —N$R^{a5}$C(═O)O$R^{c5}$, —N$R^{e5}$C(═O)N$R^{a5}R^{b5}$, —N$R^{e5}$C(═N$R^{d5}$)N$R^{a5}R^{b5}$, —N$R^{a5}$S(═O)$_2R^{c5}$, —N$R^{e5}$S(═O)$_2$N$R^{a5}R^{b5}$, nitro, —P$R^{c5}R^{f5}$, —P(═O)$R^{c5}R^{f5}$, phosphonic acid group and imino group (═N—$R^{d5}$);

2) $C_{1-6}$ alkyl, $C_{1-6}$ alkylene, $C_{2-6}$ alkenyl, $C_{2-6}$ alkynyl, phenyl, 5-6 membered heteroaryl, $C_3$-cycloalkyl and 3-10 membered aliphatic heterocyclyl, unsubstituted or optionally substituted with 1, 2, 3, 4 or 5 substituents independently selected from $R^{33}$;

$R^{a5}$, $R^{b5}$ and $R^{c5}$ are each independently selected from:

1) hydrogen;

2) $C_{1-4}$ alkyl, $C_{2-4}$ alkenyl, $C_{2-4}$ alkynyl, phenyl, 5-6 membered heteroaryl, $C_{3-10}$ cycloalkyl and 3-10 membered aliphatic heterocyclyl, unsubstituted or optionally substituted with 1, 2, 3, 4 or 5 substituents independently selected from $R^{33}$;

or, $R^{a5}$ and $R^{b5}$ attached to the same nitrogen atom, together with the nitrogen atom, form a 3-10 membered aliphatic heterocyclyl, unsubstituted or optionally substituted with 1, 2, 3, 4 or 5 substituents independently selected from $R^{33}$;

$R^{c5}$ and $R^{f5}$ are each independently selected from $C_{1-4}$ alkyl, $C_{2-4}$ alkenyl, $C_{2-4}$ alkynyl, phenyl, 5-6 membered heteroaryl, $C_{3-10}$ cycloalkyl and 3-10 membered aliphatic heterocyclyl, unsubstituted or optionally substituted with 1, 2, 3, 4 or 5 substituents independently selected from $R^{33}$;

or, $R^{c5}$ and $R^{f5}$ attached to the same phosphorous atom, together with the phosphorous atom, form a 3-10 membered aliphatic heterocyclyl, unsubstituted or optionally substituted with 1, 2, 3, 4 or 5 substituents independently selected from $R^{33}$;

$R^{d5}$ is selected from:

1) hydrogen, cyano, nitro and —S(═O)$_2R^G$;

2) $C_{1-4}$ alkyl, $C_{2-4}$ alkenyl, $C_{2-4}$ alkynyl, phenyl, 5-6 membered heteroaryl, $C_{3-10}$ cycloalkyl and 3-10 membered aliphatic heterocyclyl, unsubstituted or optionally substituted with 1, 2, 3, 4 or 5 substituents independently selected from $R^{33}$;

$R^{33}$ selected from:

1) oxo, halogen, cyano, —C(═O)$R^{a7}$, —C(═O)O$R^{a7}$, —C(═O)N$R^{a7}R^{b7}$, —C(═N$R^{d7}$)N$R^{a7}R^{b7}$, —O$R^{a7}$, —OC(═O)$R^{a7}$, —OC(═O)O$R^{c7}$, —OC(═O)N$R^{a7}R^{b7}$, —S$R^{a7}$, —S(═O)$R^{c7}$, —S(═O)$_2R^{c7}$, sulphonic acid group, —S(═O)N$R^{a7}R^{b7}$, —S(═O)$_2$N$R^{a7}R^{b7}$, —S(═O)(═N$R^{d7}$)$R^{c7}$, —N$R^{a7}R^{b7}$, —N$R^{a7}$C(═O)$R^{b7}$, —N$R^{a7}$C(═O)O$R^{c7}$, —N$R^{c7}$C(═O)N$R^{a7}R^{b7}$, —N$R^{c7}$C(═N$R^{d7}$)N$R^{a7}R^{b7}$, —N$R^{a7}$S(═O)$_2R^{c7}$, —N$R^{e7}$S(═O)$_2$N$R^{a7}R^{b7}$, nitro, —P$R^{c7}R^{f7}$, —P(═O)$R^{c7}R^{f7}$, phosphonic acid group and imino group (═N—$R^{d7}$);

2) $C_{1-4}$ alkyl, $C_{1-4}$ alkylene, $C_{2-4}$ alkenyl, $C_{2-4}$ alkynyl, phenyl, 5-6 membered heteroaryl, $C_{3-8}$ cycloalkyl and 3-8 membered aliphatic heterocyclyl, unsubstituted or optionally substituted with 1, 2, 3 or 4 substituents independently selected from $R^G$;

$R^{a7}$, $R^{b7}$ and $R^{e7}$ are each independently selected from:

1) hydrogen;

2) $C_{1-4}$ alkyl, $C_{2-4}$ alkenyl, $C_{2-4}$ alkynyl, phenyl, 5-6 membered heteroaryl, $C_{3-8}$ cycloalkyl and 3-8 membered aliphatic heterocyclyl, unsubstituted or optionally substituted with 1, 2, 3 or 4 substituents independently selected from $R^G$;

or, $R^{a7}$ and $R^{b7}$ attached to the same nitrogen atom, together with the nitrogen atom, form a 3-8 membered aliphatic heterocyclyl, unsubstituted or optionally substituted with 1, 2, 3 or 4 substituents independently selected from $R^G$;

$R^{c7}$ and $R^{f7}$ are each independently selected from $C_{1-4}$ alkyl, $C_{2-4}$ alkenyl, $C_{2-4}$ alkynyl, phenyl, 5-6 membered heteroaryl, $C_{3-8}$ cycloalkyl and 3-8 membered aliphatic heterocyclyl, unsubstituted or optionally substituted with 1, 2, 3 or 4 substituents independently selected from $R^G$;

or, $R^{c7}$ and $R^{f7}$ attached to the same phosphorous atom, together with the phosphorous atom, form a 3-8 membered aliphatic heterocyclyl, unsubstituted or optionally substituted with 1, 2, 3 or 4 substituents independently selected from $R^G$;

$R^{d7}$ is selected from:

1) hydrogen, cyano, nitro and —S(═O)$_2R^G$;

2) $C_{1-4}$ alkyl, $C_{2-4}$ alkenyl, $C_{2-4}$ alkynyl, phenyl, 5-6 membered heteroaryl, $C_{3-8}$ cycloalkyl and 3-8 membered aliphatic heterocyclyl, unsubstituted or optionally substituted with 1, 2, 3 or 4 substituents independently selected from $R^G$;

$R^G$ is selected from:

1) halogen, oxo, cyano, carboxyl, hydroxyl, $C_{1-4}$ alkoxy, amino, $C_{1-4}$ alkylamino, nitro, $C_{1-4}$ alkylthio, sulphonic acid group, $C_{1-4}$ alkyl sulfinyl, $C_{1-4}$ alkyl sulfonyl, $C_{1-4}$ alkylaminosulfonyl and $C_{1-4}$ alkylaminosulfonyl;

2) $C_{1-4}$ alkyl, $C_{1-4}$ alkylene, $C_{2-4}$ alkenyl, $C_{2-4}$ alkynyl, $C_{3-6}$ cycloalkyl and 3-8 membered aliphatic heterocyclyl, unsubstituted or optionally substituted with 1, 2, 3 or 4 substituents independently selected from oxo, halogen, hydroxyl, hydroxymethyl, carboxyl, cyano, $C_{1-3}$ alkoxy, amino, $C_{1-4}$ alkylamino, nitro and sulphonic acid group.

In some embodiments, in formula (I), $R^1$ is selected from hydrogen, fluorine, cyano, methyl and methoxy.

In some embodiments, in formula (I), $Cy^A$ is phenyl, pyridyl, pyrimidyl, pyrazolyl, imidazolyl, thiazolyl, isothiazolyl, or a bicyclyl represented by

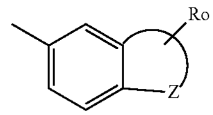

where a phenyl is fused with a 5-7 membered saturated aliphatic heterocyclyl, wherein Z represents 1-3 heteroatoms optionally selected from nitrogen and oxygen; when Z═N, said N is optionally linked to Ry; Ro is selected from oxo, F, amino, $C_{1-3}$ alkyl (optionally substituted with F, hydroxyl, amino and $C_{1-3}$ alkoxy); said aliphatic heterocyclyl may be fused with another 5-6 membered nitrogen-containing saturated aliphatic heterocyclyl to form fused ring; said phenyl, pyridyl, pyrimidyl, pyrazolyl, imidazolyl, thiazolyl, isothiazolyl, or bicyclyl represented by

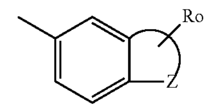

is unsubstituted or optionally substituted with 1, 2 or 3 substituents independently selected from $R^{12}$, wherein 1) when $Cy^A$ contains one $R^{12}$, the $R^{12}$ is selected from one of the followings:

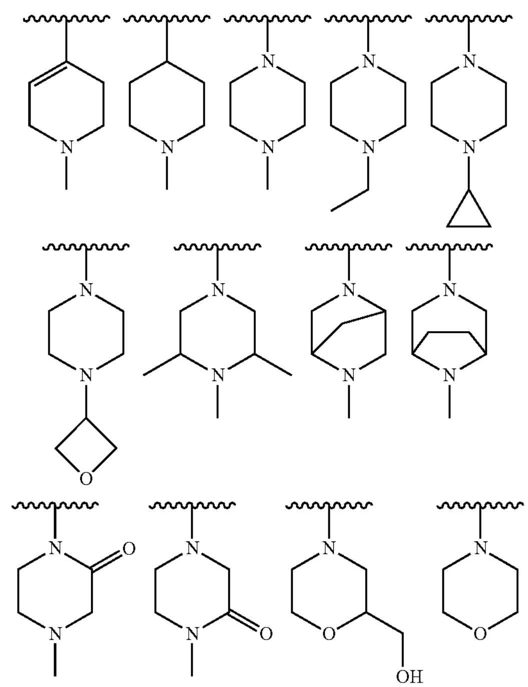

-continued

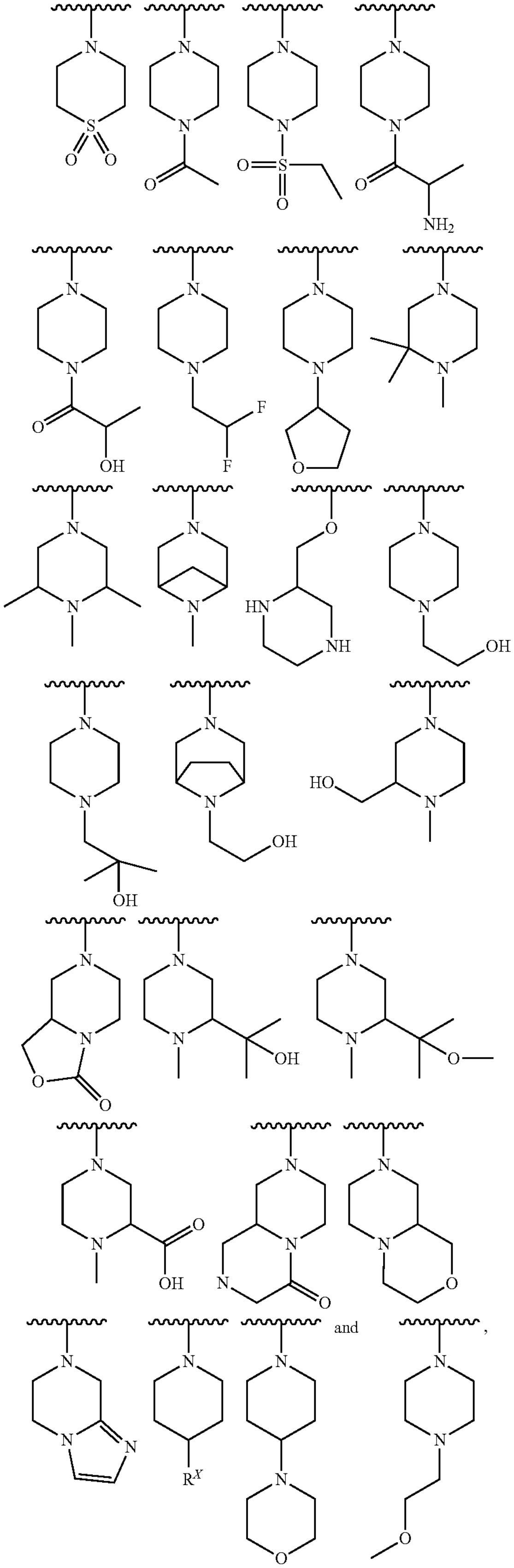

and ,

Wherein $R^x$ is selected from —OH, $C_{1-6}$ alkyl (e.g., methyl), $C_{1-6}$ alkoxy (e.g., methoxy), —$NH_2$, $C_{1-6}$ alkylamino (e.g., amino, dimethylamino)

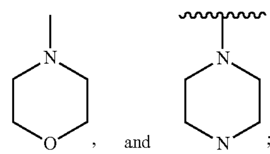

, and ;

2) when $Cy^A$ contains more than one $R^{12}$, other $R^{12}$ are each independently selected from fluorine, $C_{1-6}$ alkyl (e.g., methyl), $C_{1-6}$ alkoxy (e.g., methoxy), ($C_{1-6}$ alkylamino)methyl (e.g., (dimethylamino)methyl, (methylamino)methyl);

$Cy^B$ is selected from one of the followings:

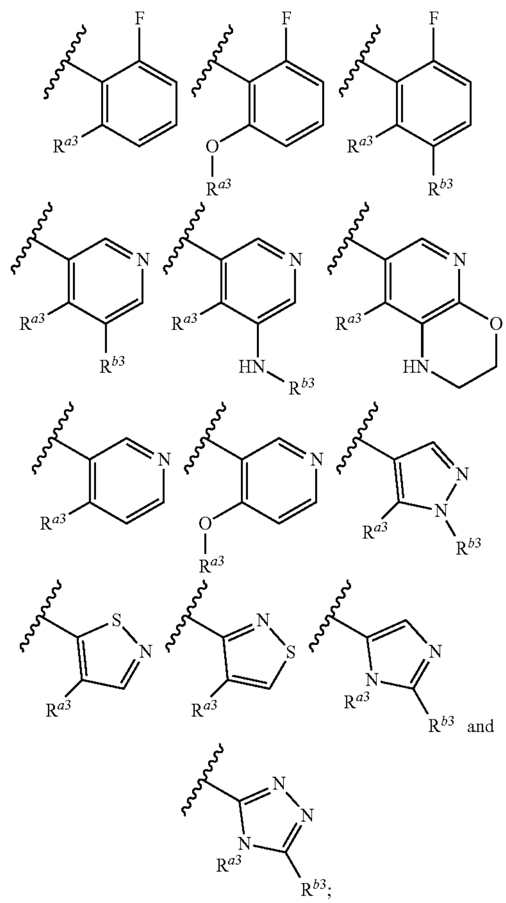

and ;

$R^{a3}$ and $R^{b3}$ are each independently selected from hydrogen, $C_{1-6}$ alkyl, and $C_{3-6}$ cycloalkyl, or $R^{a3}$ and $R^{b3}$ together with N atom to to which they are attached form a 4-6 membered saturated aliphatic heterocyclyl; said $C_{1-6}$ alkyl, $C_{3-6}$ cycloalkyl, and 4-6 membered saturated aliphatic heterocyclyl is unsubstituted or optionally substituted with substituent(s) selected from hydroxyl, $C_{1-6}$ alkyl, and fluoro-substituted $C_{1-6}$ alkyl;

$R^y$ is selected from H, $C_{1-6}$ alkyl (e.g., methyl), $C_{1-6}$ alkyl substituted with hydroxyl or halogen (e.g., hydroxyethyl, hydroxypropyl, difluoroethyl), $C_{3-6}$ cycloalkyl (e.g., cyclobutanyl, cyclobutanyl substituted with amino), 4-6 membered N-containing saturated aliphatic heterocyclyl, 5-6 membered O-containing saturated aliphatic heterocyclyl, and —C(═O)Rs, Rs is selected from $C_{1-6}$ alkyl optionally substituted with hydroxyl, amino, and 5-6 membered N-containing aliphatic heterocyclyl.

In some embodiments, In formula (I), $Cy^A$ is selected from phenyl, pyridyl, pyrimidyl, thiazolyl or a bicyclyl represented by

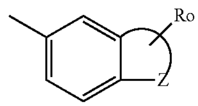

where a phenyl is fused with a 5-7 membered saturated aliphatic heterocyclyl, wherein Z represents 1-3 heteroatoms optionally selected from nitrogen and oxygen; when Z═N, Z is optionally substituted with Ry; Ro is selected from oxo, F, amino, $C_{1-3}$ alkyl (optionally substituted with F, hydroxyl, amino, and $C_{1-3}$ alkoxy); said aliphatic heterocyclyl may form fused ring with another 5-6 membered nitrogen-containing saturated aliphatic heterocyclyl heteroatom;

When $Cy^A$ is selected from phenyl, pyridyl, pyrimidyl, or thiazolyl, $R^{12}$ is selected from

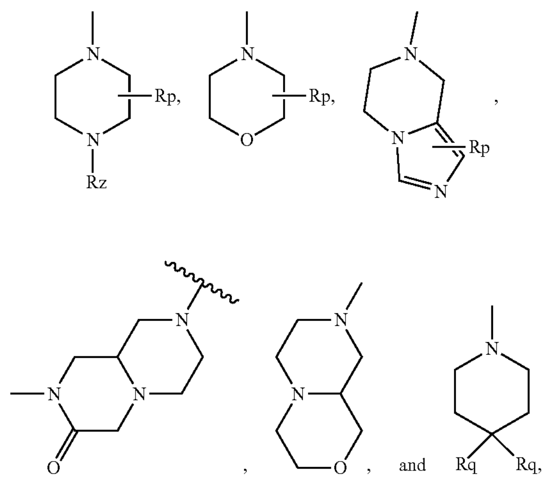

wherein $R^z$ is selected from hydrogen, $C_{1-6}$ alkyl (substituted with cyano, or methoxy), 4-6 membered oxygen-containing aliphatic heterocyclyl, or —S(═O)$_2$—$C_{1-6}$ alkyl; Rp, single or multiple substituent(s), are each optionally selected from hydrogen, $C_{1-6}$ alkyl (optionally substituted with F, hydroxyl, and amino); Rq is selected from hydroxyl, amino, $C_{1-3}$ alkyl (optionally substituted with 5-6 membered nitrogen-containing aliphatic heterocyclyl, or 5-6 membered nitrogen-containing heteroaryl), spiro heterocyclyl composed of two 4-5 membered nitrogen- and/or oxygen-containing rings, 5-6 membered aliphatic heterocyclyl containing one or two heteroatoms selected from nitrogen and oxygen; said aliphatic heterocyclyl is optionally substituted with F or $C_{1-3}$ alkyl.

In some embodiments, in formula (I), $Cy^A$ is selected from phenyl, $R^{12}$ is selected from

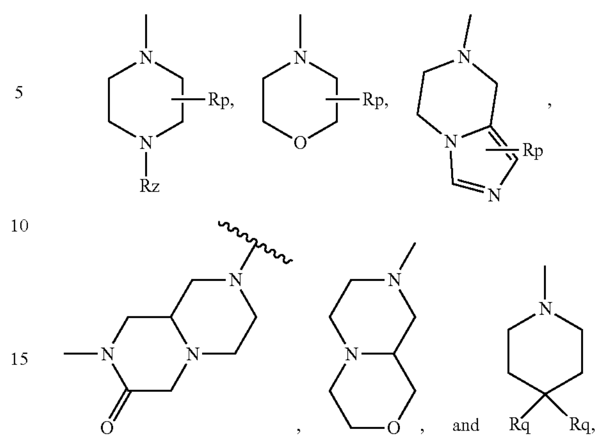

wherein $R^z$ is selected from hydrogen, $C_{1-6}$ alkyl (substituted with cyano, or methoxy), 4-6 membered oxygen-containing aliphatic heterocyclyl, or —S(═O)$_2$—$C_{1-6}$ alkyl; Rp, single or multiple substituent(s), are each optionally selected from hydrogen, $C_{1-6}$ alkyl (optionally substituted with F, hydroxyl, or amino); Rq is selected from hydroxyl, amino, $C_{1-3}$ alkyl (optionally substituted with 5-6 membered nitrogen-containing aliphatic heterocyclyl, or 5-6 membered nitrogen-containing heteroaryl), spiro heterocyclyl composed of two 4-5 membered nitrogen- and/or oxygen-containing aliphatic heterocyclyl, 5-6 membered aliphatic heterocyclyl containing one or two heteroatoms selected from nitrogen and oxygen; wherein said aliphatic heterocyclyl is optionally substituted with F or $C_{1-3}$ alkyl.

In some embodiments, in formula (I), $Cy^A$ is selected from the followings:

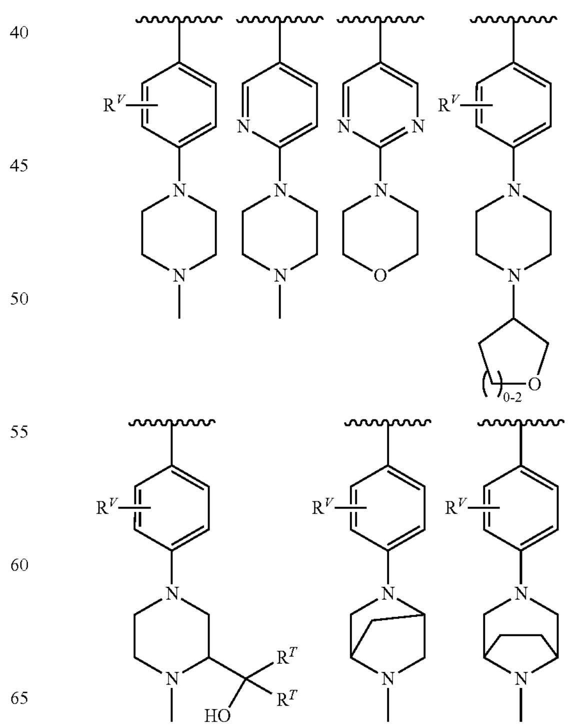

-continued

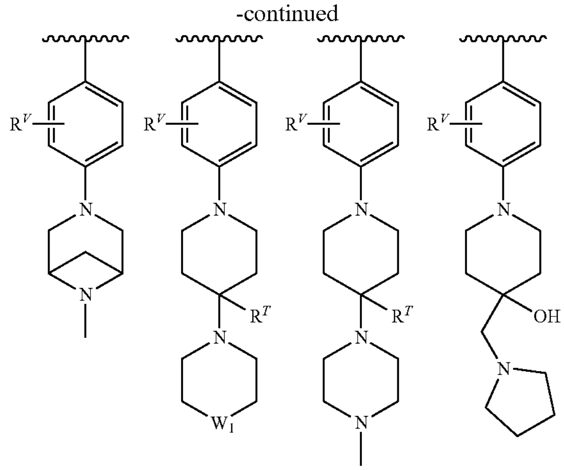

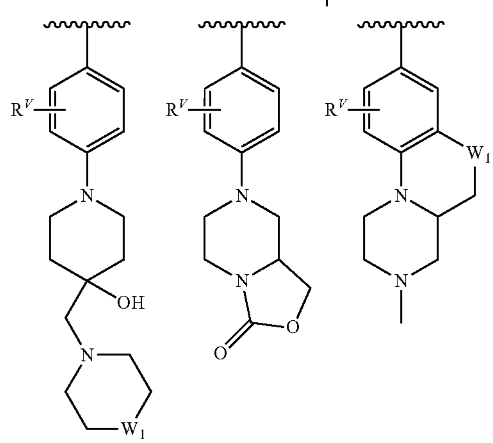

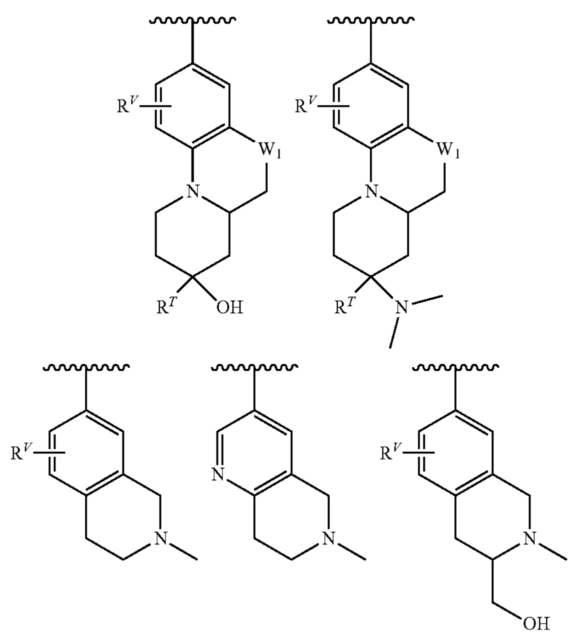

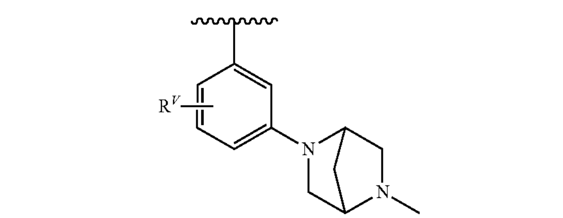

-continued

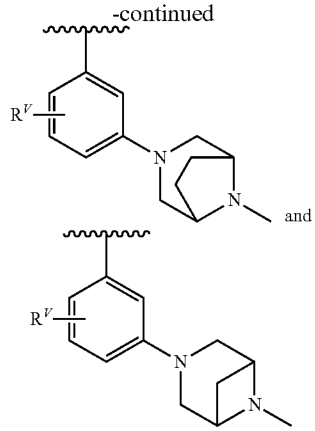

and

Wherein $W_1$ is selected from $CH_2$ or oxygen;

$R^T$ is selected from hydrogen or methyl;

$R^V$ is selected from fluorine or methyl, the amount of $R^V$ is 0, 1 or 2.

In some embodiments, in formula (I), $Cy^B$ is selected from phenyl, optionally substituted with H, F, —CN, $C_{1-3}$ alkyl (substituted with F, and amino), $C_{1-3}$ alkoxy (substituted with F), $C_{3-6}$ cycloalkoxy, and —C(═O)$NR^{a3}R^{b3}$, wherein $R^{a3}$ and $R^{b3}$ are each independently selected from hydrogen, $C_{1-6}$ alkyl, $C_{3-6}$ cycloalkyl (substituted with $C_{1-3}$ alkyl optionally substituted with F), or $R^{a3}$ and $R^{b3}$ together with the N atom to which they are attached form a 4-5 membered aliphatic heterocyclyl (optionally substituted with hydroxyl and $C_{1-3}$ alkyl).

In some embodiments, in formula (I), $Cy^B$ is selected from:

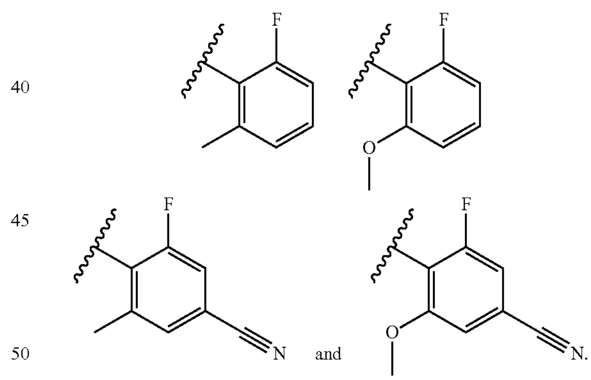

and

In some embodiments, in formula (I), when $Cy^A$ is phenyl, and $R^{12}$ is an aliphatic heterocyclyl, $R^{12}$ is linked to the meta- or para-position of said phenyl.

In some embodiments, the compounds of formula (I) include isotope labeled compounds wherein $^1H$ is deuterated.

In an aspect, the application provides a pharmaceutical composition including the compound of formula (I) or a pharmaceutically acceptable salt, hydrate, solvate, active metabolite, polymorph, isotope labeled compound, isomer or prodrug thereof, and a pharmaceutically acceptable carrier.

In an aspect, the application provides the compound of formula (I) or a pharmaceutically acceptable salt, hydrate, solvate, active metabolite, polymorph, isotope labeled compound, isomer or prodrug thereof, or a pharmaceutical composition thereof, for the prevention or treatment of a disease mediated with HPK1.

In an aspect, the application provides use of the compound of formula (I) or a pharmaceutically acceptable salt, hydrate, solvate, active metabolite, polymorph, isotope labeled compound, isomer or prodrug thereof, or a pharmaceutical composition thereof, in the preparation of a medicament for the prevention or treatment of a disease mediated with HPK1.

In some embodiments, the application provides use of the compound of formula (I) or a pharmaceutically acceptable salt, hydrate, solvate, active metabolite, polymorph, isotope labeled compound, isomer or prodrug thereof, or a pharmaceutical composition thereof, for the treatment or amelioration of one or more diseases selected from the group consisting of benign or malignant tumors, myelodysplastic syndromes and diseases caused by viruses.

In an aspect, the application provides a method for inhibiting the activity of HPK1 including administering the compound of formula (I) or a pharmaceutically acceptable salt, hydrate, solvate, active metabolite, polymorph, isotope labeled compound, isomer or prodrug thereof to a subject.

In some embodiments, the application provides a method for treating a disease or disorder mediated with HPK1 in a patient, including administering therapeutically effective amount of the compound of formula (I) or a pharmaceutically acceptable salt, hydrate, solvate, active metabolite, polymorph, isotope labeled compound, isomer or prodrug thereof to the patient.

In some embodiments, the compounds of formula (I) has the activity of inhibiting HPK1.

In some embodiments, the disease includes one or more diseases selected from the group consisting of benign or malignant tumors, myelodysplastic syndromes and diseases caused by viruses.

EMBODIMENTS

Typical embodiments embodying the features and advantages of the present application will be described in detail in the following description. It should be understood that the present application may have various variations in different embodiments, none of which is departing from the scope of the present application, and the description therein is essentially for illustrative purposes and not for the purpose of limiting the scope of the application.

In some embodiments, $R^1$ is selected from:

1) hydrogen, halogen, cyano, acetylenyl, —$OR^a$ and —$NR^aR^b$;
2) $C_{1-4}$ alkyl, $C_{3-5}$ monocyclic cycloalkyl, and 4-7 membered aliphatic heterocyclyl, unsubstituted or optionally substituted with one, two, three or four substituents independently selected from $R^{11}$.

In some embodiments, $R^1$ is selected from hydrogen, fluorine, chlorine, bromine, cyano, $C_{1-4}$ alkyl, $C_{3-4}$ cycloalkyl, 3-4 membered aliphatic heterocyclyl and —$OR^a$.

In some embodiments, $R^1$ is selected from hydrogen, fluorine, cyano, methyl, ethyl, 1-propyl, isopropyl, cyclopropyl, methoxy, ethoxy and cyclopropoxy.

In some embodiments, $R^1$ is hydrogen.

In some embodiments, $R^a$ and $R^b$ are each independently selected from hydrogen, $C_{1-3}$ alkyl, $C_{3-4}$ cycloalkyl and 3-4 membered aliphatic heterocyclyl;

or, $R^a$ and $R^b$ attached to same nitrogen atom, together with the nitrogen atom, form an unsubstituted 3-6 membered aliphatic heterocyclyl.

In some embodiments, $R^a$ and $R^b$ are each independently selected from hydrogen, methyl, ethyl and cyclopropyl.

In some embodiments, $Cy^A$ is phenyl, naphthyl, or 5, 6, 7, 8, 9 or 10 membered heteroaryl containing 1, 2 or 3 ring-forming heteroatoms selected from N, O, and S, said phenyl, naphthyl and 5, 6, 7, 8, 9 or 10 membered heteroaryl is unsubstituted or optionally substituted with 1, 2, 3 or 4 substituents independently selected from $R^{12}$.

In some embodiments, the aryl or heteroaryl of $Cy^A$ contains one $R^{12}$ selected from a cyclic group, wherein the cyclic group is selected from 6-10 membered aryl, 5-10 membered heteroaryl, $C_{3-7}$ cycloalkyl, and 3-7 membered aliphatic heterocyclylaliphatic containing 1 or 2 ring-forming heteroatoms optionally selected from N, O, and S, wherein said 6-10 membered aryl, 5-10 membered heteroaryl, $C_{3-7}$ cycloalkyl, and 3-7 membered aliphatic heterocyclyl is unsubstituted or optionally substituted with 1, 2 or 3 substituents independently selected from $R^{22}$;

or, the aryl or heteroaryl of $Cy^A$ contains 2, 3 or 4 of $R^{12}$, wherein one of the $R^{12}$ is the above mentioned cyclic group, and other $R^{12}$ are each independently selected from $C_{1-6}$ alkyl, halogen, cyano, —$OR^{a2}$ and —$NR^{a2}R^{b2}$.

In some embodiments, the aryl or heteroaryl of $Cy^A$ contains one $R^{12}$ which is a cyclic group selected from phenyl, 5-6 membered heteroaryl, $C_{3-6}$ cycloalkyl, and 4, 5, 6, and 7 membered aliphatic heterocyclylaliphatic containing 1 or 2 of ring-forming heteroatoms selected from N, O, and S, wherein said phenyl, 5-6 membered heteroaryl, $C_{3-6}$ cycloalkyl, and 4, 5, 6, and 7 membered aliphatic heterocyclyl is unsubstituted or optionally substituted with 1, 2 or 3 substituents independently selected from $R^{22}$.

or, the aryl or heteroaryl of $Cy^A$ contains 2 or 3 of $R^{12}$, wherein one of the $R^{12}$ is the above mentioned cyclic group, and other $R^{12}$ are each independently selected from $C_{1-6}$ alkyl, halogen, cyano, —$OR^{a2}$ and —$NR^{a2}R^{b2}$.

In some embodiments, $Cy^A$ is phenyl or 5-6 membered heteroaryl, optionally substituted with 1, 2, 3 or 4 substituents independently selected from $R^{12}$.

In some embodiments, $Cy^A$ is phenyl or 5-6 membered heteroaryl, optionally substituted with 1, 2, 3 or 4 substituents independently selected from $R^{12}$, wherein two $R^{12}$, together with two adjacent ring-forming atoms of the phenyl or heteroaryl to which they are attached respectively, form $C_5$, $C_6$, $C_7$ aliphatic monocyclyl or 5, 6, 7 membered aliphatic monocyclic heterocyclyl, said $C_5$, $C_6$, $C_7$ aliphatic monocyclyl or 5, 6, 7 membered aliphatic monocyclic heterocyclyl is unsubstituted or optionally substituted with 1, 2, 3 or 4 substituents independently selected from $R^{22}$.

In some embodiments, $Cy^A$ is phenyl, 5 membered or 6 membered heteroaryl containing one or two heteroatoms selected from N and S, for example, one nitrogen atom, two nitrogen atoms, or one nitrogen atom and one sulfur atom, said phenyl, 5 membered or 6 membered heteroaryl is optionally substituted with 1, 2 or 3 substituents independently selected from $R^{12}$.

In some embodiments, $Cy^A$ is phenyl, pyridyl, pyrimidyl, pyrazolyl, imidazolyl, thiazolyl, isothiazolyl, oxazolyl or isoxazolyl, which is optionally substituted with 1, 2 or 3 substituents independently selected from $R^{12}$.

In some embodiments, $Cy^A$ is phenyl, pyridyl, pyrazolyl, imidazolyl or thiazolyl, which is optionally substituted with 1, 2 or 3 substituents independently selected from $R^{12}$.

In some embodiments, the aryl or heteroaryl of $Cy^A$ contains two, three or four of $R^{12}$, wherein two $R^{12}$, together with two adjacent ring-forming atoms of the aryl or heteroaryl to which they are attached respectively, form $C_{5-8}$ aliphatic cyclyl (alicycly) or 5-8 membered aliphatic heterocyclyl containing 1, 2 or 3 ring-forming heteroatoms selected from N, O, and S, wherein said $C_{5-8}$ aliphatic cyclyl (alicycly) or 5-8 membered aliphatic heterocyclyl is unsubstituted or optionally substituted with 1, 2 or 3 substituents independently selected from $R^{22}$; other not-ring-forming $R^{12}$ are each independently selected from $C_{1-6}$ alkyl, halogen, cyano, $—OR^{a2}$ and $—NR^{a2}R^{b2}$.

In some embodiments, the aryl or heteroaryl of $Cy^A$ contains two, three or four of $R^{12}$, wherein two $R^{12}$, together with two adjacent ring-forming atoms of the aryl or heteroaryl to which they are attached respectively, form 5, 6, 7 membered aliphatic monoheterocyclyl containing 1 or 2 ring-forming heteroatoms selected from N and O, wherein said aliphatic monocyclic heterocyclyl is unsubstituted or optionally substituted with 1, 2 or 3 substituents independently selected from oxo, $R^{II}$, $—(CH_2)_{0-2}—OH$, $—(CH_2)_{0-2}—OR^{II}$, $—(CH_2)_{0-2}—NH_2$, $—(CH_2)_{0-2}—NHR^{II}$ and $—(CH_2)_{0-2}—N(R^{II})_2$; other not-ring-forming $R^{12}$ are each independently selected from $C_{1-6}$ alkyl, halogen, cyano, $—OR^{a2}$ and $—NR^{a2}R^{b2}$; RH is selected from methyl, ethyl, isopropyl, cyclopropyl and 3-oxetanebutyl.

In some embodiments, each $R^{12}$ is independently selected from:

1) oxo, halogen, cyano, $—C(═O)R^{a2}$, $—C(═O)OR^{a2}$, $—C(═O)NR^{a2}R^{b2}$, $—C(═NR^{d2})NR^{a2}R^{b2}$, $—OR^{a2}$, $—OC(═O)R^{a2}$, $—OC(═O)OR^{c2}$, $—OC(═O)NR^{a2}R^{b2}$, $—SR^{a2}$, $—S(═O)R^{c2}$, $—S(═O)_2R^{c2}$, sulphonic acid group, $—S(═O)NR^{a2}R^{b2}$, $—S(═O)_2NR^{a2}R^{b2}$, $—S(═O)(═NR^{d2})R^{c2}$, $—NR^{a2}R^{b2}$, $—NR^{a2}C(═O)R^{b2}$, $—NR^{a2}C(═O)OR^{c2}$, $—NR^{e2}C(═O)NR^{a2}R^{b2}$, $—NR^{e2}C(═NR^{d2})NR^{a2}R^{b2}$, $—NR^{a2}S(═O)_2R^{c2}$, $—NR^{e2}S(═O)_2NR^{a2}R^{b2}$ and nitro;
2) $C_{1-6}$ alkyl, $C_{2-6}$ alkenyl, $C_{2-6}$ alkynyl, 6-10 membered aryl, 5-10 membered heteroaryl, $C_{3-12}$ cycloalkyl and 3-12 membered aliphatic heterocyclyl, unsubstituted or optionally substituted with 1, 2, 3, 4, 5 or 6 substituents independently selected from $R^{22}$;
3) two $R^{12}$, together with two adjacent ring-forming atoms ring-forming atoms of the aryl or heteroaryl in $Cy^A$ to which they are attached respectively, form $C_{5-12}$ aliphatic cyclyl or 5-12 membered aliphatic heterocyclyl, unsubstituted or optionally substituted with 1, 2, 3, 4, 5 or 6 substituents independently selected from $R^{22}$.

In some embodiments, each $R^{12}$ is independently selected from:

1) oxo, halogen, cyano, $—C(═O)R^{a2}$, $—C(═O)OR^{a2}$, $—C(═O)NR^{a2}R^{b2}$, $—C(═NR^{d2})NR^{a2}R^{b2}$, $—OR^{a2}$, $—OC(═O)R^{a2}$, $—OC(═O)OR^{c2}$, $—OC(═O)NR^{a2}R^{b2}$, $—NR^{a2}R^{b2}$, $—NR^{a2}C(═O)R^{b2}$, $—NR^{a2}C(═O)OR^{c2}$, $—NR^{c2}C(═O)NR^{a2}R^{b2}$, $—NR^{c2}C(═NR^{d2})NR^{a2}R^{b2}$, $—NR^{a2}S(═O)_2R^{c2}$, $—NR^{e2}S(═O)_2NR^{a2}R^{b2}$ and nitro;
2) $C_{1-6}$ alkyl, $C_{2-6}$ alkenyl, $C_{2-6}$ alkynyl, 6-10 membered aryl, 5-10 membered heteroaryl, $C_{3-10}$ cycloalkyl and 3-10 membered aliphatic heterocyclyl, unsubstituted or optionally substituted with 1, 2, 3, 4, 5 or 6 substituents independently selected from $R^{22}$;
3) two $R^{12}$, together with two adjacent ring-forming atoms of the aryl or heteroaryl in $Cy^A$ to which they are attached respectively, form $C_{5-10}$ aliphatic cyclyl or 5-10 membered aliphatic heterocyclyl, unsubstituted or optionally substituted with 1, 2, 3, 4 or 5 substituents independently selected from $R^{22}$.

In some embodiments, each $R^{12}$ is independently selected from:

1) oxo, halogen, cyano, $—C(═O)R^{a2}$, $—C(═O)OR^{a2}$, $—C(═O)NR^{a2}R^{b2}$, $—C(═NR^{d2})NR^{a2}R^{b2}$, $—OR^{a2}$, $—OC(═O)R^{a2}$, $—OC(═O)OR^{c2}$, $—OC(═O)NR^{a2}R^{b2}$, $—NR^{a2}R^{b2}$, $—NR^{a2}C(═O)R^{b2}$, $—NR^{a2}C(═O)OR^{c2}$, $—NR^{c2}C(═O)NR^{a2}R^{b2}$, $—NR^{e2}C(═NR^{d2})NR^{a2}R^{b2}$, $—NR^{a2}S(═O)_2R^{c2}$, $—NR^{e2}S(═O)_2NR^{a2}R^{b2}$ and nitro;
2) $C_{1-6}$ alkyl, $C_{2-6}$ alkenyl, $C_{2-6}$ alkynyl, 6-10 membered aryl, 5-10 membered heteroaryl, $C_{3-10}$ cycloalkyl and 3-10 membered aliphatic heterocyclyl, unsubstituted or optionally substituted with 1, 2, 3 or 4 substituents independently selected from $R^{22}$;
3) two $R^{12}$, together with two adjacent ring-forming atoms of the aryl or heteroaryl in $Cy^A$ to which they are attached respectively, form $C_{4-8}$ aliphatic cyclyl or 4-8 membered aliphatic heterocyclyl, unsubstituted or optionally substituted with 1, 2 or 3 substituents independently selected from $R^{22}$.

In some embodiments, each $R^{12}$ is independently selected from:

1) oxo, halogen, cyano, $—C(═O)R^{a2}$, $—C(═O)NR^{a2}R^{b2}$, $—C(═NR^{d2})NR^{a2}R^{b2}$, $—OR^{a2}$, $—NR^{a2}R^{b2}$, $—NR^{a2}C(═O)R^{b2}$, $—NR^{e2}C(═O)NR^{a2}R^{b2}$, $—NR^{e2}C(═NR^{d2})NR^{a2}R^{b2}$, $—NR^{a2}S(═O)_2R^{c2}$, and $—NR^{e2}S(═O)_2NR^{a2}R^{b2}$;
2) $C_{1-6}$ alkyl, 6-10 membered aryl, 5-10 membered heteroaryl, $C_{3-10}$ cycloalkyl, and 3-10 membered aliphatic heterocyclyl, unsubstituted or optionally substituted with 1, 2, 3, 4, 5 or 6 substituents independently selected from $R^{22}$;
3) two $R^{12}$, together with two adjacent ring-forming atoms of the aryl or heteroaryl in $Cy^A$ to which they are attached respectively, form $C_{4-8}$ aliphatic cyclyl or 4-8 membered aliphatic heterocyclyl, unsubstituted or optionally substituted with 1, 2, 3 or 4 substituents independently selected from $R^{22}$.

In some embodiments, each $R^{12}$ is independently selected from:

1) oxo, halogen, cyano, $—C(═O)R^{a2}$, $—C(═O)NR^{a2}R^{b2}$, $—C(═NR^{d2})NR^{a2}R^{b2}$, $—OR^{a2}$, $—NR^{a2}R^{b2}$, $—NR^{a2}C(═O)R^{b2}$, $—NR^{a2}C(═O)OR^{c2}$, $—NR^{c2}C(═O)NR^{a2}R^{b2}$, $—NR^{e2}C(═NR^{d2})NR^{a2}R^{b2}$, $—NR^{a2}S(═O)_2R^{c2}$, and $—NR^{e2}S(═O)_2NR^{a2}R^{b2}$,
2) $C_{1-6}$ alkyl, phenyl, 5-6 membered heteroaryl, $C_{3-10}$ cycloalkyl, and 3-10 membered aliphatic heterocyclyl, unsubstituted or optionally substituted with 1, 2, 3 or 4 substituents independently selected from $R^{22}$;
3) two $R^{12}$, together with two adjacent ring-forming atoms of the aryl or heteroaryl in $Cy^A$ to which they are attached respectively, form $C_5$, $C_6$, $C_7$ aliphatic monocyclyl or 5 membered, 6 membered, 7 membered aliphatic monocyclic heterocyclyl, unsubstituted or optionally substituted with 1, 2 or 3 substituents independently selected from $R^{22}$.

In some embodiments, each $R^{12}$ independently selected from:

1) halogen, cyano, $—OR^{a2}$, $—C(═O)NR^{a2}R^{b2}$, $—NR^{a2}R^{b2}$, $—NR^{a2}C(═O)R^{b2}$, $—NR^{a2}C(═O)OR^{c2}$, $—NR^{e2}C(═O)NR^{a2}R^{b2}$, $—NR^{e2}(═NR^{d2})NR^{a2}R^{b2}$, $—NR^{a2}S(═O)_2R^{c2}$, and $—NR^{e2}S(═O)_2NR^{a2}R^{b2}$;
2) $C_{1-6}$ alkyl, phenyl, 5-6 membered heteroaryl, $C_{3-7}$ cycloalkyl, and 3-7 membered aliphatic heterocyclyl, unsubstituted or optionally substituted with 1, 2, 3 or 4 substituents independently selected from $R^{22}$.

In some embodiments, each $R^{12}$ is independently selected from:

1) halogen, $C_{1-6}$ alkyl, $C_{3-6}$ cycloalkyl, 3-7 membered aliphatic heterocyclyl, cyano, $—OR^{a2}$, $—C(=O)NR^{a2}R^{b2}$, $—NR^{a2}R^{b2}$, $—NR^{a2}C(=O)R^{b2}$, $—NR^{e2}C(=O)NR^{a2}R^{b2}$, $—NR^{e2}C(=NR^{d2})NR^{a2}R^{b2}$, $NR^{a2}S(=O)_2R^{c2}$ and $NR^{e2}S(=O)_2NR^{a2}R^{b2}$,
2) two $R^{12}$, together with two adjacent ring-forming atoms of the aryl or heteroaryl in $Cy^A$ to which they are attached respectively, form $C_{4-8}$ aliphatic cyclyl, 4-8 membered aliphatic heterocyclyl, unsubstituted or independently optionally substituted with 1, 2, 3 or 4 substituents independently selected from $R^{22}$.

In some embodiments, two $R^{12}$, together with two adjacent ring-forming atoms of the aryl or heteroaryl in $Cy^A$ to which they are attached respectively, form $C_5$, $C_6$, $C_7$ aliphatic monocyclyl and 5 membered, 6 membered, 7 membered aliphatic monocyclic heterocyclyl, unsubstituted or independently optionally substituted with 1, 2 or 3 substituents independently selected from $R^{22}$.

In some embodiments, $R^{12}$ is selected from 4 membered, 5 membered, 6 membered, 7 membered aliphatic monocyclic heterocyclyl and 7 membered, 8 membered, 9 membered, 10 membered bicylic aliphatic heterocyclyl, which is unsubstituted or optionally substituted with 1, 2, 3 substituents independently selected from $R^{22}$.

In some embodiments, $R^{12}$ is unsubstituted or optionally substituted aliphatic monocyclic heterocyclyl or aliphatic bicyclic heterocyclyl, wherein the aliphatic bicyclic heterocyclyl may be, for example, a bridged ring group, or a spiro-ring group; wherein said aliphatic dicyclic heterocyclyl comprises A1 ring and A2 ring, A1 ring is directly connected to the aryl or heteroaryl of $Cy^A$, and A1 ring can be a 3-6 membered ring, and the total number of ring-forming atoms of the aliphatic bicyclic heterocyclyl is no more than 10.

In some embodiments, aliphatic heterocyclyl of $R^{12}$ contains 1 or 2 ring-forming heteroatoms selected from N, O, and S.

In some embodiments, each $R^{12}$ is independently selected from $C_{1-6}$ alkyl, halogen, cyano, $—OR^{a2}$ and $—NR^{a2}R^{12}$.

In some embodiments, each $R^{12}$ is independently selected from:

1) $C_{1-6}$ alkyl, $C_{1-3}$ alkoxy, $C_{3-8}$ cycloalkyl, and 3-8 membered aliphatic heterocyclyl, unsubstituted or optionally substituted with 1, 2, 3 or 4 substituents independently selected from $R^{22}$; wherein 3-8 membered aliphatic heterocyclyl is monocyclic aliphatic heterocyclyl or bicyclic aliphatic heterocyclyl, said aliphatic heterocyclyl may contain ring-forming heteroatoms selected from N and/or O; $R^{22}$ is selected from oxo, hydroxyl, amino, cyano, $C_{1-3}$ alkylamino, $C_{1-3}$ alkoxy, 3-6 membered cycloalkyl and 3-6 membered aliphatic monocyclic heterocyclyl;
2) two $R^{12}$, together with two adjacent ring-forming atoms of the aryl or heteroaryl in $Cy^A$ to which they are attached respectively, form $C_5$, $C_6$, $C_7$ aliphatic monocyclyl or 5 membered, 6 membered, 7 membered aliphatic monocyclic heterocyclyl, unsubstituted or optionally substituted with 1, 2 or 3 substituents each independently selected from $R^{22}$; $R^{22}$ is selected from oxo, methyl, ethyl, isopropyl, cyclopropyl, oxetanyl, $—N(CH_3)_2$, —OH, —CN, $—OCH_3$, $—C(=O)CH_3$, $—S(=O)_2CH_2CH_3$, $—C(=O)NH_2$, $—S(=O)_2NH_2$, $—CH_2CH_2OH$, $—CH_2OH$, and $—CH_2CH_2N(CH_3)_2$.

In some embodiments, $Cy^A$ is selected from:

1) the following structures, wherein the "⌇" at the end of the chemical bond in each structure means that the structure is connected to the rest of the formula (I) through the bond:

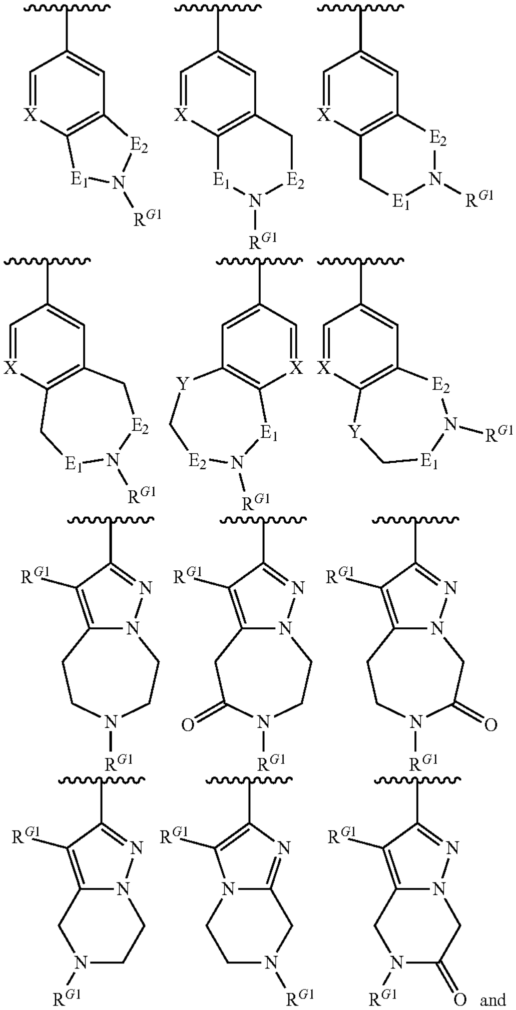

and

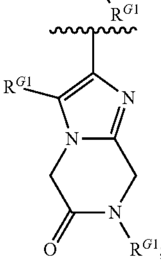

2) phenyl, pyridyl, pyrimidyl, pyrazolyl, imidazolyl, thiazolyl, isothiazolyl, oxazolyl or isoxazolyl, unsubstituted or optionally substituted with 1, 2 or 3 substituents each independently selected from $R^{12}$, wherein:

(a) each $R^{12}$ is independently selected from fluorine, chlorine, non-hydrogen $R^{G1}$, and $—OR^{G1}$;

or, (b) $Cy^A$ contains one $R^{12}$ selected from the following structures, wherein the "⌇" at the end of the chemical bond in each structure means that the structure is connected to the rest of formula (I) through the bond:

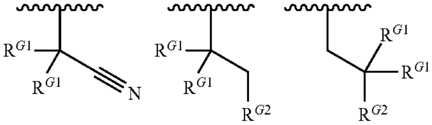
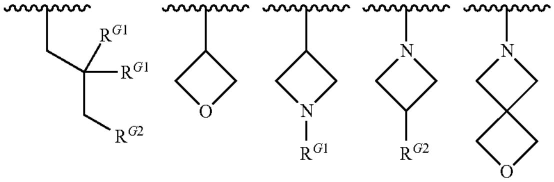
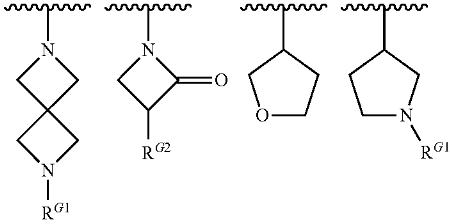
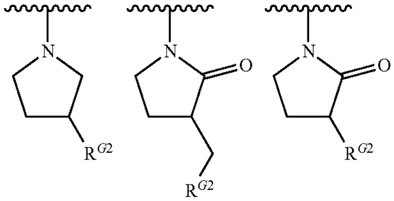
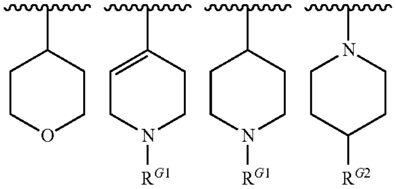
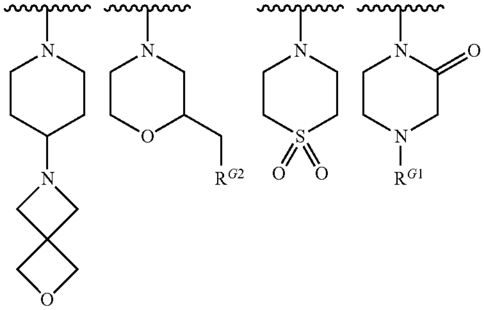
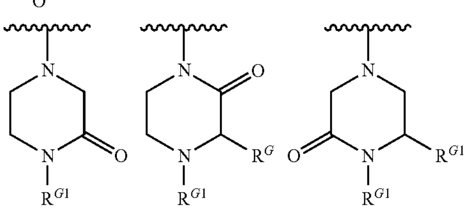
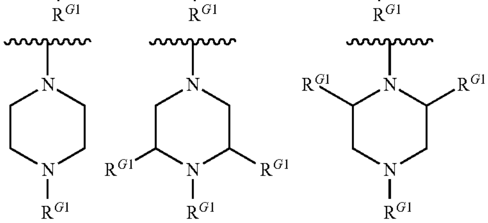
-continued
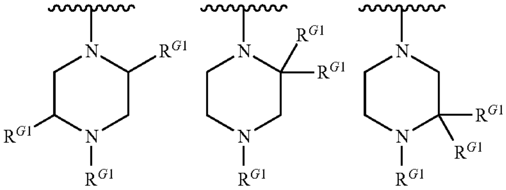
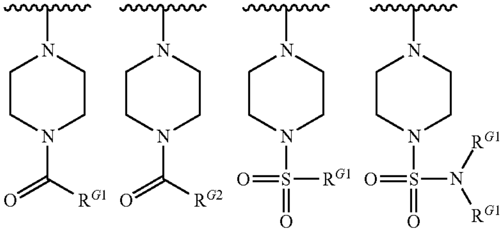
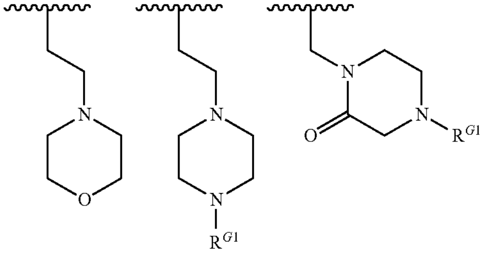
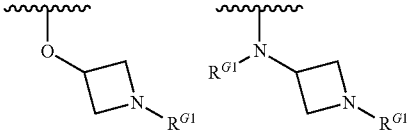
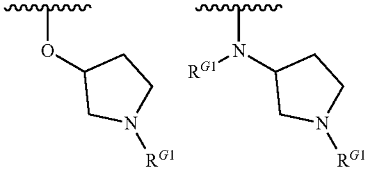
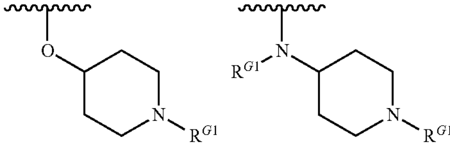
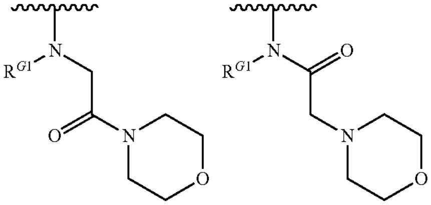
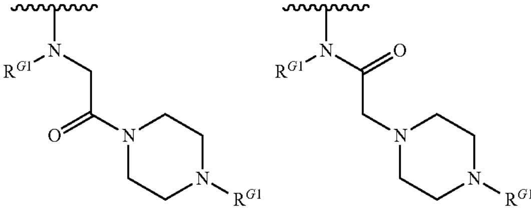

-continued

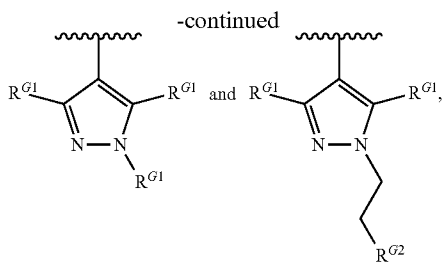

or, $Cy^A$ contains two or three $R^{12}$, wherein one of $R^{12}$ is selected from the above structures and the others of $R^{12}$ are each independently selected from fluorine, chlorine, non-hydrogen $R^{G1}$, and $—OR^{G1}$;

wherein,

X is selected from CH and N;

Y is selected from $—CH_2—$, NH and O;

$E_1$ and $E_2$ are each independently selected from $—CH_2—$ and carbonyl, but $E_1$ and $E_2$ cannot be carbonyl simultaneously;

$R^{G2}$ is selected from hydrogen, $—OR^{G1}$ and $—N(R^{G1})_2$;

Each $R^{G1}$ is independently selected from:

1) hydrogen, methyl, ethyl (optionally substituted with $C_{1-3}$ alkylamino), propyl (optionally substituted with hydroxyl and $C_{1-3}$ alkyl, such as 2-hydroxyl-2-methylpropyl), isopropyl (substituted with cyano), cyclopropyl, 3-oxetanyl and 3-methyl-3-azetidinyl;

2) two $R^{G1}$, together with the one atom to which they are attached to, form a $C_{3-6}$ monocyclyl or 3-6 membered aliphatic monocyclic heterocyclyl;

3) two $R^{G1}$ attached to two different ring-forming atoms of the same monocycle are connected to form a ring structure together with part of the ring-forming atoms of said monocycle, wherein the two connected $R^{G1}$ form a C2, C3 or C4 alkylene.

In some embodiments, $Cy^A$ is phenyl, pyridyl, pyrimidyl, pyrazolyl, imidazolyl, thiazolyl or isothiazolyl, unsubstituted or optionally substituted with 1, 2 or 3 substituents each independently selected from $R^{12}$, 1) each $R^{12}$ is independently selected from fluorine, chlorine, non-hydrogen $R^{G1}$, and $—OR^{G1}$; or, 2) $Cy^A$ contains one $R^{12}$ selected from the following structures:

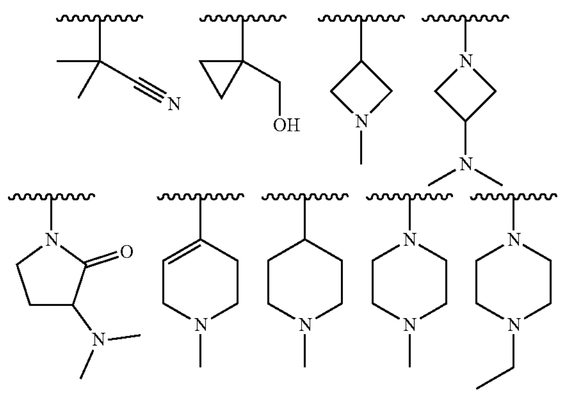

-continued

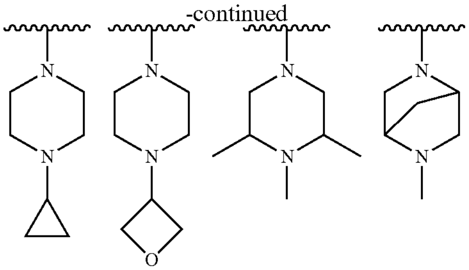

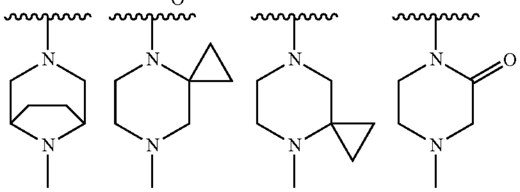

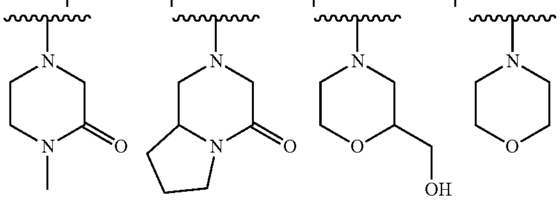

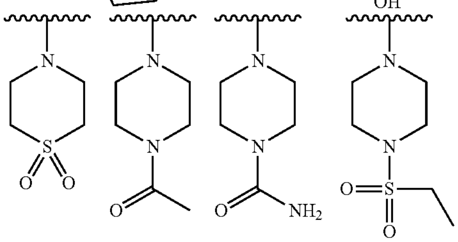

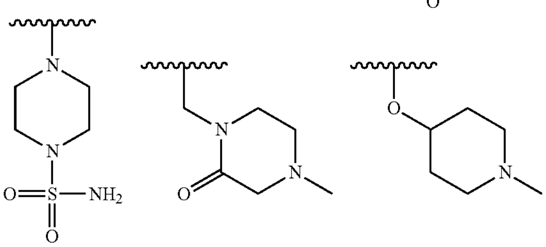

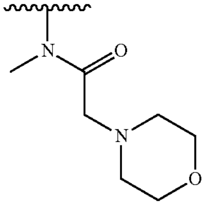

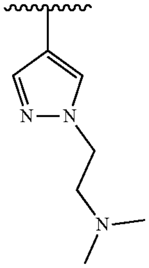

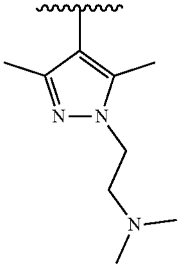

and

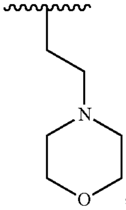

, or, $Cy^A$ contains two or three $R^{12}$, wherein one of $R^{12}$ is selected from the above structures and the others of $R^{12}$ are each independently selected from fluorine, chlorine, non-hydrogen $R^{G1}$, and —$OR^{G1}$;

Each $R^{G1}$ is independently selected from hydrogen, methyl, ethyl, isopropyl, cyclopropyl, 3-oxetanebutyl and 3-methyl-3-azetidinyl.

In some embodiments, $R^{22}$ is selected from oxo, cyano, $C_{3-7}$ cycloalkyl, 3-7 membered aliphatic heterocyclyl, $R^{H1}$, —$(CH_2)_{0-2}OH$, —$(CH_2)_{0-20}R^{H1}$, —$(CH_2)_{0-2}NH_2$, —$(CH_2)_{0-2}NHR^{11}$, —$(CH_2)_{0-2}N(R^{H1})_2$, aldehyde group, —$C(=O)R^{H1}$, —$C(=O)NH_2$, —$C(=O)NHR^{H1}$, —$C(=O)N(R^{H1})_2$, —$S(=O)_2R^{H1}$, —$S(=O)_2NH_2$, —$S(=O)_2NHR^{H1}$ and —$S(=O)_2N(R^{H1})_2$; $R^{H1}$ is independently selected from methyl, ethyl, isopropyl, cyclopropyl, 3-oxetanebutyl and 3-methyl-3-azetidinyl.

In some embodiments, $R^{22}$ is selected from oxo, cyano, methyl, ethyl, isopropyl, cyclopropyl, oxetanyl, —$N(CH_3)_2$, —OH, —CN, —$OCH_3$, —$C(=O)CH_3$, —$S(=O)_2CH_2CH_3$, —$C(=O)NH_2$, —$S(=O)_2NH_2$, —$CH_2CH_2OH$, —$CH_2OH$, and —$CH_2CH_2N(CH_3)_2$.

In some embodiments, $Cy^B$ is selected from phenyl, naphthyl and 5-10 membered heteroaryl, unsubstituted or optionally substituted with 1, 2, 3 or 4 substituents independently selected from $R^{13}$; wherein said 5-10 membered heteroaryl contains at least one ring-forming carbon atom and 1, 2, 3 or 4 ring-forming heteroatoms independently selected from N, O and S.

In some embodiments, $Cy^B$ is phenyl or 5-6 membered heteroaryl, optionally substituted with 1, 2, 3 or 4 substituents independently selected from $R^{13}$.

In some embodiments, $Cy^B$ is phenyl or 5-6 membered heteroaryl containing 1, 2 or 3 ring-forming heteroatoms selected from N and S, said phenyl or 5-6 membered heteroaryl is optionally substituted with 1, 2, or 3 substituents independently selected from $R^{13}$.

In some embodiments, $Cy^B$ is phenyl, pyridyl, pyrimidyl, pyridazinyl, pyrazolyl, imidazolyl, thiazolyl, isothiazolyl, thienyl, optionally substituted with 1, 2, or 3 substituents independently selected from $R^{13}$.

In some embodiments, $Cy^B$ is phenyl or 5-6 membered heteroaryl, optionally substituted with 1, 2, 3 or 4 substituents independently selected from $R^{13}$; wherein two $R^{13}$, together with two adjacent ring-forming atoms of the phenyl or heteroaryl of $Cy^B$ to which they are connected respectively, form a $C_{5-12}$ aliphatic cyclyl or 5-12 membered aliphatic heterocyclyl, unsubstituted or optionally substituted with 1, 2, 3, 4 or 5 substituents independently selected from $R^{23}$.

In some embodiments, $Cy^B$ is phenyl or 5-6 membered heteroaryl, optionally substituted with 1, 2, or 3 substituents independently selected from $R^{13}$; wherein two $R^{13}$, together with two adjacent ring-forming atoms of the phenyl or heteroaryl of $Cy^B$ together with the two said ring-forming atoms to which they are connected respectively, form a $C_{4-8}$ aliphatic cyclyl or 4-8 membered aliphatic heterocyclyl, unsubstituted or optionally substituted with 1, 2 or 3 substituents independently selected from $R^{23}$.

In some embodiments, $Cy^B$ is phenyl or 5-6 membered heteroaryl, optionally substituted with 1, 2, or 3 substituents independently selected from $R^{13}$; wherein two $R^{13}$, together with two adjacent ring atoms of the phenyl or heteroaryl of $Cy^B$ to which they are connected respectively, form a $C_{5-6}$ aliphatic monocyclyl or 5-6 membered aliphatic monocyclic heterocyclyl, unsubstituted or optionally substituted with 1, 2 or 3 substituents independently selected from $R^{23}$; $R^{23}$ is selected from fluorine, methyl, ethyl, isopropyl, cyclopropyl, ethylene and 3-oxetanyl.

In some embodiments, each $R^{13}$ is independently selected from:

1) oxo, halogen, cyano, —$C(=O)R^{a3}$, —$C(=O)OR^{a3}$, —$C(=O)NR^{a3}R^{b3}$, —$C(=NR^{d3})NR^{a3}R^{b3}$, —$OR^{a3}$, —$OC(=O)R^{a3}$, —$OC(=O)OR^{c3}$, —$OC(=O)NR^{a3}R^{b3}$, —$SR^{a3}$, —$S(=O)R^{c3}$, —$S(=O)_2R^{c3}$, sulphonic acid group, —$S(=O)NR^{a3}R^{b3}$, —$S(=O)_2NR^{a3}R^{b3}$, —$S(=O)(=NR^{d3})R^{c3}$, —$NR^{a3}R^{b3}$, —$NR^{a3}C(=O)R^{b3}$, —$NR^{a3}C(=O)OR^{c3}$, —$NR^{e3}C(=O)NR^{a3}R^{b3}$, —$NR^{e3}C(=NR^{d3})NR^{a3}R^{b3}$, —$NR^{a3}S(=O)_2R^{c3}$, —$NR^{e3}S(=O)_2NR^{a3}R^{b3}$ and nitro;
2) $C_{1-6}$ alkyl, $C_{2-6}$ alkenyl, $C_{2-6}$ alkynyl, 6-10 membered aryl, 5-10 membered heteroaryl, $C_{3-12}$ cycloalkyl and 3-12 membered aliphatic heterocyclyl, unsubstituted or optionally substituted with 1, 2, 3, 4, 5 or 6 substituents independently selected from $R^{23}$;
3) two $R^{13}$, together with two adjacent ring atoms of the phenyl or heteroaryl of $Cy^B$ to which they are connected respectively, form a $C_{5-12}$ aliphatic cyclyl or 5-12 membered aliphatic heterocyclyl, unsubstituted or optionally substituted with 1, 2, 3, 4 or 5 substituents independently selected from $R^{23}$.

In some embodiments, each $R^{13}$ is independently selected from:

1) oxo, halogen, cyano, —$C(=O)R^{a3}$, —$C(=O)OR^{a3}$, —$C(=O)NR^{a3}R^{b3}$, —$C(=NR^{d3})NR^{a3}R^{b3}$, —$OR^{a3}$, —$OC(=O)R^{a3}$, —$OC(=O)OR^{c3}$, —$OC(=O)NR^{a3}R^{b3}$, —$NR^{a3}R^{b3}$, —$NR^{a3}C(=O)R^{b3}$, —$NR^{a3}C(=O)OR^{c3}$, —$NR^{c3}C(=O)NR^{a3}R^{b3}$, —$NR^{c3}C(=NR^{a3})NR^{a3}R^{b3}$, —$NR^{a3}S(=O)_2R^{c3}$, —$NR^{c3}S(=O)_2NR^{a3}R^{b3}$ and nitro;
2) $C_{1-6}$ alkyl, $C_{2-6}$ alkenyl, $C_{2-6}$ alkynyl, 6-10 membered aryl, 5-10 membered heteroaryl, $C_{3-10}$ cycloalkyl and 3-10 membered aliphatic heterocyclyl, unsubstituted or optionally substituted with 1, 2, 3, 4, 5 or 6 substituents independently selected from $R^{23}$;
3) two $R^{13}$, together with two adjacent ring-forming atoms of the aryl or heteroaryl of $Cy^B$ to which they are connected respectively, form a $C_{5-10}$ aliphatic cyclyl or 5-10 membered aliphatic heterocyclyl, unsubstituted or optionally substituted with 1, 2, 3, 4 or 5 substituents independently selected from $R^{23}$.

In some embodiments, each $R^{13}$ is independently selected from:

1) oxo, halogen, cyano, —$C(=O)R^{a3}$, —$C(=O)OR^{a3}$, —$C(=O)NR^{a3}R^{b3}$, —$C(=NR^{d3})NR^{a3}R^{b3}$, —$OR^{a3}$, —$OC(=O)R^{a3}$, —$OC(=O)OR^{c3}$, —$OC(=O)NR^{a3}R^{b3}$, —$NR^{a3}R^{b3}$, —$NR^{a3}C(=O)R^{b3}$, —$NR^{a3}C(=O)OR^{c3}$, —$NR^{e3}C(=O)NR^{a3}R^{b3}$, —$NR^{c3}C(=NR^{d3})NR^{a3}R^{b3}$, —$NR^{a3}S(=O)_2R^{c3}$, —$NR^{e3}S(=O)_2NR^{a3}R^{b3}$ and nitro;
2) $C_{1-6}$ alkyl, $C_{2-6}$ alkenyl, $C_{2-6}$ alkynyl, 6-10 membered aryl, 5-10 membered heteroaryl, $C_{3-10}$ cycloalkyl and 3-10 membered aliphatic heterocyclyl, unsubstituted or optionally substituted with 1, 2, 3 or 4 substituents independently selected from $R^{23}$;
3) two $R^{13}$, together with two adjacent ring-forming atoms of the aryl or heteroaryl of $Cy^B$ to which they are connected respectively, form a $C_{4-8}$ aliphatic cyclyl or 4-8 membered aliphatic heterocyclyl, unsubstituted or optionally substituted with 1, 2 or 3 substituents independently selected from $R^{23}$.

In some embodiments, each $R^{13}$ is independently selected from:

1) oxo, halogen, cyano, —$C(=O)R^{a3}$, —$C(=O)NR^{a3}R^{b3}$, —$C(=NR^{d3})NR^{a3}R^{b3}$, —$OR^{a3}$, —$NR^{a3}R^{b3}$, —$NR^{a3}C(=O)R^{b3}$, —$NR^{c3}C(=O)$ $NR^{a3}R^{b3}$, —$NR^{c3}C$(═$NR^{d3}$)$NR^{a3}R^{b3}$, —$NR^{a3}S$(═O)$_2$ $R^{c3}$ and —$NR^{c3}S$(═O)$_2NR^{a3}R^{b3}$;

2) $C_{1-6}$ alkyl, 6-10 membered aryl, 5-10 membered heteroaryl, $C_{3-10}$ cycloalkyl and 3-10 membered aliphatic heterocyclyl, unsubstituted or optionally substituted with 1, 2, 3, 4, 5 or 6 substituents independently selected from $R^{23}$;

3) two $R^{13}$, together with two adjacent ring-forming atoms of the aryl or heteroaryl of $Cy^B$ to which they are connected respectively, form a $C_{4-8}$ aliphatic cyclyl or 4-8 membered aliphatic heterocyclyl, unsubstituted or optionally substituted with 1, 2, 3 or 4 substituents independently selected from $R^{23}$.

In some embodiments, each $R^{13}$ is independently selected from:

1) oxo, halogen, cyano, —C(═O)$R^{a3}$, —C(═O)$NR^{a3}R^{b3}$, —C(═$NR^{d3}$)$NR^{a3}R^{b3}$, —$OR^{a3}$, —$NR^{a3}R^{b3}$, —$NR^{a3}C$(═O)$R^{b3}$, —$NR^{a3}C$(═O)$OR^{c3}$, —$NR^{c3}C$(═O)$NR^{a3}R^{b3}$, —$NR^{c3}C$(═$NR^{a3}$)$NR^{a3}R^{b3}$, —$NR^{a3}S$(═O)$_2R^{c3}$, and —$NR^{e3}S$(═O)$_2NR^{a3}R^{b3}$;

2) $C_{1-6}$ alkyl, phenyl, 5-6 membered heteroaryl, $C_{3-10}$ cycloalkyl and 3-10 membered aliphatic heterocyclyl, unsubstituted or optionally substituted with 1, 2, 3 or 4 substituents independently selected from $R^{23}$;

3) two $R^{13}$, together with two adjacent ring-forming atoms of the aryl or heteroaryl of $Cy^B$ to which they are connected respectively, form a $C_5$, $C_6$, $C_7$ aliphatic monocyclyl or 5 membered, 6 membered, 7 membered aliphatic monocyclic heterocyclyl, unsubstituted or optionally substituted with 1, 2 or 3 substituents independently selected from $R^{23}$.

In some embodiments, each $R^{13}$ is independently selected from:

1) oxo, halogen, cyano, $C_{1-4}$ alkyl, $C_{3-6}$ cycloalkyl, —C(═O)$R^{a3}$, —C(═O)$NR^{a3}R^{b3}$, —$OR^{a3}$, —$NR^{a3}R^{b3}$, —$NR^{a3}C$(═O)$R^{b3}$, —$NR^{e3}C$(═O)$NR^{a3}R^{b3}$ and —$NR^{e3}C$(═$NR^{d3}$)$NR^{a3}R^{b3}$, 2) two $R^{13}$, together with two adjacent ring-forming atoms of the aryl or heteroaryl of $Cy^B$ to which they are connected respectively, form a $C_{4-8}$ aliphatic cyclyl or 4-8 membered aliphatic heterocyclyl, unsubstituted or optionally substituted with 1, 2, 3 or 4 substituents independently selected from $R^{23}$.

In some embodiments, each $R^{13}$ is independently selected from:

1) oxo, fluorine, chlorine, cyano, $C_{1-3}$ alkyl, $C_{3-4}$ cycloalkyl, —C(═O)$R^{a3}$, —C(═O)$NR^{a3}R^{b3}$, —$OR^{a3}$, —$NR^{a3}R^{b3}$, —$NR^{a3}C$(═O)$R^{b3}$, —$NR^{e3}C$(═O)$NR^{a3}R^{b3}$ and —$NR^{e3}C$(═$NR^{d3}$)$NR^{a3}R^{b3}$, 2) two $R^{13}$, together with two adjacent ring-forming atoms of the aryl or heteroaryl of $Cy^B$ to which they are connected respectively, form a $C_{5-6}$ aliphatic monocyclyl or 5-6 membered aliphatic monocyclic heterocyclyl, unsubstituted or optionally substituted with 1, 2 or 3 substituents independently selected from $R^{23}$.

In some embodiments, each $R^{13}$ independently selected from:

1) halogen and cyano;

2) $C_{1-4}$ alkyl, $C_{3-6}$ cycloalkyl and 3-6 membered aliphatic heterocyclyl, unsubstituted or optionally substituted with 1, 2 or 3 substituents each independently selected from fluorine, cyano, —$OR^{a5}$ and —$NR^{a5}R^{b5}$, wherein $R^{a5}$ and $R^{b5}$ are each independently selected from hydrogen and $C_{1-6}$ alkyl, or, $R^{a5}$ and $R^{b5}$ attached to the same N atom, together with the N atom, form a 3-6 membered aliphatic heterocyclyl.

In some embodiments, each $R^{13}$ is independently selected from halogen, cyano, —$OR^{a3}$ and —$NR^{a3}R^{b3}$, wherein $R^{a3}$ and $R^{b3}$ are each independently selected from:

1) hydrogen;

2) $C_{1-6}$ alkyl, $C_{3-6}$ cycloalkyl, and 3-6 membered aliphatic heterocyclyl, unsubstituted or optionally substituted with 1, 2 or 3 substituents independently selected from fluorine, cyano, —$OR^{a5}$ and —$NR^{a5}R^{b5}$, wherein Ras and $R^{b5}$ are each independently selected from hydrogen and $C_{1-4}$ alkyl, or, $R^{a5}$ and $R^{b5}$ attached to the same N atom, together with said N atom, form a 3-6 membered aliphatic heterocyclyl.

In some embodiments, $R^{13}$ is independently selected from:

1) fluorine, chlorine, cyano, $C_{1-3}$ alkyl, $C_{3-4}$ cycloalkyl, —$OR^{a3}$ and —$NR^{a3}R^{b3}$, 2) two $R^{13}$, together with two adjacent ring-forming atoms of the aryl or heteroaryl of $Cy^B$ to which they connected respectively, form a $C_{5-6}$ aliphatic monocyclyl or 5-6 membered aliphatic monocyclic heterocyclyl, unsubstituted or optionally substituted with 1, 2 or 3 substituents independently selected from $R^{23}$;

$R^{a3}$ and $R^{b3}$ are each independently selected from hydrogen, $C_{1-4}$ alkyl and $C_{3-6}$ cycloalkyl, or, $R^{a3}$ and $R^{b3}$ attached to the same N atom, together said N atom, form a 3-6 membered aliphatic heterocyclyl; $R^{23}$ selected from $C_{1-6}$ alkyl and $C_{3-6}$ cycloalkyl.

In some embodiments, two $R^{13}$, together with two adjacent ring-forming atoms of the aryl or heteroaryl of $Cy^B$ to which they attached respectively, form a $C_{3-7}$ aliphatic cyclyl or 3-7 membered aliphatic heterocyclyl, unsubstituted or optionally substituted with 1, 2 or 3 substituents independently selected from oxo, fluorine, cyano, —$OR^{a5}$ and —$NR^{a5}R^{b5}$, wherein said 3-7 membered aliphatic heterocyclyl contains 1 or 2 ring-forming heteroatoms selected from N, O and S; $R^{a5}$ and $R^{b5}$ are each independently selected from hydrogen and $C_{1-4}$ alkyl, or, $R^{a5}$ and $R^{b5}$ attached to the same N atom, together with said N atom, form a 3-6 membered aliphatic heterocyclyl.

In some embodiments, each $R^{13}$ independently selected from halogen, amino, $C_{1-3}$ alkyl, substituted $C_{1-3}$ alkyl, $C_{1-3}$ alkoxy, substituted $C_{1-3}$ alkoxy, $C_{3-6}$ cycloalkoxy, $C_{1-3}$ alkylamino and —C(═O)$NR^{a3}R^{b3}$; wherein the substituent of substituted $C_{1-3}$ alkyl is selected from one, two or three of halogen, hydroxyl, $C_{1-3}$ alkoxy, and $C_{1-3}$ alkyl; the substituent of substituted $C_{1-3}$ alkoxy is selected from one, two or three halogens; $R^{a3}$ and $R^{b3}$ are each independently selected from hydrogen and $C_{1-3}$ alkyl, or, $R^{a3}$, $R^{b3}$ attached to the same N atom, together with said N atom, form a 3-6 membered aliphatic heterocyclyl, unsubstituted or optionally substituted with one or two substituents selected from $C_{1-3}$ alkyl, $C_{1-3}$ alkoxy, and hydroxyl.

In some embodiments, each $R^{13}$ is independently selected from —F, —Cl, —$NH_2$, —$CH_3$, —$CH_2CH_3$, —$CH(CH_3)CH_3$, —$CF_3$, —$CHF_2$, —$CH_2OCH_3$, —$OCH_3$, —$OCH_2CH_3$, —$OCH(CH_3)CH_3$, —$OCHF_2$, —$O(C_3H_5)$ (cyclopropoxy), —$CH_2NHCH_3$, —$CH_2N(CH_3)_2$, —$NHCH_3$, —$N(CH_3)_2$, —$NHCH_2CH_3$, —$N(CH_3)(CH_2CH_3)$, —$N(CH_2CH_3)_2$, —$NR^{a3}R^{b3}$, —C(═O)$NHCH_3$, —C(═O)$N(CH_3)_2$, and —C(═O)$NR^{a3}R^{b3}$; in-$NR^{a3}R^{b3}$ and —C(═O)$NR^{a3}R^{b3}$, $R^{a3}$, $R^{b3}$ attached to the same N atom, together with said N atom, form a 4 or 5 membered saturated aliphatic monocyclic heterocyclyl, unsubstituted or optionally substituted with one or two substituents selected from methyl, hydroxyl, and methoxy.

In some embodiments, two $R^{13}$, together with two adjacent ring-forming atoms of the aryl or heteroaryl of $Cy^B$ to which they connected respectively, form a 5 membered or 6 membered aliphatic monocyclic heterocyclyl containing one or two ring-forming heteroatoms selected from N and O, said aliphatic monocyclic heterocyclyl is unsubstituted or optionally substituted with 1 or 2 substituents independently selected from $R^{23}$; $R^{23}$ may be oxo, fluorine, methyl, —$CH_2OH$, —$NHCH_3$.

In some embodiments, $Cy^B$ is selected from the following structures, wherein the "⌇" at the end of the chemical bond in each structure means that the structures are connected to the rest of formula (I) through the bond:

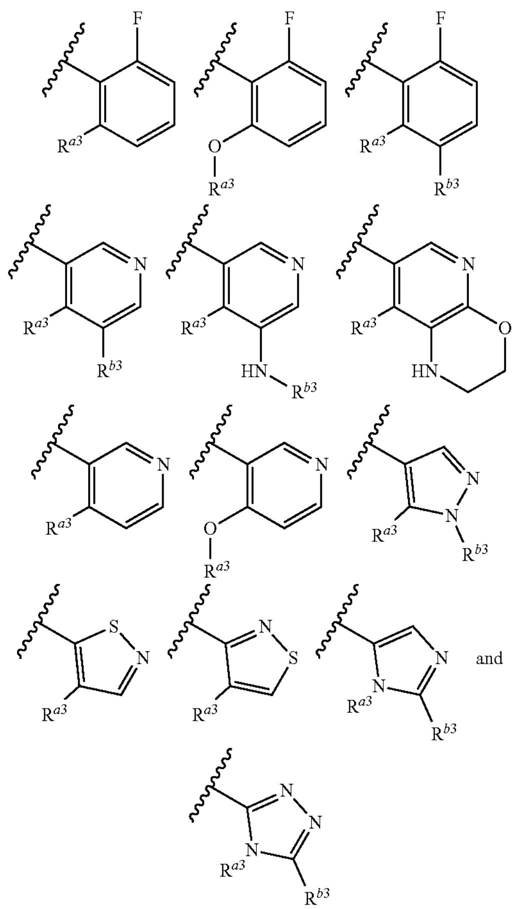

wherein, $R^{a3}$ and $R^{b3}$ are each independently selected from hydrogent and $C_{1-6}$ alkyl, or, $R^{a3}$ and $R^{b3}$, together with two adjacent ring-forming atoms to which they are attached respectively, form a 5-6 membered aliphatic monocyclyl or 5-6 membered aliphatic monocyclic heterocyclyl.

In some embodiments, $R^1$ is hydrogen;

$Cy^A$ is selected from phenyl, naphthyl and 5-10 membered heteroaryl, unsubstituted or optionally substituted with 1, 2, 3 or 4 substituents independently selected from $R^{12}$; wherein 5-membered heteroaryl contains at least two ring-forming carbon atoms and 1, 2, 3 or 4 ring-forming heteroatoms independently selected from N, O and S;

$R^{12}$ is selected from:

1) oxo, halogen, cyano, —C(═O)$R^{a2}$, carboxyl, —C(═O)$NR^{a2}R^{b2}$, —$OR^{a2}$, —$NR^{a2}R^{b2}$, —$NR^{a2}$C(═O)$R^{c2}$, —$NR^{e2}$C(═O)$NR^{a2}R^{b2}$, —$NR^{e2}$C(═$NR^{d2}$)$NR^{a2}R^{b2}$, —$NR^{a2}$S(═O)$_2R^{c2}$ and —$NR^{e2}$S(═O)$_2NR^{a2}R^{b2}$, 2) $C_{1-6}$ alkyl, $C_{2-6}$ alkenyl, $C_{2-6}$ alkynyl, phenyl, 5-6 membered heteroaryl, $C_{3-7}$ monocyclic cycloalkyl, $C_{6-10}$ bicyclic cycloalkyl, 3-7 membered aliphatic monocyclic heterocyclyl and 6-10 membered biocyclic aliphatic heterocyclyl, unsubstituted or optionally substituted with 1, 2, 3 or 4 substituents independently selected from $R^{22}$;

3) two $R^{12}$, together with two adjacent ring-forming atoms of the aryl or heteroaryl in $Cy^A$ to which they connected respectively, form a $C_{5-10}$ aliphatic cyclyl or 5-10 membered aliphatic heterocyclyl, unsubstituted or optionally substituted with 1, 2 or 3 substituents independently selected from $R^{22}$; wherein 5-10 membered aliphatic heterocyclyl contains one or two ring-forming heteroatoms independently selected from N, O and S;

$R^{a2}$, $R^{b2}$ and $R^{e2}$ are each independently selected from:

1) hydrogen;

2) $C_{1-4}$ alkyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^{22}$;

or, $R^{a2}$ and $R^{b2}$, together with the same N atom to which they are attached, form a 3-8 membered aliphatic heterocyclyl, unsubstituted or optionally substituted with 1, 2 or 3 substituents independently selected from $R^{22}$, wherein 3-8 membered aliphatic heterocyclyl contains 1 or 2 ring-forming heteroatoms, for example, contains only said N atom, or contains said N atom and another heteroatom independently selected from N, O and S atom;

$R^{c2}$ is selected from $C_{1-4}$ alkyl, $C_{2-3}$ alkenyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^{22}$;

$R^{d2}$ is selected from hydrogen, $C_{1-4}$ alkyl, $C_{3-6}$ cycloalkyl, 3-6 membered aliphatic heterocyclyl, cyano, nitro and —S(═O)$_2R^G$;

$R^{22}$ is selected from:

1) oxo, halogen, cyano, carboxyl, —C(═O)$R^{a4}$, —C(═O)$NR^{a4}R^{b4}$, —C(═$NR^{d4}$)$NR^{a4}R^{b4}$, —$OR^{a4}$, —S(═O)$R^{c4}$, —S(═O)$_2R^{c4}$, —S(═O)$_2NR^{a4}R^{b4}$, —S(═O)(═$NR^{d4}$)$R^{c4}$, —$NR^{a4}R^{b4}$, —$NR^{a4}$C(═O)$R^{b4}$, —$NR^{e4}$C(═O)$NR^{a4}R^{b4}$, —$NR^{e4}$C(═$NR^{d4}$)$NR^{a4}R^{b4}$, —$NR^{a4}$S(═O)$_2R^{c4}$, —$NR^{e4}$S(═O)$_2NR^{a4}R^{b4}$ and imino group (═N—$R^{d4}$);

2) $C_{1-4}$ alkyl, $C_{1-4}$ alkylene, phenyl, 5-6 membered heteroaryl, $C_{3-7}$ cycloalkyl and 3-7 membered aliphatic heterocyclyl, unsubstituted or optionally substituted with 1, 2 or 3 substituents independently selected from $R^{32}$;

$R^{a4}$, $R^{b4}$ and $R^{e4}$ are each independently selected from:

1) hydrogen;

2) $C_{1-4}$ alkyl, $C_{3-6}$ monocyclic cycloalkyl and 3-6 membered aliphatic monocyclic heterocyclyl, unsubstituted or optionally substituted with 1, 2 or 3 substituents independently selected from $R^{32}$;

or, $R^{a4}$ and $R^{b4}$, together with the same N atom to which they are attached, form a 3-6 membered aliphatic monocyclic heterocyclyl or 6-7 membered bicyclic aliphatic heterocyclyl, unsubstituted or optionally substituted with 1, 2 or 3 substituents independently selected from $R^{32}$; wherein 3-6 membered aliphatic monocyclic heterocyclyl and 6-7 membered bicyclic aliphatic heterocyclyl contain one or two ring-forming heteroatoms, for example, contains only said N atom, or contains said N atom and another heteroatom independently selected from N, O and S atom;

$R^{c4}$ is selected from $C_{1-4}$ alkyl, $C_{2-3}$ alkenyl, $C_{3-6}$ monocyclic cycloalkyl and 3-6 membered aliphatic monocyclic heterocyclyl, unsubstituted or optionally substituted with 1, 2 or 3 substituents independently selected from $R^{32}$;

$R^{d4}$ is selected from hydrogen, $C_{1-4}$ alkyl, $C_{3-6}$ monocyclic cycloalkyl, 3-6 membered aliphatic monocyclic heterocyclyl, cyano, nitro and $-S(=O)_2R^G$;

$R^{32}$ is selected from oxo, halogen, cyano, hydroxyl, $-OR^G$, amino, $-NHR^G$, $-N(R^G)_2$, aldehyde group, $-C(=O)R^G$, $-S(=O)_2R^G$, carboxyl, $-C(=O)OR^G$, $-C(=O)NH_2$, $-C(=O)-NHR^G$, $-C(=O)N(R^G)_2$, $-S(=O)_2NH_2$, $-S(=O)_2-NHR^G$ and $-S(=O)_2N(R^G)_2$;

$Cy^B$ selected from phenyl, naphthyl and 5-10 membered heteroaryl, unsubstituted or optionally substituted with 1, 2, 3 or 4 substituents independently selected from $R^{13}$, wherein 5-membered heteroaryl contains at least two ring-forming carbon atoms and 1, 2, 3 or 4 ring-forming heteroatoms independently selected from N, O and S;

$R^{13}$ is selected from:

1) oxo, halogen, cyano, $-C(=O)R^{a3}$, carboxyl, $-C(=O)NR^{a3}R^{b3}$, $-OR^{a3}$, $-NR^{a3}R^{b3}$, $-NR^{a3}C(=O)R^{b3}$, $-NR^{e3}C(=O)NR^{a3}R^{b3}$, $-NR^{e3}C(=NR^{d3})NR^{a3}R^{b3}$, $-NR^{a3}S(=O)_2R^{c3}$ and $-NR^{c3}S(=O)_2NR^{a3}R^{b3}$;

2) $C_{1-6}$ alkyl, $C_{2-6}$ alkenyl, $C_{2-6}$ alkynyl, phenyl, 5-6 membered heteroaryl, $C_{3-7}$ monocyclic cycloalkyl, $C_{6-10}$ bicyclic cycloalkyl, 3-7 membered aliphatic monocyclic heterocyclyl and 6-10 membered bicyclic aliphatic heterocyclyl, unsubstituted or optionally substituted with 1, 2, 3 or 4 substituents independently selected from $R^{23}$;

3) two $R^{13}$, together with two adjacent ring-forming atoms of the aryl or heteroaryl in $Cy^B$ to which they are attached respectively, form a $C_{5-10}$ aliphatic cyclyl or 5-10 membered aliphatic heterocyclyl, unsubstituted or optionally substituted with 1, 2 or 3 substituents independently selected from $R^{23}$, wherein said 5-10 membered aliphatic heterocyclyl contains 1 or 2 ring-forming heteroatoms independently selected from N, O and S;

$R^{a3}$, $R^{b3}$ and $R^{e3}$ are each independently selected from:

1) hydrogen;

2) $C_{1-4}$ alkyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^{23}$;

or, $R^{a3}$ and $R^{b3}$ together with the same N atom to which they are attached form a 3-8 membered aliphatic heterocyclyl, unsubstituted or optionally substituted with 1, 2 or 3 substituents independently selected from $R^{23}$; wherein 3-8 membered aliphatic heterocyclyl contains one or two ring-forming heteroatoms, for example, contains only said N atom, or contains said N atom and another heteroatom independently selected from N, O and S;

$R^{c3}$ is selected from $C_{1-4}$ alkyl, $C_{2-3}$ alkenyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^{23}$;

$R^{d3}$ is selected from hydrogen, $C_{1-4}$ alkyl, $C_{3-6}$ cycloalkyl, 3-6 membered aliphatic heterocyclyl, cyano, nitro and $-S(=O)_2R^G$;

$R^{23}$ is selected from:

1) oxo, halogen, cyano, carboxyl, $-C(=O)R^{a5}$, $-C(=O)NR^{a5}R^{b5}$, $-C(=NR^{d5})NR^{a5}R^{b5}$, $-OR^{a5}$, $-S(=O)R^{c5}$, $-S(=O)_2R^{c5}$, $-S(=O)_2NR^{a5}R^{b5}$, $-S(=O)(=NR^{d5})R^{c5}$, $-NR^{a5}R^{b5}$, $-NR^{a5}C(=O)R^{b5}$, $-NR^{e5}C(=O)NR^{a5}R^{b5}$, $-NR^{e5}C(=NR^{d5})NR^{a5}R^{b5}$, $-NR^{a5}S(=O)_2R^{e5}$, $-NR^{e5}S(=O)_2NR^{a5}R^{b5}$ and imino group ($=N-R^{d5}$);

2) $C_{1-5}$ alkyl, $C_{1-5}$ alkylene, phenyl, 5-6 membered heteroaryl, $C_{3-7}$ cycloalkyl and 3-7 membered aliphatic heterocyclyl, unsubstituted or optionally substituted with 1, 2 or 3 substituents independently selected from $R^{33}$;

$R^{a5}$, $R^{b5}$ and $R^{e5}$ are each independently selected from:

1) hydrogen;

2) $C_{1-4}$ alkyl, $C_{3-6}$ monocyclic cycloalkyl and 3-6 membered aliphatic monocyclic heterocyclyl, unsubstituted or optionally substituted with 1, 2 or 3 substituents independently selected from $R^{33}$;

or, $R^{a5}$ and $R^{b5}$ together with the same N atom to which they are attached form a 3-6 membered aliphatic monocyclic heterocyclyl or 6-7 membered bicyclic aliphatic heterocyclyl, unsubstituted or optionally substituted with 1, 2 or 3 substituents independently selected from $R^{33}$; wherein 3-6 membered aliphatic monocyclic heterocyclyl and 6-7 membered bicyclic aliphatic heterocyclyl contains one or two ring-forming heteroatoms, for example, contains only said N atom, or contains said N atom and another heteroatom independently selected from N, O and S;

$R^{c5}$ is selected from $C_{1-4}$ alkyl, $C_{2-3}$ alkenyl, $C_{3-6}$ monocyclic cycloalkyl and 3-6 membered aliphatic monocyclic heterocyclyl, unsubstituted or optionally substituted with 1, 2 or 3 substituents independently selected from $R^{33}$;

$R^{d5}$ is selected from hydrogen, $C_{1-4}$ alkyl, $C_{3-6}$ monocyclic cycloalkyl, 3-6 membered aliphatic monocyclic heterocyclyl, cyano, nitro and $-S(=O)_2R^{GA}$;

$R^{33}$ is selected from oxo, halogen, cyano, hydroxyl, $-OR^{GA}$, amino, $-NHR^{GA}$ and $-N(R^{GA})_2$;

Each $R^{GA}$ are each independently selected from:

$C_{1-4}$ alkyl, $C_{1-4}$ alkylene, $C_{3-6}$ cycloalkyl and 4-6 membered aliphatic heterocyclyl, unsubstituted or optionally substituted with 1, 2 or 3 fluorine atoms;

or, two $R^{GA}$ together with the same N atom to which they are attached form a 4-6 membered aliphatic monocyclic heterocyclyl, unsubstituted or optionally substituted with 1, 2 or 3 fluorine atoms; wherein 4-6 membered aliphatic monocyclic heterocyclyl contains one or two ring-forming heteroatoms, for example, contains only said N atom, or contains said N atom and another heteroatom independently selected from N, O and S.

In some embodiments, the application provides a pharmaceutical composition including the compound of formula (I) or a pharmaceutically acceptable salt, hydrate, solvate, active metabolite, polymorph, isotope labeled compound, isomer or prodrug thereof and a pharmaceutically acceptable carrier.

The pharmaceutical combination may be prepared in a manner well known in the pharmaceutical field, and may be administered by various routes. The mode of administration may be topical (including transdermal, epidermal, ocular and mucosal, including intranasal, vaginal, and rectal delivery), pulmonary (e.g., by inhalation or insufflation of powders or aerosols, including by nebulizer; intratracheal or intranasal), oral or parenteral.

In some embodiments, the composition is suitable for parenteral administration, including intravenous, intraarterial, subcutaneous, intraperitoneal, intramuscular or infusion; or intracranial, such as intrathecal or intraventricular administration. Parenteral administration may be in the form of a single bolus dose, or (e.g.) continuous perfusion pump.

In some embodiments, the composition is suitable for topical administration, which may include transdermal patches, ointments, lotions, creams, gels, drops, suppositories, sprays, liquids and powders. Conventional pharmaceutical carriers, aqueous, powdered or oily matrices, thickeners and the like may be necessary or desired.

In some embodiments, the application provides use of the compound of formula (I) or a pharmaceutically acceptable salt, hydrate, solvate, active metabolite, polymorph, isotope labeled compound, isomer or prodrug thereof, or a pharmaceutical composition thereof, for the prevention or treatment of a disease mediated with HPK1.

In some embodiments, the application provides a method for regulating, for example, inhibiting, the activity of HPK1, including administering the compound of formula (I) or a pharmaceutically acceptable salt, hydrate, solvate, active metabolite, polymorph, isotope labeled compound, isomer or prodrug thereof, or a pharmaceutical composition thereof to a patient, in order to stimulate and/or boost immunity to cancers or viral diseases.

In some embodiments, the application provides a method for preventing, ameliorating or treating a disease mediated with HPK1 in a patient, including administering therapeutically effective amount of the compound of formula (I) or a pharmaceutically acceptable salt, hydrate, solvate, active metabolite, polymorph, isotope labeled compound, isomer or prodrug thereof, or a pharmaceutical composition thereof to the patient.

In some embodiments, the application provides use of the compound of formula (I) or a pharmaceutically acceptable salt, hydrate, solvate, active metabolite, polymorph, isotope labeled compound, isomer or prodrug thereof, or a pharmaceutical composition thereof, for the treatment or amelioration of benign or malignant tumors, myelodysplastic syndromes and diseases caused by viruses.

In some embodiments, the application provides use of the compound of formula (I) or a pharmaceutically acceptable salt, hydrate, solvate, active metabolite, polymorph, isotope labeled compound, isomer or prodrug thereof, or a pharmaceutical composition thereof, for the treatment or amelioration of benign or malignant tumors.

In some embodiments, the application provides use of the compound of formula (I) or a pharmaceutically acceptable salt, hydrate, solvate, active metabolite, polymorph, isotope labeled compound, isomer or prodrug thereof, or a pharmaceutical composition thereof, for the treatment or amelioration of diseases caused by viruses.

In some embodiments, the application provides use of the compound of formula (I) or a pharmaceutically acceptable salt, hydrate, solvate, active metabolite, polymorph, isotope labeled compound, isomer or prodrug thereof, or a pharmaceutical composition thereof, in the preparation of a medicament for the treatment or amelioration of one or more particular diseases selected from benign or malignant tumors, myelodysplastic syndromes and diseases caused by viruses.

In some embodiments, the application provides use of the compound of formula (I) or a pharmaceutically acceptable salt, hydrate, solvate, active metabolite, polymorph, isotope labeled compound, isomer or prodrug thereof, or a pharmaceutical composition thereof, in the preparation of a medicament for the treatment or amelioration of benign or malignant tumors.

In some embodiments, the application provides use of the compound of formula (I) or a pharmaceutically acceptable salt, hydrate, solvate, active metabolite, polymorph, isotope labeled compound, isomer or prodrug thereof, or a pharmaceutical composition thereof, in the preparation of a medicament for the treatment or amelioration of diseased caused by viruses.

In some embodiments, the malignant tumors include one or more of leukemia, lymphoma, multiple myeloma, lung cancer, hepatocellular carcinoma, cholangiocarcinoma, gallbladder cancer, gastric cancer, colorectal cancer, intestinal leiomyosarcoma, breast cancer, ovarian cancer, cervical cancer, endometrial cancer, vaginal cancer, malignant teratoma, pancreatic cancer, pancreatic ductal adenocarcinoma, nasopharyngeal cancer, oral cancer, laryngeal cancer, esophageal squamous cell carcinoma, thyroid cancer, kidney cancer, bladder cancer, malignant brain tumor, rhabdomyosarcoma, osteosarcoma, chondrosarcoma, osteofibrosarcoma, malignant thymoma, malignant peripheral nerve sheath tumor, prostate cancer, testicular cancer, penile cancer and other malignant tumors, as well as benign and malignant tumors of the skin (including but not limited to melanoma, basal cell carcinoma, squamous cell carcinoma).

In some embodiments, the tumor is a tumor producing PGE2 (e.g., COX-2 overexpressed tumor) and/or an adenosine-producing tumor (e.g., CD39 and CD73 overexpressed tumor), such as colorectal cancer, breast cancer, pancreatic cancer, lung cancer and ovarian cancer.

In some embodiments, the virus includes one or more of hepatitis virus, human immunodeficiency virus, human papillomavirus, herpes simplex virus, measles virus, norovirus, Boca virus, Coxsackie virus, Ebola virus, enterovirus, lymphocytic meningitis virus, influenza virus, SARS virus and novel coronavirus.

Definition of Terms

In this disclosure, unless otherwise specified, a definition of a certain group applies to all groups containing this group. For example, the definition of alkyl is applicable to C1-C6 alkyl, C1-C3 alkyl, etc.; the definition of C1-C6 alkyl is applicable to "C1-C6 alkoxy", etc., and the following definitions are applicable to the claims and the description.

When a structure contains multiple substituents represented by the same symbol, the substituents may be the same or different; For example, the $Cy^B$ contains two $R^{13}$ as substituents, wherein the two $R^{13}$ may be both methoxy, or one may be methoxy, and the other may be methyl.

The term "halogen" includes fluorine, chlorine, bromine, and iodine.

The term "$C_{m-n}$" (where m and n is an integer, and indicates the range that includes the end point) represents corresponding groups containing m-n carbon atoms, for example, $C_{1-6}$ alkyl represents an alkyl containing 1-6 carbon atoms, and $C_{2-6}$ alkenyl represents an alkenyl containing 2-6 carbon atoms.

The term "n membered" (where n is an integer) usually describes the number of ring-forming atoms, where the number of ring-forming atoms is n. "m-n membered" indicates the range that includes the end point, representing that the corresponding ring structure contains m-n ring-forming atoms. For example, piperidinyl is an example of a 6-membered heterocyclyl, and pyrazolyl is an example of a 5-membered heteroaryl.

The term "substituted" refers to a hydrogen of a structure is displaced by a "substituent". Unless otherwise indicated, the term "substituted" means any degree of substitution as long as said substitution is permitted. The choice of substituents is independent and the substitution may be in any chemically accessible position. It should be understood that substitution on a given atom is limited by chemical valence. It should be understood that substitution on a given atom produces chemically stable molecules. One divalent substituent (e.g., oxo) will displace two hydrogen atoms.

"The rest of the compound" refers to the portion of the whole molecular structure except for the "substituent" described. The rest of the compound is connected to the substituent by one or more unsaturated valences. The rest of the compound may contain one or more "junctions", and two or more junctions may be on the same atom or different atoms.

The term "alkyl" refers to a straight-chain or branched-chain saturated hydrocarbon group. Alkyl is a group formed by the loss of a hydrogen of an alkane. The examples of alkyl include methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, 1,2,2-trimethylpropyl and the like.

The term "alkenyl" refers to a straight or branched chain hydrocarbon group having one or more carbon-carbon double bonds. Alkenyl are a group formed by the loss of a hydrogen atom in an olefin. The examples of the alkenyl may be vinyl, 1-propenyl, 2-propenyl, allyl, 1-butenyl, 2-butenyl, (E)-but-2-ene-1-yl, (Z)-but-2-ene-1-yl, 2-methylpropy-1-ene-1-yl, 1,3-butadiene-1-yl, 1,3-butadiene-2-yl and the like.

The term "alkynyl" refers to a straight or branched chain hydrocarbon group having one or more carbon-carbon triple bonds. Alkynyl is a group formed by the loss of one hydrogen atom from an alkyne. Examples of alkynyl may be ethynyl, 1-propynyl, propargyl, 1-butynyl, but-2-yn-1-yl, but-3-yn-1-yl, but-3-ene-1-alkynyl, 3-methylpent-2-ene-4-yn-1-yl and the like.

The term "alkylene" refers to a divalent group formed by losing two hydrogen atoms on the carbon atom of an alkane at the same time, wherein the two valences may be connected to the same atom, or connected to two atoms respectively. For example, methylene ($—CH_2—$ or $=CH_2$), 1,1-ethylene ($—CH(CH_3)—$ or $=CH—CH_3$), 1,2-ethylene ($—CH_2CH_2—$), but-1,4-diyl, but-1,3-diyl, 2,2-dimethylprop-1,3-diyl, etc.

The term "alkoxy" refers to a group with formula "—O-alkyl", wherein the alkyl group is as defined above. Alkoxy may be, for example, methoxy, ethoxy, n-propoxy, isopropoxy, n-butoxy, tert-butoxy and n-hexoxy and the like.

The term "alkylthio" refers to a group of formula "—S-alkyl", wherein the alkyl group is as defined above. "alkylthio" may be, for example, methylthio, ethylthio, n-propylthio, isopropylthio, n-butylthio, tert-butylthio and n-hexylthio and the like.

The term "alkylamino" includes a group of formula "—NH-alkyl" and a group of formula "—N-(alkyl)$_2$", wherein the alkyl group is as defined above. The group of formula "—NH-alkyl" may be, for example, methylamino, ethylamino, isopropylamino and n-hexylamino and the like; The group of formula "—N-(alkyl)$_2$" may be, for example, dimethylamino, diethylamino, methylethylamino, methylisopropylamino and ethyl-n-hexylamino and the like.

The term "alkyl sulfinyl" refers to a group of formula "—S(═O)-alkyl", wherein the alkyl group is as defined above. For example, it may be methyl sulfinyl, ethyl sulfinyl, isopropyl sulfinyl and the like.

The term "alkyl sulfonyl" refers to a group of formula "—S(═O)$_2$-alkyl", wherein the alkyl group is as defined above. For example, it may be methyl sulfonyl, ethyl sulfoyl, isopropyl sulfonyl and the like.

The term "alkylaminosulfinyl" comprises a group of formula "—S(═O)—NH-alkyl" and a group of formula "—S(═O)—N(alkyl)$_2$", wherein the alkyl group is as defined above. The group of formula "—S(═O)—NH-alkyl" may be, for example, methylaminosulfinyl, ethylaminosulfinyl, isopropylaminosulfinyl, tert-butylaminosulfinyl and the like. The group of formula "—S(═O)—N(alkyl)$_2$" may be, for example, dimethylaminosulfinyl, diethylaminosulfinyl, methylethylaminosulfinyl, ethyl isobutylaminosulfinyl and the like.

The term "alkylaminosulfonyl" comprises a group of formula "—S(═O)$_2$—NH-alkyl" and a group of formula "—S(═O)$_2$—N(alkyl)$_2$", wherein the alkyl group is as defined above. The group of formula "—S(═O)$_2$—NH-alkyl" may be, for example, methylaminosulfonyl, ethylaminosulfonyl, isopropylaminosulfonyl, tert-butylaminosulfonyl, etc. The group of formula "—S(═O)$_2$—N(alkyl)$_2$" may be, for example, dimethylaminosulfonyl, diethylaminosulfonyl, methyl isopropylaminosulfonyl, ethyl tert-butylaminosulfonyl and the like.

The term "carbonyl" refers to a group of formula "—(C═O)—", which may also be represented by "—C(O)—".

The term "cyano" refers to a group of formula "—C≡N", which may also be represented by "—CN".

The term "hydroxymethyl" refers to a group of formula "$—CH_2OH$".

The term "oxo" refers to an oxygen atom as a divalent substituent, when connected to a carbon atom to form a carbonyl group, or to the heteroatom to form a sulfinyl or sulfonyl, or N-oxide group and the like. In some embodiments, cycloalkyl and heterocyclyl may optionally be substituted by one or two oxo groups.

The term "imino group" or "═N—R", refers to an amino group as a divalent substituent, wherein two valents of the same nitrogen atom are connected to one atom selected from the rest of the compound to form a double bond, and the third valence of the nitrogen atom is connected to the R group defined by the context. The nitrogen atom may form imide, amidine or guanidine when connected to a carbon atom, or forms a sulfinyl imide or the like when connected to a heteroatom.

The term "cyclyl" includes aliphatic and aromatic monocyclyl or polycyclyl. The aliphatic monocyclyl contains a cyclyl, including cyclized alkyl and alkenyl. Aliphatic polycyclyl contains two or more cyclyls wherein at least one cyclyl is an aliphatic monocyclyl (including cyclized alkyl and alkenyl), the other cyclyls may be aliphatic and/or aromatic cyclyls. In aliphatic polycyclyl, any one of the rings is connected to at least one another ring to form a spiro ring (two rings share a ring-forming atom) or a bridged ring (two rings share two or more ring-forming atoms). The polycyclyl is connected to the rest of the compound by a ring carbon atom. It may be, for example, cyclopropyl, cyclobutyl, cyclopentyl, cyclohexyl, cyclopentenyl, cyclohexadienyl, dicyclo[3.1.0]hexyl, norbornyl, norpinanyl, dicyclo[1.1.1]pentyl, 1H-inden-1-yl, 2,3-dihydro-1H-inden- 2-yl and the like. When a cyclyl only contains saturated rings, the cyclyl is a saturated cyclyl, also named as the "cycloalkyl".

The term "cycloalkoxy" refers to a group of formula "—O-cycloalkyl", wherein the cycloalkyl is as defined above. It may be, for example, cyclopropoxy.

The cyclyl includes a "cyclylene", i.e., the cyclyl is connected by two chemical valences to two connection points of the rest of the compound, and the two chemical valences described may be on the same carbon atom of the cyclylene, or may be on two different carbon atoms of the cyclylene. The two connection points may be located on the same atom of the rest of the compound, or located on two different atoms of the rest of the compound. For example, it may be 1,1-cyclobutylene, 1,3-cyclobutylene, and the like.

The term "aryl" refers to an aromatic monocyclyl or polycyclyl. For example, it may be phenyl, naphthyl, and the like.

The term "heterocyclyl" refers to a monocyclylic or polycyclic group having at least one ring-forming heteroatom selected from oxygen, nitrogen, sulfur and phosphorus. The poly-heterocyclyl contains two or more rings, wherein at least one ring has at least one ring-forming heteroatom selected from oxygen, nitrogen, sulfur and phosphorus, and the other ring may have ring-forming heteroatoms or not. In poly-heterocyclyl, any one of the rings is connected to at least one other ring to form a spiro ring (two rings share a ring-forming atom) or a bridged ring (two rings share two or more ring-forming atoms). The heterocyclyl may be connected to the rest of the compound by an optional ring-forming carbon atom, or by an optional ring-forming heteroatom. In some embodiments, any of the ring carbon atoms in the heterocyclyl may be substituted by an oxo group to form a carbonyl group. In some embodiments, any ring nitrogen atom in the heterocyclyl may be N-oxide. In some embodiments, any ring nitrogen atom in the heterocyclyl may be quaternary ammonium ion.

Heterocyclyl includes aromatic heterocyclyl (i.e., "heteroaryl") and aliphatic heterocyclyl.

The term "heteroaryl" refers to an aromatic monoheterocyclyl or polyheterocyclyl having at least one ring-forming heteroatom selected from oxygen, nitrogen and sulfur. The heteroaryl group may be connected to the rest of the compound by an optional carbon atom, or by an optional heteroatom, provided that the chemical valence of the carbon atom or heteroatom allows. In some embodiments, any of the ring-forming carbon atoms in the heteroaryl may be substituted by an oxo group to form a carbonyl group. In some embodiments, any ring-forming nitrogen atom in the heteroaryl may be N-oxide. In some embodiments, any ring nitrogen atom in the heteroaryl may be quaternary ammonium ion. For example, the heteroaryl may be pyrrolyl (including pyrrol-1-yl, pyrrol-2-yl and pyrrol-3-yl), pyrazolyl, imidazolyl, oxazolyl, isoxazolyl, thiazolyl, isothiazolyl, triazolyl, tetrazolyl, pyridyl, pyridin-2 (1H)-one-1-yl, pyridin-4 (1H)-one-1-yl, pyrazinyl, pyrimidinyl, pyridazinyl, pyrazin-3 (2H)-one-2-yl, 1,2,4-triazinyl, 1,3,5-triazinyl, indolyl, benzofuranyl, benzothienyl, indazolyl, benzoimidazolyl, benzisothiazolyl, quinolinyl, isoquinolinyl, naphthyridinyl, imidazo[1,2-b]thiazolyl, purinyl, etc., The term "aliphatic heterocyclyl" includes monocyclic or polycyclic aliphatic heterocyclyl. The monocyclic aliphatic heterocyclyl (aliphatic monoheterocyclyl) may not contain double bond or contain one or more double bonds in the rings. The polycyclic aliphatic heterocyclyl (aliphatic polyheterocyclyl) contains at least one alicycle, and other rings may be aliphatic or aromatic rings. The polycyclic aliphatic heterocyclyl may not contain a double bond or contain one or more double bonds in the rings. For example, it may be azetidinyl, oxetanyl, tetrahydropyrrolyl, tetrahydrofuranyl, 2-oxo-oxazolidinyl, piperidinyl, 3-oxo-piperidinyl, piperazinyl, morpholinyl, azepanyl, 2-oxa-6-azaspiro[3.3]heptyl, 1,2,3,4-tetrahydroquinolinyl, etc.

The term "heterocyclyl" includes a heterocyclylene, i.e., a heterocyclyl is connected to two points of attachment to the rest of the compound through two valences, and the two valences may be in the same ring-forming atom of the heterocyclylene. It may also be located on the two ring-forming atoms of the heterocyclylene group. The two connection points may be located on the same atom in the rest of the compound, or may be located on two atoms in the rest of the compound. For example, 1,1-(3-oxetanylene), 1,3-(2-azacyclopentylene), and the like.

The term "fused rings" refers to a bridged ring system formed by two rings sharing two adjacent ring-forming atoms. The two rings may be saturated alicyclic, unsaturated alicyclic or aromatic rings. The two adjacent ring-forming atoms are optionally carbon atoms or heteroatoms.

The term "n-membered oxaalkylene" refers to a divalent group formed by replacing one or more carbon atoms in the main chain of an n-membered alkylene with oxygen atom(s). The two valences as described may be on the same atom of the rest of the compound, or may be on two atoms of the rest of the compound. For example, 2-oxa-1,3-propylene (—CH2OCH2-) is an example of 3-membered oxaalkylene. 2-oxa-1,4-butylene (—CH2OCH2CH2-) is an example of a 4-membered oxaalkylene and the like. An alkylene group in which only branched-chain carbon atom (s) is replaced by oxygen atom(s) should not be considered "oxaalkylene"; for example, in 2-methyl-1,3-propylene, when the branched-chain methyl is replaced by oxygen, and the resulted group (—CH2CH(OH)CH2-) should be regarded as 2-hydroxy substituted 1,3-propylene.

The term "n-membered azaalkylene" refers to a divalent group formed by replacing one or more carbon atoms in the main chain of an n-membered alkylene with nitrogen atom (s), and the two valences described may be on the same atom of the rest of the compound, or on two separate atoms of the rest of the compound. For example, 2-aza-1,3-propylene (—CH2OHCH2-) is an example of 3-membered azaalkylene, and aza-1,2-ethylene (—CH2NH—) is an example of a 2-membered azaalkylene, and the like. An alkylene group in which only branched-chain carbon atom(s) is substituted with nitrogen atom(s) should not be considered "azaalkylene"; for example, in 2-methyl-1,3-propylene, when the branched-chain methyl is replaced by nitrogen, and the resulted group (—CH2CH(NH2)CH2-) should be regarded as 2-amino substituted 1,3-propylene.

The term "isomer" refers to isomers that result from different spatial arrangements of atoms in a molecule. "Stereoisomers" of the compounds described herein refers to all stereoisomers. For example, when the compound has asymmetric carbon atoms, enantiomers and diastereomers are produced; when the compound has carbon-carbon double bonds, carbon-nitrogen double bonds, or ring structures, cis- or trans-isomers are produced. Unless otherwise indicated, the compounds described herein include all isomers thereof, such as optical isomers, geometric isomers, rotational isomers, tautomers, stably existing conformational isomers, and the like; and the compounds may exist as a mixture of isomers or as isolated isomers.

Methods for preparing optically active products from optically inactive starting materials are known in the art, e.g., by resolution of racemic mixtures or by stereoselective synthesis.

Resolution of racemic mixtures of compounds may be carried out by any of a number of methods known in the art. One method involves fractional recrystallization using a chiral resolving acid that is an optically active salt-forming organic acid. Suitable resolving agents for fractional recrystallization may be optically active acids such as D-tartaric acid, L-tartaric acid, diacetyltartaric acid, dibenzoyltartaric acid, mandelic acid, malic acid, camphorsulfonic acid, etc. Other suitable resolving agents for fractional recrystallization include, for example, α-methylbenzylamine, 2-phenylglycinol, cyclohexylethylamine and the like in stereoisomerically pure form.

Methods for resolution of racemic mixtures also include, for example, the separation of diastereomers obtained by reaction with appropriate optically active species such as chiral alcohols or Mosher's acid chlorides, and then conversion (such as hydrolysis) to the corresponding single optical isomer. For example, it may be performed by elution on a chromatographic column packed with an optically active resolving agent. Suitable chromatographic column and elution solvents may be determined by those skilled in the art.

The term "isotope labeled compounds" refers to a compound of the present application in which one or more atoms are replaced by a particular isotopic atom thereof. For example, the isotopic atom in the compound of the present application may include various isotopes of elements H, C, N, O, F, P, S, Cl and I, such as $^{2}H$, $^{3}H$, $^{13}C$, $^{14}C$, $^{15}N$, $^{17}O$, $^{18}O$, $^{18}F$, $^{30}P$, $^{32}P$, $^{35}S$, $^{36}S$, $^{123}I$, $^{124}I$ and $^{125}I$, etc. This application includes various isotope labeled compounds as defined. For example, they may be those compounds in which radioactive isotopes such as $^{3}H$ and $^{14}C$ are present, or those in which non-radioactive isotopes such as $^{2}H$ and $^{13}C$ are present. Such isotope labeled compounds are suitable for metabolic studies (using $^{14}C$), reaction kinetic studies (using e.g, $^{2}H$ or $^{3}H$), detection or imaging techniques such as positron emission tomography (PET) or single photon emission computed tomography (SPECT), including drug or substrate tissue distribution analysis; or radiotherapy for patients, etc.

In particular, $^{18}F$ compounds may be particularly desirable for PET or SPECT studies. Isotope labeled compounds of formula (I) may generally be prepared by conventional techniques known to those skilled in the art or by methods analogous to those described in the accompanying examples and preparations using an appropriate isotope labeled reagent in place of the unlabeled reagents.

Furthermore, substitution with heavier isotopes, especially deuterium (i.e, $^{2}H$ or D), may yield certain therapeutic advantages resulting from greater metabolic stability, such as increased in vivo half-life or reduced dose requirements or improved therapeutic index, and thus in some cases it may be preferred.

The term "pharmaceutically acceptable" refers to those compounds, materials, compositions and/or dosage forms, which are within the scope of sound medical judgment, suitable for use in contact with human and animal tissue without excessive of toxicity, irritation, allergic reactions or other problems or complications commensurate with a reasonable benefit/risk ratio.

The term "a pharmaceutically acceptable salt" refers to a salt that retains the biological activity and properties of the compounds of the present application and generally have no biologically or otherwise undesirable effects. In many cases, the compounds of the present application are capable of forming acid and/or base addition salts via the presence of amino and/or carboxyl groups or the like.

The term "pharmaceutically acceptable acid addition salts" may be formed with inorganic and organic acids.

The term "pharmaceutically acceptable base addition salts" may be formed with inorganic and organic bases.

All compounds and pharmaceutically acceptable salts thereof may be found (e.g., hydrates and solvates) with other substances (e.g., solvents, including water and other solvents, etc.) or may be isolated. When in the solid state, the compounds described herein and salts thereof may exist in various forms, including hydrates and solvates. Hydrates and solvates of compounds and salts thereof described herein include those in which water and solvents may be isotopically labeled, such as $D_2O$, methanol-$d_3$, methanol-$d_4$, acetone-$d_6$, DMSO-$d_6$. The presence of hydrates and solvates may be identified by those skilled in the art using means such as nuclear magnetic resonance (NMR).

The term "polymorph" refers to compounds of the present application that exist in different crystal lattice forms, as well as in amorphous form. Polymorphs of the compounds of the present application and salts thereof also include mixtures of various lattice forms, as well as mixtures of one or several lattice forms and amorphous form. The presence of polymorphs may be identified by those skilled in the art using means such as X-ray diffraction.

Therefore, unless expressly stated otherwise, references to compounds and salts thereof in this specification are to be understood to encompass any solid state form of the compounds.

The term "active metabolite" refers to an active derivative of a compound that is formed when the compound is metabolized.

The term "a pharmaceutically acceptable prodrug" refers to any pharmaceutically acceptable ester, salt of the ester, amide or other derivative of the compound of the present application, which, upon administration to a subject, is capable of directly or indirectly providing the compound of the present application or its pharmacologically active metabolites or residues. Particularly preferred derivatives or prodrugs are those that increase the bioavailability of the compound of the present application when administered to a patient (e.g., make orally administered compounds more readily absorbed into the blood), or promote the delivery of the compound to biological organs or the site of action.

The term "a pharmaceutical composition" refers to a biologically active compound optionally in admixture with at least one pharmaceutically acceptable chemical component or agent, which is a "carrier" that facilitates for introducing the active compound into cells or tissues, include but are not limited to stabilizers, diluents, suspending agents, thickening agents and/or excipients. The pharmaceutical composition includes, but are not limited to, the following forms: tablets, pills, powders, lozenges, sachets, cachets, elixirs, suspensions, emulsions, solutions, syrups, aerosols (solid or dissolved in liquid vehicles), ointments, soft and hard gelatin capsules, suppositories, transdermal patches, sterile injectable solutions and sterile packaged powders, etc.

The term "pharmaceutically acceptable carriers" includes solvents, dispersion media, coatings, surfactants, antioxidants, preservatives (e.g., antibacterial, antifungal), isotonic agents, absorption delaying agents, salts, preservatives, pharmaceutical stabilizers, binders, excipients, disintegrants, lubricants, sweeteners, flavoring agents, dyes, and the like, well known to those skilled in the art, and combinations thereof. Unless being incompatible with the active compound, any conventional carrier is included in the therapeutic or pharmaceutical compositions.

The term "therapeutically effective amount" refers to the amount of the compound of the present application that induces a biological or medical response in a subject, such as reducing or inhibiting activity of enzyme or protein or ameliorating symptoms, alleviating a condition, slowing or delaying disease progression, or preventing disease, etc., The term "subject" or "patient" refers to an individual, including mammals and non-mammals, suffering from a disease, disorder, condition, or the like. Examples of mammal include, but are not limited to, any member of the class mammalia: humans; non-human primates (e.g., chimpanzees and other apes and monkeys); livestock, such as cattle, horses, sheep, goats, pigs; other domesticated animals, such as rabbits, dogs, and cats; laboratory animals, including rodents, such as rats, mice, and guinea pigs, and the like. Examples of non-mammals include, but are not limited to, birds, fish, and the like.

Synthesis

The compounds of the present application and their salts may be prepared using known organic synthesis techniques and may be prepared according to any of some synthetic routes such as those in the schemes below.

The reactions used to prepare the compounds of the present application may be carried out in suitable solvents. Suitable solvents may be substantially unreactive with the starting materials (reactants), intermediates or products at temperatures at which the reaction is carried out (e.g., temperatures that may range from the melting point to the boiling point of the solvent). A given reaction may be carried out in one solvent or a mixture of solvents. Depending on a particular reaction step, one skilled in the art may select an appropriate solvent for a particular reaction step.

The preparation of the compounds of the present application may involve the protection and deprotection of various chemical groups. The need for protection and deprotection and the selection of appropriate protecting groups may be readily determined by those skilled in the art.

The following schemes provide general guidance related to the preparation of the compounds of the present application. Those skilled in the art will appreciate that general knowledge of organic chemistry may be used to modify or optimize the methods shown in the schemes to prepare the various compounds of the present application.

Compounds of formula (I) may be prepared according to the methods as illustrated in the schemes below.

Various compounds of formula (I) may be prepared using the methods illustrated in Scheme 1. In the method shown in Scheme 1, the compound of formula 1-1 is transformed by diazotization and coupling reaction to the compound of formula 1-2. The compound of formula 1-2 is converted to the compound of formula 1-3 by ring closure reactions such as thermal ring closure, as well as acid or base catalyzed ring closure reactions. The compound of formula 1-3 is amidated to form the compound of formula 1-4. The compound of formula 1-4 is chlorinated and dehydrated (e.g., chlorination and dehydration in the presence of phosphorus oxychloride) to form the compound of formula 1-5. The compound of formula 1-5 is converted to the compound of formula 1-6 by condensation and ring-closing with hydrazine (or hydrazine hydrate). The compound of formula 1-6 undergoes Sandmeyer or similar reactions to form the halogenated (e.g., chloro, bromo, or iodo) compound of formula 1-7. The NH group of the pyrazolyl of formula 1-7 is protected by a suitable protecting group to form the compound of formula 1-8. The compound of formula 1-8 is then transformed by various cross-coupling reactions (e.g., Suzuki reaction, Stille reaction, etc.) to the compound of formula 1-9. Finally, the compound of formula (I) is generated by deprotection. By selection of suitable catalyst (e.g. SPhos-Pd-G2), the compound of formula 1-7 may directly undergo various cross-coupling reactions (e.g. Suzuki reaction, Stille reaction, etc.) and subsequent reactions (such as reductive amination, carboxylic acid-amine condensation, etc.) to form the desired compound of formula (I).

Scheme 1

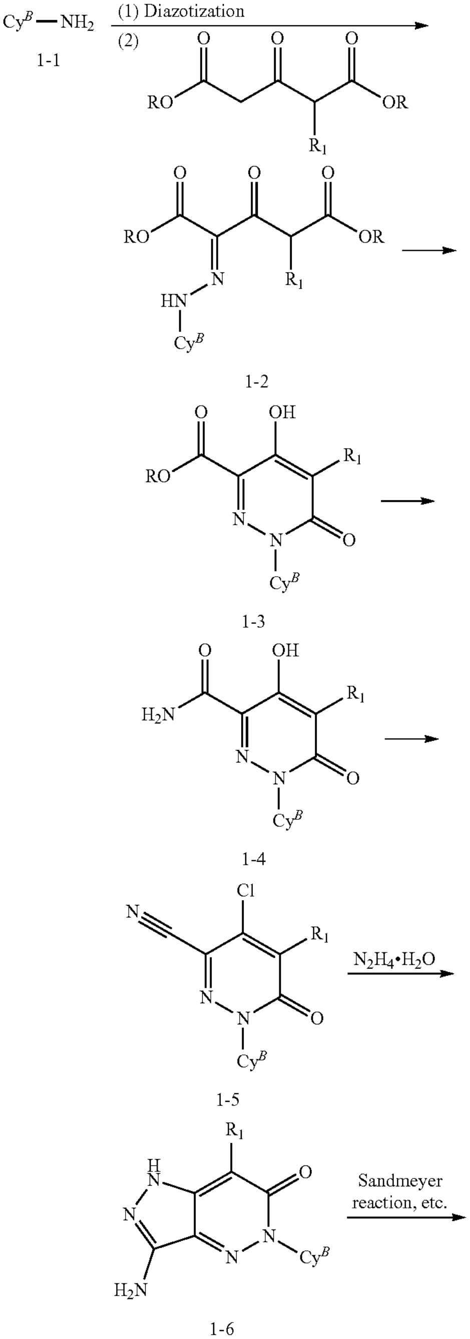

-continued

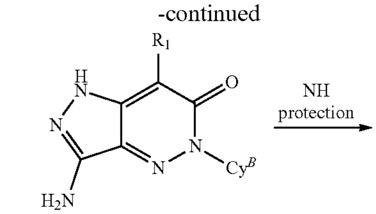

1-7

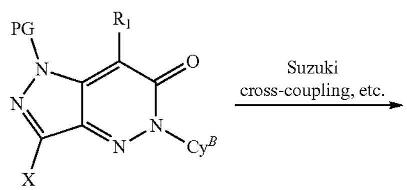

1-8

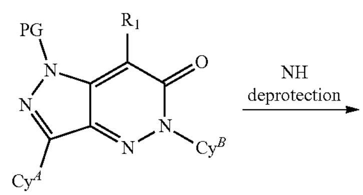

1-9

-continued

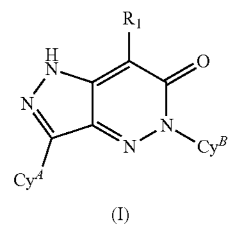

(I)

Alternatively, the compounds of formula (I) may be prepared using the methods illustrated in Scheme 2. In the method shown in Scheme 2, firstly, the compound of formula 1-1 is transformed to the compound of formula 1-3 by the same method as shown in Scheme 1. The compound of formula 1-3 is then chlorinated to form the compound of formula 2-4. The compound of formula 2-4 is condensed with excessive hydrazine (or hydrazine hydrate) to form the compound of formula 2-5A; or the compound of formula 2-4 is condensed with one equivalent of hydrazine (or hydrazine hydrate) to form the compound of formula 2-5B. The compound of formula 2-5A or 2-5B may undergo ring closure reactions (e.g., thermal ring closure, and acid- or base-catalyzed ring closure reactions) to form the compound of formula 2-6. The compound of formula 2-6 is halogenated (e.g., chloro, bromo, etc.) to form the compound of formula 1-7. The compound of formula 1-7 may be transformed in a manner as shown in Scheme 1 to form the desired compound of formula (I). Scheme 2 is subdivided into Scheme 2A and Scheme 2B according to different intermediates of formula 2-5A or formula 2-5B.

Scheme 2

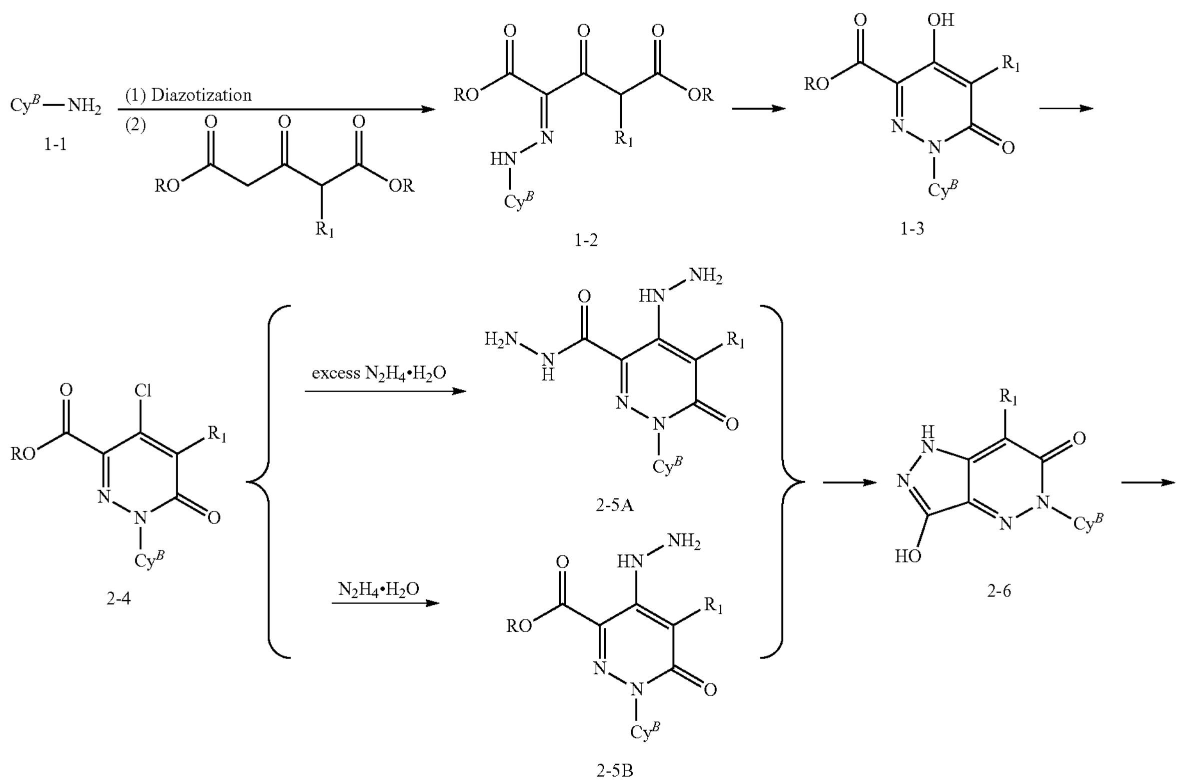

1-1 1-2 1-3 2-4 2-5A 2-5B 2-6

-continued

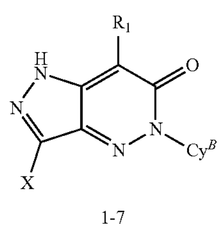

1-7

NH protection

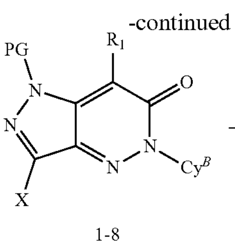

1-8

Suzuki coupling

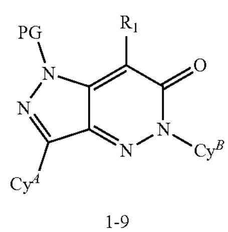

1-9

NH deprotection

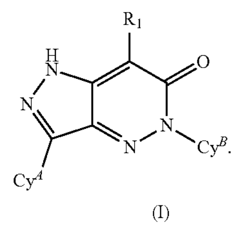

(I)

Alternatively, the compounds of formula (I) may be prepared using the method illustrated in Scheme 3A. In the method shown in Scheme 3A, the carboxylic acid derivative compound of formula 3-la (wherein X is a halogen or a halogen-like group, such as bromine, iodine, etc.; L1 is an aromatic or heteroaromatic ring; LG is a leaving group such as halogen, alkoxy, —N(Me)OMe, etc.) is converted to the compound of formula 3-2a by condensation. The compound of formula 1-1 is diazotizated and coupled with the compound of formula 3-2a to form the compound of formula 3-3. The compound of formula 3-3 is transformed to the compound of formula 3-4 by ring closure reaction. The compound of formula 3-4 is condensed with hydrazine (or hydrazine hydrate) to form the compound of formula 3-5A. The NH group of pyrazolyl in the compound of formula 3-5A is protected with an appropriate protecting group to form the compound of formula 3-6. The compound of formula 3-6 undergoes various cross-coupling reactions (e.g., Suzuki reaction, Stille reaction, Buchwald-Hartwig amination, etc.) to form the compound of formula 1-9. Finally, the compound of formula (I) is formed by deprotection of compound 1-9. By selection of suitable catalyst, the compound of formula 3-5A can then be converted to the desired compound of formula (I) through various cross-coupling reactions (e.g. Suzuki reaction, Stille reaction, Buchwald-Hartwig amination, etc.).

Scheme 3A

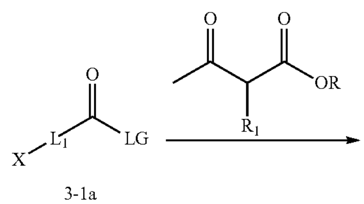

3-1a

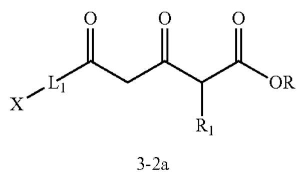

3-2a

-continued

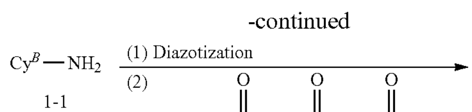

1-1

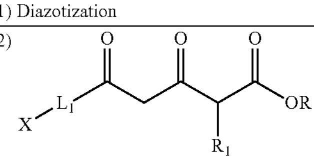

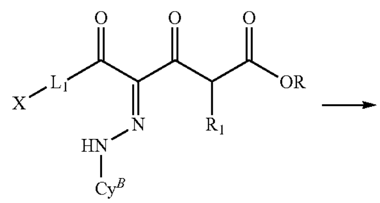

3-3

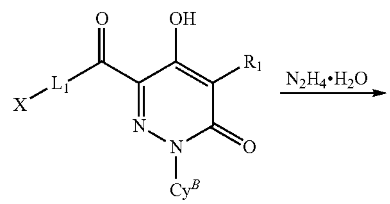

3-4

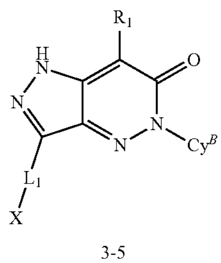

3-5

NH protection

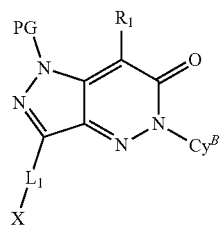

3-6

Cross-coupling reaction (Suzuki, Buchwald-Hartwig, etc.)

-continued

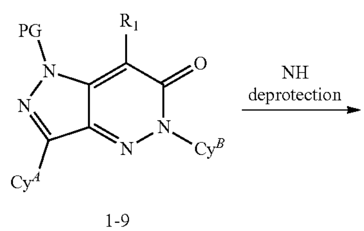

1-9

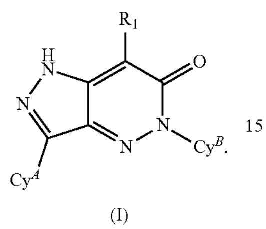

(I)

Alternatively, the compound of formula (I) may be prepared by the method illustrated in Scheme 3B. The compound of formula 3-4 is condensed with a substituted hydrazine to form the compound of formula 3-5B. The compound of formula 3-5B undergoes various cross-coupling reactions (e.g. Suzuki reaction, Stille reaction, Buchwald-Hartwig amination, etc.) to form the compound of formula 1-9B. Finally, the compound of formula (I) is formed by deprotection of the compound 1-9B.

Scheme 3B

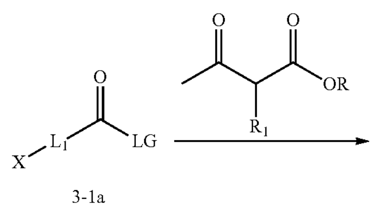

3-1a

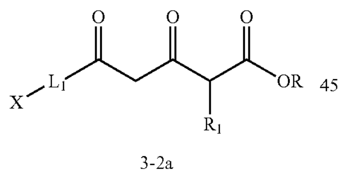

3-2a

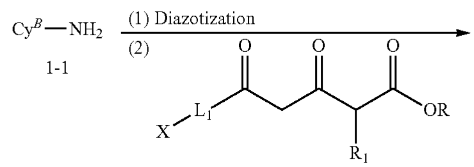

1-1

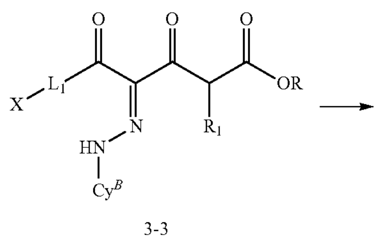

3-3

-continued

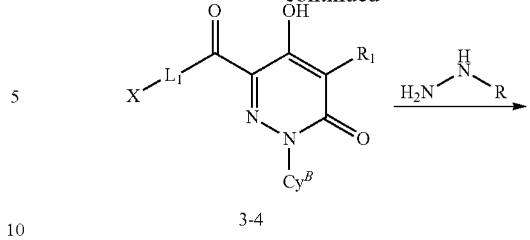

3-4

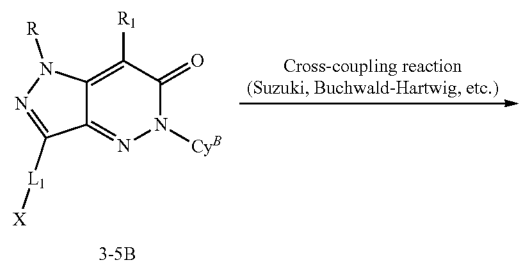

3-5B

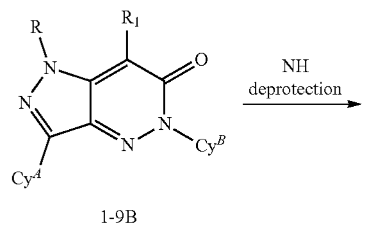

1-9B

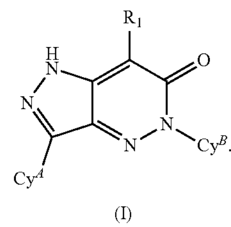

(I)

Alternatively, the compound of formula (I) may be prepared using the method illustrated in Scheme 4. In the method shown in Scheme 4, the carboxylic acid derivative compound of formula 3-1a (wherein X is a halogen or a halogen-like group, such as bromine, iodine, etc.; L1 is an aromatic or heteroaromatic ring; LG is a leaving group such as halogen, alkoxy, —N(Me)OMe, etc.) is converted to the compound of formula 4-3 by condensation; or the aldehyde compound of formula 4-1 is converted to the compound of formula 4-3 by addition reaction and then oxidation (such as using Dess-Martin periodinane). The compound of formula 1-1 is diazotized and then coupled with the compound of formula 4-3 to form the compound of formula 4-4. The compound of formula 4-4 is subjected to ring closure reaction to generate the compound of formula 3-4. The compound of formula 3-4 can then be converted to the desired compound of formula (I) in a manner as shown in Schemes 3A or 3B.

Scheme 4

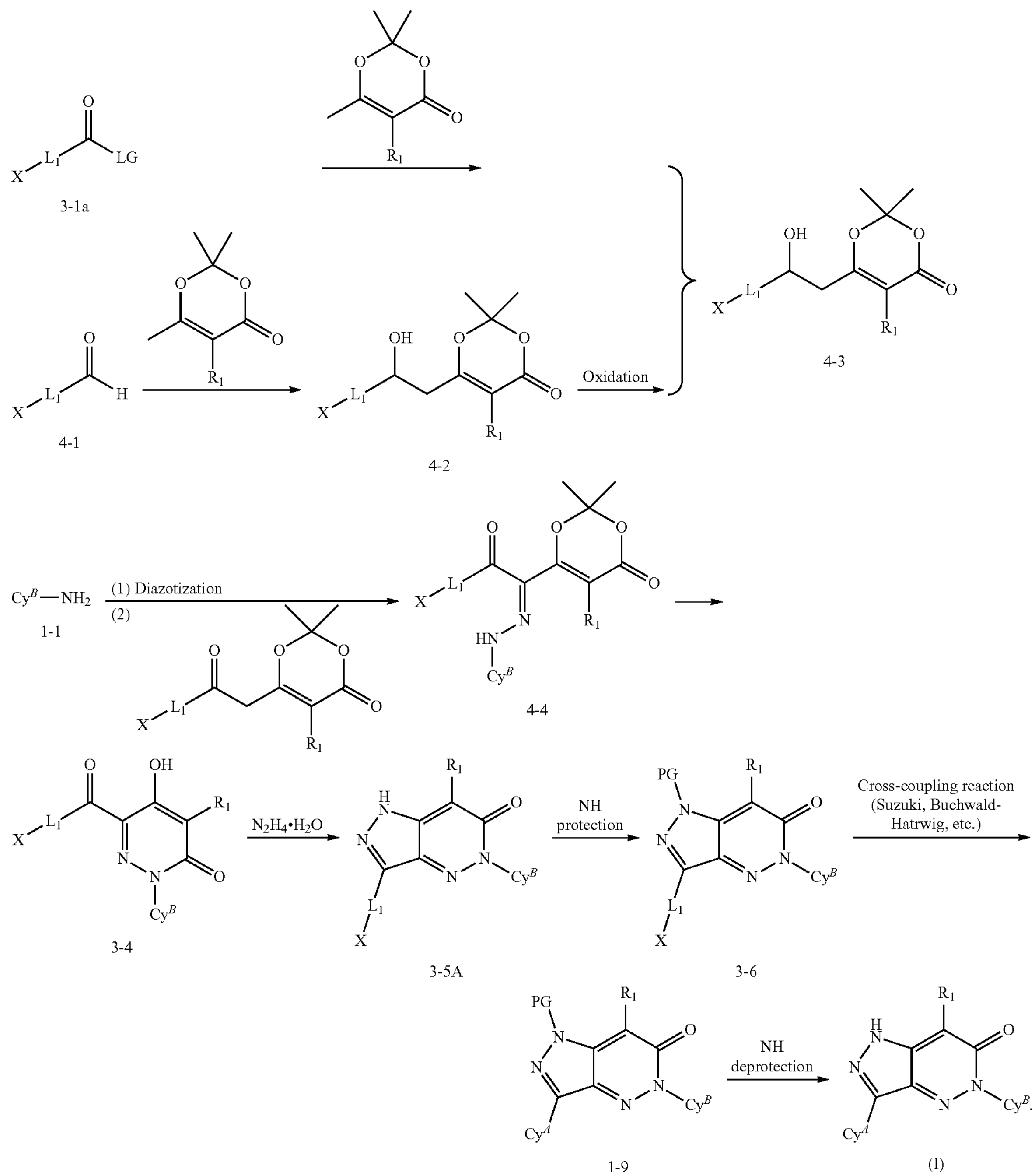

All methods described in this specification may be performed in any suitable order unless otherwise indicated or clearly contradicted by context. All examples or exemplary language (e.g., "such as") provided in this specification are used only to better clarify the invention, and are not intended to limit the scope of the application as otherwise claimed.

Hereinafter, the preparation and properties of the compounds of formula (I) in some embodiments will be further described with reference to specific examples. Among them, the starting materials used are known and commercially available, or may be synthesized using or according to methods known in the art.

Unless otherwise specified, all reactions in the examples were carried out under continuous magnetic stirring, and the reaction temperature was in degrees Celsius.

The reactions may be monitored according to any suitable method known in the art, such as nuclear magnetic resonance spectroscopy (NMR), infrared spectroscopy (IR), spectrophotometry (e.g., UV-Vis spectroscopy), liquid mass spectrometry (LC-MS), mass spectrometry, high performance liquid chromatography, thin layer chromatography and so on. The products may be purified by any suitable method known in the art, such as column chromatography (normal or reverse phase), preparative thin layer chromatography, trituration, recrystallization, and the like.

Generally, 100-200 mesh silica gel from Qingdao Haiyang Chemical Co., Ltd. is used as carrier (stationary phase) in normal phase column chromatography. Silica gel 60 F254 silica gel plate from Merck Ltd. is used in thin layer chromatography (TLC), and GF254 preparative silica gel plate from Anhui Liangchen Silicon Material Co., Ltd. is used in preparative thin layer chromatography (pre-TLC).

The structures of the compounds in the examples were determined by nuclear magnetic resonance spectroscopy (NMR) and/or liquid chromatography-mass spectrometry (LC-MS). The nuclear magnetic resonance spectrum was measured by Bruker AVANCE-400 nuclear magnetic resonance apparatus, and the solvent was usually deuterated dimethyl sulfoxide (DMSO-$d_6$) or deuterated chloroform ($CDCl_3$). NMR chemical shifts (δ) were given in parts per million (ppm) using tetramethylsilane (TMS) as the internal standard. LC-MS was performed on an Agilent 1100 series liquid chromatograph and a Bruker HCT-Ultra ion trap mass spectrometer.

Abbreviation Table

DIPEA N,N-diisopropylethylamine

BINAP 1,1'-binaphthalene-2,2'-bisdiphenylphosphine $Pd_2(dba)_3$ tris(dibenzylideneacetone) dipalladium $Pd(dppf)Cl_2$ (1,1'-bis(diphenylphosphino) ferrocene) palladium dichloride $Pd(dppf)Cl_2$-DCM (1,1'-bis(diphenylphosphino) ferrocene) palladium dichloride-dichloromethane adduct SPhos-Pd-G2 chloro(2-dicyclohexylphosphino-2',6'-dimethoxy-1,1'-biphenyl)(2'-amino)-1,1'-biphenyl-2-yl) palladium (II)

EXAMPLE 1

Compound 1: Preparation of 5-(2-fluoro-6-methylphenyl)-3-(4-(4-methylpiperazin-1-yl)phenyl)-1H-pyrazolo[4,3-c]pyridazin-6(5H)-one (Scheme 1)

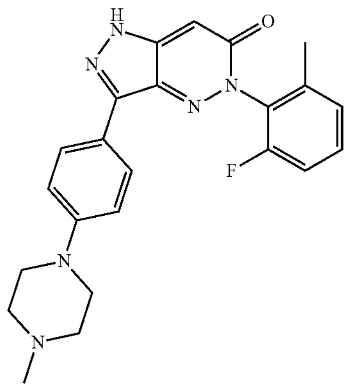 [SMILES: Cc1cccc(F)c1-n1nc2c(-c3ccc(N4CCN(C)CC4)cc3)n[nH]c2cc1=O]

Step 1: Preparation of dimethyl 2-(2-(2-fluoro-6-methylphenyl) hydrazino)-3-oxo-glutarate

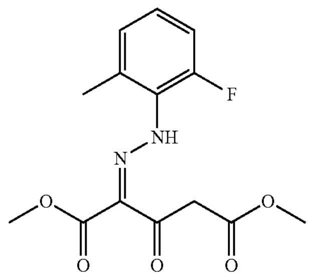

To a there-necked flask containing 2-fluoro-6-methylaniline (5.0 g, 40 mmol) was added hydrochloric acid (4M, 54 mL). The mixture was cooled to 0° C. An aqueous solution (30 mL) of sodium nitrite (2.8 g, 40 mmol) was added dropwise, while keeping the temperature of the reaction mixture at 5-10° C. After stirring for additional 2 hours at 5-10° C., the mixture formed was then added rapidly to a vigorously stirred solution of dimethyl 3-oxo-glutarate (7.0 g, 40 mmol) and sodium acetate (21.0 g, 264 mmol) in a solvent mixture of ethanol (30 mL) and water (60 mL) at room temperature, the product precipitated. The reaction mixture was further stirred at room temperature for 2 hours and then filtered with suction. The filter cake was dried to give crude dimethyl 2-(2-(2-fluoro-6-methylphenyl) hydrazino)-3-oxo-glutarate (6.0 g) as a yellow solid. The crude product was directly used in the next step.

ESI-MS: m/z=310.9 ($[M+H]^+$).

Step 2: Preparation of methyl 1-(2-fluoro-6-methylphenyl)-4-hydroxy-6-oxo-1,6-dihydropyridazine-3-carboxylate

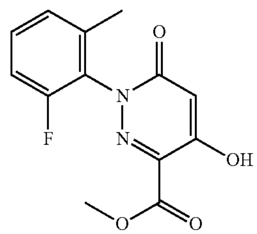 [SMILES: COC(=O)c1nn(-c2c(C)cccc2F)c(=O)cc1O]

Dimethyl 2-(2-(2-fluoro-6-methylphenyl) hydrazino)-3-oxo-glutarate (6.0 g, 19 mmol) was dissolved in 1,2-dichlorobenzene (100 mL) in a sealed tube, and was heated to reflux. After heating for 4 hours, the reaction mixture was cooled to room temperature, and cyclohexane (300 mL) was added dropwise. The product was crystallized and filtered with suction. The filter cake was dried to give methyl 1-(2-fluoro-6-methylphenyl)-4-hydroxy-6-oxo-1,6-dihydropyridazine-3-carboxylate as a brown solid (2.0 g, 7.2 mmol). Yield: 37%.

ESI-MS: m/z=279.1 ($[M+H]^+$).

Step 3: Preparation of 1-(2-fluoro-6-methylphenyl)-4-hydroxy-6-oxo-1,6-dihydropyridazine-3-carboxamide

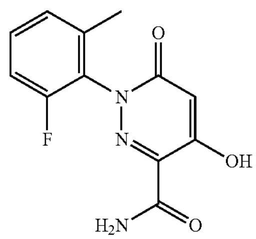 [SMILES: Cc1cccc(F)c1-n1nc(C(N)=O)c(O)cc1=O]

Methyl 1-(2-fluoro-6-methylphenyl)-4-hydroxy-6-oxo-1,6-dihydropyridazine-3-carboxylate (2.0 g, 7.2 mmol) was dissolved in ammonia in methanol (7N, 20 mL) in a sealed tube, and was heated to reflux overnight. The reaction mixture was cooled to room temperature and concentrated to dryness to give the crude product of 1-(2-fluoro-6-methylphenyl)-4-hydroxy-6-oxo-1,6-dihydropyridazine-3-carboxamide (1.6 g) as oil. The crude product was directly used in the next step.

ESI-MS: m/z=264.1 ($[M+H]^+$).

Step 4: Preparation of 4-chloro-1-(2-fluoro-6-methylphenyl)-6-oxo-1,6-dihydropyridazine-3-carbonitrile

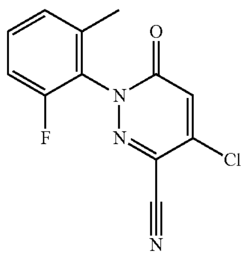 [SMILES: Cc1cccc(F)c1-n1nc(C#N)c(Cl)cc1=O]

To a solution of 4-chloro-1-(2-fluoro-6-methylphenyl)-6-oxo-1,6-dihydropyridazine-3-carbonitrile (1.6 g) in acetonitrile (16 mL) was added phosphorus oxychloride (8 mL) and heated to reflux overnight. The reaction mixture was poured into ice and stirred for 1 hour, and then extracted with ethyl acetate for three times (30 mL×3). The organic phases were combined, dried, filtered and concentrated to dryness. The residue was purified by column chromatography (petroleum ether/ethyl acetate: 20/1 to 10/1) to give 4-chloro-1-(2-fluoro-6-methylphenyl)-6-oxo-1,6-dihydropyridazine-3-carbonitrile as a white solid (800 mg, 3.04 mmol). Overall yield for two steps: 50%.

ESI-MS: m/z=264.0 ($[M+H]^+$).

Step 5: Preparation of 3-amino-5-(2-fluoro-6-methylphenyl)-1H-pyrazolo[4,3-c]pyridazin-6(5H)-one

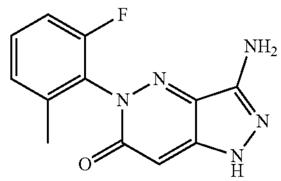 [SMILES: Cc1cccc(F)c1-n1nc2c(N)n[nH]c2cc1=O]

4-Chloro-1-(2-fluoro-6-methylphenyl)-6-oxo-1,6-dihydropyridazine-3-carbonitrile (800 mg, 3.04 mmol) was dissolved in ethanol (8 mL), and 98% hydrazine hydrate (760 mg, 15 mmol) was added. The reaction tube was sealed and heated to 100° C. overnight. The reaction mixture was cooled to room temperature, and the product was precipitated and filtered. The filter cake was dried to give 3-amino-5-(2-fluoro-6-methylphenyl)-1H-pyrazolo[4,3-c]pyridazin-6(5H)-one (600 mg, 2.3 mmol) as a red solid. Yield: 75%.

ESI-MS: m/z=260.1 ($[M+H]^1$).

Step 6. Preparation of 3-bromo-5-(2-fluoro-6-methylphenyl)-1H-pyrazolo[4,3-c]pyridazin-6(5H)-one

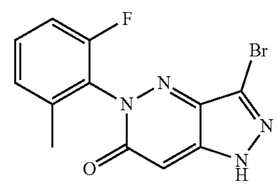 [SMILES: Cc1cccc(F)c1-n1nc2c(Br)n[nH]c2cc1=O]

3-Amino-5-(2-fluoro-6-methylphenyl)-1H-pyrazolo[4,3-c]pyridazin-6(5H)-one (600 mg, 2.3 mmol) was dissolved in acetonitrile (12 mL), and tert-butyl nitrite (240 mg) was added dropwise at 0° C. The reaction mixture was stirred at 0° C. for 10 minutes, then copper bromide (510 mg) was added and further stirred for 20 minutes. The reaction mixture was poured into water (20 mL) and filtered. The filtrate was extracted with ethyl acetate (20 mL×3) for three times. The combined organic phase was washed with brine, dried, filtered, and concentrated to give crude 3-bromo-5-(2-fluoro-6-methylphenyl)-1H-pyrazolo[4,3-c]pyridazine-6(5H)-one (400 mg). The crude product was directly used in the next step.

ESI-MS: m/z=323.0 ($[M+H]^+$).

Step 7: Preparation of Compound 1

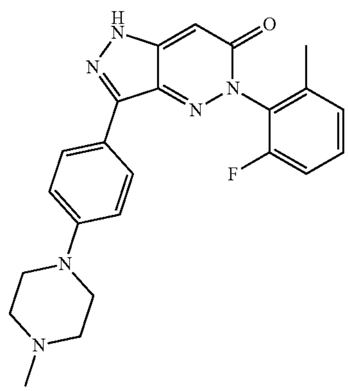

To a single-necked flask was added crude 3-bromo-5-(2-fluoro-6-methylphenyl)-1H-pyrazolo[4,3-c]pyridazin-6(5H)-one (400 mg, 1.24 mmol), (4-(4-methylpiperazin-1-yl)phenyl)boronic acid pinacol ester (376 mg, 1.24 mmol), potassium carbonate (340 mg, 2.48 mmol), Pd(dppf)$Cl_2$-DCM (108 mg, 0.147 mmol), 1,4-dioxane (2 mL) and water (2 mL). The mixture was heated to 80° C. under nitrogen and stirred for 3 hours. The reaction mixture was cooled to room temperature and concentrated. The residue was purified by preparative high pressure liquid chromatography (pre-HPLC) to give compound 1 (as the trifluoroacetate salt, 5.3 mg, 0.010 mmol) as a brown solid.

EXAMPLE 2

Compound 2: Preparation of 5-(2-methoxy-6-methylphenyl)-3-(4-(4-methylpiperazin-1-yl)phenyl)-1H-pyrazolo[4,3-c]pyridazin-6(5H)-one (Scheme 2A)

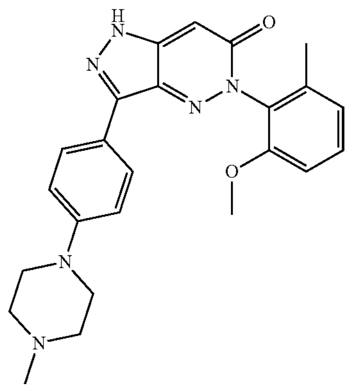 [SMILES: COc1cccc(C)c1-n1nc2c(-c3ccc(N4CCN(C)CC4)cc3)n[nH]c2cc1=O]

Step 1: Preparation of dimethyl 2-(2-(2-methoxy-6-methylphenyl)hydrazino)-3-oxo-glutarate

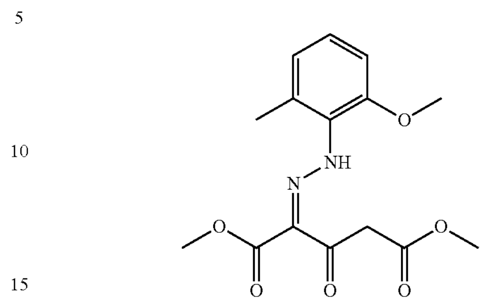

This compound was prepared according to the procedure described in Example 1 (step 1) using 2-methoxy-6-methylaniline instead of 2-fluoro-6-methylaniline as the starting material. Yield: 79%.

ESI-MS: m/z=323.2 ($[M+H]^1$).

Step 2: Preparation of methyl 4-hydroxy-1-(2-methoxy-6-methylphenyl)-6-oxo-1,6-dihydropyridazine-3-carboxylate

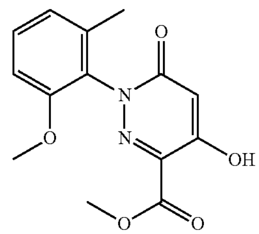 [SMILES: COC(=O)c1nn(-c2c(C)cccc2OC)c(=O)cc1O]

This compound was prepared according to the procedure described in Example 1 (step 2) using dimethyl 2-(2-(2-(2-methoxy-6-methylphenyl) hydrazino)-3-oxo-glutarate instead of dimethyl 2-(2-(2-fluoro-6-methylphenyl) hydrazino)-3-oxo-glutarate as starting material. Yield: 83%.

ESI-MS: m/z=291.2 ($[M+H]^+$).

Step 3: Preparation of methyl 4-chloro-1-(2-methoxy-6-methylphenyl)-6-oxo-1,6-dihydropyridazine-3-carboxylate

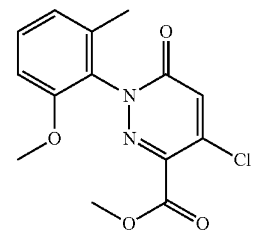 [SMILES: COC(=O)c1nn(-c2c(C)cccc2OC)c(=O)cc1Cl]

To phosphorus oxychloride (15 mL) was added methyl 4-hydroxy-1-(2-methoxy-6-methylphenyl)-6-oxo-1,6-dihydropyridazine-3-carboxylate (3.12 g, 10.8 mmol), and heated to 100° C. under nitrogen for 14 hours. The reaction was complete. The reaction mixture was cooled to room temperature, concentrated to dryness, and the residue was purified by column chromatography (petroleum ether/ethyl acetate: 3/1) to obtain methyl 4-chloro-1-(2-methoxy-6-methylphenyl)-6-oxo-1,6-dihydropyridazine-3-carboxylate (2.39 g, 7.74 mmol) as an orange solid. Yield: 72%.

ESI-MS: m/z=309.1 ($[M+H]^+$).

Step 4: Preparation of 4-hydrazino-1-(2-methoxy-6-methylphenyl)-6-oxo-1,6-dihydropyridazine-3-carbohydrazide

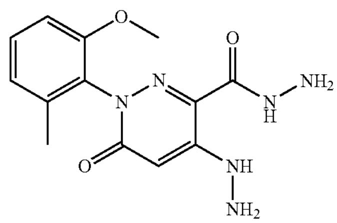 [SMILES: COc1cccc(C)c1-n1nc(C(=O)NN)c(NN)cc1=O]

Methyl 4-chloro-1-(2-methoxy-6-methylphenyl)-6-oxo-1,6-dihydropyridazine-3-carboxylate (2.39 g, 7.74 mmol), hydrazine hydrate (1.45 g, 23.2 mmol) and DIPEA (3.84 mL, 23.2 mmol) were added into absolute ethanol (24 mL), and was heated to 80° C. under nitrogen for 2 hours. The reaction was complete. The reaction mixture was cooled to 0° C. A precipitate was formed, and collected by filtration. The filter cake was rinsed with cold absolute ethanol (about 0° C.) and dried in vacuo to give 4-hydrazino-1-(2-methoxy-6-methylphenyl)-6-oxo-1,6-dihydropyridazine-3-carbohydrazide (2.06 g, 6.77 mmol) as a yellow solid. Yield: 88%.

ESI-MS: m/z=305.2 ($[M+H]^+$).

Step 5: Preparation of 5-(2-methoxy-6-methylphenyl)-1H-pyrazolo[4,3-c]pyridazin-3,6(2H,5H)-dione

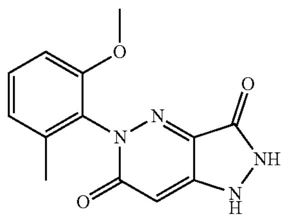 [SMILES: COc1cccc(C)c1-n1nc2c(=O)[nH][nH]c2cc1=O]

4-hydrazino-1-(2-methoxy-6-methylphenyl)-6-oxo-1,6-dihydropyridazine-3-carbohydrazide (2.06 g, 6.78 mmol), glacial acetic acid (2.33 mL, 40.7 mmol) and DIPEA (5.60 mL, 33.9 mmol) were added into n-butanol (20 mL), and heated to 120° C. under nitrogen for 15 hours. The reaction was complete. The reaction mixture was cooled to room temperature and concentrated to dryness. The residue was purified by column chromatography (dichloromethane/methanol: 40/1 to 8/1) to give 5-(2-methoxy-6-methylphenyl)-1H-pyrazolo[4,3-c]pyridazin-3,6 (2H,5H)-dione (1.67 g, 6.14 mmol) as a reddish-brown solid. Yield: 90%.

ESI-MS: m/z=273.1 ($[M+H]^+$).

Step 6: Preparation of 3-chloro-5-(2-methoxy-6-methylphenyl)-1H-pyrazolo[4,3-c]pyridazin-6(5H)-one

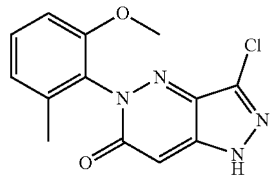 [SMILES: COc1cccc(C)c1-n1nc2c(Cl)n[nH]c2cc1=O]

To a solution of 5-(2-methoxy-6-methylphenyl)-1H-pyrazolo[4,3-c]pyridazin-3,6 (2H,5H)-dione (200 mg, 0.74 mmol) in acetonitrile (100 mL) was added phosphorus oxychloride (334 μL, 3.67 mmol) and benzyltrimethylammonium chloride (136 mg, 0.74 mmol). The mixture was heated to 70° C. under nitrogen, and stirred for 18 hours. The reaction mixture was cooled to room temperature, and concentrated to dryness. The residue was purified by thin layer chromatography (dichloromethane/methanol: 20/1) to give 3-chloro-5-(2-methoxy-6-methylphenyl)-1H-pyrazolo[4,3-c]pyridazin-6(5H)-one (95 mg, 0.33 mmol) as a yellow solid. Yield: 44%.

ESI-MS: m/z=291.2 ($[M+H]^+$).

Step 7: Preparation of Compound 2

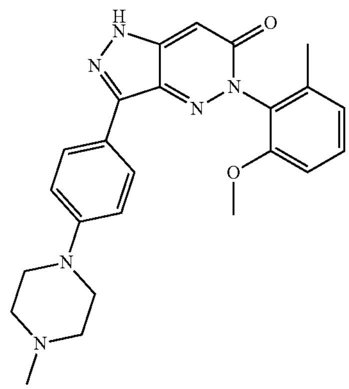 [SMILES: COc1cccc(C)c1-n1nc2c(-c3ccc(N4CCN(C)CC4)cc3)n[nH]c2cc1=O]

3-Chloro-5-(2-methoxy-6-methylphenyl)-1H-pyrazolo[4,3-c]pyridazin-6(5H)-one (50 mg, 0.17 mmol), 4-(4-methyl-1-piperazinyl)phenylboronic acid (76 mg, 0.34 mmol), SPhos-Pd-G2 (10 mg, 0.014 mmol) and potassium phosphate (110 mg, 0.52 mmol) were added to a mixture of 1,4-dioxane (4 mL) and water (1 mL). The mixture was heated to 100° C. under nitrogen for 14 hours to complete the reaction. The reaction mixture was cooled to room temperature and concentrated to dryness. The residue was purified by thin layer chromatography (dichloromethane/methanol: 20/1) to give a crude product, which was slurried with methanol (1 mL) in ice-water bath to give compound 2 (61 mg, 0.14 mmol) as a yellow solid. Yield: 82%.

EXAMPLE 4

Compound 4: 5-(2,4-dimethoxyphenyl)-3-(4-(1-methyl-1,2,3,6-tetrahydropyridin-4-yl)phenyl)-1H-pyrazolo[4,3-c]pyridazin-6(5H)-one (Scheme 3A)

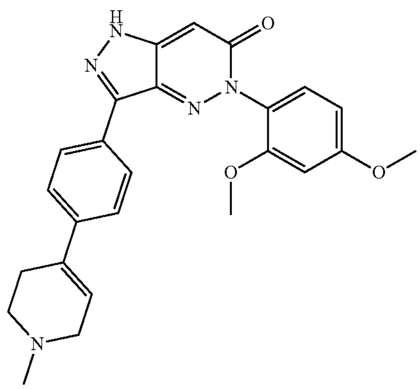 [SMILES: COc1ccc(-n2nc3c(-c4ccc(C5=CCN(C)CC5)cc4)n[nH]c3cc2=O)c(OC)c1]

Step 1: Preparation of 4-bromo-N-methoxy-N-methylbenzamide

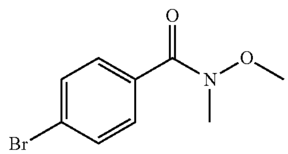

To a solution of 4-bromobenzoyl chloride (5.0 g, 22.8 mmol) in dichloromethane (50 mL) cooled in ice-water bath under nitrogen Was added N,O-dimethylhydroxylamine hydrochloride (2.667 g, 27.34 mmol) and triethylamine (6.32 mL, 45.6 mmol) successively. The mixture was warmed to room temperature gradually and further stirred for 2 hours. Dilute hydrochloric acid (0.1M, 100 mL) was added to quench the reaction. The reaction mixture was extracted with dichloromethane for three times (100 mL×3). The combined organic phase was washed with brine, dried and filtered. The filtrate was concentrated to dryness under reduced pressure to give 4-bromo-N-methoxy-N-methylbenzamide (5.46 g, 22.4 mmol) as a yellow oil. Yield: 98%. ESI-MS: m/z=244.0 ($[M+H]^+$).

Step 2: Preparation of methyl 5-(4-bromophenyl)-3,5-dioxopentanoate

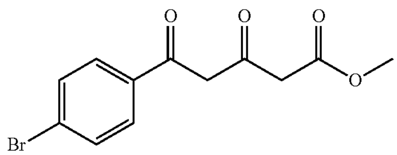 [SMILES: COC(=O)CC(=O)CC(=O)c1ccc(Br)cc1]

To an ice water bath-cooled suspension of sodium hydride (360 mg, 9.01 mmol) in dry tetrahydrofuran (20 mL) under nitrogen was added methyl acetoacetate (951 mg, 8.19 mmol) dropwise with stirring. The mixture was stirred for 0.5 hour at the same temperature. The reaction was then cooled to −70° C. in a dry ice-acetone bath, and n-butyllithium (2.5M in n-hexane, 3.3 mL, 8.2 mmol) was added dropwise. The mixture was stirred for 10 minutes with the temperature maintained. Then, a solution of 4-bromo-N-methoxy-N-methylbenzamide (2.00 g, 8.19 mmol) in tetrahydrofuran (10 mL) was added dropwise, and then stirred for 1 hour. The reaction was warmed to 0° C., and quenched with saturated ammonium chloride solution (100 mL). The reaction mixture was extracted with ethyl acetate (100 mL×2). The combined organic phase was washed with saturated brine (100 mL), dried over anhydrous sodium sulfate, and then filtered. The filtrate was concentrated under reduced pressure, and the residue was purified by column chromatography (petroleum ether/ethyl acetate: 10/1) to give methyl 5-(4-bromophenyl)-3,5-dioxopentanoate (1.346 g, 4.5 mmol)) as a yellow oil. Yield: 54%.

ESI-MS: m/z=299.0 ($[M+H]^+$).

Step 3: Preparation of methyl 5-(4-bromophenyl)-4-(2-(2,4-dimethoxyphenyl) hydrazino)-3,5-dioxopentanoate

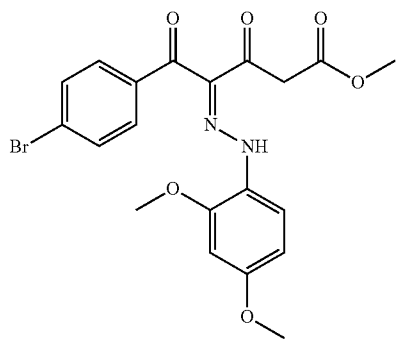 [SMILES: COC(=O)CC(=O)/C(=N\Nc1ccc(OC)cc1OC)C(=O)c1ccc(Br)cc1]

To an ice bath-cooled mixture of 2,4-dimethoxyaniline (200 mg, 1.31 mmol) in water (1.6 mL) was added concentrated hydrochloric acid (0.8 mL) and aqueous solution (1.2 mL) of sodium nitrite (90 mg, 1.31 mmol) dropwise, successively. The resultant solution was stirred for 0.5 hours with the temperature maintained to obtain a diazonium salt solution. To a solution of methyl 5-(4-bromophenyl)-3,5-dioxopentanoate (391 mg, 1.31 mmol) and sodium acetate (643 mg, 7.83 mmol) in absolute ethanol (1.2 mL) and water (2.4 mL) was added the above obtained diazonium salt solution dropwise. After the addition, the mixture was stirred at room temperature for 2 hours. The reaction mixture was extracted with dichloromethane for three times (20 mL×3), dried over anhydrous sodium sulfate, and filtered. The filtrate was concentrated under reduced pressure, and the residue was purified by column chromatography (petroleum ether/ethyl acetate: 10/1 to 1/8) to give methyl 5-(4-bromophenyl)-4-(2-(2,4)-dimethoxyphenyl) hydrazino)-3,5-dioxopentanoate (325 mg, 0.70 mmol) as an orange solid. Yield: 54%.

ESI-MS: m/z=463.1 ($[M+H]^+$).

Step 4: Preparation of 6-(4-bromobenzoyl)-2-(2,4-dimethoxyphenyl)-5-hydroxypyridazin-3 (2H)-one

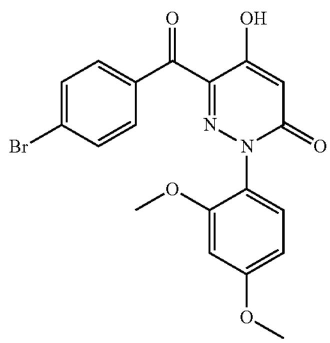 [SMILES: COc1ccc(-n2nc(C(=O)c3ccc(Br)cc3)c(O)cc2=O)c(OC)c1]

Methyl 5-(4-bromophenyl)-4-(2-(2,4-dimethoxyphenyl) hydrazinomethylene)-3,5-dioxopentanoate (100 mg, 0.22 mmol) was dissolved in o-dichlorobenzene (2 mL), heated to 175° C. and stirred for 5 hours under nitrogen. The reaction mixture was cooled to room temperature, diluted with ethyl acetate (10 mL), and extracted with saturated sodium bicarbonate solution for three times (10 mL×3). The combined aqueous phases was adjusted to pH=4-5 with saturated citric acid solution, and extracted with ethyl acetate twice (20 mL×2). The organic phases were combined, dried over anhydrous sodium sulfate, and filtered. The filtrate was concentrated to dryness under reduced pressure to give 6-(4-bromobenzoyl)-2-(2,4-dimethoxyphenyl)-5-hydroxypyridazin-3 (2H)-one (67 mg, 0.16 mmol) as a yellow solid. Yield: 72%.

ESI-MS: m/z=431.1 ($[M+H]^+$).

Step 5: Preparation of 3-(4-bromophenyl)-5-(2,4-dimethoxyphenyl)-1H-pyrazolo[4,3-c]pyridazin-6 (5H)-one

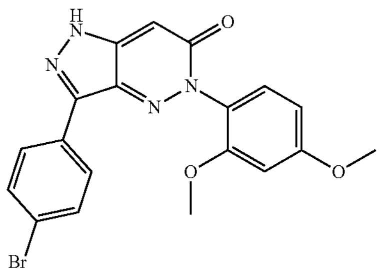 [SMILES: COc1ccc(-n2nc3c(-c4ccc(Br)cc4)n[nH]c3cc2=O)c(OC)c1]

To a solution of 6-(4-bromobenzoyl)-2-(2,4-dimethoxyphenyl)-5-hydroxypyridazin-3 (2H)-one (47 mg, 0.11 mmol) in n-butanol (2 mL) was added glacial acetic acid (31 μL, 0.55 mmol) and hydrazine hydrate (33 μL, 0.55 mmol). The mixture was heated to 120° C. under nitrogen and stirred for 15 hours. The reaction mixture was cooled to room temperature. Precipitate formed. The solid was collected by filtration and dried in vacuo to give 3-(4-bromophenyl)-5-(2,4-dimethoxyphenyl)-1H-pyrazolo[4,3-c] pyridazine-6(5H)-one (27 mg, 0.063 mmol) as a yellow solid. Yield: 58%.

ESI-MS: m/z=427.1 ($[M+H]^+$).

Step 6: Preparation of Compound 4

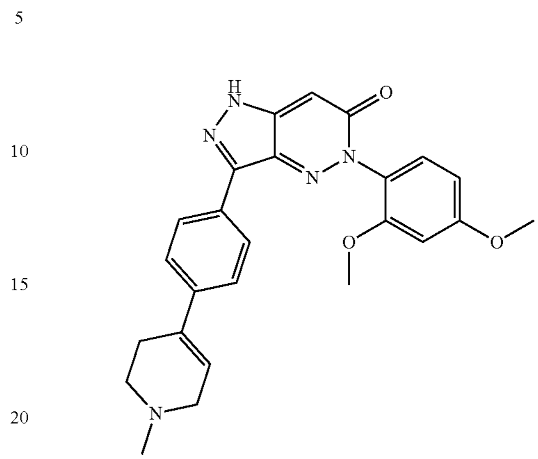

3-(4-Bromophenyl)-5-(2,4-dimethoxyphenyl)-1H-pyrazolo[4,3-c]pyridazin-6(5H)-one (10.0 mg, 0.023 mmol), 1-methyl-1,2,3,6-tetrahydropyridine-4-boronic acid pinacol ester (10.4 mg, 0.047 mmol), SPhos-Pd-G2 (1.7 mg, 0.002 mmol) and potassium phosphate (14.9 mg, 0.070 mmol) were added to a solvent mixture of 1,4-dioxane (1.6 mL) and water (0.4 mL). The resultant mixture was heated to 100° C. under nitrogen and stirred for 15 hours. The reaction mixture was cooled to room temperature, concentrated to dryness, and the residue was purified by thin layer chromatography (dichloromethane/methanol: 10/1) to obtain the crude product, which was slurried with methanol (0.5 mL) at room temperature to obtain compound 4 (3.4 mg, 0.0077 mmol) as a yellow solid. Yield: 33%.

EXAMPLE 23

Compound 23: 5-(2-fluoro-6-methoxyphenyl)-3-(4-(1-methyl-1,2,3,6-tetrahydro-pyridin-4-yl)phenyl)-1H-pyrazolo[4,3-c]pyridazin-6(5H)-one (Scheme 4)

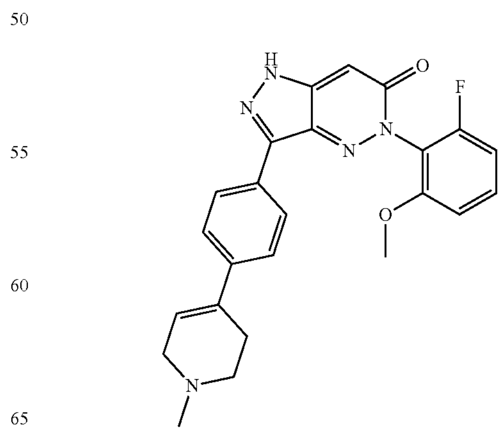

Step 1: Preparation of 2-methoxy-6-fluorophenyldiazonium tetrafluoroborate

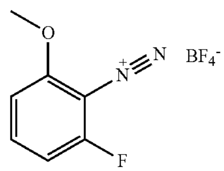

To dry methyl tert-butyl ether (8 mL) cooled to −5° C. under nitrogen was added boron trifluoride diethyl ether complex (1.1 mL, 8.9 mmol) and a solution of 2-fluoro-6-methoxyaniline (614 mg, 4.35 mmol) in dry methyl tert-butyl ether (3 mL) successively. After stirring for 15 minutes, the reaction mixture was cooled to −15° C. A solution of tert-butyl nitrite (0.62 mL, 5.2 mmol) in dry methyl tert-butyl ether (3 mL) was added dropwise. After the addition, the reaction mixture was gradually warmed to 0° C. Dry tetrahydrofuran (5 mL) was added, and stirring was continued at 0° C. for 2 hours. The reaction mixture was filtered, and the filter cake was washed with methyl tert-butyl, collected, and dried at room temperature to give 2-methoxy-6-fluorophenyldiazonium tetrafluoroborate (955 mg, 3.98 mmol) as a gray solid, Yield: 91%.

Step 2: Preparation of 6-(2-(4-bromophenyl)-1-(2-(2-fluoro-6-methoxyphenyl)-hydrazino)-2-oxo-ethyl)-2,2-dimethyl-4H-1,3-dioxin-4-one

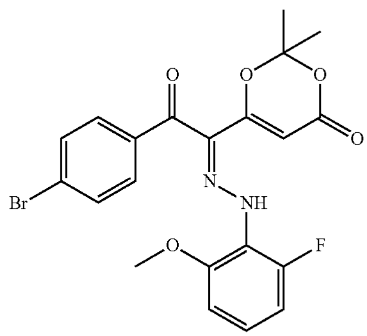 [SMILES: COc1cccc(F)c1N/N=C(/C(=O)c1ccc(Br)cc1)C1=CC(=O)OC(C)(C)O1]

To a solution of 6-(2-(4-bromophenyl)-2-oxo-ethyl)-2,2-dimethyl-4H-1,3-dioxin-4-one (694 mg, 2.13 mmol) in ethanol (20 mL) was added sodium acetate (506 mg, 6.16 mmol), and cooled to −5° C. To the above mixture was added a solution of 2-methoxy-6-fluorophenyldiazonium tetrafluoroborate (539 mg, 2.25 mmol) in acetonitrile (3 mL) dropwise, and stirred for 20 minutes. The reaction mixture was poured into a mixture of ethyl acetate and aqueous ammonium chloride solution with stirring. After phase separation, the aqueous phase was extracted with ethyl acetate. The combined organic phase was dried and concentrated to give the crude product of 6-(2-(4-bromophenyl)-1-(2-(2-fluoro-6-methoxyphenyl) hydrazino)-2-oxo-ethyl)-2,2-dimethyl-4H-1,3-dioxin-4-one. The crude product was used directly in the next step without purification.

ESI-MS: m/z=477.1 ($[M+H]^+$).

Step 3: Preparation of 6-(4-bromobenzoyl)-2-(2-fluoro-6-methoxyphenyl)-5-hydroxypyridazin-3(2H)-one

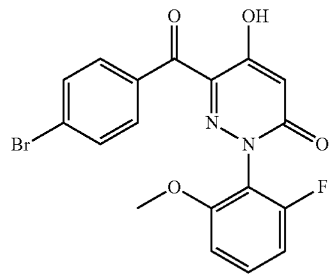 [SMILES: COc1cccc(F)c1-n1nc(C(=O)c2ccc(Br)cc2)c(O)cc1=O]

To a solution of 6-(2-(4-bromophenyl)-1-(2-(2-fluoro-6-methoxyphenyl) hydrazino)-2-oxo-ethyl)-2,2-dimethyl-4H-1,3-dioxin-4-one (970 mg, 2.03 mmol) in 1,2-dichlorobenzene (4 mL) was added glacial acetic acid (485 μL), and heated to 130° C. for 1 hour. The reaction mixture was cooled to room temperature, and poured into n-heptane (120 mL) cooled in an ice-water bath with stirring. The resultant precipitate was collected by filtration, dried in vacuo to give 6-(4-bromobenzoyl)-2-(2-fluoro-6-methoxyphenyl)-5-hydroxypyridazin-3(2H)-one (518 mg, 1.23 mmol) as an orange-red solid. Yield: 61%.

ESI-MS: m/z=419.1 ($[M+H]^+$).

Step 4: Preparation of 3-(4-bromophenyl)-5-(2-fluoro-6-methoxyphenyl)-1H-pyrazolo[4,3-c]pyridazin-6(5H)-one

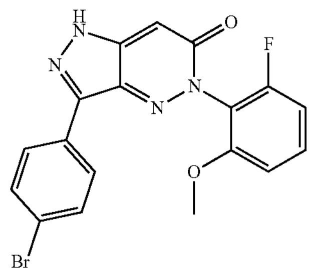 [SMILES: COc1cccc(F)c1-n1nc2c(-c3ccc(Br)cc3)n[nH]c2cc1=O]

This compound was prepared according to the procedure described in Example 4 (step 5) using 6-(4-bromobenzoyl)-2-(2-fluoro-6-methoxyphenyl)-5-hydroxypyridazine-3(2H)-one instead of 6-(4-bromobenzoyl)-2-(2,4-dimethoxyphenyl)-5-hydroxypyridazin-3(2H)-one as starting material. Yield: 70%.

ESI-MS: m/z=415.1 ($[M+H]^+$).

Step 5: Preparation of Compound 23

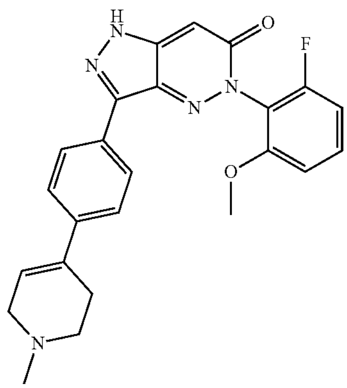 [SMILES: COc1cccc(F)c1-n1nc2c(-c3ccc(C4=CCN(C)CC4)cc3)n[nH]c2cc1=O]

This compound was prepared according to the procedure described in Example 4 (step 6) using 3-(4-bromophenyl)-5-(2-fluoro-6-methoxyphenyl)-1H-pyrazolo[4,3-c] pyridazin-6(5H)-one instead of 3-(4-bromophenyl)-5-(2,4-dimethoxyphenyl)-1H-pyrazolo[4,3-c]pyridazin-6(5H)-one as starting material with yield of 58%.

EXAMPLE 24

Compound 24: 5-(2-fluoro-6-methoxyphenyl)-3-(4-(1-methylpiperidin-4-yl)phenyl)-1H-pyrazolo[4,3-c] pyridazin-6(5H)-one

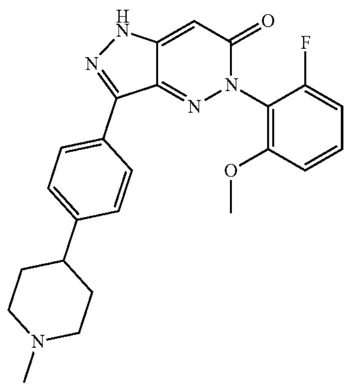 [SMILES: COc1cccc(F)c1-n1nc2c(-c3ccc(C4CCN(C)CC4)cc3)n[nH]c2cc1=O]

To a solution of compound 23 (60 mg, 014 mmol) in a solvent mixture of anhydrous methanol (6 mL) and tetrahydrofuran (6 mL) was added 10% Pd/C (12 mg), and stirred at room temperature overnight under a hydrogen atmosphere. The Pd/C was removed by filtration, and the filtrate was concentrated to dryness. The residue was purified by thin layer chromatography (dichloromethane/anhydrous methanol: 10/1) to give 5-(2-fluoro-6-methoxyphenyl)-3-(4-(1-methylpiperidin-4-yl)phenyl)-1H-pyrazolo[4,3-c] pyridazin-6(5H)-one (32 mg, 0.074 mmol). Yield: 53%.

EXAMPLE 25

Compound 25: 5-(2,4-dimethoxyphenyl)-3-(4-(4-methylpiperazin-1-yl)phenyl)-1H-pyrazolo[4,3-c]pyridazin-6 (5H)-one (Scheme 3B)

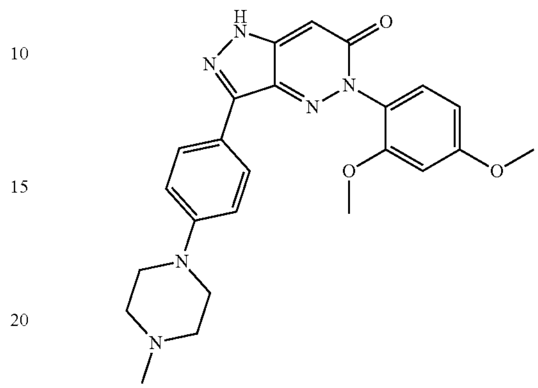

Step 1: Preparation of 3-(4-Bromophenyl)-1-(2,4-dimethoxybenzyl)-5-(2,4-dimethoxyphenyl)-1H-pyrazolo[4,3-c]pyridazin-6(5H)-one

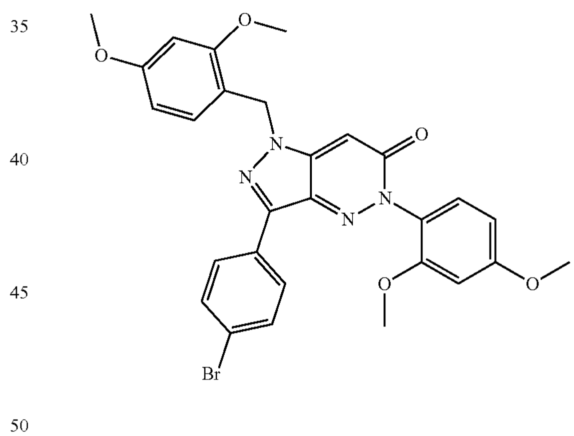

6-(4-bromobenzoyl)-2-(2,4-dimethoxyphenyl)-5-hydroxypyridazin-3 (2H)-one was prepared according to the procedure described in Example 4 (step 4). 6-(4-bromobenzoyl)-2-(2,4-dimethoxyphenyl)-5-hydroxypyridazin-3 (2H)-one (840 mg, 1.95 mmol), 2,4-dimethoxyphenylhydrazine dihydrochloride (646 mg, 2.53 mmol) and anhydrous sodium acetate (479 mg, 5.84 mmol) were added to n-butanol (10 mL), heated to 100° C. for 1 hour. The reaction mixture was cooled to room temperature, and the precipitate was collected by filtration. The solid was purified by column chromatography (petroleum ether/ethyl acetate: 1/9 to 0/10) to give 3-(4-bromophenyl)-1-(2,4-dimethoxybenzyl)-5-(2,4-dimethoxyphenyl)-1H-pyrazolo[4,3-c]pyridazin-6(5H)-one (532 mg, 0.92 mmol). Yield: 36%.

ESI-MS: m/z=577.2 ($[M+H]^+$).

Step 2: Preparation of 1-(2,4-dimethoxybenzyl)-5-(2,4-dimethoxyphenyl)-3-(4-(4-methylpiperazin-1-yl)phenyl)-1H-pyrazolo[4,3-c]pyridazin-6(5H)-one

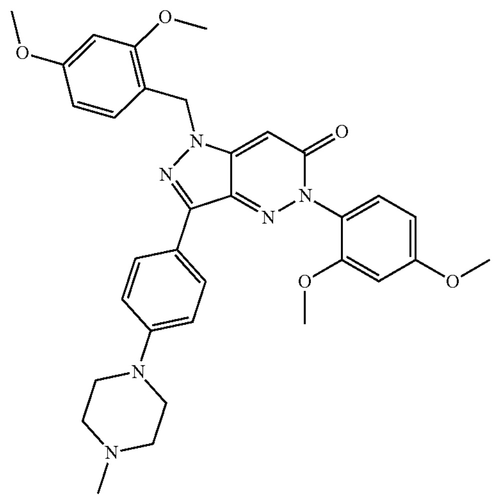

To a mixture of 3-(4-bromophenyl)-1-(2,4-dimethoxy benzyl)-5-(2,4-dimethoxyphenyl)-1H-pyrazolo[4,3-c] pyridazin-6(5H)-one (450 mg, 0.78 mmol), methylpiperazine (390 mg, 3.9 mmol), $Pd_2(dba)_3$ (71 mg, 0.078 mmol) and BINAP (121 mg, 0.195 mmol) in toluene (9 mL) was added a solution of sodium tert-pentoxide in toluene (3.5M, 1.1 mL) under nitrogen. The resultant mixture was heated to 100° C. and stirred overnight. The reaction mixture was diluted with dichloromethane and washed with water. The organic phase was dried and concentrated. The residue was purified by column chromatography (dichloromethane/methanol: 100/1 to 30/1) to give 1-(2,4-dimethoxybenzyl)-5-(2,4-dimethoxyphenyl)-3-(4-(4-methylpiperazin-1-yl) phenyl)-1H-pyrazolo[4,3-c]pyridazin-6(5H)-one (203 mg, 0.34 mmol) as an orange-red solid. Yield: 44%.

ESI-MS: m/z=597.4 ($[M+H]^+$).

Step 3: Preparation of Compound 25

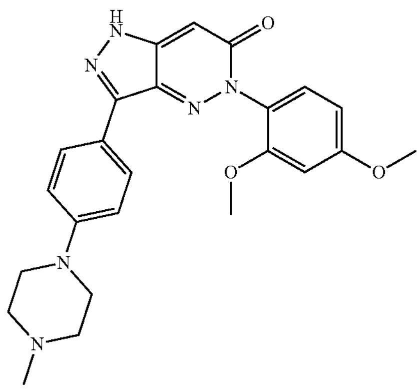 [SMILES: COc1ccc(-n2nc3c(-c4ccc(N5CCN(C)CC5)cc4)n[nH]c3cc2=O)c(OC)c1]

To a solution of 1-(2,4-dimethoxybenzyl)-5-(2,4-dimethoxyphenyl)-3-(4-(4-methylpiperazin-1-yl)phenyl)-1H-pyrazolo[4,3-c]pyridazin-6(5H)-one (200 mg, 0.34 mmol) in trifluoroacetic acid (6 mL) was added anisole (0.3 mL), and heated to 80° C. for 2 hours. The reaction mixture was cooled to room temperature, diluted with water (20 mL), and extracted with ethyl acetate for three times. The aqueous phase was adjusted to pH=8 with sodium carbonate solution, and solid precipitated. The solid was collected by filtration, dried, and slurried with methanol to give compound 25 (90 mg, 0.20 mmol) as an orange solid. Yield: 60%.

EXAMPLE 29

Compound 33: 5-(2-fluoro-6-methoxyphenyl)-3-(4-(4-methyl-3-oxo-piperazin-1-yl)phenyl)-1H-pyrazolo[4,3-c]pyridazin-6(5H)-one (Scheme 2B)

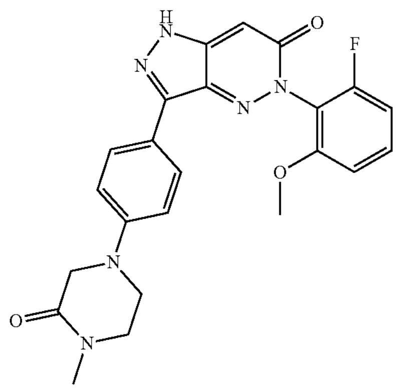 [SMILES: COc1cccc(F)c1-n1nc2c(-c3ccc(N4CCN(C)C(=O)C4)cc3)n[nH]c2cc1=O]

Step 1: Preparation of dimethyl 2-(2-(2-(2-fluoro-6-methoxyphenyl) hydrazino)-3-oxo-glutarate

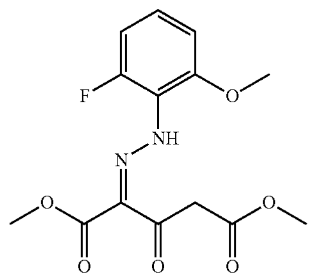

This compound was prepared according to the procedure described in Example 2 (step 1) using 2-fluoro-6-methoxyaniline instead of 2-methoxy-6-methylaniline as the starting material. Yield: 94%.

ESI-MS: m/z=327.2 ($[M+H]^1$).

Step 2: Preparation of methyl 4-hydroxy-1-(2-fluoro-6-methoxyphenyl)-6-oxo-1,6-dihydro-pyridazine-3-carboxylate

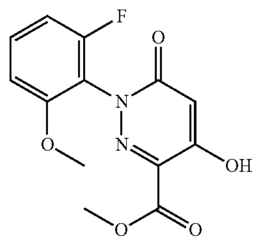 [SMILES: COC(=O)c1nn(-c2c(F)cccc2OC)c(=O)cc1O]

This compound was prepared according to the procedure described in Example 2 (step 2) using dimethyl 2-(2-(2-(2-fluoro-6-methoxyphenyl) hydrazino)-3-oxo-glutarate instead of dimethyl 2-(2-(2-(2-methoxy-6-methylphenyl) hydrazino)-3-oxo-glutarate as starting material. Yield: 90%.

ESI-MS: m/z=295.2 ([M+H][1]).

Step 3: Preparation of methyl 4-chloro-1-(2-fluoro-6-methoxyphenyl)-6-oxo-1,6-dihydropyridazine-3-carboxylate

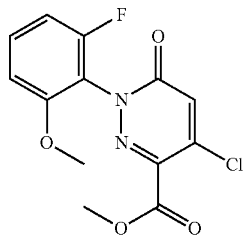 [SMILES: COC(=O)c1nn(-c2c(F)cccc2OC)c(=O)cc1Cl]

This compound was prepared according to the procedure described in Example 2 (step 3) using methyl 4-hydroxy-1-(2-fluoro-6-methoxyphenyl)-6-oxo-1,6-dihydropyridazine-3-carboxylate instead of methyl 4-hydroxy-1-(2-methoxy-6-methylphenyl)-6-oxo-1,6-dihydropyridazine-3-carboxylate as starting material. Yield: 84%.

ESI-MS: m/z=313.2 ($[M+H]^+$).

Step 4: Preparation of methyl 4-hydrazino-1-(2-fluoro-6-methoxyphenyl)-6-oxo-1,6-dihydro-pyridazine-3-carboxylate

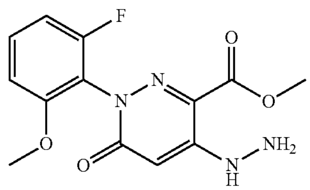 [SMILES: COC(=O)c1nn(-c2c(F)cccc2OC)c(=O)cc1NN]

To a suspension of methyl 4-chloro-1-(2-fluoro-6-methoxyphenyl)-6-oxo-1,6-dihydropyridazine-3-carboxylate (4.0 g, 12.8 mmol, 1.0 eq) and DIPEA (8.4 mL, 51.3 mmol, 4.0 eq) in ethanol (40 mL) was added a solution of 98% hydrazine hydrate (785 mg, 15.4 mmol, 1.2 eq) in ethanol (40 mL) at room temperature. After the addition, the mixture was stirred at room temperature for 4 hours. The reaction mixture was diluted with water (150 mL) and extracted with ethyl acetate for three times. The organic phases were combined, washed with brine, dried, filtered and concentrated to dryness. The residue was purified by column chromatography (dichloromethane/methanol: 100/1) to give methyl 4-hydrazino-1-(2-fluoro-6-methoxyphenyl)-6-oxo-1,6-dihydropyridazine-3-carboxylate (2.3 g) as a yellow solid. Yield: 59%.

ESI-MS: m/z=309.1 ($[M+H]^+$).

Step 5: Preparation of 5-(2-fluoro-6-methoxyphenyl)-1H-pyrazolo[4,3-c]pyridazine-3,6(2H,5H)-dione

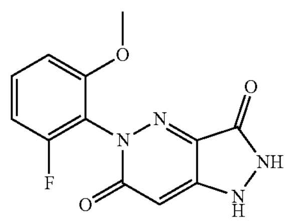 [SMILES: COc1cccc(F)c1-n1nc2c(=O)[nH][nH]c2cc1=O]

To a solution of methyl 4-hydrazino-1-(2-fluoro-6-methoxyphenyl)-6-oxo-1,6-dihydropyridazine-3-carboxylate (1.6 g, 5.19 mmol, 1.0 eq) in a solvent mixture of methanol (15 mL) and tetrahydrofuran (15 mL) was added aqueous solution (15 mL) of lithium hydroxide monohydrate (436 mg, 10.38 mmol, 2.0 eq), and the mixture was stirred at room temperature for 2 hours. The reaction mixture was concentrated to dryness. The residue was purified by column chromatography (dichloromethane/methanol: 15/1) to give 5-(2-fluoro-6-methoxyphenyl)-1H-pyrazolo[4,3-c]pyridazine-3,6 (2H,5H)-dione (1.4 g) as a brown-red solid. Yield: 99%.

ESI-MS: m/z=277.2 ($[M+H]^+$).

Step 6: Preparation of 3-chloro-5-(2-fluoro-6-methoxyphenyl)-1H-pyrazolo[4,3-c]pyridazin-6(5H)-one

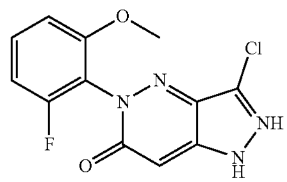 [SMILES: COc1cccc(F)c1-n1nc2c(Cl)n[nH]c2cc1=O]

This compound was prepared according to the procedure described in Example 2 (step 6) using 5-(2-fluoro-6-methoxyphenyl)-1H-pyrazolo[4,3-c]pyridazine-3,6(2H,5H)-dione instead of 5-(2-methoxy-6-methylphenyl)-1H-pyrazolo[4,3-c]pyridazine-3,6(2H,5H)-dione as starting material. Yield: 28%.

ESI-MS: m/z=295.1 ($[M+H]^+$).

Step 7: Preparation of Compound 33

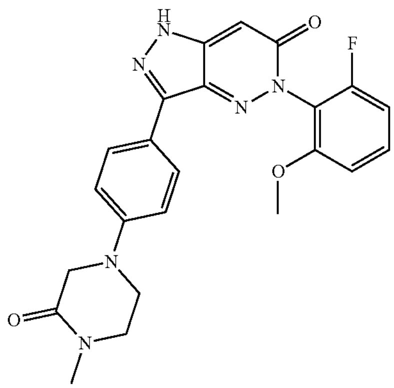 [SMILES: COc1cccc(F)c1-n1nc2c(-c3ccc(N4CCN(C)C(=O)C4)cc3)n[nH]c2cc1=O]

This compound was prepared according to the procedure described in Example 2 (step 7) using 3-chloro-5-(2-fluoro-6-methoxyphenyl)-1H-pyrazolo[4,3-c]pyridazine-6(5H)-one instead of 3-chloro-5-(2-methoxy-6-methylphenyl)-1H-pyrazolo[4,3-c]pyridazine-6(5H)-one, and using (4-(4-methyl-3-oxo-piperazin-1-yl)phenyl) boronic acid pinacol ester instead of 4-(4-methyl-1-piperazinyl)phenylboronic acid as starting materials. Yield: 25%.

EXAMPLE 30

Compound 34: 5-(2-fluoro-6-cyclopropylphenyl)-3-(4-(4-methylpiperazin-1-yl)phenyl)-1H-pyrazolo[4,3-c]pyridazin-6(5H)-one (Scheme 3A)

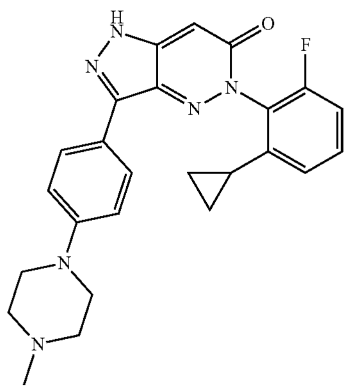 [SMILES: CN1CCN(c2ccc(-c3n[nH]c4cc(=O)n(-c5c(F)cccc5C5CC5)nc34)cc2)CC1]

Step 1: Preparation of tert-butyl(2-fluoro-6-cyclopropylphenyl)carbamate

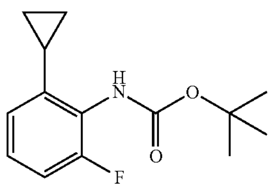 [SMILES: CC(C)(C)OC(=O)Nc1c(F)cccc1C1CC1]

This compound was prepared according to the procedure described in Example 29 (step 2) using cyclopropylboronic acid instead of 4,4,5,5-tetramethyl-2-(prop-1-en-2-yl)-1,3,2-dioxaborane as the starting material. Yield: 65%.

ESI-MS: m/z=196.1 ($[M+H-C_4H_8]^1$).

Step 2: Preparation of 2-fluoro-6-cyclopropylaniline

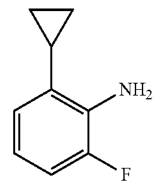 [SMILES: Nc1c(F)cccc1C1CC1]

This compound was prepared according to the procedure described in Example 29 (step 4) using tert-butyl(2-fluoro-6-cyclopropylphenyl) carbamate as starting material. Yield: 87%. ESI-MS: m/z=152.1 ($[M+H]^+$).

Step 3: Preparation of 2-cyclopropyl-6-fluorophenyldiazonium tetrafluoroborate

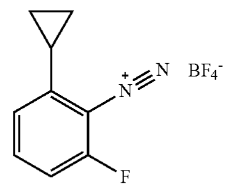

To a solvent mixture of dry methyl tert-butyl ether (3 mL) and dry tetrahydrofuran (3 mL) cooled to −5° C. was added boron trifluoride ether complex (489 μL, 3.97 mmol) and a solution of 2-fluoro-6-cyclopropylaniline (300 mg, 1.98 mmol) in dry tetrahydrofuran (3 mL) successively, under nitrogen. After stirring for 15 minutes, the reaction mixture was cooled to −15° C. A solution of tert-butyl nitrite (246 mg, 2.38 mmol) in dry methyl tert-butyl ether (3 mL) was added dropwise. After the addition, the reaction mixture was gradually warmed to 0° C., and further stirred for 1.5 hours. The reaction mixture was filtered, and the filter cake was washed with methyl tert-butyl (50 mL) and dried at room temperature to give 2-cyclopropyl-6-fluorophenyldiazonium tetrafluoroborate (426 mg, 1.70 mmol) was a white solid. Yield: 86%.

ESI-MS: m/z=163.1 ($[M+H-BF_4]^+$).

Step 4: Preparation of methyl 5-(4-bromophenyl)-4-(2-(2-fluoro-6-cyclopropylphenyl)hydrazino)-3,5-dioxopentanoate

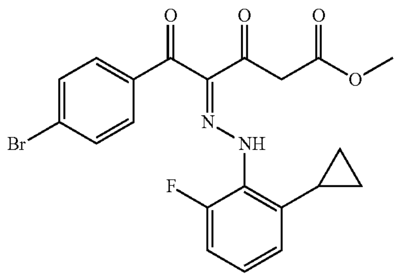 [SMILES: COC(=O)CC(=O)/C(=N\Nc1c(F)cccc1C1CC1)C(=O)c1ccc(Br)cc1]

To a mixture of methyl 5-(4-bromophenyl)-3,5-dioxopentanoate (920 mg, 3.07 mmol) and anhydrous sodium acetate (757 mg, 9.22 mmol) in absolute ethanol (20 mL) cooled to −15° C. was added a solution of 2-cyclopropyl-6-fluorophenyldiazonium tetrafluoroborate (384 mg, 1.54 mmol) in acetonitrile (4 mL) dropwise. After the addition, the reaction mixture was gradually warmed to 0° C. and further stirred for 1.5 hours. The reaction mixture was concentrated under reduced pressure, diluted with water (60 mL), and extracted with ethyl acetate (20 mL*3). The combined organic phase was washed with saturated brine (60 mL), dried over anhydrous sodium sulfate, and filtered with suction. The filtrate was concentrated to dryness. The residue was purified by column chromatography (petroleum ether/ethyl acetate: 15/1) to give methyl 5-(4-bromophenyl)-4-(2-(2-fluoro-6-cyclopropylphenyl) hydrazino)-3,5-dioxopentanoate (435 mg, 0.94 mmol) as a yellow solid. Yield: 61%.

ESI-MS: m/z=461.0 ($[M+H]^+$).

Step 5: Preparation of 6-(4-bromobenzoyl)-2-(2-fluoro-6-cyclopropylphenyl)-5-hydroxypyridazin-3 (2H)-one

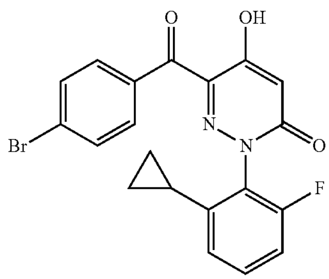 [SMILES: O=C(c1ccc(Br)cc1)c1nn(-c2c(F)cccc2C2CC2)c(=O)cc1O]

This compound was prepared according to the procedure described in Example 4 (step 4) using methyl 5-(4-bromophenyl)-4-(2-(2-fluoro-6-cyclopropylphenyl) hydrazinomethylene)-3,5-dioxopentanoate instead of methyl 5-(4-bromophenyl)-4-(2-(2,4-dimethoxyphenyl) hydrazinomethylene)-3,5-dioxopentanoate as the starting material. Yield: 38%.

ESI-MS: m/z=429.0 ($[M+H]^+$).

Step 6: Preparation of 3-(4-bromophenyl)-5-(2-fluoro-6-cyclopropylphenyl)-1H-pyrazolo[4,3-c] pyridazin-6(5H)-one

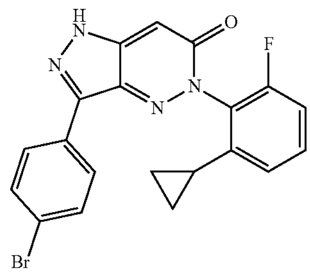 [SMILES: O=c1cc2[nH]nc(-c3ccc(Br)cc3)c2nn1-c1c(F)cccc1C1CC1]

This compound was prepared according to the procedure described in Example 4 (step 5) using 6-(4-bromobenzoyl)-2-(2-fluoro-6-cyclopropylphenyl)-5-hydroxypyridazine-3 (2H)-one instead of 6-(4-bromobenzoyl)-2-(2,4-dimethoxyphenyl)-5-hydroxypyridazin-3 (2H)-one as starting material. Yield: 71%.

ESI-MS: m/z=425.1 ($[M+H]^+$).

Step 7: Preparation of 3-(4-bromophenyl)-5-(2-cyclopropyl-6-fluorophenyl)-1-(2-(trimethylsilyl) ethoxymethyl)-1H-pyrazolo[4,3-c]pyridazin-6(5H)-one

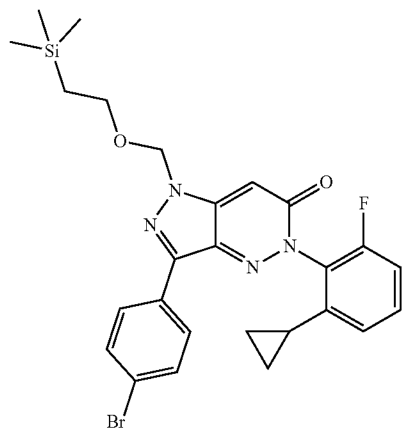 [SMILES: C[Si](C)(C)CCOCn1nc(-c2ccc(Br)cc2)c2nn(-c3c(F)cccc3C3CC3)c(=O)cc21]

To a solution of 3-(4-bromophenyl)-5-(2-fluoro-6-cyclopropylphenyl)-1H-pyrazolo[4,3-c]pyridazin-6(5H)-one (92 mg, 0.22 mmol) in dry N,N-dimethylformamide (5 mL) at 0° C. was added sodium hydride (26 mg, 0.65 mmol) under nitrogen, and the mixture was stirred at 0° C. for 20 min. 2-(Trimethylsilyl) ethoxymethyl chloride (111 mg, 0.67 mmol) was then added dropwise, and the mixture was warmed to room temperature and stirred for 2 hours. The reaction mixture was poured into water (50 mL), extracted with ethyl acetate for three times (15 mL*3). The combined organic phase was washed with saturated brine (50 mL*3), dried over anhydrous sodium sulfate, and filtered with suction. The filtrate was concentrated to dryness, and the residue was purified by column chromatography (petroleum ether/ethyl acetate: 5/1) to give 3-(4-bromophenyl)-5-(2-cyclopropyl-6-fluorophenyl)-1-(2-(trimethylsilyl)ethoxymethyl)-1H-pyrazolo[4,3-c]pyridazin-6(5H)-one (82 mg, 0.15 mmol) as a yellow solid. Yield: 67%.

ESI-MS: m/z=555.0 ($[M+H]^1$)

Step 8: Preparation of 5-(2-cyclopropyl-6-fluorophenyl)-3-(4-(4-methylpiperazin-1-yl)phenyl)-1-(2-(trimethylsilyl)ethoxymethyl)-1H-pyrazolo[4,3-c]pyridazin-6(5H)-one

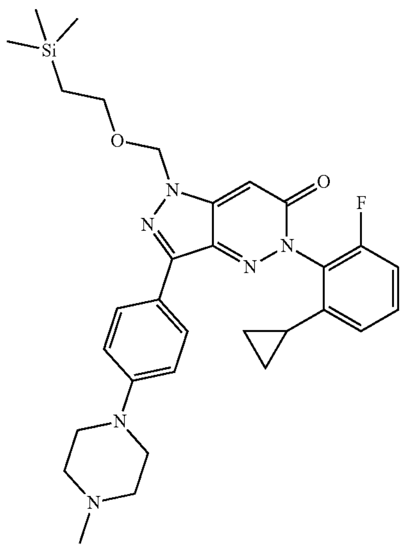 [SMILES: CN1CCN(c2ccc(-c3nn(COCC[Si](C)(C)C)c4cc(=O)n(-c5c(F)cccc5C5CC5)nc34)cc2)CC1]

To a mixture of 3-(4-bromophenyl)-5-(2-cyclopropyl-6-fluorophenyl)-1-(2-(trimethylsilyl) ethoxymethyl)-1H-pyrazolo[4,3-c]pyridazin-6(5H)-one (82 mg, 0.15 mmol), methylpiperazine (74 mg, 0.74 mmol), $Pd_2(dba)_3$ (13 mg, 0.015 mmol) and BINAP (23 mg, 0.037 mmol) in toluene (7 mL) was added a solution of sodium tert-pentoxide in toluene (3.5 M, 0.21 mL) under nitrogen. The mixture was heated to 100° C. and stirred overnight. The reaction mixture was poured into saturated aqueous ammonium chloride solution (60 mL), and extracted with ethyl acetate for three times (20 mL*3). The combined organic phase was washed with saturated brine, dried over anhydrous sodium sulfate, and filtered with suction. The filtrate was concentrated to dryness, and the residue was purified by column chromatography (ethyl acetate/triethylamine: 100/3) to give 5-(2-cyclopropyl-6-fluorophenyl)-3-(4-(4-methylpiperazin-1-yl) phenyl)-1-(2-(trimethylsilyl) ethoxymethyl)-1H-pyrazolo[4,3-c]pyridazin-6(5H)-one (36 mg, 0.063 mmol) as a red solid. Yield: 42%.

ESI-MS: m/z=575.2 ($[M+H]^+$).

Step 9: Preparation of Compound 34

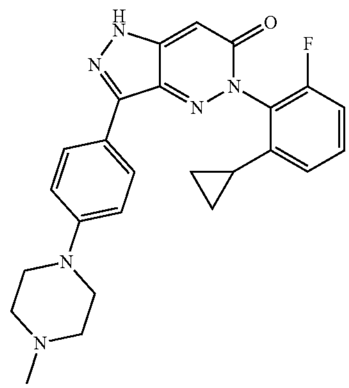 [SMILES: CN1CCN(c2ccc(-c3n[nH]c4cc(=O)n(-c5c(F)cccc5C5CC5)nc34)cc2)CC1]

To a solution of 5-(2-cyclopropyl-6-fluorophenyl)-3-(4-(4-methylpiperazin-1-yl)phenyl)-1-(2-(trimethylsilyl) ethoxymethyl)-1H-pyrazolo[4,3-c]pyridazin-6(5H)-one (36 mg, 0.063 mmol) in dichloromethane (10 mL) was added trifluoroacetic acid (2.5 mL) at 0° C. The reaction mixture was warmed to room temperature and stirred for 2 hours. The reaction mixture was neutralized with saturated aqueous sodium carbonate solution, extracted with dichloromethane for three times (30 mL*3). The combined organic phase was washed with saturated brine, dried over anhydrous sodium sulfate, and filtered with suction. The filtrate was concentrated to dryness. The residue was re-dissolved in methanol (5 mL), and a small amount of aqueous ammonia was added. After stirring at room temperature for 1 hour, the mixture was concentrated to dryness, and the residue was purified by thin layer chromatography (DCM/MeOH: 10/1) to give compound 34 (10 mg, 0.022 mmol) as a red solid. Yield: 36%.

Other compounds in the Examples were synthesized by methods similar to those described in the above synthetic schemes, and their characterization data are listed in the table below.

| Example | Compound | Structural Formula | Spectrum Data | Synthetic Scheme |
| --- | --- | --- | --- | --- |
| Example 1 | Compound 1 | 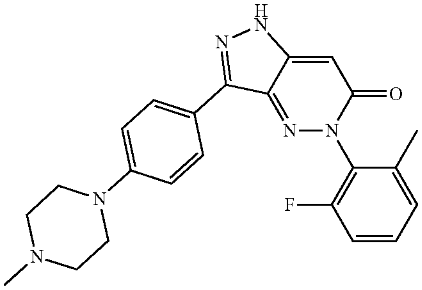 [SMILES: Cc1cccc(F)c1-n1nc2c(-c3ccc(N4CCN(C)CC4)cc3)n[nH]c2cc1=O] | ESI-MS: m/z = 419.2 ($[M + H]^+$). $^1H$ NMR (400 MHz, DMSO-$d_6$) δ 12.91 (s, 1H), 9.65 (s, 1H), 8.01 (d, J = 8.8 Hz, 2H), 7.52-7.46 (m, 1H), 7.30 (t, J = 7.8 Hz, 2H), 7.13 (d, J = 9.2 Hz, 1H), 6.71 (s, 1H), 3.96-3.92 (m, 2H), 3.55-3.52 (m, 2H), 3.18-3.10 (m, 2H), 3.04-2.98 (m, 2H), 2.85 (s, 3H), 2.10 (s, 3H). | 1 |

-continued

| Example | Compound | Structural Formula | Spectrum Data | Synthetic Scheme |
|---|---|---|---|---|
| Example 2 | Compound 2 | 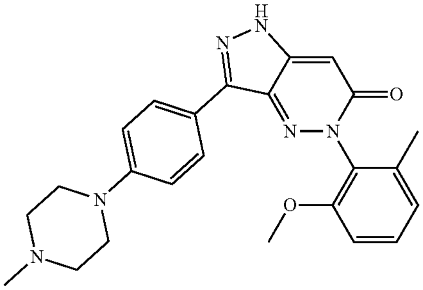 | ESI-MS: m/z = 431.2 ([M + H]$^+$). $^1$H NMR (400 MHz, DMSO-$d_6$) δ 12.71 (s, 1H), 7.95 (d, J = 9.0 Hz, 2H), 7.39 (t, J = 8.0 Hz, 1H), 7.10-6.96 (m, 4H), 6.59 (s, 1H), 3.69 (s, 3H), 3.24-3.16 (m, 4H), 2.47-2.37 (m, 4H), 2.21 (s, 3H), 1.99 (s, 3H). | 2A |
| Example 3 | Compound 3 | 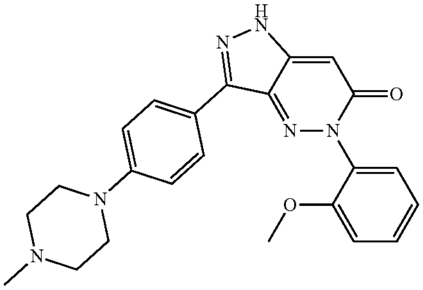 | ESI-MS: m/z = 417.3 ([M + H]$^+$). $^1$H NMR (400 MHz, DMSO-$d_6$) δ 12.68 (s, 1H), 7.97 (d, J = 9.0 Hz, 2H), 7.52-7.48 (m, 1H), 7.41 (dd, J = 7.7, 1.6 Hz, 1H), 7.24 (dd, J = 8.4, 0.8 Hz, 1H), 7.11 (td, J = 7.6, 1.0 Hz, 1H), 7.02 (d, J = 9.0 Hz, 2H), 6.55 (s, 1H), 3.74 (s, 3H), 3.24-3.17 (m, 4H), 2.46-2.40 (m, 4H), 2.21 (s, 3H). | 2A |
| Example 4 | Compound 4 | 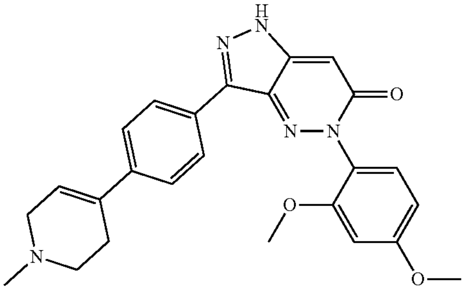 | ESI-MS: m/z = 444.3 ([M + H]$^+$). $^1$H NMR (400 MHz, DMSO-$d_6$) δ 12.90 (s, 1H), 8.09 (d, J = 8.5 Hz, 2H), 7.56 (d, J = 8.5 Hz, 2H), 7.32 (d, J = 8.6 Hz, 1H), 6.76 (d, J = 2.5 Hz, 1H), 6.66 (dd, J 8.6, 2.5 Hz, 1H), 6.59 (s, 1H), 6.27-6.22 (m 1H), 3.86 (s, 3H), 3.73 (s, 3H), 3.05-3.00 (m, 2H), 2.60-2.54 (m, 2H), 2.50-2.45 (m, 2H), 2.28 (s, 3H). | 3A |
| Example 5 | Compound 5 | 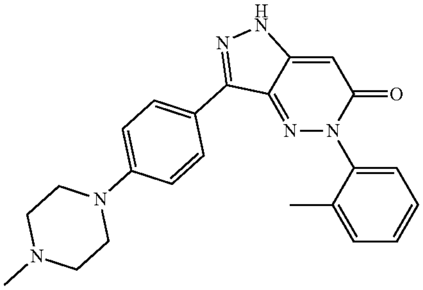 [SMILES: Cc1ccccc1-n1nc2c(-c3ccc(N4CCN(C)CC4)cc3)n[nH]c2cc1=O] | ESI-MS: m/z = 401.3 ([M + H]$^+$). $^1$H NMR (400 MHz, DMSO-$d_6$) δ 12.73 (s, 1H), 7.98 (d, J = 9.0 Hz, 2H), 7.45-7.35 (m, 4H), 7.02 (d, J = 9.0 Hz, 2H), 6.62 (s, 1H), 3.30 (s, 3H), 3.23-3.18 (m, 4H), 2.46-2.40 (m, 4H), 2.07 (s, 3H). | 2A |
| Example 6 | Compound 6 | 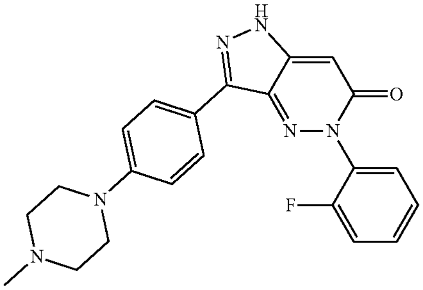 | ESI-MS: m/z = 405.3 ([M + H]$^+$). $^1$H NMR (400 MHz, DMSO-$d_6$) δ 12.77 (s, 1H), 7.99 (d, J = 9.0 Hz, 2H), 7.69-7.55 (m, 2H), 750-7.38 (m, 2H), 7.03 (d, J = 9.0 Hz, 2H), 6.63 (s, 1H), 3.24-3.19 (m, 4H), 2.46-2.40 (m, 4H), 2.21 (s, 3H). | 2A |

-continued

| Example | Compound | Structural Formula | Spectrum Data | Synthetic Scheme |
|---|---|---|---|---|
| Example 7 | Compound 7 | 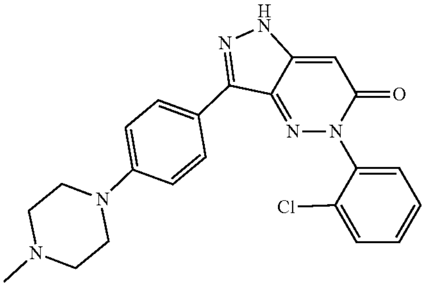 [SMILES: CN1CCN(c2ccc(-c3n[nH]c4cc(=O)n(-c5ccccc5Cl)nc34)cc2)CC1] | ESI-MS: m/z = 421.3 ([M + H]$^+$). $^1$HNMR (400 MHz, DMSO-$d_6$) δ 12.78 (s, 1H), 7.97 (d, J = 9.0 Hz, 2H), 7.73-7.69 (m, 1H), 7.68-7.64 (m, 1H), 7.61-7.53 (m, 2H), 7.03 (d, J = 9.0Hz,2H), 6.64 (s, 1H), 3.23-3.18 (m, 4H), 2.46-2.40 (m, 4H), 2.21 (s, 3H). | 2A |
| Example 8 | Compound 8 | 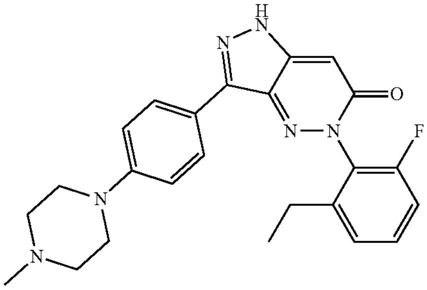 [SMILES: CCc1cccc(F)c1-n1nc2c(-c3ccc(N4CCN(C)CC4)cc3)n[nH]c2cc1=O] | ESI-MS: m/z = 433.3 ([M + H]$^+$). $^1$H NMR (400 MHz, DMSO-d6) δ 12.82 (s, 1H), 7.96 (d, J = 9.0 Hz, 2H), 7.57-7.50 (m, 1H), 7.34-7.26 (m, 2H), 7.03 (d, J = 9.0 Hz, 1H), 6.67 (s, 1H), 3.24-3.16 (m, 2 H), 2.45-2.35 (m, 6H), 2.21 (s, 3H), 1.06 (t, J = 7.6 Hz, 3H). | 2A |
| Example 9 | Compound 9 | 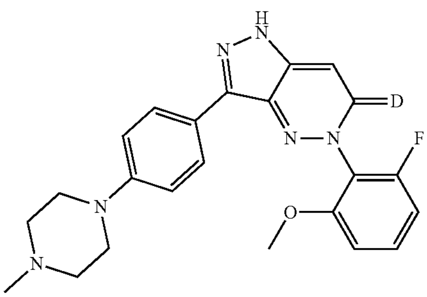 | ESI-MS: m/z = 435.3 ([M + H]$^+$). $^1$H NMR (400 MHz, DMSO-$d_6$) δ 12.77 (s, 1H), 9.75 (d, J = 9.0 Hz, 2H), 7.59-7.52 (m, 1H), 7.12 (d, J = 8.6 Hz, 1H), 7.09-7.02 (m, 3H), 6.61 (s, 1H), 3.78 (s, 3H), 3.24-3.17 (m, 4H), 2.46-2.40 (m, 4H), 2.21 (s, 3H). | 2A |
| Example 10 | Compound 10 | 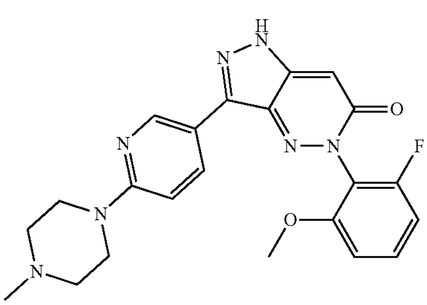 [SMILES: COc1cccc(F)c1-n1nc2c(-c3ccc(N4CCN(C)CC4)nc3)n[nH]c2cc1=O] | ESI-MS: m/z = 436.3 (M + H]$^+$). $^1$H NMR (400 MHz, DMSO-$d_6$) δ 12.84 (s, 1H), 8.82 (d, J = 2.2 Hz, 1H), 8.13 (dd, J = 9.0,2.4 Hz, 1H), 7.60-7.521 (m, 1H), 7.12 (d, J = 8.6 Hz, 1H), 7.09-7.03 (m, 1H), 6.96 (d, J = 9.0 Hz, 1H), 6.64 (s,1H), 3.79 (s, 3H), 3.60-3.52 (m, 4H), 2.42-2.35 (m, 4H), 2.21 (s, 3H). | 2A |
| Example 11 | Compound 11 | 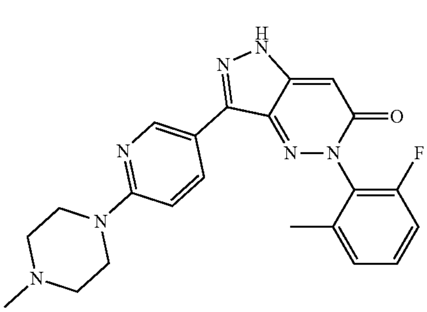 [SMILES: Cc1cccc(F)c1-n1nc2c(-c3ccc(N4CCN(C)CC4)nc3)n[nH]c2cc1=O] | ESI-MS: m/z = 420.3 ([M + H]$^+$). $^1$HNMR (400 MHz, DMSO-$d_6$) δ 12.89 (s, 1H), 8.83 (d, J = 2.2 Hz, 1H), 8.13 (dd, J = 9.0, 2.4 Hz, 1H), 7.53-7.45 (m, 1H), 7.33-7.25 (m, 2H), 6.96 (d, J = 9.0 Hz, 1H), 6.70 (s, 1H), 3.60-3.52 (m, 4H), 2.41-2.34 (m, 4H), 2.21 (s, 3H), 2.10 (s, 3H). | 2A |

-continued

| Example | Compound | Structural Formula | Spectrum Data | Synthetic Scheme |
|---|---|---|---|---|
| Example 12 | Compound 12 | 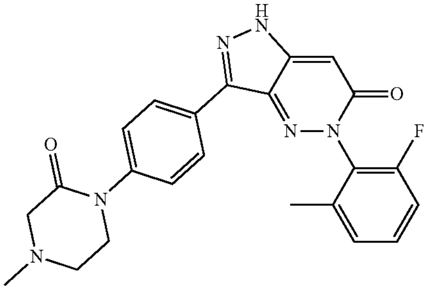 [SMILES: Cc1cccc(F)c1-n1nc2c(-c3ccc(N4CCN(C)CC4=O)cc3)n[nH]c2cc1=O] | ESI-MS: m/z = 433.3 ([M + H]+). $^1$H NMR (400 MHz, DMSO-$d_6$) δ 12.89 (s, 1H), 8.83 (d, J = 2.2 Hz, 1H), 8.13 (dd, J = 9.0,2.4 Hz,1H), 7.53-7.45 (m, 1H), 7.33-7.25 (m, 2H), 6.96 (d, J = 9.0 Hz, 1H), 6.70 (s, 1H), 3.60-3.52 (m, 4H), 2.41-2.34 (m, 4H), 2.21 (s, 3H), 2.10 (s, 3H). | 2A |
| Example 13 | Compound 13 | 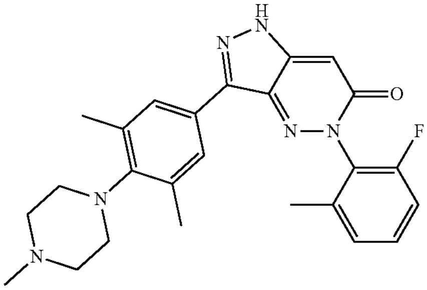 [SMILES: Cc1cc(-c2n[nH]c3cc(=O)n(-c4c(C)cccc4F)nc23)cc(C)c1N1CCN(C)CC1] | ESI-MS: m/z = 447.3 ([M + H]+). $^1$H NMR (400 MHz, DMSO-$d_6$) δ 12.97 (s, 1H), 7.70 (s, 2H), 7.52-7.46 (m, 1H), 7.32-7.26 (m, 2H), 6.71 (s, 1H), 3.60-3.52 (m, 4H), 2.41-2.34 (m, 4H), 2.28 (s, 6H), 2.23 (s, 3H), 2.11 (s, 3H). | 2A |
| Example 14 | Compound 14 | 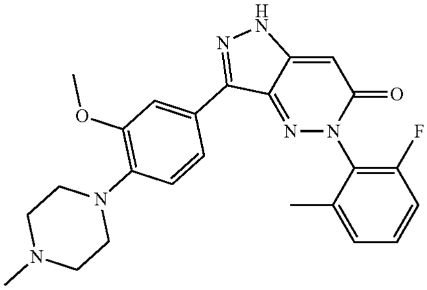 [SMILES: COc1cc(-c2n[nH]c3cc(=O)n(-c4c(C)cccc4F)nc23)ccc1N1CCN(C)CC1] | ESI-MS: m/z = 449.3 ([M + H]+). $^1$H NMR (400 MHz, DMSO-$d_6$) δ 12.92 (s, 1H), 7.70 (dd, J = 8.2, 1.8 Hz, 1H), 7.61 (d, J = 1.8 Hz, 1H), 7.53-7.45 (m, 1H), 7.33-7.25 (m, 2H), 6.98 (d, J = 8.3 Hz, 1H), 6.71 (s, 1H), 3.80 (s, 3H), 3.02 (br, 4H), 2.47 (br, 4H), 2.22 (s, 3H), 2.11 (s, 3H). | 2A |
| Example 15 | Compound 15 | 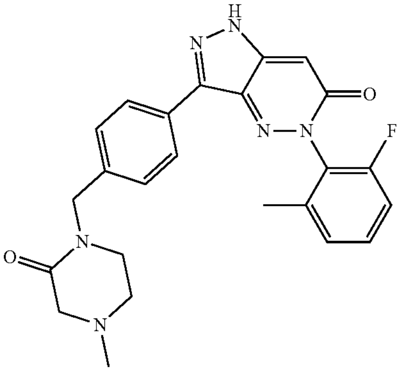 [SMILES: Cc1cccc(F)c1-n1nc2c(-c3ccc(CN4CCN(C)CC4=O)cc3)n[nH]c2cc1=O] | ESI-MS: m/z = 447.3 ([M + H]+). $^1$H NMR (400 MHz, DMSO-$d_6$) δ 13.08 (s, 1H), 8.08 (d, J = 8.3 Hz, 2H), 7.53-7.45 (m, 1H), 7.37-7.26 (m, 4H), 6.76 (s, 1H), 4.54 (s, 2H), 3.21 (t, J = 5.5 Hz, 2H), 3.01 (s, 2H), 2.56 (t, J = 5.4 Hz, 2H), 2.20 (s, 3H), 2.10 (s, 3H). | 2A |
| Example 16 | Compound 16 | 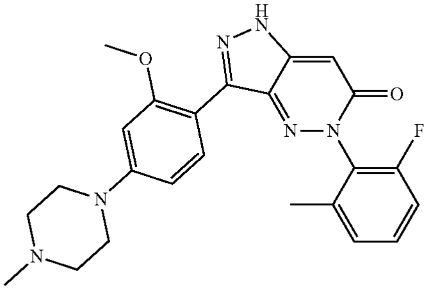 [SMILES: COc1cc(N2CCN(C)CC2)ccc1-c1n[nH]c2cc(=O)n(-c3c(C)cccc3F)nc12] | ESI-MS: m/z = 449.3 ([M + H]+). $^1$H NMR (400 MHz, DMSO-$d_6$) δ 12.78 (s, 1H), 7.48-7.39 (m, 2H), 7.28-7.22 (m, 2H), 6.63 (s, 1H), 6.61-6.56 (m, 2H), 3.71 (s, 3H), 3.25-3.20 (m, 4H), 2.46-2.41 (m, 4H), 2.21 (s, 3H), 2.07 (s, 3H). | 2A |

-continued

| Example | Compound | Structural Formula | Spectrum Data | Synthetic Scheme |
|---|---|---|---|---|
| Example 17 | Compound 17 | 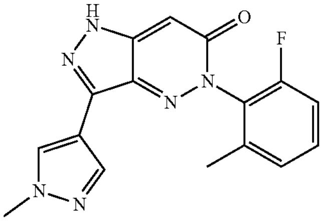 [SMILES: Cc1cccc(F)c1-n1nc2c(-c3cnn(C)c3)n[nH]c2cc1=O] | ESI-MS: m/z = 325.3 ([M + H]$^+$). $^1$H NMR (400 MHz, DMSO-$d_6$) δ 12.77 (s, 1H), 8.21 (s, 1H), 7.93 (s, 1H), 7.52-7.45 (m, 2H), 7.32-7.25 (m, 2H), 6.66 (s, 1H), 3.89 (s, 3H), 2.09 (s, 3H). | 2A |
| Example 18 | Compound 18 | 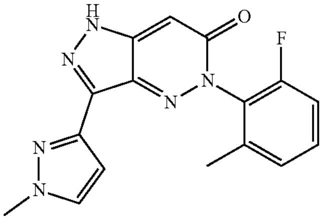 [SMILES: Cc1cccc(F)c1-n1nc2c(-c3ccn(C)n3)n[nH]c2cc1=O] | ESI-MS: m/z = 325.3 ([M + H]$^+$). $^1$H NMR (400 MHz, DMSO-$d_6$) δ 12.95 (s, 1H), 7.79 (d, J = 2.2 Hz, 1H), 7.52-7.45 (m, 1H), 7.32-7.24 (m, 2H), 6.74 (d, J = 2.2 Hz, 1H), 6.70 (s, 1H), 3.90 (s, 3H), 2.07 (s, 3H). | 2A |
| Example 19 | Compound 19 | 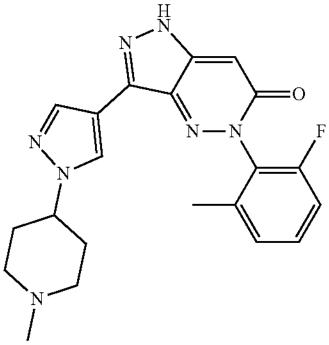 [SMILES: Cc1cccc(F)c1-n1nc2c(-c3cnn(C4CCN(C)CC4)c3)n[nH]c2cc1=O] | ESI-MS: m/z = 408.2 ([M + H]$^+$). $^1$H NMR (400 MHz, DMSO-$d_6$) δ 12.77 (s, 1H), 8.26 (s, 1H), 7.97 (s, 1H), 7.52-7.44 (m, 1H), 7.32-7.26 (m, 2H), 6.66 (s, 1H), 4.31-4.22 (m, 1H), 2.90-2.84 (m, 2H), 2.22 (s, 3H), 2.12-1.90 (m, 9H). | 2A |
| Example 20 | Compound 20 | 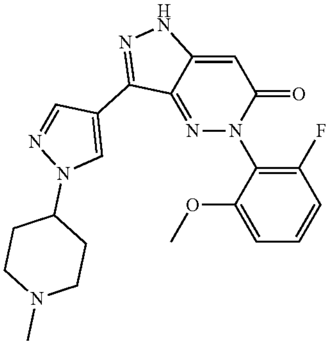 [SMILES: COc1cccc(F)c1-n1nc2c(-c3cnn(C4CCN(C)CC4)c3)n[nH]c2cc1=O] | ESI-MS: m/z = 424.2 ([M + H]$^+$). $^1$H NMR (400 MHz, DMSO-$d_6$) δ 12.73 (s, 1H), 8.24 (s, 1H), 7.96 (s, 1H), 7.60-7.50 (m, 1H), 7.12 (d, J = 8.6 Hz, 1H), 7.06 (t, J = 8.7 Hz, 1H), 6.60 (s, 1H), 4.31-4.21 (m, 1H), 3.78 (s, 3H), 2.90-2.81 (m, 2H), 2.20 (s, 3H), 2.08-1.90 (m, 6H). | 2A |
| Example 21 | Compound 21 | 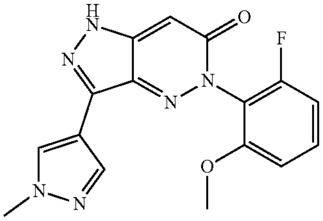 [SMILES: COc1cccc(F)c1-n1nc2c(-c3cnn(C)c3)n[nH]c2cc1=O] | ESI-MS: m/z = 341.2 ([M + H]$^+$). $^1$H NMR (400 MHz, DMSO-$d_6$) 8 12.73 (s, 1H), 8.20 (s, 1H), 7.93 (s, 1H), 7.59-7.51 (m, 1H), 7.12 (d, J = 8.6 Hz, 1H), 7.05 (t, J = 8.7 Hz, 1H), 6.61 (s, 1H), 3.89 (s, 3H), 3.78 (s, 3H). | 2A |

-continued

| Example | Compound | Structural Formula | Spectrum Data | Synthetic Scheme |
|---|---|---|---|---|
| Example 22 | Compound 22 | 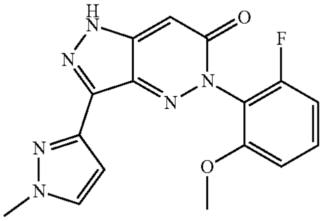 [SMILES: COc1cccc(F)c1-n1nc2c(-c3ccn(C)n3)n[nH]c2cc1=O] | ESI-MS: m/z = 341.2 ([M + H]$^+$). $^1$H NMR (400 MHz, DMSO-$d_6$) δ 12.91 (s, 1H), 7.79 (d, J= 1.9 Hz, 1H), 7.60-7.51 (m, 1H),7.14-7.02 (m, 2H), 6.73 (d, J = 1.9 Hz, 1H), 6.64 (s, 1H), 3.90 (s, 3H), 3.78 (s, 3H). | 2A |
| Example 23 | Compound 23 | 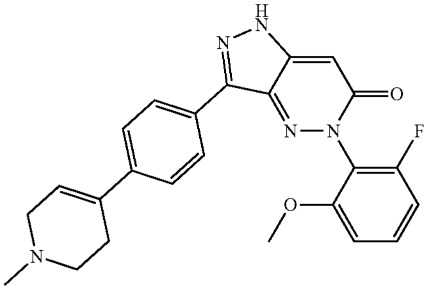 [SMILES: COc1cccc(F)c1-n1nc2c(-c3ccc(C4=CCN(C)CC4)cc3)n[nH]c2cc1=O] | ESI-MS: m/z = 432.4 ([M + H]$^+$). $^1$H NMR (400 MHz, DMSO-$d_6$) δ 13.04 (br, 1H), 8.07 (d, J = 8.4 Hz, 2H), 7.61-7.53 (m 3H), 7.15-7.03 (m, 2H), 6.70 (s, 1H), 6.25 (s, 1H), 3.79 (s, 3H), 3.12 (s, 2H), 2.70-2.62 (m, 2H), 2.56-2.50 (m, 2H), 2.34 (s, 3H). | 4 |
| Example 24 | Compound 24 | 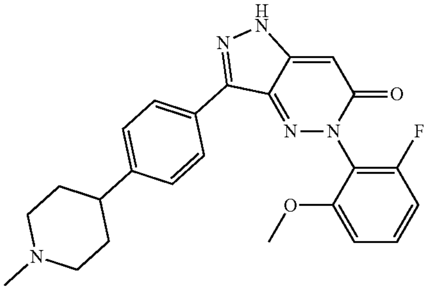 [SMILES: COc1cccc(F)c1-n1nc2c(-c3ccc(C4CCN(C)CC4)cc3)n[nH]c2cc1=O] | ESI-MS: m/z = 434.4 ([M + H]$^+$). $^1$H NMR (400 MHz, DMSO-$d_6$) δ 12.96 (br, 1H), 8.02 (d, J = 8.2 Hz, 1H), 7.60-7.52 (m, 1H), 7.37 (d, J = 8.2 Hz, 1H), 7.12 (d, J = 8.6 Hz, 1H), 7.06 (t, J = 8.92 Hz, 1H), 6.68 (s, 1H), 2.86 (d, J = 11.2 Hz, 2H), 2.50-2.42 (m, 1H), 2.19 (s, 3H), 1.97 (t, J = 10.6 Hz, 2H), 1.77-1.60 (m, 4H). | 4 |
| Example 25 | Compound 25 | 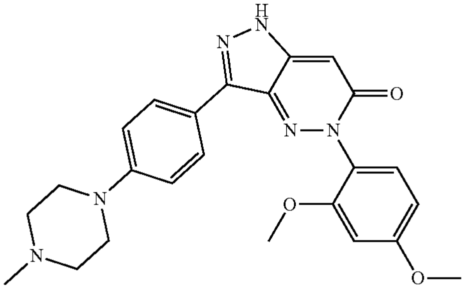 | ESI-MS: m/z = 447.3 ([M + H]$^+$). $^1$H NMR (400 MHz, DMSO-$d_6$) δ 12.65 (s, 1H), 9.78 (d, J = 9.0 Hz, 2H), 7.30 (d, J = 8.6 Hz, 1H), 7.02 (d, J = 9.0 Hz, 2H), 6.76 (d, J = 2.5 Hz, 1H), 6.65 (dd, J = 8.6, 2.6 Hz, 1H), 6.51 (s, 1H), 3.85 (s, 3H), 3.73 (s, 3H), 3.23-3.18 (m, 4H), 2.45-2.41 (m, 4H), 2.21 (s, 3H). | 3B |
| Example 26 | Compound 26 | 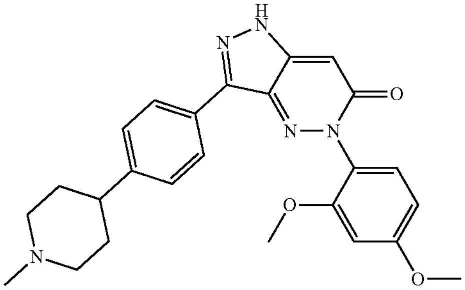 | ESI-MS: m/z = 446.3 ([M + H]$^+$). $^1$H NMR (400 MHz, DMSO-$d_6$) δ 12.88 (s, 1H), 8.05 (d, J = 8.3 Hz, 2H), 7.37 (d, J = 8.4 Hz,2H), 7.31 (d, J = 8.6 Hz, 1H), 6.76 (d, J = 2.5 Hz, 1H), 6.66 (dd, J = 8.6, 2.5 Hz, 1H), 6.59 (s, 1H), 3.86 (s, 3H), 373 (s, 3H), 3.08-2.98 (m, 2H), 2.62-2.52 (m, 1H), 2.40-2.20 (m, 5H), 1.84-1.68 (m, 4H). | 3A |

-continued

| Example | Compound | Structural Formula | Spectrum Data | Synthetic Scheme |
|---|---|---|---|---|
| Example 27 | Compound 27 | 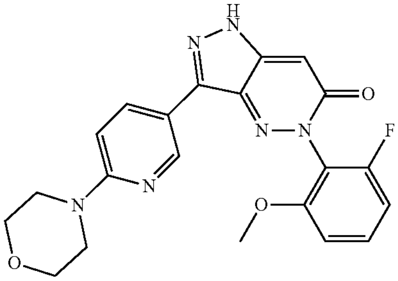 [SMILES: COc1cccc(F)c1-n1nc2c(-c3ccc(N4CCOCC4)nc3)n[nH]c2cc1=O] | ESI-MS: m/z = 423.3 ([M + H]$^+$). $^1$H NMR (400 MHz, DMSO-$d_6$) δ 12.88 (s, 1H), 8.84 (d, J = 2.2 Hz, 1H), 8.16 (dd, J = 9.0,2.4 Hz, 1H), 7.60-7.52 (m, 1H), 7.12 (d, J = 8.6 Hz, 1H), 7.06 (t, J = 8.8 Hz, 1H), 6.97 (d, J = 9.0 Hz, 1H), 6.65(s, 1H), 3.79 (s, 3H), 3.72-3.66 (m, 4H), 3.54-3.50 (m, 4H). | 2A |
| Example 28 | Compound 28 | 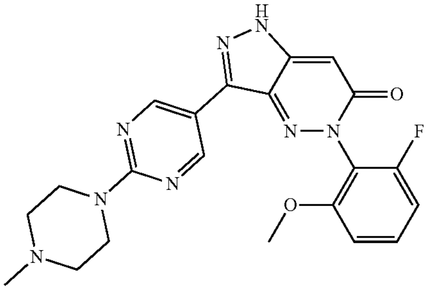 [SMILES: COc1cccc(F)c1-n1nc2c(-c3cnc(N4CCN(C)CC4)nc3)n[nH]c2cc1=O] | ESI-MS: m/z = 437.3 ([M + H]$^+$). $^1$H NMR (400 MHz, DMSO-$d_6$) δ 12.97 (br, 1H), 8.94 (s, 2H), 7.60-7.52 (m, 1H), 7.12 (d, J = 8.6 Hz, 1H), 7.06 (t, J = 8.8 Hz, 1H), 6.68 (s, 1H), 3.82-3.76 (m, 7H), 3.38-3.32 (m, 4H), 2.20 (s, 3H). | 2A |
| Example 29 | Compound 29 | 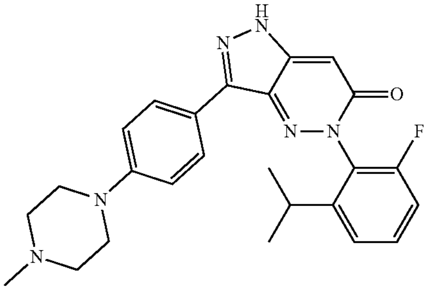 [SMILES: CC(C)c1cccc(F)c1-n1nc2c(-c3ccc(N4CCN(C)CC4)cc3)n[nH]c2cc1=O] | ESI-MS: m/z = 447.3 ([M + H]$^+$). $^1$H NMR (400 MHz, DMSO-$d_6$) δ 12.83 (s, 1H), 7.96 (d, J = 9.0 Hz, 2H), 7.57-7.50 (m, 1H), 7.39 (d, J = 7.9 Hz, 1H), 7.31-7.25 (m, 1H), 7.03 (d, J = 9.0 Hz, 2H), 6.66 (s, 1H), 3.24-3.16 (m, 4H), 2.61 (sept, 1H), 2.45-2.35 (m, 4H), 2.21 (s, 3H), 1.15-1.11 (m, 6H). | 2A |
| Example 30 | Compound 32 | 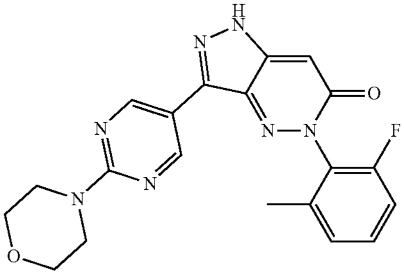 [SMILES: Cc1cccc(F)c1-n1nc2c(-c3cnc(N4CCOCC4)nc3)n[nH]c2cc1=O] | ESI-MS: 408.1 [M + H]$^+$ $^1$H NMR (400 MHz, DMSO-$d_6$) δ 13.04 (s, 1H), 8.98 (s, 2H), 7.52-7.46 (m, 1H), 7.32-7.27 (m, 2H), 6.75 (s, 1H), 3.77 (t, J = 4.4 Hz, 4H), 3.66 (t, J = 4.4 Hz, 4H), 2.10 (s, 3H). | 2A |
| Example 31 | Compound 33 | 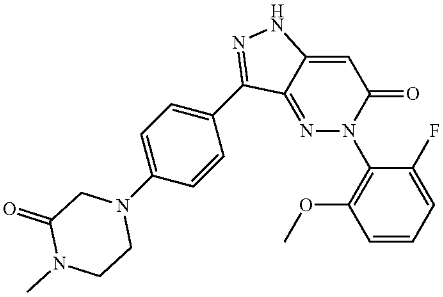 [SMILES: COc1cccc(F)c1-n1nc2c(-c3ccc(N4CCN(C)C(=O)C4)cc3)n[nH]c2cc1=O] | ESI-MS: m/z = 449.1 ([M + H]$^+$). $^1$H NMR (400 MHz, DMSO-$d_6$) δ 12.81 (brs, 1H), 7.98 (d, J = 8.9 Hz, 2H), 7.56 (q, J = 7.9 Hz, 1H), 7.15-7.02 (m, 4H), 6.63 (s, 1H), 3.83 (s, 2H), 3.79 (s, 3H), 3.59-3.53 (m, 2H), 3.47-3.41 (m, 2H), 3.32 (s, 3H). | 2B |

-continued

| Example | Compound | Structural Formula | Spectrum Data | Synthetic Scheme |
|---|---|---|---|---|
| Example 32 | Compound 34 | 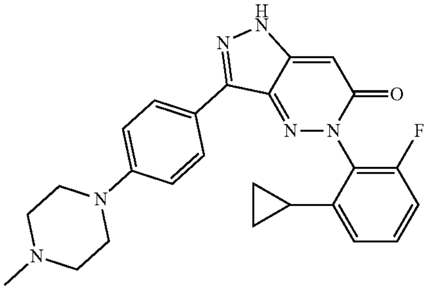 [SMILES: CN1CCN(c2ccc(-c3n[nH]c4cc(=O)n(-c5c(F)cccc5C5CC5)nc34)cc2)CC1] | ESI-MS: m/z = 445.2 ([M + H]$^+$). $^1$H NMR (400 MHz, DMSO-$d_6$) δ 12.83 (s, 1H), 7.96 (d, J = 9.0 Hz, 2H), 7.51-7.44 (m, 1H), 7.26 (t, J = 8.8 Hz, 1H), 7.06-6.96 (m, 3H), 6.67 (s, 1H), 3.24-3.18 (m, 4H), 2.45-2.39 (m, 4H), 2.21 (s, 3H),1.61-1.52 (m, 1H), 0.82-0.62 (m, 4H). | 3A |
| Example 33 | Compound 42 | 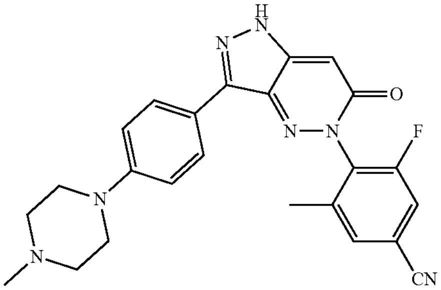 [SMILES: Cc1cc(C#N)cc(F)c1-n1nc2c(-c3ccc(N4CCN(C)CC4)cc3)n[nH]c2cc1=O] | ESI-MS: 444.3 [M + H]$^+$ $^1$H NMR (400 MHz, DMSO-$d_6$) δ 12.89 (s, 1H), 8.01 (d, J = 9.2 Hz, 1H), 7.95 (d, J = 8.8Hz,2H),7.89 (s, 1H), 7.03 (d, J = 8.8 Hz, 2H), 6.71 (s, 1H), 3.23-3.20 (m, 4H), 2.45-2.41 (m, 4H), 2.21 (s, 3H), 2.17 (s, 3H). | 2A |
| Example 34 | Compound 47 | 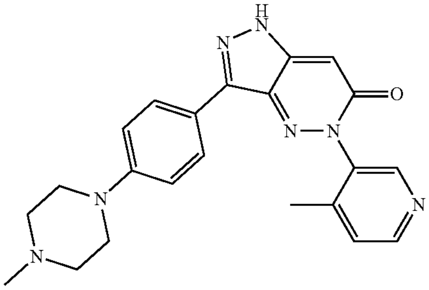 [SMILES: Cc1ccncc1-n1nc2c(-c3ccc(N4CCN(C)CC4)cc3)n[nH]c2cc1=O] | ESI-MS: m/z = 402.2 ([M + H]$^+$). $^1$H NMR (400 MHz, DMSO-$d_6$) δ 12.81 (brs, 1H), 8.59-8.55 (m, 2H), 7.98 (d, J = 8.8 Hz, 2H), 7.49 (d, J = 4.2, 1H), 7.03 (d, J = 8.0 Hz, 2H), 6.66 (s, 1H), 3.32-3.21 (m, 4H), 2.58-2.42 (m, 4H), 2.25 (s, 3H), 2.15 (s, 3H). | 4 |
| Example 35 | Compound 48 | 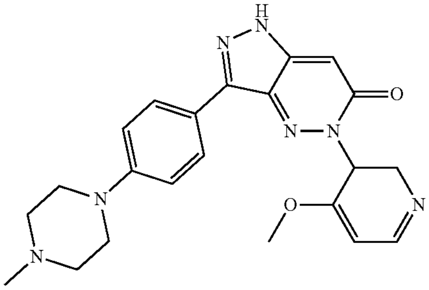 [SMILES: COC1=CC=NCC1n1nc2c(-c3ccc(N4CCN(C)CC4)cc3)n[nH]c2cc1=O] | ESI-MS: m/z = 418.1 ([M + H]$^+$). $^1$H NMR (400 MHz, DMSO-$d_6$) δ 12.76 (brs, 1H), 8.68-8.48 (m, 2H), 7.97 (d, J = 8.4 Hz, 2H), 7.33 (d, J = 5.6 Hz, 1H), 7.02 (d, J = 8.4 Hz, 2H), 6.59 (s, 1H), 3.85 (s, 3H), 3.29-3.08 (m, 4H), 2.48-2.31 (m, 4H), 2.21 (s, 3H). | 4 |
| Example 36 | Compound 55 | 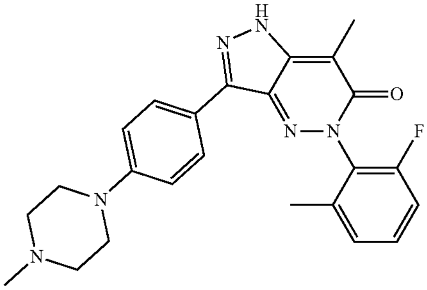 [SMILES: Cc1cccc(F)c1-n1nc2c(-c3ccc(N4CCN(C)CC4)cc3)n[nH]c2c(C)c1=O] | ESI-MS: 433.2 [M + H]$^+$ $^1$HNMR (400 MHz, DMSO-$d_6$) δ 12.90 (s, 1H), 7.98 (d, J = 8.8 Hz, 2H), 7.51-7.45 (m, 1H), 7.32-7.27 (m, 2H), 7.03 (d, J = 9.2 Hz, 2H), 3.20 (t, J = 4.8 Hz, 4H), 2.43 (t, J = 4.8 Hz, 4H), 2.28 (s, 3H), 2.21 (s, 3H), 2.07 (s, 3H). | 3A |

-continued

| Example | Compound | Structural Formula | Spectrum Data | Synthetic Scheme |
|---|---|---|---|---|
| Example 37 | Compound 58 | 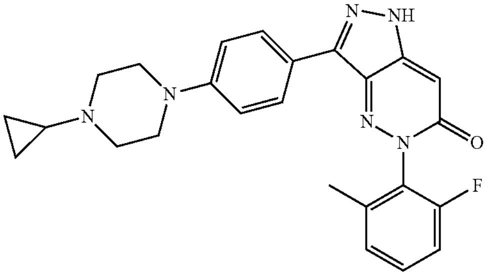 [SMILES: Cc1cccc(F)c1-n1nc2c(-c3ccc(N4CCN(C5CC5)CC4)cc3)n[nH]c2cc1=O] | ESI-MS: 445.3 [M + H]$^+$ $^1$H NMR (400 MHz, DMSO-$d_6$) δ 12.84 (s, 1H), 7.96 (d, J = 8.9 Hz, 2H), 7.55-7.44 (m, 1H),, 7.35-7.25 (m, 2H), 7.04 (d, J = 8.6 Hz, 2H), 6.68 (s, 1H), 3.17 (br, 4H), 2.67 (br, 4H), 2.10 (s, 3H), 1.65 (br, 1H), 0.56-0.30 (m, 4H). | 4 |
| Example 38 | Compound 61 | 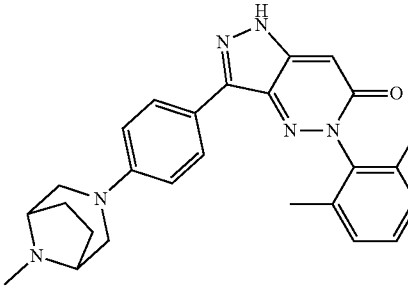 | ESI-MS: 445.3[M + H]$^+$ $^1$H NMR (700 MHz, DMSO-$d_6$) δ 12.82 (s, 1H), 7.94 (d, J = 8.9 Hz, 2H), 7.51-7.46 (m, 1H), 7.32-7.28 (m, 2H), 6.95-6.89 (m, 2H), 6.67 (s, 1H), 3.51-3.44 (m, 2H), 3.42-3.35 (m, 2H), 3.06 - 2.84 (m, 2H), 2.33 (brs, 3H), 2.09 (s, 3H), 2.06 - 1.94 (m, 2H), 1.79-1.52 (m, 2H). | 2A |
| Example 39 | Compound 72 | 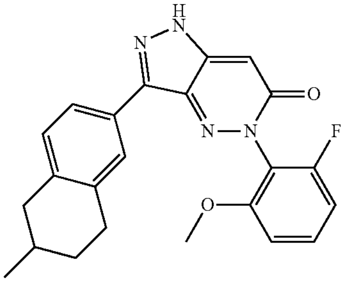 [SMILES: COc1cccc(F)c1-n1nc2c(-c3ccc4c(c3)CCC(C)C4)n[nH]c2cc1=O] | ESI-MS: 406.3 [M + H]$^+$ $^1$H NMR (400 MHz, DMSO-$d_6$) δ 13.01 (s, 1H), 8.05-7.75 (m, 2H), 7.63-7.45 (m, 1H), 7.22-6.99 (m, 3H), 6.69 (s, 1H), 3.79 (s, 3H), 3.53 (s, 2H), 2.86 (s, 2H), 2.62 (s, 2H), 2.35 (s, 3H). | 2A |
| Example 40 | Compound 73 | 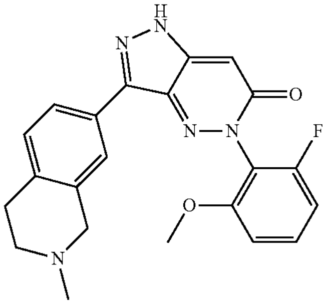 [SMILES: COc1cccc(F)c1-n1nc2c(-c3ccc4c(c3)CN(C)CC4)n[nH]c2cc1=O] | ESI-MS: m/z = 406.2 ([M + H]$^+$). $^1$H NMR (400 MHz, DMSO-$d_6$) δ 12.80 (brs, 1H), 7.77 (s, 1H), 7.61-7.51 (m, 1H), 7.12 (d, J = 8.6 Hz, 1H), 7.06 (t, J = 8.9 Hz, 1H), 6.63 (s, 1H), 3.79 (s, 3H), 3.75-3.68 (m, 4H), 3.51-3.44 (m, 4H). | 2A |
| Example 41 | Compound 74 | 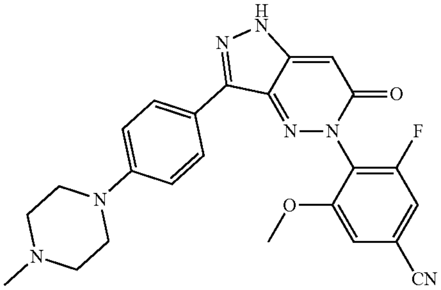 [SMILES: COc1cc(C#N)cc(F)c1-n1nc2c(-c3ccc(N4CCN(C)CC4)cc3)n[nH]c2cc1=O] | ESI-MS: m/z = 460.2 ([M + H]$^+$). $^1$H NMR (400 MHz, DMSO-$d_6$) δ 12.91 (brs, 1H), 7.96 (d, J = 8.7 Hz, 2H), 7.85-7.70 (m, 2H), 7.08 (d, J = 8.7 Hz, 2H), 6.85 (s, 1H), 3.87 (s, 3H), 3.39-3.30 (m, 4H), 3.02-2.78 (m, 4H), 2.55 (s, 3H). | 4 |

-continued

| Example | Compound | Structural Formula | Spectrum Data | Synthetic Scheme |
|---|---|---|---|---|
| Example 42 | Compound 75 | 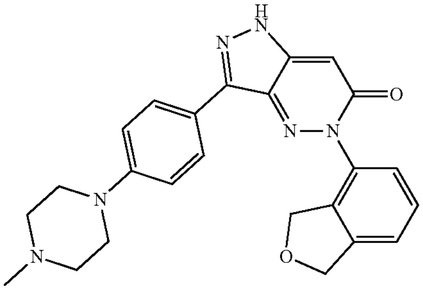 [SMILES: CN1CCN(c2ccc(-c3n[nH]c4cc(=O)n(-c5cccc6c5COC6)nc34)cc2)CC1] | ESI-MS: m/z = 429.2 ([M + H]$^+$). $^1$H NMR (400 MHz, DMSO-$d_6$) δ 12.76 (brs, 1H), 8.01 (d, J = 8.8 Hz, 2H), 7.53-7.42 (m, 3H), 7.04(d, J = 8.9 Hz, 2H), 6.62 (s, 1H), 5.11 (s, 2H), 4.95 (s, 2H), 3.27-3.17 (m, 4H), 2.48-2.41 (m, 4H), 2.22 (s, 3H). | 4 |
| Example 43 | Compound 76 | 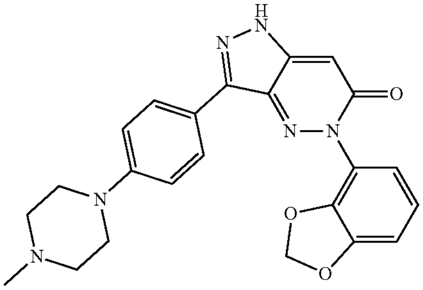 [SMILES: CN1CCN(c2ccc(-c3n[nH]c4cc(=O)n(-c5cccc6c5OCO6)nc34)cc2)CC1] | ESI-MS: m/z = 431.2 ([M + H]$^+$). $^1$H NMR (400 MHz, DMSO-$d_6$) δ 12.75 (brs, 1H), 8.01 (d, J = 8.8 Hz, 2H), 7.15-6.96 (m, 5H), 6.60 (s, 1H), 6.10 (s, 2H), 3.28-3.17 (m, 4H), 2.47-2.36 (m, 4H), 2.22 (s, 3H). | 4 |
| Example 44 | Compound 77 | 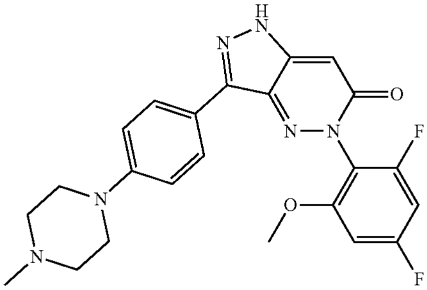 [SMILES: COc1cc(F)cc(F)c1-n1nc2c(-c3ccc(N4CCN(C)CC4)cc3)n[nH]c2cc1=O] | ESI-MS: 453.2 [M + H]$^+$ 1H NMR (400 MHz, DMSO-$d_6$) δ 12.81 (s, 1H), 7.95 (d, J = 9.0 Hz, 2H), 7.17-7.08 (m, 2H), 7.04 (d, J = 9.0 Hz, 2H), 6.62 (s, 1H), 3.80 (s, 3H), 3.25-3.19 (m, 4H), 2.47-2.42 (m, 4H), 2.22 (s, 3H). | 2A |
| Example 45 | Compound 78 | 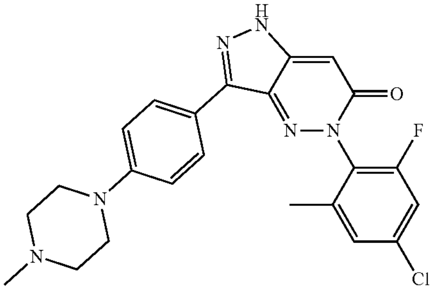 [SMILES: Cc1cc(Cl)cc(F)c1-n1nc2c(-c3ccc(N4CCN(C)CC4)cc3)n[nH]c2cc1=O] | ESI-MS: 453.1 [M + H]$^+$ | 2A |
| Example 46 | Compound 79 | 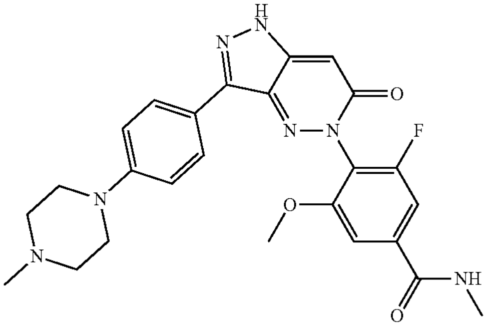 | ESI-MS: 492.2 [M + H]$^+$ $^1$H NMR (400 MHz, DMSO-$d_6$) δ 12.83 (s, 1H), 8.70 (d, J = 4.3 Hz, 1H), 7.95 (d, J = 8.3 Hz, 2H), 7.54 (s, 1H), 7.47 (d, J = 10.0 Hz, 1H), 7.03 (d, J = 8.4 Hz, 2H), 6.64 (s, 1H), 3.85 (s, 3H), 3.23-3.18 (m, 4H), 2.85 (d, J = 3.5 Hz, 3H), 2.46-2.40 (m, 4H), 2.21 (s, 3H). | 4 |

-continued

| Example | Compound | Structural Formula | Spectrum Data | Synthetic Scheme |
|---|---|---|---|---|
| Example 47 | Compound 80 | 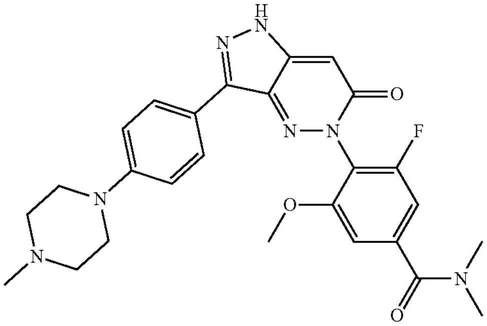 | ESI-MS: 506.1 [M + H]+ $^1$H NMR (400 MHz, DMSO-$d_6$) δ 12.83 (s, 1H), 7.95 (d, J = 8.6 Hz, 2H), 7.17-7.11 (m, 2H), 7.04 (d, J = 8.6 Hz, 2H), 6.64 (s, 1H), 3.81 (s, 3H), 3.24-3.17 (m, 4H), 3.03 (s, 3H), 3.00 (s, 3H), 2.46-2.40 (m, 4H), 2.21 (s, 3H). | 4 |
| Example 48 | Compound 81 | 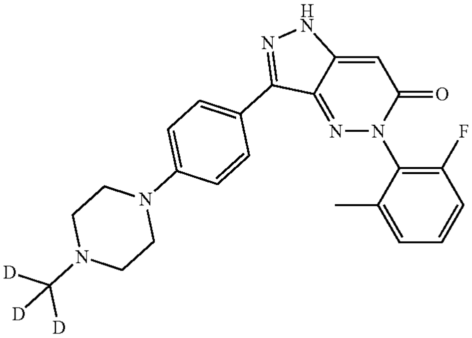 [SMILES: [2H]C([2H])([2H])N1CCN(c2ccc(-c3n[nH]c4cc(=O)n(-c5c(C)cccc5F)nc34)cc2)CC1] | ESI-MS: 422.3 [M + H]+ $^1$H NMR (400 MHz, DMSO-$d_6$) δ 12.81 (s, 1H), 7.96 (d, J = 8.8 Hz, 2H), 7.52-7.46 (m, 1H), 7.32-7.26 (m, 2H), 7.03 (d, J = 9.0 Hz, 1H), 6.67 (s, 1H), 3.23-3.19 (m, 2H), 2.46-2.42 (m, 4H), 2.10 (s, 3H). | 2A |
| Example 49 | Compound 82 | 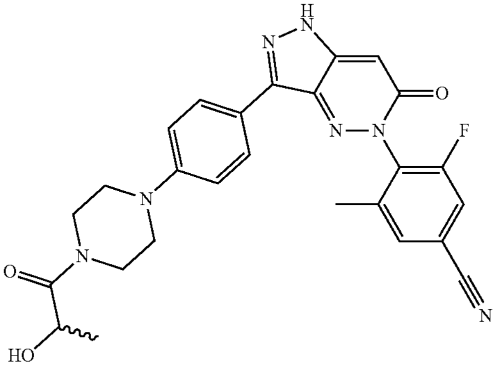 [SMILES: Cc1cc(C#N)cc(F)c1-n1nc2c(-c3ccc(N4CCN(C(=O)C(C)O)CC4)cc3)n[nH]c2cc1=O] | ESI-MS: 501.3 [M + H]+ $^1$H NMR (700 MHz, DMSO-$d_6$) δ 8.02-8.00 (m, 1H), 8.00-7.95 (m, 2H), 7.90 (s, 1H), 7.08-7.04 (m, 2H), 6.73-6.71 (m, 1H), 3.83-3.78 (m, 1H), 3.70-3.54 (m, 4H), 3.28-3.15 (m, 6H), 2.17 (s, 3H), 1.10-1.09 (m, 3H). | 2B |
| Example 50 | Compound 83 | 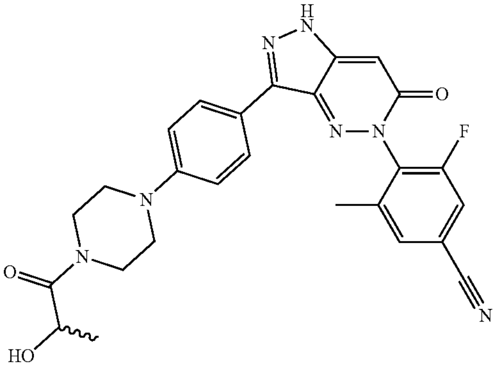 [SMILES: Cc1cc(C#N)cc(F)c1-n1nc2c(-c3ccc(N4CCN(C(=O)C(C)O)CC4)cc3)n[nH]c2cc1=O] | ESI-MS: 502.2 [M + H]+ $^1$H NMR (700 MHz, DMSO-$d_6$) δ 12.93 (s, 1H), 8.02 (dd, J = 9.2, 1.7 Hz, 1H), 7.98 (d, J = 9.0 Hz, 2H), 7.90 (s, 1H), 7.07 (d, J = 9.0 Hz, 2H), 6.73 (s, 1H), 4.98 (d, J = 6.9 Hz, 1H), 4.48-4.44 (m, 1H), 3.73-3.62 (m, 3H), 3.58-3.52 (m, 1H), 3.30-3.16 (m, 4H), 2.17 (s, 3H), 1.20 (d, J = 6.6 Hz, 3H). | 2B |

-continued

| Example | Compound | Structural Formula | Spectrum Data | Synthetic Scheme |
|---|---|---|---|---|
| Example 51 | Compound 84 | 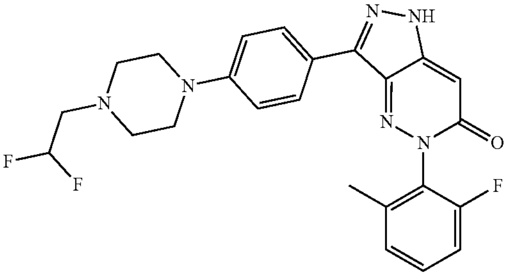 [SMILES: Cc1cccc(F)c1-n1nc2c(-c3ccc(N4CCN(CC(F)F)CC4)cc3)n[nH]c2cc1=O] | ESI-MS: 469.1 $[M + H]^+$ $^1HNMR$ (400 MHz, DMSO-$d_6$) δ 12.86 (s, 1H), 7.97 (d, J = 9.0 Hz, 2H), 7.54-7.45 (m, 1H), 7.35-7.26 (m, 2H), 7.04 (d, J = 9.0 Hz, 2H), 6.68 (s, 1H), 6.18 (tt, J = 55.6, 4.3 Hz, 1H), 3.26 - 3.20 (m, 4H), 2.78 (td, J = 15.6, 4.1 Hz, 2H), 2.69-2.62 (m, 4H), 2.10 (s, 3H). | 4 |
| Example 52 | Compound 85 | 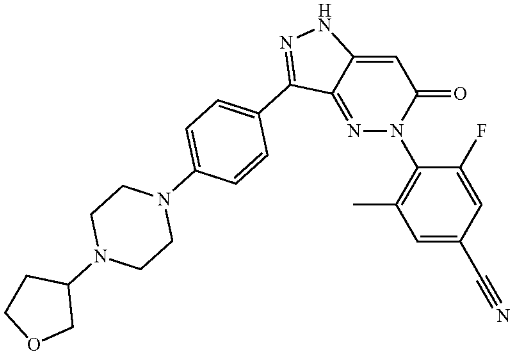 [SMILES: Cc1cc(C#N)cc(F)c1-n1nc2c(-c3ccc(N4CCN(C5CCOC5)CC4)cc3)n[nH]c2cc1=O] | ESI-MS: 500.3 $[M + H]^+$ $^1H$ NMR (400 MHz, DMSO-$d_6$) δ 12.91 (s, 1H), 8.04-7.98 (m, 1H), 7.95 (d, J = 8.9 Hz, 2H), 7.88 (s, 1H), 7.02 (d, J = 8.9 Hz, 2H), 6.71 (s, 1H), 3.83-3.75 (m, 2H), 3.68-3.62 (m, 1H), 3.54-3.49 (m, 1H), 3.21 (t, J = 5.0 Hz, 4H), 2.95-2.87 (m, 1H), 2.60-2.42 (m, 4H), 2.17 (m, 3H), 2.03-1.94 (m, 1H), 1.81-1.71 (m, 1H). | 2B |
| Example 53 | Compound 86 | 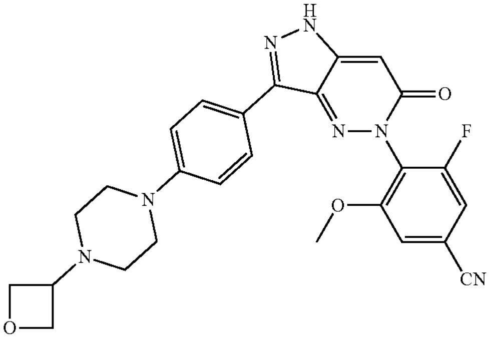 [SMILES: COc1cc(C#N)cc(F)c1-n1nc2c(-c3ccc(N4CCN(C5COC5)CC4)cc3)n[nH]c2cc1=O] | ESI-MS: 502.2 $[M + H]^+$ $^1H$ NMR (400 MHz, DMSO-$d_6$) δ 12.87 (s, 1H), 7.94 (d, J = 8.9 Hz, 2H), 7.79 (d, J = 8.9 Hz, 1H), 7.73 (s, 1H), 7.04 (d, J = 8.9 Hz, 2H), 6.67 (s, 1H), 4.56 (t, J = 6.5 Hz, 2H), 4.47 (t, J = 6.5 Hz, 2H), 3.87 (s, 3H), 3.47-3.40 (m, 1H), 3.26-3.23 (m, 4H), 2.41-2.37 (m, 4H). | 2A |
| Example 54 | Compound 87 | 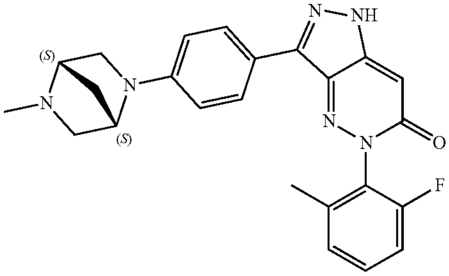 | ESI-MS: 431.2 $[M + H]^+$ $^1H$ NMR (400 MHz, DMSO-$d_6$) δ 12.72 (s, 1H), 7.93 (d, J = 8.8 Hz, 2H), 7.53-7.44 (m, 1H), 7.33-7.27 (m, 2H), 6.68 (d, J = 8.9 Hz, 2H), 6.64 (s, 1H), 4.35 (s, 2H), 3.46 (br, 1H), 3.30-3.28 (m, 1H), 3.21 (d, J = 9.3 Hz, 2H), 2.79 (d, J = 9.4 Hz, 1H), 2.52-2.50 (m, 1H), 2.27 (brs, 3H), 2.10 (s, 3H), 1.93-1.86 (m, 1H), 1.81-1.75 (s, 1H). | 4 |

-continued

| Example | Compound | Structural Formula | Spectrum Data | Synthetic Scheme |
|---|---|---|---|---|
| Example 55 | Compound 88 | 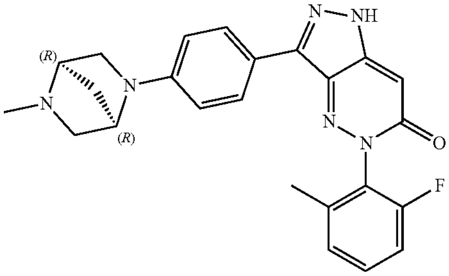 | ESI-MS: 431.2 [M + H]+ $^1$H NMR (400 MHz, DMSO-d6) δ 12.72 (s, 1H), 7.93 (d, J = 8.8 Hz, 2H), 7.53-7.44 (m, 1H), 7.33-7.27 (m, 2H), 6.68 (d, J = 8.9 Hz, 2H), 6.64 (s, 1H), 4.35 (s, 2H), 3.46 (br, 1H), 3.30-3.28 (m, 1H), 3.21 (d, J = 9.3 Hz, 2H), 2.79 (d, J = 9.4 Hz, 1H), 2.52-2.50 (m, 1H), 2.27 (brs, 3H), 2.10 (s, 3H), 1.93-1.86 (m, 1H), 1.81-1.75 (s, 1H). | 4 |
| Example 56 | Compound 89 | 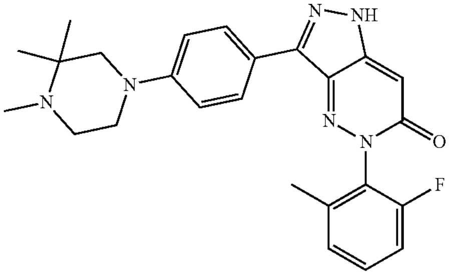 [SMILES: Cc1cccc(F)c1-n1nc2c(-c3ccc(N4CCN(C)C(C)(C)C4)cc3)n[nH]c2cc1=O] | ESI-MS: 447.1 [M + H]+ $^1$HNMR (400 MHz, DMSO-$d_6$) δ 12.85 (s, 1H), 7.95 (d, J = 8.9 Hz, 2H), 7.53-7.44 (m, 1H), 7.34-7.25 (m, 2H), 7.02 (d, J = 8.9 Hz, 2H), 6.67 (s, 1H), 3.20 (br, 2H), 2.99 (br, 2H), 2.63-2.52 (m, 2H), 2.16 (br, 3H), 2.10 (s, 3H), 1.01 (s, 6H). | 4 |
| Example 57 | Compound 90 | 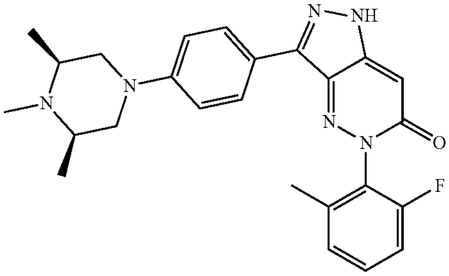 [SMILES: Cc1cccc(F)c1-n1nc2c(-c3ccc(N4C[C@@H](C)N(C)[C@@H](C)C4)cc3)n[nH]c2cc1=O] | ESI-MS: 447.1 [M + H]+ $^1$H NMR (400 MHz, DMSO-$d_6$) δ 12.81 (s, 1H), 7.96 (d, J = 9.0 Hz, 2H), 7.58-7.42 (m, 1H), 7.36-7.25 (m, 2H), 7.03 (d, J = 9.0 Hz, 2H), 6.67 (s, 1H), 3.66 (d, J = 11.7 Hz, 2H), 2.48-2.42 (m, 2H), 2.29-2.14 (m, 5H), 2.10 (s, 3H), 1.06 (d, J = 6.1 Hz, 6H). | 4 |
| Example 58 | Compound 91 | 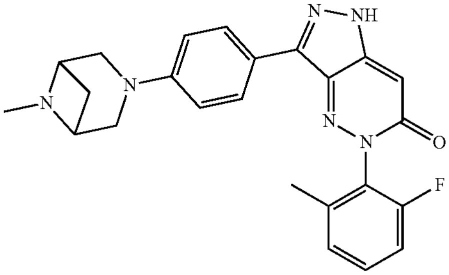 [SMILES: Cc1cccc(F)c1-n1nc2c(-c3ccc(N4CC5CC(C4)N5C)cc3)n[nH]c2cc1=O] | ESI-MS: 431.2 [M + H]+ $^1$H NMR (400 MHz, DMSO-$d_6$) δ 12.74 (br, 1H), 7.99 (d, J = 9.0 Hz, 2H), 7.52-7.46 (m, 1H), 7.32-7.26 (m, 2H), 6.84 (d, J = 9.0 Hz, 2H), 6.64 (s,1H), 3.56 (d, J = 5.8 Hz, 2H), 3.47 (d, J = 11.2 Hz, 2H), 3.30-3.27 (m, 2H), 2.42 (q, J = 6.7 Hz, 1H), 2.10 (s, 3H), 1.99 (s, 3H), 1.50 (d, J = 8.2 Hz, 1H). | 4 |

-continued

| Example | Compound | Structural Formula | Spectrum Data | Synthetic Scheme |
|---|---|---|---|---|
| Example 59 | Compound 92 | 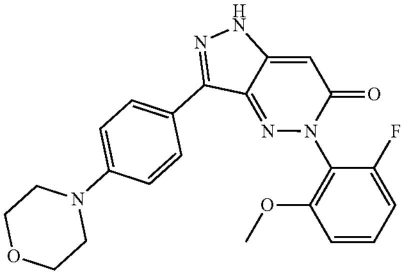 [SMILES: COc1cccc(F)c1-n1nc2c(-c3ccc(N4CCOCC4)cc3)n[nH]c2cc1=O] | ESI-MS: 422.2 [M + H]$^+$ $^1$H NMR (400 MHz, DMSO-$d_6$) δ 12.81 (s, 1H), 7.97 (d, J = 8.8 Hz, H), 7.59-7.53 (m, 1H), 7.12 (d, J = 8.4 Hz, 1H), 7.09-7.04 (m, 3H), 6.63 (s, 1H), 3.78 (s, 3H), 3.73 (t, J = 4.8 Hz, 4H), 3.18 (t, J = 4.8 Hz, 4H). | 2A |
| Example 60 | Compound 93 | 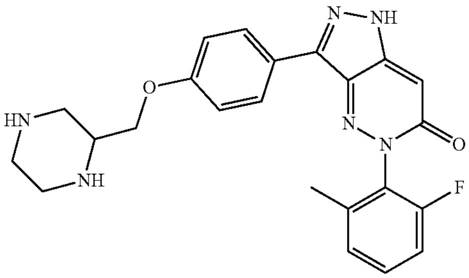 [SMILES: Cc1cccc(F)c1-n1nc2c(-c3ccc(OCC4CNCCN4)cc3)n[nH]c2cc1=O] | ESI-MS: 435.2 [M + H]$^+$ $^1$H NMR (400 MHz, DMSO-$d_6$) δ 13.05 (s, 1H), 9.79 (br, 3H), 8.10 (d, J = 8.5 Hz, 2H), 7.54-7.45 (m, 1H), 7.34-7.26 (m, 2H), 7.17 (d, J = 8.6 Hz, 2H), 6.74 (s, 1H), 4.38-4.28 (m, 2H), 4.01-3.92 (m, 1H), 3.66-3.17 (m, 4H), 2.10 (s, 3H). | 4 |
| Example 61 | Compound 94 | 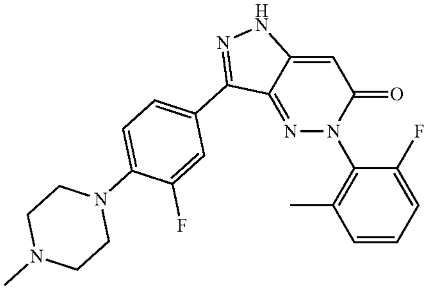 [SMILES: Cc1cccc(F)c1-n1nc2c(-c3ccc(N4CCN(C)CC4)c(F)c3)n[nH]c2cc1=O] | ESI-MS: 437.2 [M + H]$^+$ $^1$H NMR (400 MHz, DMSO-$d_6$) δ 12.89 (br, 1H), 7.87 (dd, J = 8.4, 2.0 Hz, 1H), 7.75 (dd, J = 14.2, 2.0 Hz, 1H), 7.55 - 7.46 (m, 1H), 7.33 - 7.27 (m, 2H), 7.15 (t, J = 8.9 Hz, 1H), 6.72 (s, 1H), 3.10-3.04 (m, 4H), 2.48-2.43 (m, 4H), 2.21 (s, 3H), 2.10 (s, 3H). | 2A |
| Example 62 | Compound 95 | 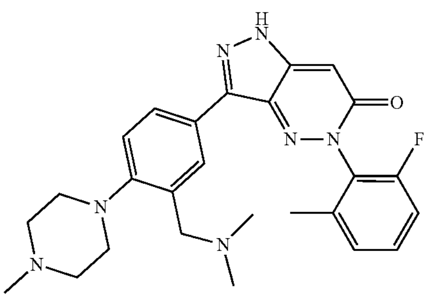 [SMILES: Cc1cccc(F)c1-n1nc2c(-c3ccc(N4CCN(C)CC4)c(CN(C)C)c3)n[nH]c2cc1=O] | ESI-MS: 476.4 [M + H]$^+$ $^1$H NMR (400 MHz, DMSO-$d_6$) δ 13.04 (s, 1H), 8.18 (s, 1H), 8.00 (d, J = 8.1 Hz, 1H), 7.49 (q, J = 7.0 Hz, 1H), 7.35-7.19 (m, 3H), 6.74 (s, 1H), 3.59 (br, 2H), 3.00 (s, 4H), 2.70 (br, 4H), 2.39 (s, 3H), 2.27 (s, 6H), 2.12 (s, 3H). | 2A |
| Example 63 | Compound 96 | 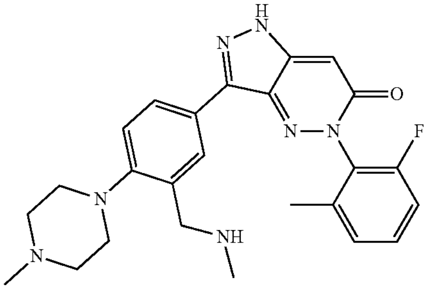 [SMILES: CNCc1cc(-c2n[nH]c3cc(=O)n(-c4c(C)cccc4F)nc23)ccc1N1CCN(C)CC1] | ESI-MS: 462.4 [M + H]$^+$ | 2A |

-continued

| Example | Compound | Structural Formula | Spectrum Data | Synthetic Scheme |
|---|---|---|---|---|
| Example 64 | Compound 97 | 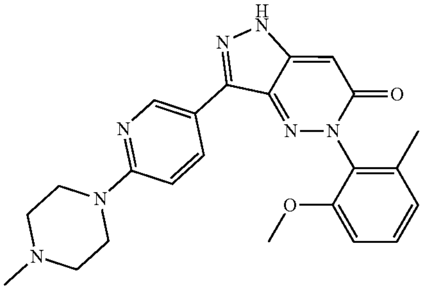 | ESI-MS: 432.2 $[M+H]^+$ $^1$HNMR (400 MHz, DMSO-$d_6$), δ 12.79 (s, 1H), 8.82 (d, J = 2.2 Hz, 1H), 8.12 (dd, J = 9.0, 2.4 Hz, 1H), 7.39 (t, J = 8.0 Hz, 1H), 7.06 (d, J = 8.2 Hz,1H), 6.99 (d, J = 7.6 Hz, 1H), 6.95 (d, J = 9.0 Hz, 1H), 6.62 (s, 1H), 3.70 (s, 3H), 3.60-3.50 (m, 4H), 2.42-2.32 (m, 4H), 2.20 (s, 3H), 2.00 (s, 3H). | 2A |
| Example 65 | Compound 98 | 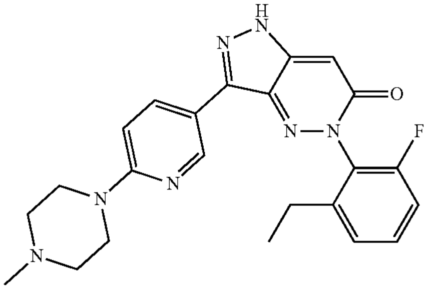 [SMILES: CCc1cccc(F)c1-n1nc2c(-c3ccc(N4CCN(C)CC4)nc3)n[nH]c2cc1=O] | ESI-MS: 434.2 $[M+H]^+$ $^1$HNMR (400 MHz, DMSO-$d_6$) δ 12.92 (s, 1H), 8.83 (d, J = 2.4 Hz, 1H), 8.14 (dd, J = 9.2, 2.4 Hz, 1H), 7.57-7.51 (m, 1H), 7.33-7.28 (m, 2H), 6.97 (d, J = 9.2 Hz, 1H), 6.71 (s, 1H), 3.59-3.52 (m, 4H), 2.47-2.34 (m, 6H), 2.22 (s, 3H), 1.06 (t, J = 7.6 Hz, 3H). | 2A |
| Example 66 | Compound 99 | 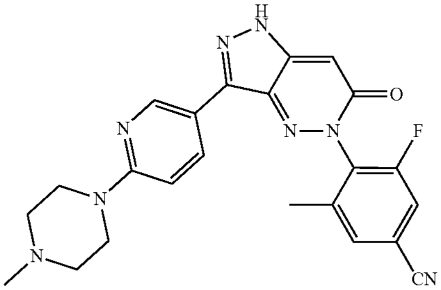 | ESI-MS: 445.2 $[M+H]^+$ $^1$H NMR (400 MHz, DMSO-$d_6$) δ 12.99 (br, 1H), 8.82 (s, 1H), 8.13 (d, J = 8.0 Hz, 1H), 8.01 (d, J = 9.2 Hz, 1H), 7.89 (s, 1H), 6.96 (d, J = 9.2 Hz, 1H), 6.74 (s, 1H), 3.56 (s, 4H), 2.38 (s, 4H), 2.21 (s, 3H), 2.17 (s, 3H). | 2A |
| Example 67 | Compound 100 | 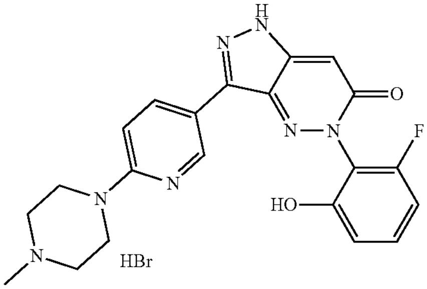 [SMILES: CN1CCN(c2ccc(-c3n[nH]c4cc(=O)n(-c5c(O)cccc5F)nc34)cn2)CC1 ; Br] | ESI-MS: 422.1 $[M+H]^+$ $^1$H NMR (400 MHz, DMSO-$d_6$) δ 12.82 (s,1H), 10.37 (s, 1H), 8.85 (d, J = 2.4 Hz, 1H), 8.14 (dd, J = 8.8, 2.4 Hz, 1H), 7.40-7.33 (m, 1H), 6.97 (d, J = 9.2 Hz, 1H), 6.83-6.89 (m, 2H), 6.64 (s, 1H), 3.60-3.54 (m, 4H), 2.44-2.37 (m, 4H), 2.22 (s, 3H). | 2A |
| Example 68 | Compound 101 | 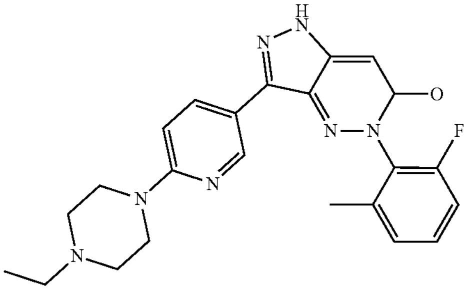 [SMILES: CCN1CCN(c2ccc(-c3n[nH]c4c3=NN(c3c(C)cccc3F)C(O)C=4)cn2)CC1] | ESI-MS: m/z = 434.2 ($[M+H]^+$). $^1$H NMR (400 MHz, DMSO-$d_6$) δ 12.96 (brs, 1H), 8.83 (s, 1H), 8.14 (d, J = 8.9 Hz, 1H), 7.55-7.42 (m, 1H), 7.35-7.22 (m, 2H), 6.95 (d, J = 9.0 Hz, 1H), 6.67 (s, 1H), 3.65-3.46 (m, 4H), 2.46-2.38 (m, 4H), 2.38-2.26 (m, 2H), 2.10 (s, 3H), 1.02 (t, J = 7.0 Hz, 3H). | 2B |

-continued

| Example | Compound | Structural Formula | Spectrum Data | Synthetic Scheme |
|---|---|---|---|---|
| Example 69 | Compound 102 | 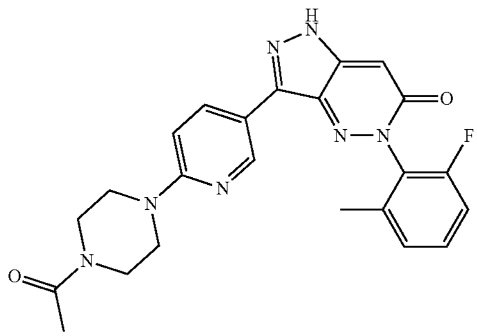 [SMILES: CC(=O)N1CCN(c2ccc(-c3n[nH]c4cc(=O)n(-c5c(C)cccc5F)nc34)cn2)CC1] | ESI-MS: m/z = 448.2 ([M + H]$^+$). $^1$H NMR (400 MHz, DMSO-$d_6$) δ 12.93 (brs, 1H), 8.85 (d, J = 2.2 Hz, 2H), 8.17 (d, J = 9.2 Hz, 1H), 7.54-7.46 (m, 1H), 7.34-7.26 (m, 2H), 6.99 (d, J = 9.1 Hz, 1H), 6.71 (s, 1H), 3.67-3.60 (m, 2H), 3.59-3.49 (m, 6H), 2.10 (s, 3H), 2.04(s, 3H). | 2B |
| Example 70 | Compound 103 | 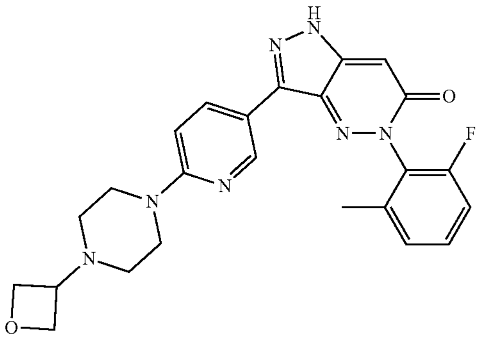 [SMILES: Cc1cccc(F)c1-n1nc2c(-c3ccc(N4CCN(C5COC5)CC4)nc3)n[nH]c2cc1=O] | ESI-MS: m/z = 462.2 ([M + H]$^+$). $^1$H NMR (400 MHz, DMSO-$d_6$) δ 12.92 (brs, 1H), 8.85 (s, 1H), 8.15 (d, J = 9.2 Hz, 1H), 7.55-7.45 (m, 1H), 7.35-7.26 (m, 2H), 6.99 (d,J=8.6 Hz, 1H), 6.71 (s, 1H), 4.64-4.39 (m, 4H), 3.69-3.49 (m, 4H), 3.48-3.36 (m, 1H), 2.41-2.24 (m, 4H), 2.11 (s, 3H). | 2B |
| Example 71 | Compound 104 | 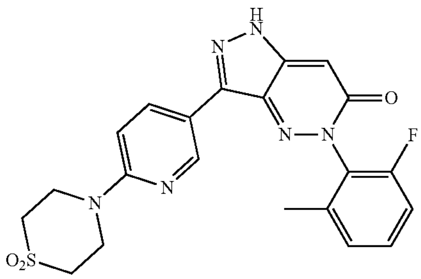 [SMILES: Cc1cccc(F)c1-n1nc2c(-c3ccc(N4CCS(=O)(=O)CC4)nc3)n[nH]c2cc1=O] | ESI-MS: m/z =455.1 ([M + H]$^+$). $^1$H NMR (400 MHz, DMSO-$d_6$) δ 12.97 (brs, 1H), 8.88 (d,J = 2.2 Hz, 1H), 8.21 (d, J = 9.0, 2.3 Hz, 1H), 7.55-7.44 (m, 1H), 7.35-7.25 (m, 2H), 7.17 (d, J = 9.0 Hz, 1H), 6.73 (s, 1H), 4.20-3.99 (m, 4H), 3.19-3.05 (m, 4H), 2.10 (s, 3H). | 2B |
| Example 72 | Compound 105 | 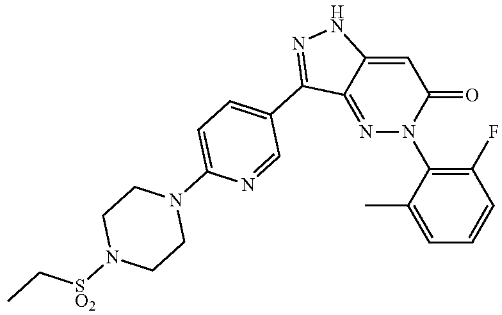 [SMILES: CCS(=O)(=O)N1CCN(c2ccc(-c3n[nH]c4cc(=O)n(-c5c(C)cccc5F)nc34)cn2)CC1] | ESI-MS: 498.1 [M + H]$^+$ $^1$H NMR (400 MHz, DMSO-$d_6$) δ 12.94 (s, 1H), 8.86 (d, J = 2.0 Hz, 1H), 8.18 (dd, J = 9.2, 2.4 Hz, 1H), 7.52-7.47 (m, 1H), 7.34-7.26 (m, 2H), 7.03 (d, J = 8.8 Hz, 1H), 6.72 (s, 1H), 3.71-3.65 (m, 4H), 3.29-3.22 (m, 4H), 3.08 (q, J = 7.6 Hz, 2H), 2.10 (s, 3H), 1.21 (t.,J = 7.2 Hz, 3H). | 2B |
| Example 73 | Compound 106 | 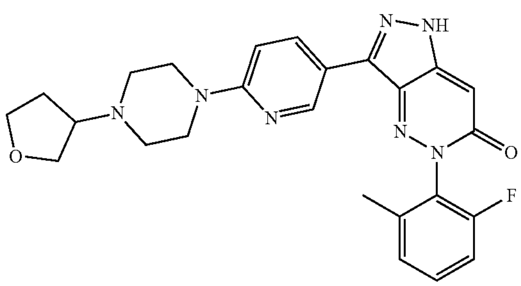 [SMILES: Cc1cccc(F)c1-n1nc2c(-c3ccc(N4CCN(C5CCOC5)CC4)nc3)n[nH]c2cc1=O] | ESI-MS: 476.2 [M + H]$^+$ $^1$H NMR (400 MHz, DMSO-$d_6$) δ 12.91 (s, 1H), 8.83 (d, J = 2.0 Hz, 1H), 8.14 (dd, J = 9.2, 2.4Hz, 1H), 7.52-7.47 (m, 1H), 7.34-7.26 (m, 2H), 6.96 (d, J = 8.8 Hz, 1H), 6.70 (s, 1H), 3.83-3.74 (m, 2H), 3.64 (q, J = 7.6 Hz, 1H), 3.58-3.48 | 2A |

-continued

| Example | Compound | Structural Formula | Spectrum Data | Synthetic Scheme |
|---|---|---|---|---|
| | | | (m, 5H), 2.94-2.87 (m, 1H), 2.55-2.47 (m, 1H), 2.43-2.38 (m, 2H), 2.10 (s, 3H), 2.02-1.94 (m, 1H), 1.80-1.71 (m, 1H). | |
| Example 74 | Compound 107 | 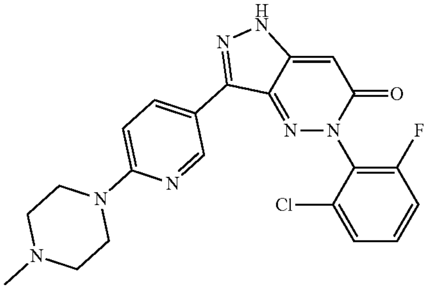 [SMILES: CN1CCN(c2ccc(-c3n[nH]c4cc(=O)n(-c5c(F)cccc5Cl)nc34)cn2)CC1] | ESI-MS: 440.1 [M + H]$^+$ $^1$H NMR (400 MHz, DMSO-$d_6$) δ 12.97 (s, 1H), 8.83 (d, J = 2.2 Hz, 1H), 8.13 (dd, J = 9.0, 2.4 Hz, 1H), 7.70-7.60 (m, 2H), 7.57-7.52 (m, 1H), 6.98 (d, J = 9.0 Hz, 2H), 6.74 (s, 1H), 3.62-3.52 (m, 4H), 2.48-2.38 (m, 4H), 2.24 (s, 3H). | 2A |
| Example 75 | Compound 108 | 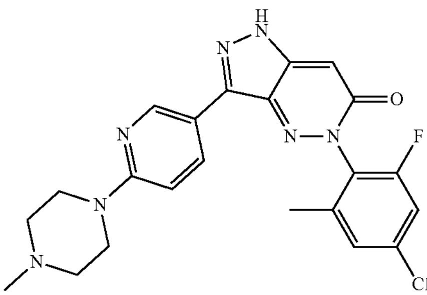 | ESI-MS: 454.3 [M + H]$^+$ $^1$H NMR (400 MHz, DMSO-$d_6$) δ 12.82 (br, 1H), 8.83 (d, J = 2.3 Hz, 1H), 8.13 (dd, J = 9.0, 2.4 Hz, 1H), 7.58 (dd, J = 9.3, 2.3 Hz, 1H), 7.46 (s,1H),6.96 (d, J = 9.0 Hz, 1H), 6.72 (s, 1H), 3.58-3.54 (m, 4H), 2.39-2.36 (m, 4H), 2.21 (s, 3H), 2.11 (s, 3H). | 2A |
| Example 76 | Compound 109 | 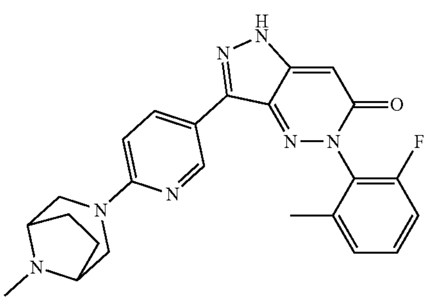 [SMILES: Cc1cccc(F)c1-n1nc2c(-c3ccc(N4CC5CCC(C4)N5C)nc3)n[nH]c2cc1=O] | ESI-MS: 446.3 [M + H]$^+$ $^1$H NMR (400 MHz, DMSO-$d_6$) δ 12.88 (s, 1H), 8.81 (s, 1H) 8.12-8.10 (m, 1H), 7.52-7.48 (m, 1H), 7.31-7.28 (m, 2H), 6.82 (d, J = 9.2 Hz, 1H), 6.69 (s,1H), 3.86 (d, J = 11.2 Hz, 2H), 3.23 (s, 2H), 2.99 (d, J = 11.2 Hz, 2H), 2.24 (s, 3H), 2.10 (s, 3H), 1.94-1.92 (m, 2H), 1.57-1.46 (m, 2H). | 2A |
| Example 77 | Compound 110 | 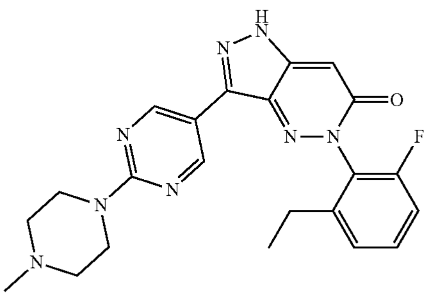 [SMILES: CCc1cccc(F)c1-n1nc2c(-c3cnc(N4CCN(C)CC4)nc3)n[nH]c2cc1=O] | ESI-MS: 435.2 [M + H]$^+$ $^1$H NMR (400 MHz, DMSO-$d_6$,) δ 13.03 (s, 1H), 8.95 (s, 2H), 7.57-7.51 (m, 1H), 7.33-7.25 (m, 2H), 6.74 (s, 1H), 3.79 (t, J = 4.4 Hz, 4H), 2.45-2.38 (m, 2H), 2.35 (t, J = 4.4 Hz, 4H), 2.20 (s, 3H), 1.05 (t, J = 7.6 Hz, 3H). | 2A |

-continued

| Example | Compound | Structural Formula | Spectrum Data | Synthetic Scheme |
|---|---|---|---|---|
| Example 78 | Compound 111 | 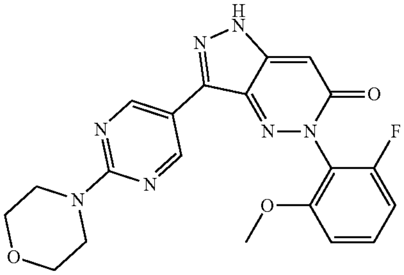 [SMILES: COc1cccc(F)c1-n1nc2c(-c3cnc(N4CCOCC4)nc3)n[nH]c2cc1=O] | ESI-MS: m/z = 424.1 ([M + H]$^+$). $^1$H NMR (400 MHz, DMSO-$d_6$) δ 13.00 (brs, 1H), 8.97 (s, 2H), 7.56 (q, J = 8.0 Hz, 1H), 7.12 (d, J = 8.6 Hz, 1H), 7.06 (t, J = 8.9 Hz, 1H), 6.70 (s, 1H), 3.80-3.74 (m, 7H), 3.70-3.61 (m, 4H). | 2B |
| Example 79 | Compound 112 | 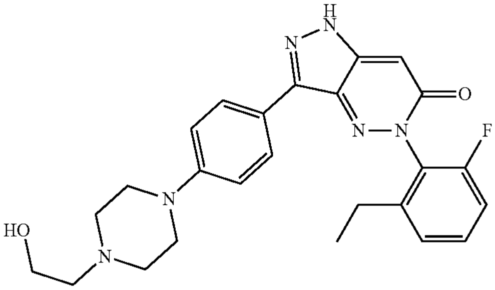 | ESI-MS: 463.4 [M + H]$^+$ $^1$H NMR (700 MHz, DMSO-$d_6$) δ 12.86 (s, 1H), 7.97 (d, J = 9.0 Hz, 2H), 7.56-7.52 (m, 1H), 7.33-7.30 (m, 2H), 7.03 (d, J = 9.0 Hz, 2H), 6.68 (s, 1H), 4.44 (s, 1H), 3.53 (q, J = 5.8 Hz, 2H), 3.22-3.19 (m, 4H), 2.56-2.52 (m, 4H), 2.45-2.37 (m, 4H), 1.06 (t, J =7.6 Hz, 3H). | 2A |
| Example 80 | Compound 113 | 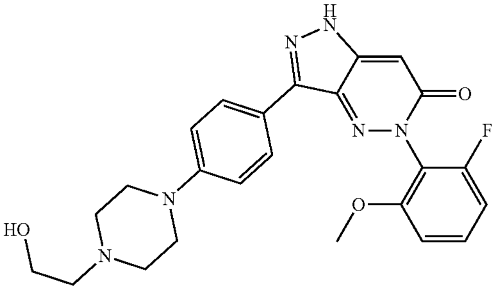 [SMILES: COc1cccc(F)c1-n1nc2c(-c3ccc(N4CCN(CCO)CC4)cc3)n[nH]c2cc1=O] | ESI-MS: 465.3 [M + H]$^+$ $^1$H NMR (400 MHz, DMSO-$d_6$) δ 12.77 (s, 1H), 7.95 (d, J = 8.9 Hz, 2H), 7.60-7.51 (m, 1H), 7.17-6.98 (m, 4H), 6.61 (s, 1H), 4.41 (t, J = 5.3 Hz, 1H), 3.78 (s, 3H), 3.53 (q, J = 6.0 Hz, 2H), 3.24-3.17 (m, 4H), 2.60 - 2.52 (m, 4H), 2.42 (t, J = 6.2 Hz, 2H). | 2A |
| Example 81 | Compound 114 | 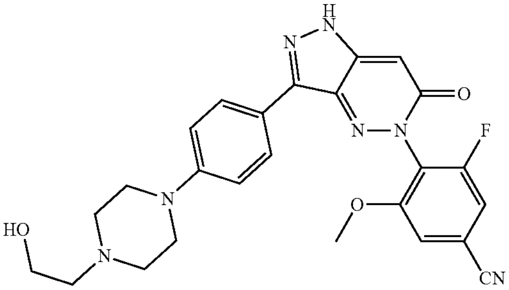 [SMILES: COc1cc(C#N)cc(F)c1-n1nc2c(-c3ccc(N4CCN(CCO)CC4)cc3)n[nH]c2cc1=O] | ESI-MS: 490.2 [M + H]$^+$ $^1$H NMR (400 MHz, DMSO-$d_6$) δ 12.88 (s, 1H), 7.93 (d, J = 8.9 Hz, 2H), 7.78 (dd, J = 8.9, 1.5 Hz, 1H), 7.73 (s, 1H), 7.03 (d, J = 8.9 Hz, 2H), 6.66 (s, 1H), 4.43 (s, 1H), 3.87 (s, 3H), 3.26-3.12 (m, 6H), 2.60-2.52 (m, 4H), 2.47-2.40 (m, 2H). | 2B |
| Example 82 | Compound 115 | 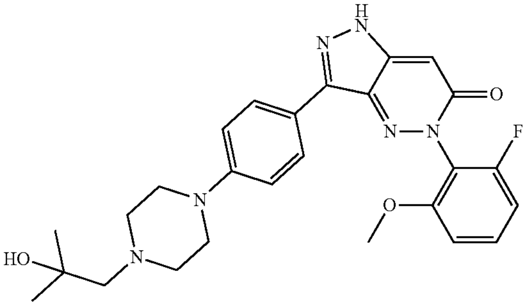 | ESI-MS: 493.3 [M + H]$^+$ $^1$H NMR (400 MHz, DMSO-$d_6$) δ 1 2.78 (s, 1H), 7.95 (d, J = 9.0 Hz, 2H), 7.61-7.50 (m, 1H), 7.12 (d, J = 8.6 Hz, 1H), 7.09-6.96 (m, 3H), 6.62 (s, 1H), 4.12 (s, 1H), 3.78 (s, 3H), 3.27 - 3.12 (m, 4H), 2.72-2.59 (m, 4H), 2.23 (s, 2H), 1.10 (s, 6H). | 2A |

-continued

| Example | Compound | Structural Formula | Spectrum Data | Synthetic Scheme |
|---|---|---|---|---|
| Example 83 | Compound 116 | 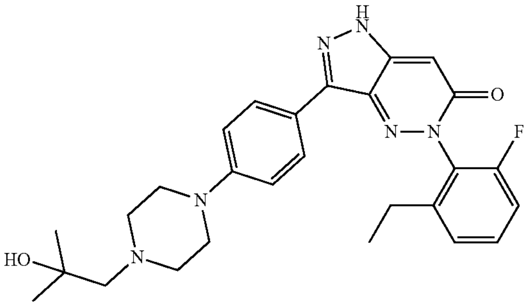 | ESI-MS: 494.3 [M + H]$^+$ $^1$H NMR (700 MHz, DMSO-$d_6$) δ 12.83 (s, 1H), 7.96 (d, J = 8.9 Hz, 2H), 7.56-7.51 (m, 1H), 7.33-7.28 (m, 2H), 7.02 (d, J = 9.0 Hz, 2H),6.67 (s, 1H), 4.12 (s, 1H), 3.24-3.18 (m, 4H), 2.68-2.60 (m, 4H), 2.45-2.37 (m, 2H), 2.24 (s, 2H), 1.10 (s, 6H), 1.06 (t, J = 7.6 Hz, 3H). | 2A |
| Example 84 | Compound 117 | 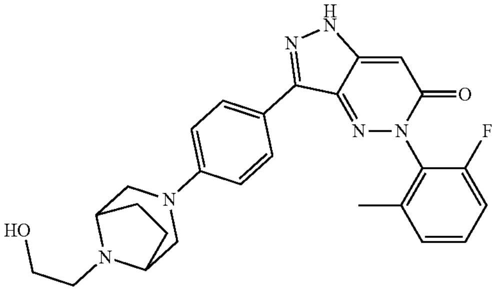 [SMILES: Cc1cccc(F)c1-n1nc2c(-c3ccc(N4CC5CCC(C4)N5CCO)cc3)n[nH]c2cc1=O] | ESI-MS: 475.1 [M + H]$^+$ $^1$H NMR (400 MHz, DMSO-$d_6$) δ 12.77 (s, 1H), 7.94 (d, J = 8.9 Hz, 2H), 7.53-7.46 (m, 1H), 7.33-7.25 (m, 2H), 6.89 (d, J = 9.0 Hz, 2H), 6.66 (s, 1H), 4.36 (t, J = 5.3 Hz, 1H), 3.50 (q, J = 5.9 Hz, 2H), 3.45-3.33 (m, 4H), 2.88 (d, J = 9.8 Hz, 2H), 2.43 (t, J = 6.2 Hz, 2H), 2.09 (s, 3H), 1.95- 1.83 (m, 2H), 1.65-1.54 (m, 2H). | 2A |
| Example 85 | Compound 118 | 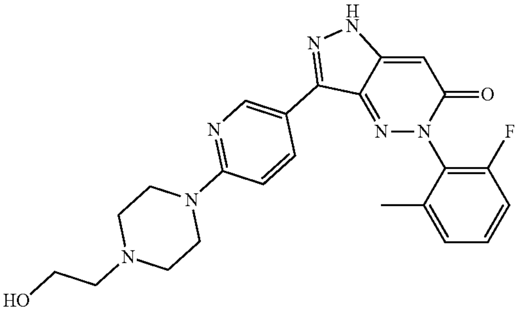 [SMILES: Cc1cccc(F)c1-n1nc2c(-c3ccc(N4CCN(CCO)CC4)nc3)n[nH]c2cc1=O] | ESI-MS: 450.2 [M + H]$^+$ $^1$H NMR (400 MHz, $CD_3OD$) δ 8.98 (d, J = 2.0 Hz, 1H), 8.31 (dd, J = 8.8, 2.4 Hz, 1H), 7.52-7.46 (m, 1H), 7.28 (d, J = 8.0 Hz, 1H), 7.21 (t, J = 8.8 Hz, 1H), 6.92 (d, J = 8.8 Hz, 1H), 6.74 (s, 1H), 3.74 (t, J = 5.6 Hz, 2H), 3.66 (t, J = 5.2 Hz, 4H), 2.66 (t, J = 5.2 Hz, 4H), 2.61 (t, J = 5.6 Hz, 2H), 2.18 (s, 3H). | 2A |
| Example 86 | Compound 119 | 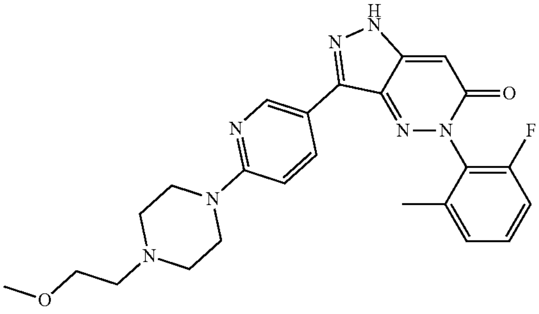 [SMILES: COCCN1CCN(c2ccc(-c3n[nH]c4cc(=O)n(-c5c(C)cccc5F)nc34)cn2)CC1] | ESI-MS: 464.2 [M + H]$^+$ $^1$H NMR (400 MHz, DMSO-$d_6$) δ 12.90 (s, 1H), 8.83 (d, J = 2.4 Hz, 1H), 8.14 (dd, J = 9.2, 2.4 Hz, 1H), 7.52-7.47 (m, 1H), 7.33-7.26 (m, 2H), 6.96 (d, J = 8.8 Hz, 1H), 6.70 (s, 1H), 3.58-3.51 (m, 4H), 3.46 (t, J = 6.0 Hz, 2H), 3.24 (s, 3H), 2.52-2.45 (m, 6H), 2.10 (s, 3H). | 2A |
| Example 87 | Compound 120 | 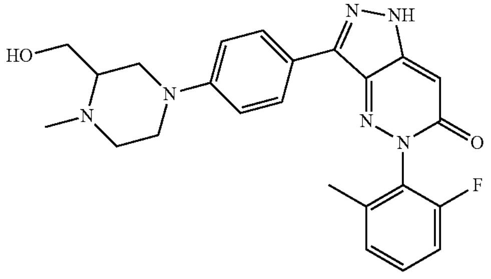 [SMILES: Cc1cccc(F)c1-n1nc2c(-c3ccc(N4CCN(C)C(CO)C4)cc3)n[nH]c2cc1=O] | ESI-MS: 449.2 [M + H]$^+$ $^1$H NMR (400 MHz, DMSO-$d_6$) δ 12.83 (s, 1H), 7.97 (d, J = 8.9 Hz, 2H), 7.53-7.45 (m, 1H), 7.34-7.25 (m, 2H), 7.02 (d, J = 9.0 Hz, 2H), 6.67 (s, 1H), 4.60-4.54 (m, 2H), 3.75 (d, J = 11.6 Hz, 1H), 3.69-3.57 (m, 2H), 3.40-3.34 (m, 1H), 2.89-2.73 (m, 2H), 2.62-2.53 (m, 1H), 2.30-2.19 (m, 4H), 2.14-2.06 (m, 4H). | 4 |

-continued

| Example | Compound | Structural Formula | Spectrum Data | Synthetic Scheme |
|---|---|---|---|---|
| Example 88 | Compound 121 | 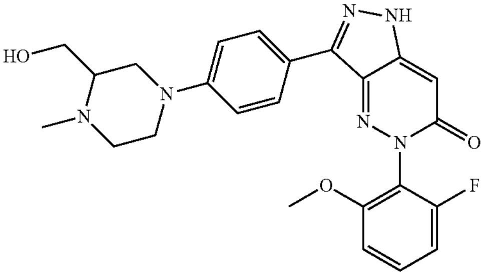 [SMILES: COc1cccc(F)c1-n1nc2c(-c3ccc(N4CCN(C)C(CO)C4)cc3)n[nH]c2cc1=O] | ESI-MS: 465.2 $[M + H]^+$ $^1H$ NMR (400 MHz, DMSO-$d_6$) δ 12.75 (br, 1H), 7.95 (d, J = 8.9 Hz, 2H), 7.59-7.51 (m, 1H), 7.14-6.99 (m, 4H), 6.60 (s, 1H), 4.56 (s, 1H), 3.78 (s, 3H), 3.77-3.71 (m, 1H), 3.69-3.56 (m, 2H), 3.40-3.34 (m, 1H), 2.88-2.74 (m, 2H), 2.58 (dd, J = 12.0, 10.2 Hz, 1H), 2.28-2.20 (m, 4H), 2.15-2.06 (m, 1H). | 2A |
| Example 89 | Compound 122 | 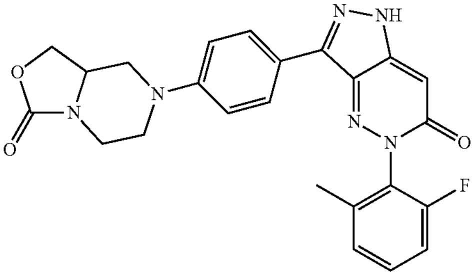 [SMILES: Cc1cccc(F)c1-n1nc2c(-c3ccc(N4CCN5C(=O)OCC5C4)cc3)n[nH]c2cc1=O] | ESI-MS: 461.2 $[M +H]^+$ $^1H$ NMR (400 MHz, DMSO-$d_6$) 8 12.87 (s, 1H), 7.99 (d, J = 8.9 Hz, 2H), 7.53-7.45 (m, 1H), 7.35-7.25 (m, 2H), 7.13-7.04 (m, 2H), 6.69 (s, 1H), 4.41 (t, J = 8.1 Hz, 1H), 4.01-3.90 (m, 3H), 3.85-3.75 (m, 1H), 3.62 (dd, J = 13.3, 3.2 Hz, 1H), 3.16-3.07 (m, 1H), 2.85 - 2.62 (m, 2H), 2.10 (s, 3H). | 4 |
| Example 90 | Compound 123 | 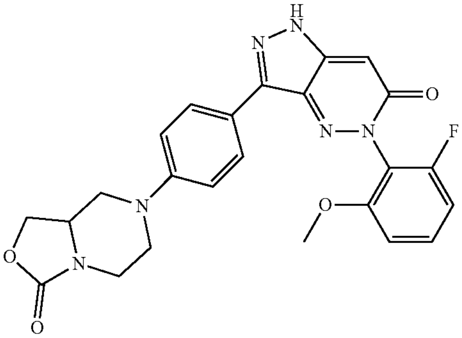 [SMILES: COc1cccc(F)c1-n1nc2c(-c3ccc(N4CCN5C(=O)OCC5C4)cc3)n[nH]c2cc1=O] | ESI-MS: 477.2 $[M + H]^+$ $^1H$ NMR (400 MHz, DMSO-$d_6$) δ 12.81 (s, 1H), 7.97 (d, J = 8.9 Hz, 2H), 7.66-7.47 (m, 1H), 7.15-7.01 (m, 4H), 6.63 (s, 1H), 4.46-4.36 (m, 1H), 4.03-3.89 (m, 3H), 3.84-3.75 (m, 4H), 3.62 (dd, J = 13.1, 2.6 Hz, 1H), 3.17-3.07 (m, 1H), 2.82-2.65 (m, 2H). | 2A |
| Example 91 | Compound 124 | 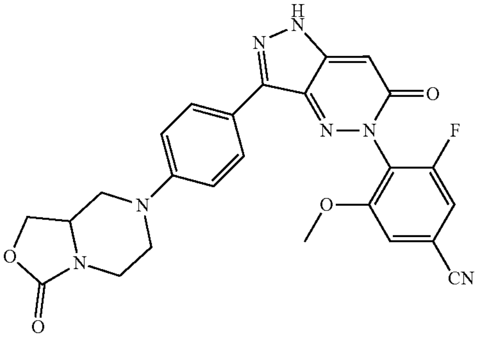 [SMILES: COc1cc(C#N)cc(F)c1-n1nc2c(-c3ccc(N4CCN5C(=O)OCC5C4)cc3)n[nH]c2cc1=O] | ESI-MS: 502.2 $[M + H]^+$ $^1H$ NMR (400 MHz, DMSO-$d_6$) δ 12.89 (s, 1H), 7.96 (d, J = 9.0 Hz, 2H), 7.78 (dd, J = 8.9, 1.4 Hz, 1H), 7.74-7.70 (m, 1H), 7.08 (d, J = 9.0 Hz, 2H), 6.67 (s, 1H), 4.41 (t, J = 8.1 Hz, 1H), 4.02-3.91 (m, 3H), 3.86 (s, 3H), 3.83-3.76 (m, 1H), 3.62 (dd, J = 13.1, 2.7 Hz, 1H), 3.12 (td, J = 12.7, 3.6 Hz, 1H), 2.82-2.65 (m, 2H). | 2B |

-continued

| Example | Compound | Structural Formula | Spectrum Data | Synthetic Scheme |
|---|---|---|---|---|
| Example 92 | Compound 125 | 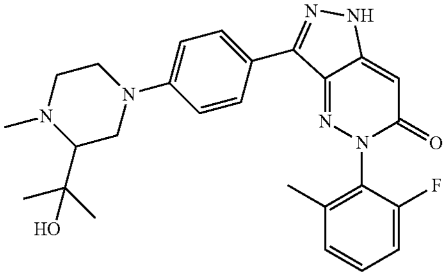 [SMILES: Cc1cccc(F)c1-n1nc2c(-c3ccc(N4CCN(C)C(C(C)(C)O)C4)cc3)n[nH]c2cc1=O] | ESI-MS: 477.1 $[M + H]^+$ $^1H$ NMR (400 MHz, DMSO-$d_6$) δ 12.79 (s, 1H), 7.96 (d, J = 8.8 Hz, 2H), 7.59-7.52 (m, 1H), 7.33-7.26 (m, 2H), 6.93 (d, J = 8.8 Hz, 2H), 6.66 (s, 1H), 4.29 (s, 1H), 3.65-3.58 (m, 1H), 3.56-3.49 (m, 1H), 2.98-2.81 (m, 3H), 2.62-2.55 (m, 1H), 2.41 (s, 3H), 2.28-2.20 (m, 1H), 2.10 (s, 3H), 1.13 (s, 3H), 1.11 (s, 3H). | 2A |
| Example 93 | Compound 126 | 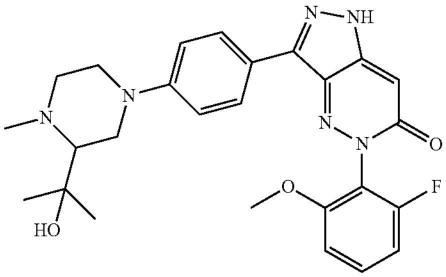 [SMILES: COc1cccc(F)c1-n1nc2c(-c3ccc(N4CCN(C)C(C(C)(C)O)C4)cc3)n[nH]c2cc1=O] | ESI-MS: 493.3$[M + H]^+$ $^1H$ NMR (400 MHz, DMSO-$d_6$) δ 12.74 (s, 1H), 7.95 (d, J = 8.9 Hz, 2H), 7.65-7.50 (m, 1H), 7.12 (d, J = 8.6 Hz, 1H), 7.06 (t, J = 8.8 Hz, 1H), 6.93 (d, J = 9.0 Hz, 2H), 6.61 (s, 1H), 4.29 (s, 1H), 3.78 (s, 3H), 3.61 (dd, J = 12.8, 3.9 Hz, 1H), 3.58-3.48 (m, 1H), 3.01-2.77 (m, 3H), 2.63-5.52 (m, 1H), 2.40 (s, 3H), 2.24 (dd, J = 9.1, 3.9 Hz, 1H), 1.13 (s, 3H) , 1.11 (s, 3H). | 2A |
| Example 94 | Compound 127 | 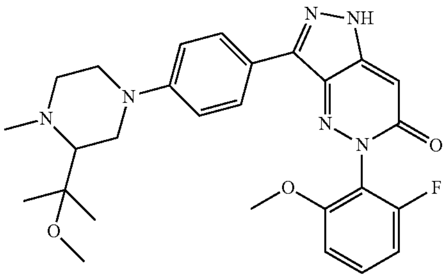 [SMILES: COc1cccc(F)c1-n1nc2c(-c3ccc(N4CCN(C)C(C(C)(C)OC)C4)cc3)n[nH]c2cc1=O] | ESI-MS: 507.3 $[M + H]^+$ $^1H$ NMR (400 MHz, DMSO-$d_6$) δ 12.73 (s, 1H), 7.95 (d, J = 8.8 Hz, 2H), 7.59-7.52 (m, 1H), 7.12 (d, J = 8.6 Hz, 1H), 7.06 (t, J = 8.8 Hz, 1H), 6.93 (d, J = 8.8 Hz, 2H), 6.60 (s, 1H), 3.78 (s, 3H), 3.60-3.52 (m, 2H), 3.11 (s, 3H), 2.95-2.80 (m, 3H), 2.62-2.55 (m, 1H), 2.44 (dd, J = 9.0, 3.6 Hz, 1H), 2.39 (s, 3H), 1.15 (s, 3H), 1.11 (s, 3H). | 2A |
| Example 95 | Compound 128 | 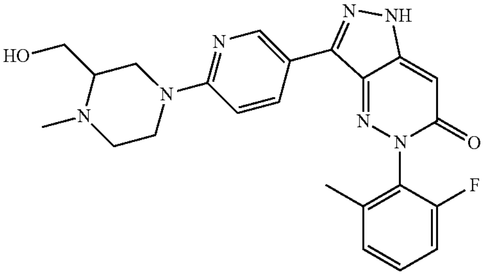 [SMILES: Cc1cccc(F)c1-n1nc2c(-c3ccc(N4CCN(C)C(CO)C4)nc3)n[nH]c2cc1=O] | ESI-MS: 450.3 $[M + H]^+$ $^1H$ NMR (400 MHz, DMSO-$d_6$) δ 12.83 (br, 1H), 8.83 (d, J = 2.2 Hz, 1H), 8.13 (dd, J = 9.0, 2.4 Hz, 1H), 7.54-7.44 (m, 1H), 7.34-7.25 (m, 2H), 6.93 (d, J = 9.1 Hz, 1H), 6.69 (s, 1H), 4.60 (br, 1H), 4.29 (d, J = 12.0 Hz, 1H), 4.10 (d, J = 12.2 Hz, 1H), 3.65 (dd, J = 11.0, 3.6 Hz, 1H), 3.02 - 2.94 (m, 1H), 2.81-2.69 (m, 2H), 2.23 (s, 3H), 2.19-2.13 (m, 1H), 2.10 (s, 3H), 2.07-1.92 (m, 1H). | 2A |

-continued

| Example | Compound | Structural Formula | Spectrum Data | Synthetic Scheme |
| --- | --- | --- | --- | --- |
| Example 96 | Compound 129 | 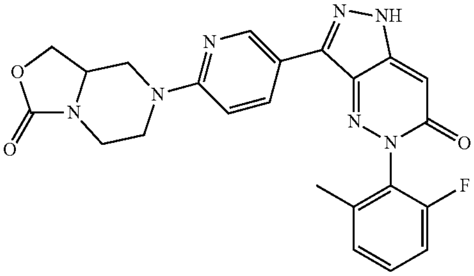 | ESI-MS: 436.1 [M + H]$^+$ $^1$H NMR (400 MHz, DMSO-$d_6$) δ 12.95 (s, 1H), 8.85 (d, J = 2.2 Hz, 1H), 8.17 (dd, J = 9.0, 2.4 Hz, 1H), 7.54-7.45 (m, 1H), 7.35-7.26 (m, 2H), 7.04 (d, J = 9.1 Hz, 1H), 6.72 (s, 1H), 4.58 (dd, J = 13.0, 2.8 Hz, 1H), 4.44-4.35 (m, 2H), 3.99 (dd, J = 8.8, 5.6 Hz, 1H), 3.92 - 3.79 (m, 1H), 3.65-3.58 (m, 1H), 3.07-2.99 (m, 1H), 2.96-2.79 (m, 2H), 2.10 (s, 3H). | 2A |
| Example 97 | Compound 130 | 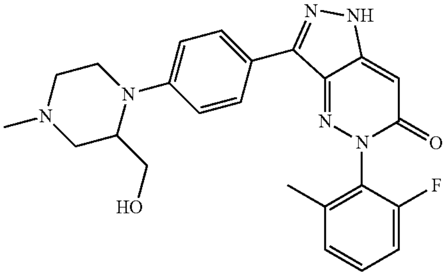 [SMILES: Cc1cccc(F)c1-n1nc2c(-c3ccc(N4CCN(C)CC4CO)cc3)n[nH]c2cc1=O] | ESI-MS: 449.2 [M + H]$^+$ $^1$H NMR (400 MHz, DMSO-$d_6$) δ 12.92 (s, 1H; NH), 8.02-7.90 (m, 2H), 7.55-7.43 (m, 1H), 7.35-7.24 (m, 2H), 7.03-6.94 m, 2H), 6.66 (s, 1H), 3.84-3.78 (m, 1H), 3.74-3.65 (m, 1H), 3.52-3.44 (m, 1H), 3.07-3.01 (m, 1H), 3.00-2.90 (m, 1H), 2.84-2.77(m, 1H), 2.20 (s, 3H), 2.10 (d, J = 3.5 Hz, 3H), 2.06-1.93 (m, 3H). | 4 |
| Example 98 | Compound 131 | 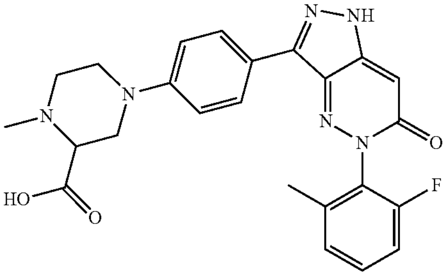 [SMILES: Cc1cccc(F)c1-n1nc2c(-c3ccc(N4CCN(C)C(C(=O)O)C4)cc3)n[nH]c2cc1=O] | ESI-MS: 463.3 [M + H]$^+$ $^1$H NMR (400 MHz, DMSO-$d_6$) δ 12.97 (s, 1H), 10.58 (br, 1H), 8.02 (d, J = 8.8 Hz, 2H), 7.52-7.46 (m, 1H), 7.34-7.28 (m, 2H), 7.15 (d, J = 8.4 Hz, 2H), 6.71 (s, 1H), 4.34-4.24 (m, 1H), 4.18-4.04 (m, 1H), 3.94-3.80 (m, 1H), 3.36-3.20 (m, 4H), 2.92 (s, 3H), 2.10 (s, 3H). | 2A |
| Example 99 | Compound 132 | 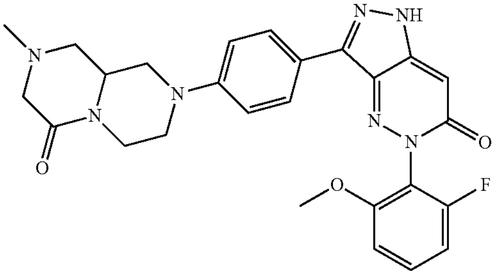 [SMILES: COc1cccc(F)c1-n1nc2c(-c3ccc(N4CCN5C(=O)CN(C)CC5C4)cc3)n[nH]c2cc1=O] | ESI-MS: 504.3 [M + H]$^+$ $^1$H NMR (400 MHz, DMSO-$d_6$) δ 12.80 (s, 1H), 7.97 (d, J = 9.0 Hz, 2H), 7.59-7.53 (m,1H), 7.14-7.04 (m, 4H), 6.62 (s, 1H), 4.44-4.36 (m, 1H), 3.84-3.77 (m, 5H), 3.65-3.56 (m, 1H), 3.07 (d, J = 15.6 Hz, 1H), 2.92-2.87 (m, 1H), 2.84-2.75 (m, 2H), 2.71-2.56 (m, 2H), 2.26 (dd, J = 11.8, 8.0 Hz, 1H), 2.21 (s, 3H). | 2A |
| Example 100 | Compound 133 | 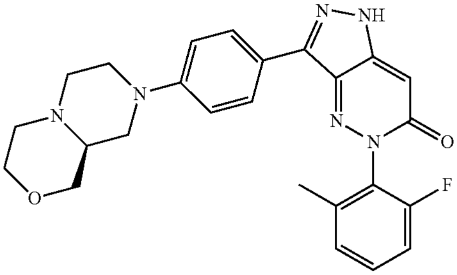 [SMILES: Cc1cccc(F)c1-n1nc2c(-c3ccc(N4CCN5CCOC[C@@H]5C4)cc3)n[nH]c2cc1=O] | ESI-MS: 461.3 [M + H]$^+$ $^1$H NMR (400 MHz, DMSO-$d_6$) δ 12.81 (s, 1H), 7.96 (d, J = 8.9 Hz, 2H), 7.52-7.46 (m, 1H), 7.32-7.27 (m, 2H), 7.03 (d, J = 8.9 Hz, 2H), 6.67 (s, 1H), 3.79-3.69 (m, 3H), 3.60 (d, J = 11.5 Hz, 1H), 3.56-3.49 (m,1H), 3.15 (t, J = | 2A |

-continued

| Example | Compound | Structural Formula | Spectrum Data | Synthetic Scheme |
|---|---|---|---|---|
| | | | 10.4 Hz, 1H), 2.85-2.76 (m, 2H), 2.67 (d, J = 11.5 Hz, 1H), 2.36-2.16 (m, 4H), 2.10 (s, 3H). | |
| Example 101 | Compound 134 | 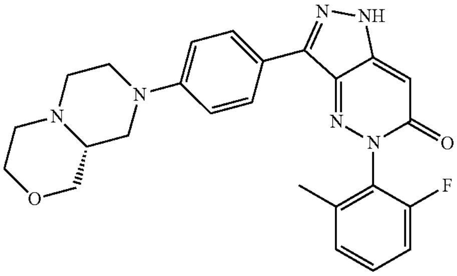 [SMILES: Cc1cccc(F)c1-n1nc2c(-c3ccc(N4CCN5CCOC[C@H]5C4)cc3)n[nH]c2cc1=O] | ESI-MS: 461.3 $[M + H]^+$ $^1$HNMR (400 MHz, DMSO-$d_6$) δ 12.81 (s, 1H), 7.96 (d, J = 8.9 Hz, 2H), 7.52-7.46 (m, 1H), 7.32-7.27 (m, 2H), 7.03 (d, J = 8.9 Hz, 2H), 6.67 (s, 1H), 3.79-3.69 (m, 3H), 3.60 (d, J = 11.5 Hz, 1H), 3.56-3.49 (m, 1H), 3.15 (t, J = 10.4 Hz, 1H), 2.85-2.76 (m, 2H), 2.67 (d, J = 11.5 Hz, 1H), 2.36-2.16 (m, 4H), 2.10 (s, 3H). | 2A |
| Example 102 | Compound 135 | 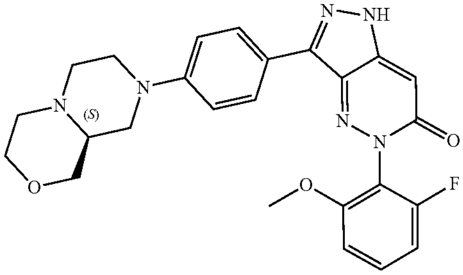 | ESI-MS: 477.2 $[M + H]^+$ $^1$H NMR (400 MHz, DMSO-$d_6$) δ 12.78 (s, 1H), 7.95 (d, J = 8.9 Hz, 2H), 7.59-7.52 (m, 1H), 7.12 (d, J = 8.6 Hz, 1H), 7.09-7.02 (m, 3H), 6.61 (s, 1H), 3.78-3.69 (m, 6H), 3.60 (d, J = 11.5 Hz, 1H), 3.56-3.49 (m, 1H), 3.15 (t, J = 10.4 Hz, 1H), 2.85-2.76 (m, 2H), 2.67 (d, J = 11.5 Hz, 1H), 2.36-2.16 (m, 4H). | 2A |
| Example 103 | Compound 136 | 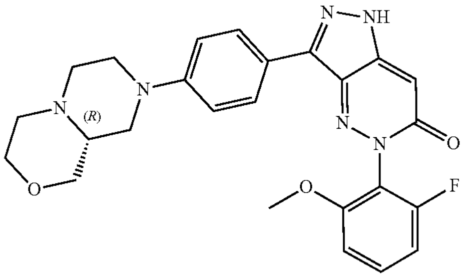 | ESI-MS: 477.2 $[M + H]^+$ $^1$HNMR (400 MHz, DMSO-$d_6$) δ 12.80 (s, 1H), 7.95 (d, J = 8.9 Hz, 2H), 7.59-7.52 (m, 1H), 7.12 (d, J = 8.6 Hz, 1H), 7.09-7.02 (m, 3H), 6.62 (s, 1H), 3.78-3.69 (m, 6H), 3.60 (d, J = 11.5 Hz, 1H), 3.56-3.49 (m, 1H), 3.15 (t, J = 10.4 Hz, 1H), 2.85-2.76 (m, 2H), 2.67 (d, J = 11.5 Hz, 1H), 2.36-2.16 (m, 4H). | 2A |
| Example 104 | Compound 137 | 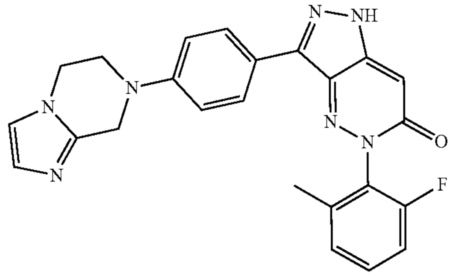 [SMILES: Cc1cccc(F)c1-n1nc2c(-c3ccc(N4CCn5ccnc5C4)cc3)n[nH]c2cc1=O] | ESI-MS: 442.2 $[M + H]^+$ $^1$H NMR (400 MHz, DMSO-$d_6$) δ 12.85 (s, 1H), 8.03-8.00 (m, 2H), 7.53-7.46 (m, 1H), 7.33-7.27 (m, 2H), 7.19-7.16 (m, 2H), 7.10 (d, J=1.0 Hz, 1H), 6.88 (d, J = 1.2 Hz, 1H), 6.69 (s, 1H), 4.47 (s, 2H), 4.09 (t, J = 5.3 Hz, 2H), 3.79 (t, J = 5.3 Hz, 2H), 2.10 (s, 3H). | 4 |

-continued

| Example | Compound | Structural Formula | Spectrum Data | Synthetic Scheme |
|---|---|---|---|---|
| Example 105 | Compound 138 | 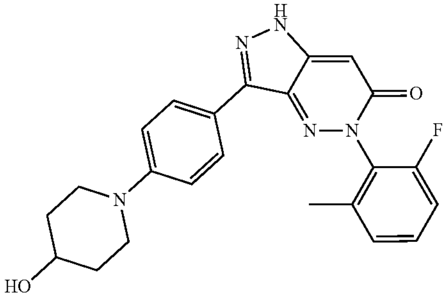 [SMILES: Cc1cccc(F)c1-n1nc2c(-c3ccc(N4CCC(O)CC4)cc3)n[nH]c2cc1=O] | ESI-MS: 420.2 $[M+H]^+$ $^1H$ NMR (400 MHz, DMSO-$d_6$) δ 12.80 (s, 1H), 7.95 (d, J = 8.9 Hz, 2H), 7.52-7.46 (m, 1H), 7.33-7.27 (m, 2H), 7.02 (d, J = 8.9 Hz, 2H), 6.67 (s, 1H), 4.67 (d, J = 4.2 Hz, 1H), 3.69-3.59 (m, 3H), 2.98-2.88 (m, 2H), 2.10 (s, 3H), 1.84-1.72 (m, 2H), 1.47-1.36 (m, 2H). | 4 |
| Example 106 | Compound 139 | 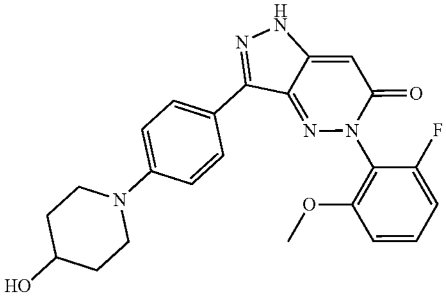 [SMILES: COc1cccc(F)c1-n1nc2c(-c3ccc(N4CCC(O)CC4)cc3)n[nH]c2cc1=O] | ESI-MS: 436.2 $[M+H]^+$ $^1H$ NMR (400 MHz, DMSO-$d_6$) δ 12.77 (s, 1H), 7.93 (d, J= 8.8 Hz, 2H), 7.59-7.53 (m, 1H), 7.13-7.01 (m, 4H), 6.61 (s, 1H), 4.68 (d, J = 4.4 Hz, 1H), 3.78 (s, 3H), 3.68-3.60 (m, 3H), 2.97-2.90 (m, 2H), 1.84-1.74 (m, 2H), 1.48-1.36 (m, 2H). | 2A |
| Example 107 | Compound 140 | 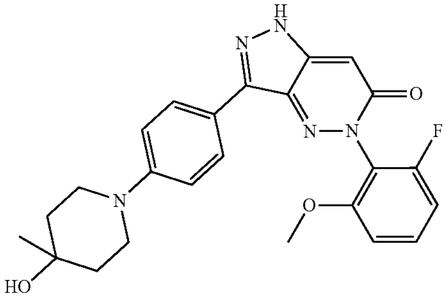 [SMILES: COc1cccc(F)c1-n1nc2c(-c3ccc(N4CCC(C)(O)CC4)cc3)n[nH]c2cc1=O] | ESI-MS: 450.2 $[M+H]^+$ $^1H$ NMR (400 MHz, DMSO-$d_6$) δ 12.77 (br, 1H), 7.93 (d, J = 8.8 Hz, 2H), 7.59-7.52 (m,1H), 7.12 (d, J = 8.8 Hz, 1H), 7.09-7.00 (m, 3H) , 6.61(s, 1H), 4.32 (s, 1H), 3.78 (s, 3H), 3.44-3.30 (m, 2H), 3.22-3.16 (m, 2H), 1.54-1.50 (m, 4H), 1.13 (s, 3H). | 2A |
| Example 108 | Compound 141 | 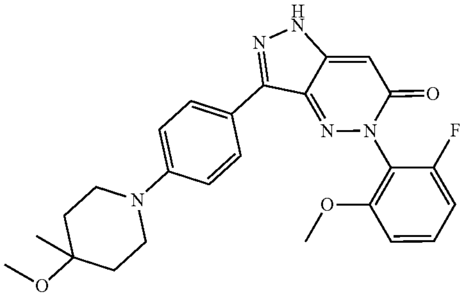 [SMILES: COc1cccc(F)c1-n1nc2c(-c3ccc(N4CCC(C)(OC)CC4)cc3)n[nH]c2cc1=O] | ESI-MS: 464.3 $[M+H]^+$ $^1H$ NMR (400 MHz, DMSO-$d_6$) δ 12.77 (s, 1H), 7.93 (d, J = 8.8 Hz, 2H), 7.59-7.52 (m, 1H), 7.12 (d, J = 8.6 Hz, 1H), 7.09-7.00 (m, 3H), 6.61 (s, 1H), 3.79 (s, 3H), 3.46-3.39 (m, 2H), 3.12 (s, 3H), 3.12-3.04 (m, 2H), 1.77-1.70 (m, 2H), 1.57-1.48 (m, 2H), 1.12 (s, 3H). | |

-continued

| Example | Compound | Structural Formula | Spectrum Data | Synthetic Scheme |
| --- | --- | --- | --- | --- |
| Example 109 | Compound 142 | 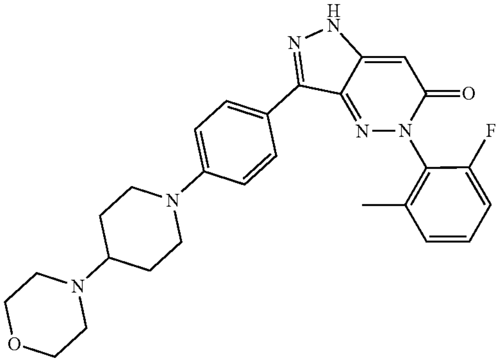 [SMILES: Cc1cccc(F)c1-n1nc2c(-c3ccc(N4CCC(N5CCOCC5)CC4)cc3)n[nH]c2cc1=O] | ESI-MS: 489.2 $[M+H]^+$ $^1H$ NMR (400 MHz, DMSO-$d_6$) δ 12.81 (s, 1H), 7.95 (d, J = 9.0 Hz, 2H), 7.52 - 7.46 (m, 1H), 7.33-7.26 (m, 2H), 7.03 (d, J = 9.1 Hz, 2H), 6.67 (s, 1H), 3.88-3.77 (m, 2H), 3.60-3.51 (m, 4H), 2.79-2.69 (m, 2H), 2.48-2.42 (m, 4H), 2.35-2.27 (m, 1H), 2.10 (s, 3H), 1.87-1.78 (m, 2H), 1.50-1.38 (m, 2H). | 4 |
| Example 110 | Compound 143 | 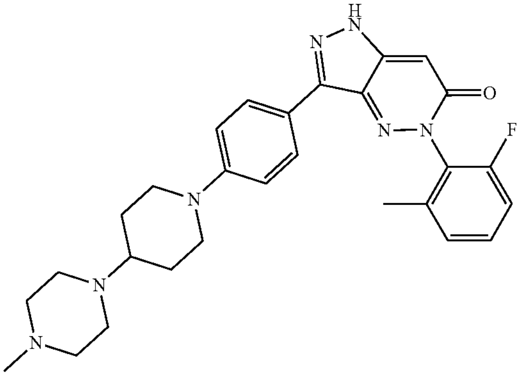 [SMILES: Cc1cccc(F)c1-n1nc2c(-c3ccc(N4CCC(N5CCN(C)CC5)CC4)cc3)n[nH]c2cc1=O] | ESI-MS: 502.2 $[M+H]^+$ $^1H$ NMR (400 MHz, DMSO-$d_6$) δ 12.80 (s, 1H), 7.95 (d, J = 9.0 Hz, 2H), 7.53-7.45 (m, 1H), 7.34-7.25 (m, 2H), 7.02 (d, J = 9.0 Hz, 2H), 6.67 (s, 1H), 3.82 (d, J = 12.5 Hz, 2H), 3.32 (s, 2H), 2.79-2.69 (m, 2H), 2.52-2.43 (m, 2H), 2.40-2.21 (m, 5H), 2.15 (s, 3H), 2.10 (s, 3H), 1.84-1.75 (m, 2H), 1.51-1.38 (m, 2H). | 4 |
| Example 111 | Compound 144 | 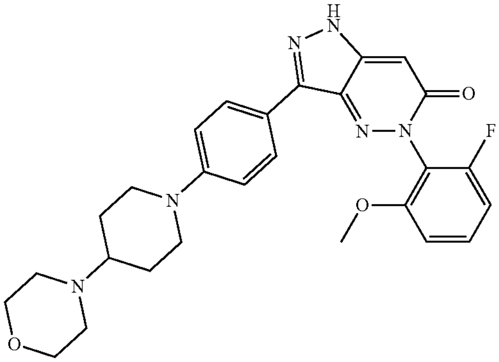 [SMILES: COc1cccc(F)c1-n1nc2c(-c3ccc(N4CCC(N5CCOCC5)CC4)cc3)n[nH]c2cc1=O] | ESI-MS: 505.3 $[M+H]^+$ $^1$HNMR (400 MHz, DMSO-$d_6$) δ 12.75 (s, 1H), 7.93 (d, J = 9.0 Hz, 2H), 7.59-7.52 (m, 1H), 7.12 (d, J = 8.6 Hz, 1H), 7.09-7.01 (m, 3H), 6.61 (s, 1H), 3.85-3.77 (m, 5H), 3.57-3.53 (m, 4H), 2.78-2.70 (m, 2H), 2.48-2.43 (m, 4H), 2.36-2.26 (m, 1H), 1.87-1.80 (m, 2H), 1.50-1.39 (m, 2H). | 2A |
| Example 112 | Compound 145 | 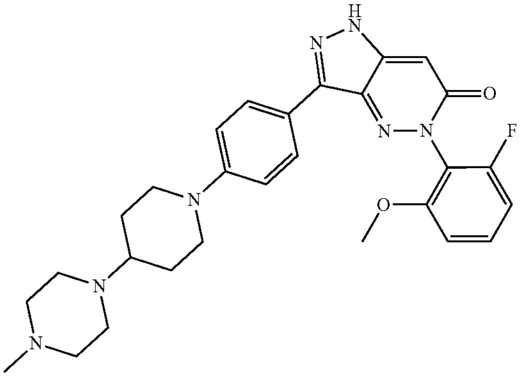 [SMILES: COc1cccc(F)c1-n1nc2c(-c3ccc(N4CCC(N5CCN(C)CC5)CC4)cc3)n[nH]c2cc1=O] | ESI-MS: 518.3 $[M+H]^+$ $^1H$ NMR (400 MHz, DMSO-d6) δ 12.77 (s, 1H), 7.93 (d, J = 9.0 Hz, 2H), 7.59-7.52 (m, 1H), 7.12 (d, J = 8.6 Hz, 1H), 7.09-7.01 (m, 3H), 6.61 (s, 1H), 3.85-3.77 (m, 5H), 2.78-2.70 (m, 2H), 2.50-2.43 (m, 2H), 2.40-2.26 (m, 5H), 2.15 (s, 3H), 1.84-1.76 (m, 2H), 1.50-1.39 (m, 2H). | 2A |

-continued

| Example | Compound | Structural Formula | Spectrum Data | Synthetic Scheme |
|---|---|---|---|---|
| Example 113 | Compound 146 | 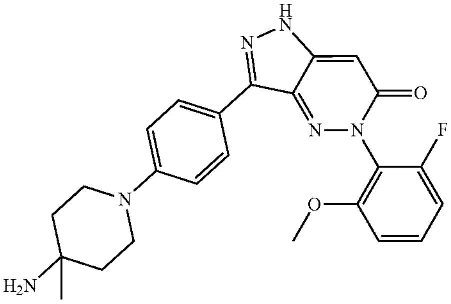 [SMILES: COc1cccc(F)c1-n1nc2c(-c3ccc(N4CCC(C)(N)CC4)cc3)n[nH]c2cc1=O] | ESI-MS: 449.3 $[M + H]^+$ $^1H$ NMR (400 MHz, DMSO-$d_6$) δ 7.95 (d, J = 8.9 Hz, 2H), 7.59-7.52 (m, 1H), 7.12 (d, J = 8.6 Hz, 1H), 7.09-7.02 (m, 3H), 6.61 (s, 1H), 3.78 (s, 3H), 3.55-3.46 (m, 2H), 3.23-3.15 (m, 2H), 1.70-1.58 (m,4H), 1.24 (s, 3H). | 4 |
| Example 114 | Compound 147 | 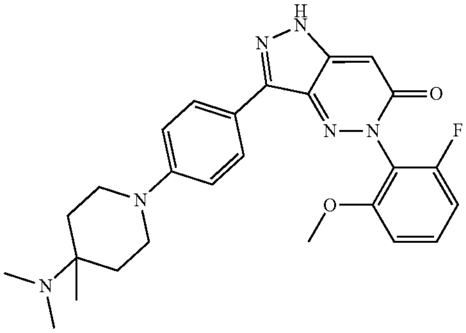 [SMILES: COc1cccc(F)c1-n1nc2c(-c3ccc(N4CCC(C)(N(C)C)CC4)cc3)n[nH]c2cc1=O] | ESI-MS: 477.3 $[M + H]^+$ $^1$HNMR (400 MHz, DMSO-$d_6$) δ 12.81 (s, 1H), 7.96 (d, J = 8.9 Hz, 2H), 7.59-7.52 (m, 1H), 7.14-7.02 (m, 4H), 6.62 (s, 1H), 3.90-3.60 (m, 5H), 2.97 (br, 2H), 2.61 (br, 6H), 1.83 (br, 4H), 1.26 (br, 3H). | 4 |
| Example 115 | Compound 148 | 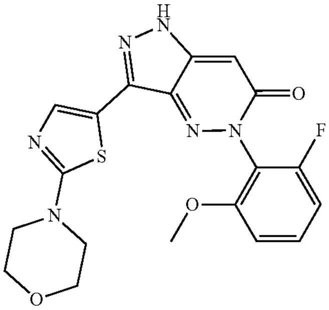 [SMILES: COc1cccc(F)c1-n1nc2c(-c3cnc(N4CCOCC4)s3)n[nH]c2cc1=O] | ESI-MS: m/z = 429.1 ($[M + H]^+$). $^1H$ NMR (400 MHz, DMSO-$d_6$) δ 12.80 (brs, 1H), 7.77 (s, 1H), 7.61-7.51 (m, 1H), 7.12 (d, J = 8.6 Hz, 1H), 7.06 (t, J = 8.9 Hz, 1H), 6.63 (s, 1H), 3.79 (s, 3H), 3.75-3.68 (m, 4H), 3.51-3.44 (m, 4H). | 2A |
| Example 116 | Compound 149 | 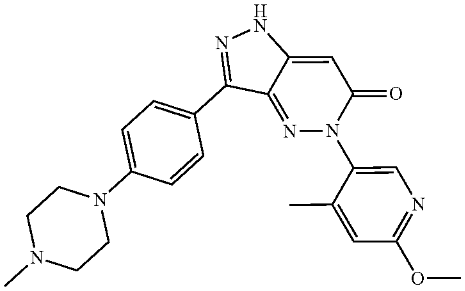 | ESI-MS: m/z = 432.2 ($[M + H]^+$). $^1H$ NMR (400 MHz, DMSO-$d_6$) δ 12.78 (brs, 1H), 8.20 (s, 1H), 7.99 (d, J = 8.8 Hz, 2H), 7.03 (d, J = 8.8, 2H), 6.90 (s, 1H), 6.63 (s, 1H), 3.91 (s, 3H), 3.26-3.12 (m, 4H), 2.54-2.48 (m, 4H), 2.24 (s, 3H), 2.08 (s, 3H). | 4 |
| Example 117 | Compound 150 | 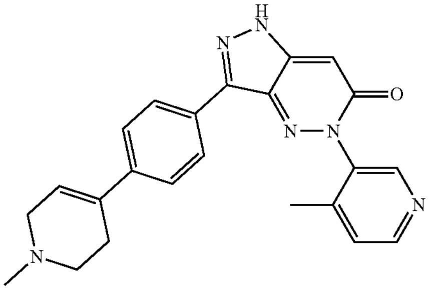 [SMILES: Cc1ccncc1-n1nc2c(-c3ccc(C4=CCN(C)CC4)cc3)n[nH]c2cc1=O] | ESI-MS: 399.2 $[M + H]^+$ $^1H$ NMR (400 MHz, DMSO-$d_6$) δ 13.07 (s, 1H), 8.66-8.54 (m, 2H), 8.11 (d, J = 8.0 Hz, 2H), 7.58 (d, J = 8.1 Hz, 2H), 7.50 (d, J = 4.8 Hz, 1H), 6.74 (s, 1H), 6.26 (s, 1H), 3.32 (s, 2H), 3.06 (s, 2H), 2.64-2.56 (m, 2H), 2.30 (s, 3H), 2.16 (s, 3H). | 4 |

-continued

| Example | Compound | Structural Formula | Spectrum Data | Synthetic Scheme |
|---|---|---|---|---|
| Example 118 | Compound 151 | 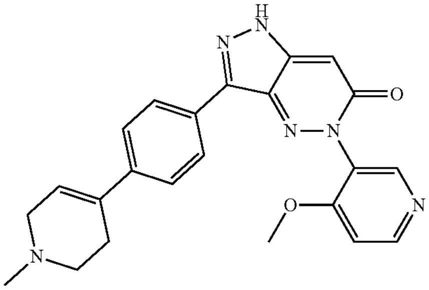 [SMILES: COc1ccncc1-n1nc2c(-c3ccc(C4=CCN(C)CC4)cc3)n[nH]c2cc1=O] | ESI-MS: 415[M + H]$^+$ $^1$H NMR (400 MHz, DMSO-$d_6$) δ 13.01 (s, 1H), 8.61 (d, J = 5.8 Hz, 1H), 8.53 (s, 1H), 8.09 (d, J = 8.5 Hz, 2H), 7.57 (d, J = 8.5 Hz, 2H), 7.34 (d, J = 5.8 Hz, 1H), 6.67 (s, 1H), 6.25 (s, 1H), 3.85 (s, 3H), 3.36-3.32 (m, 2H), 3.07-2.99 (m, 2H), 2.58 (t, J = 5.5 Hz, 2H), 2.28 (s, 3H). | 4 |
| Example 119 | Compound 152 | 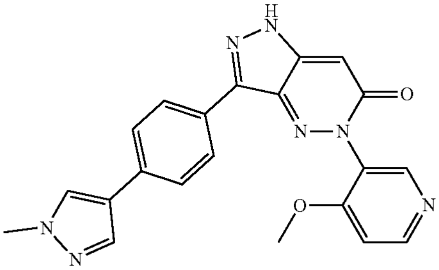 [SMILES: COc1ccncc1-n1nc2c(-c3ccc(-c4cnn(C)c4)cc3)n[nH]c2cc1=O] | ESI-MS: 400.1[M + H]$^+$ $^1$H NMR (400 MHz, DMSO-$d_6$) δ 12.99 (s, 1H), 8.61 (d, J = 5.8 Hz, 1H), 8.54 (s, 1H), 8.16 (s, 1H), 8.11 (d, J = 8.5 Hz, 2H), 7.89 (s, 1H), 7.69 (d, J = 8.5 Hz, 2H), 7.34 (d, J = 5.8 Hz, 1H), 6.67 (s, 1H), 3.87 (s, 3H), 3.86 (s, 3H). | 4 |
| Example 120 | Compound 153 | 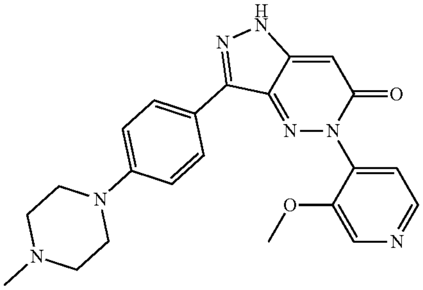 [SMILES: COc1cnccc1-n1nc2c(-c3ccc(N4CCN(C)CC4)cc3)n[nH]c2cc1=O] | ESI-MS: m/z = 418.2 ([M + H]$^+$). $^1$H NMR (300 MHz, DMSO-$d_6$) δ 12.78 (brs, 1H), 8.65 (s, 1H), 8.42 (d, J = 2.7 Hz, 1H), 7.97 (d ,J = 9.0 Hz, 2H), 7.56 (d, J= 4.8 Hz, 1H), 7.03 (d, J = 9.0Hz, 2H), 6.60 (s, 1H), 3.89 (s, 3H), 3.28-3.18 (m, 4H), 2.48-2.38 (m, 4H), 2.23 (s, 3H). | 4 |
| Example 121 | Compound 154 | 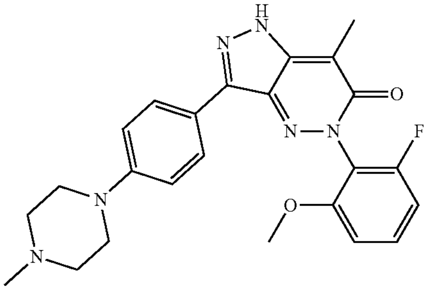 [SMILES: COc1cccc(F)c1-n1nc2c(-c3ccc(N4CCN(C)CC4)cc3)n[nH]c2c(C)c1=O] | ESI-MS: 449.2 [M + H]$^+$ $^1$H NMR (400 MHz, DMSO-$d_6$) δ 12.86 (s, 1H), 7.96 (d, J = 9.2 Hz, 2H), 7.58-7.52 (m, 1H), 7.11 (d, J = 8.8 Hz, 1H), 7.08-7.01 (m, 1H), 3.77 (s, 3H), 3.22-3.18 (m, 4H), 2.46-2.42 (m, 4H), 2.25 (s, 3H), 2.21 (s, 3H). | 3A |
| Example 122 | Compound 155 | 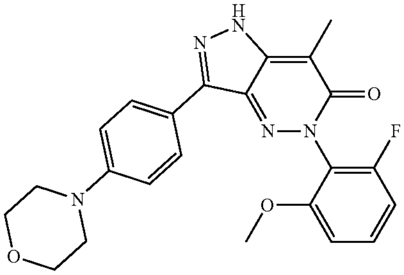 [SMILES: COc1cccc(F)c1-n1nc2c(-c3ccc(N4CCOCC4)cc3)n[nH]c2c(C)c1=O] | ESI-MS: 436.2 [M + H]$^+$ $^1$H NMR (400 MHz, DMSO-$d_6$) δ 12.88 (s, 1H), 7.99 (d, J = 8.8 Hz, 2H), 7.58-7.51 (m, 1H), 7.13-7.02 (m, 4H), 3.77 (s, 3H), 3.76-3.70 (m, 4H), 3.20-3.14 (m, 4H), 2.26 (s, 3H). | 3A |

-continued

| Example | Compound | Structural Formula | Spectrum Data | Synthetic Scheme |
|---|---|---|---|---|
| Example 123 | Compound 156 | 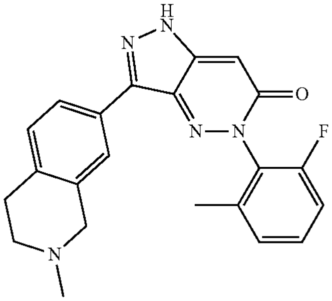 [SMILES: Cc1cccc(F)c1-n1nc2c(-c3ccc4c(c3)CN(C)CC4)n[nH]c2cc1=O] | ESI-MS: 390.3 $[M + H]^+$ $^1H$ NMR (400 MHz, DMSO-$d_6$) δ 13.11 (s, 1H), 7.93 (d, J = 8.1 Hz, 1H), 7.81 (s, 1H), 7.54-7.44 (m, 1H), 7.35-7.23 (m, 3H), 6.76 (s, 1H), 3.91 (br, 2H), 2.97 (br, 4H), 2.58 (s, 3H), 2.10 (s, 3H). | 2A |
| Example 124 | Compound 157 | 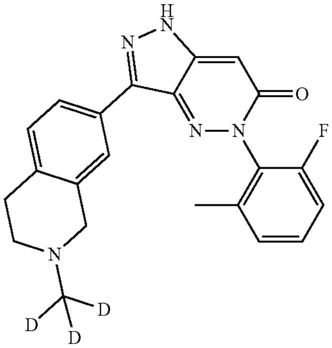 [SMILES: [2H]C([2H])([2H])N1CCc2ccc(-c3n[nH]c4cc(=O)n(-c5c(C)cccc5F)nc34)cc2C1] | ESI-MS: 393.2 $[M + H]^+$ $^1HNMR$ (400 MHz, DMSO-$d_6$) δ 13.02 (s, 1H), 7.87 (dd, J = 8.0, 1.4 Hz, 1H), 7.76 (s, 1H), 7.52-7.46 (m, 1H), 7.32-7.26 (m, 2H), 7.22 (d, J = 8.0 Hz, 1H), 6.74 (s, 1H), 3.52 (br, 2H), 2.83 (t, J = 5.7 Hz, 2H), 2.61 (d, J = 5.7 Hz, 2H), 2.10 (s, 3H). | 2A |
| Example 125 | Compound 158 | 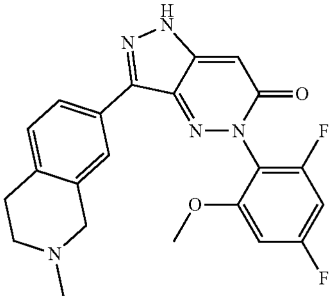 [SMILES: COc1cc(F)cc(F)c1-n1nc2c(-c3ccc4c(c3)CN(C)CC4)n[nH]c2cc1=O] | ESI-MS: 424.2 $[M + H]^+$ $^1H$ NMR (400 MHz, DMSO-$d_6$) δ 13.05 (s, 1H), 7.85 (dd, J = 8.0, 1.5 Hz, 1H), 7.75 (s, 1H), 7.23 (d, J = 8.0 Hz, 1H), 7.17 - 7.09 (m, 2H), 6.69 (s, 1H), 3.80 (s, 3H), 3.52 (s, 2H), 2.84 (t, J = 5.8 Hz, 2H), 2.60 (t, J = 5.9 Hz, 2H), 2.34 (s, 3H). | 2A |
| Example 126 | Compound 159 | 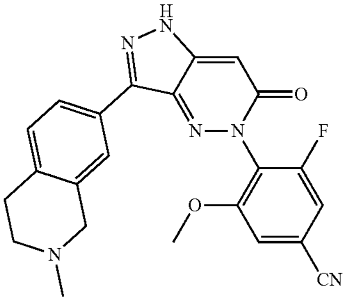 [SMILES: COc1cc(C#N)cc(F)c1-n1nc2c(-c3ccc4c(c3)CN(C)CC4)n[nH]c2cc1=O] | ESI-MS: 431.1 $[M + H]^+$ $^1H$ NMR (400 MHz, DMSO-$d_6$) δ 13.07 (s, 1H), 7.84 (dd, J = 8.0, 1.8 Hz, 1H), 7.79 (dd, J = 9.0, 1.3 Hz, 1H), 7.76 - 7.72 (m, 2H), 7.22 (d, J = 8.0 Hz, 1H), 6.73 (s, 1H), 3.87 (s, 3H), 3.52 (s, 2H), 2.84 (t, J = 5.9 Hz, 2H), 2.61 (t, J = 5.9 Hz, 2H), 2.34 (s, 3H). | 2B |
| Example 127 | Compound 160 | 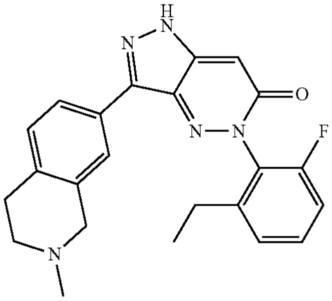 [SMILES: CCc1cccc(F)c1-n1nc2c(-c3ccc4c(c3)CN(C)CC4)n[nH]c2cc1=O] | ESI-MS: 404.3 $[M + H]^+$ $^1H$ NMR (400 MHz, DMSO-$d_6$) δ 13.05 (s, 1H), 7.87 (dd, J = 8.0, 1.6 Hz, 1H), 7.77 (s, 1H), 7.57-7.51 (m, 1H), 7.34-7.28 (m, 2H), 7.22 (d, J = 8.0 Hz, 1H), 6.73 (s, 1H), 3.50 (s, 2H), 2.83 (t, J = 5.6 Hz, 2H), 2.59 (t, J =6.0 Hz, 2H), 2.47-2.36 (m, 2H), 2.33 (s, 3H), 1.07 (t, J = 7.6 Hz, 3H). | 2A |

-continued

| Example | Compound | Structural Formula | Spectrum Data | Synthetic Scheme |
|---|---|---|---|---|
| Example 128 | Compound 161 | 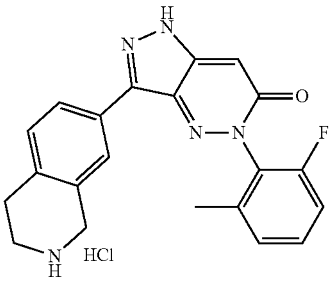 [SMILES: Cc1cccc(F)c1-n1nc2c(-c3ccc4c(c3)CNCC4)n[nH]c2cc1=O ; Cl] | ESI-MS: 376.3 $[M + H]^+$ $^1H$ NMR (400 MHz, DMSO-$d_6$) δ 13.19 (s, 1H), 9.25 (s, 2H), 8.00 (dd, J = 8.0, 1.5 Hz, 1H), 7.94-7.91 (m, 1H), 7.54-7.46 (m, 1H), 7.36 (d, J = 8.1 Hz, 1H), 7.33-7.27 (m, 2H), 6.78 (s, 1H), 4.33 (t, J = 4.0 Hz, 2H), 3.41-3.33 (m, 2H), 3.03 (t, J = 6.2 Hz, 2H), 2.10 (s, 3H). | 2A |
| Example 129 | Compound 162 | 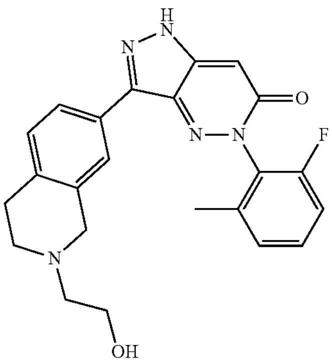 [SMILES: Cc1cccc(F)c1-n1nc2c(-c3ccc4c(c3)CN(CCO)CC4)n[nH]c2cc1=O] | ESI-MS: 420.2 $[M + H]^+$ $^1H$ NMR (400 MHz, DMSO-d6) δ 13.04 (s, 1H), 7.91-7.83 (m, 1H), 7.75 (s, 1H), 7.54-7.45 (m, 1H), 7.36-7.26 (m, 2H), 7.21 (d, J = 8.0 Hz, 1H), 6.74(s, 1H), 4.44 (t, J = 5.2 Hz, 1H), 3.63 (s, 2H), 3.58 (q, J = 5.7 Hz, 2H), 2.82 (t, J = 5.5 Hz, 2H), 2.71 (t, J = 5.5 Hz, 2H), 2.56 (t, J = 6.2 Hz, 2H), 2.10 (s, 3H). | 2A |
| Example 131 | Compound 163 | 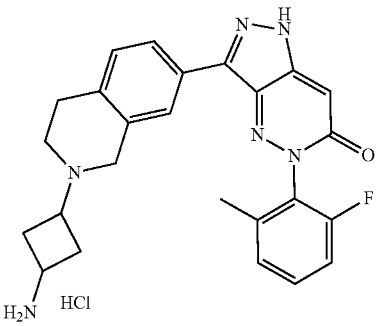 [SMILES: Cc1cccc(F)c1-n1nc2c(-c3ccc4c(c3)CN(C3CC(N)C3)CC4)n[nH]c2cc1=O ; Cl] | ESI-MS: 445.3 $[M + H]^+$ $^1H$ NMR (400 MHz, DMSO-$d_6$) δ 13.22 (s, 1H), 11.70 (br, 1H), 8.41 (br, 3H), 8.02 (d, J = 8.2 Hz, 1H), 7.92 (s, 1H), 7.54-7.45 (m, 1H), 7.39 (d, J = 8.1 Hz, 1H), 7.35 - 7.25 (m, 2H), 6.78 (s, 1H), 4.66-4.54 (m, 1H), 4.30-4.18 (m, 1H), 3.77-3.58 (m, 2H), 3.33-3.16 (m, 2H), 3.13-3.01 (m, 1H), 2.78-2.60 (m, 4H), 2.11-2.09 (m, 3H). | 2A |
| Example 132 | Compound 164 | 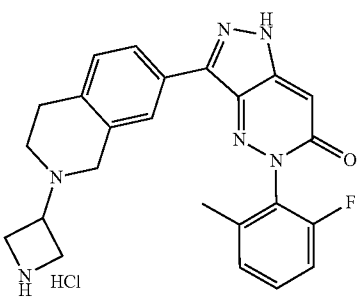 [SMILES: Cc1cccc(F)c1-n1nc2c(-c3ccc4c(c3)CN(C3CNC3)CC4)n[nH]c2cc1=O ; Cl] | ESI-MS: 431.3 $[M + H]^+$ $^1H$ NMR (400 MHz, DMSO-$d_6$) δ 13.21 (s, 1H), 12.80 (br, 1H), 9.63 (s, 1H), 9.17 (s, 1H), 8.01 (d, J = 8.0 Hz, 1H), 7.85 (s, 1H), 7.54 -7.45 (m, 1H), 7.38 (d, J = 8.2 Hz, 1H), 7.34-7.26 (m, 2H), 6.77 (s, 1H), 4.84-4.08 (m, 8H), 3.32-3.04 (m, 3H), 2.10 (s, 3H). | 2A |

-continued

| Example | Compound | Structural Formula | Spectrum Data | Synthetic Scheme |
|---|---|---|---|---|
| Example 133 | Compound 165 | 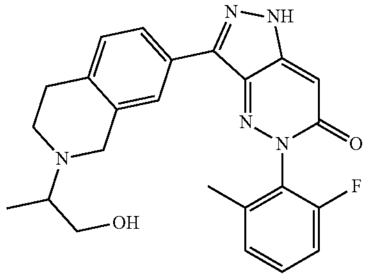 [SMILES: Cc1cccc(F)c1-n1nc2c(-c3ccc4c(c3)CN(C(C)CO)CC4)n[nH]c2cc1=O] | ESI-MS: 434.3 [M + H]+ $^1$H NMR (400 MHz, DMSO-$d_6$) δ 13.02 (s, 1H), 7.85 (d, J = 8.0 Hz, 1H), 7.76 (s, 1H), 7.52-7.46 (m, 1H), 7.32-7.27 (m, 2H), 7.20 (d, J = 8.0 Hz, 1H), 6.73 (s, 1H), 4.31 (s, 1H), 3.82-3.69 (m, 2H), 3.58-3.48 (m, 1H), 3.40-3.30 (m, 1H), 2.90-2.60 (m, 5H), 2.10 (s, 3H), 1.00 (d, J = 6.4 Hz, 3H). | 2A |
| Example 134 | Compound 166 | 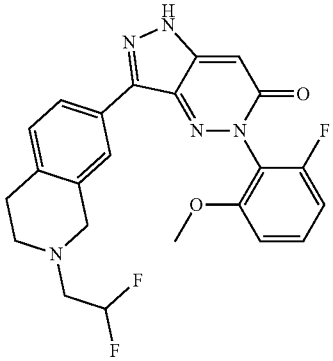 [SMILES: COc1cccc(F)c1-n1nc2c(-c3ccc4c(c3)CN(CC(F)F)CC4)n[nH]c2cc1=O] | ESI-MS: 456.2 [M + H]+ $^1$H NMR (400 MHz, DMSO-$d_6$) δ 13.01 (s, 1H), 7.87 (dd, J = 8.0, 1.5 Hz, 1H), 7.74 (d, J = 1.3 Hz, 1H), 7.60-7.52 (m, 1H), 7.23 (d, J = 8.0 Hz, 1H), 7.13 (d, J = 8.6 Hz, 1H), 7.10-7.03 (m, 1H), 6.69 (s, 1H), 6.22 (tt, J = 55.7, 4.3 Hz, 1H), 3.78 (s, 3H), 3.76 (s, 2H), 2.91 (td, J = 15.6, 4.3 Hz, 2H), 2.84 (s, 4H). | 2A |
| Example 135 | Compound 167 | 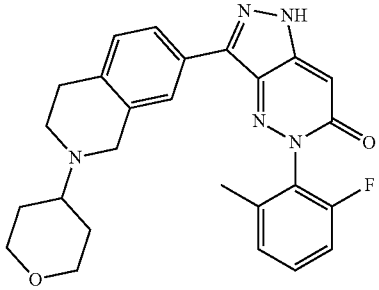 [SMILES: Cc1cccc(F)c1-n1nc2c(-c3ccc4c(c3)CN(C3CCOCC3)CC4)n[nH]c2cc1=O] | ESI-MS: 460.4 [M + H]+ $^1$H NMR (400 MHz, DMSO-$d_6$) δ 13.06 (s, 1H), 7.86 (dd, J = 8.0, 1.6 Hz, 1H), 7.77 (s, 1H), 7.52-7.47 (m, 1H), 7.32-7.28 (m, 2H), 7.21 (d, J = 8.0 Hz, 1H), 6.74 (s, 1H), 3.91 (dd, J = 10.8, 3.2 Hz, 2H), 3.74 (s, 2H), 3.32-3.26 (m, 2H), 2.84-2.74 (m, 2H), 2.67-2.56 (m, 1H), 2.10 (s, 3H), 1.76 (d, J = 12.0 Hz, 2H), 1.56-1.46 (m, 2H) | 2A |
| Example 136 | Compound 168 | 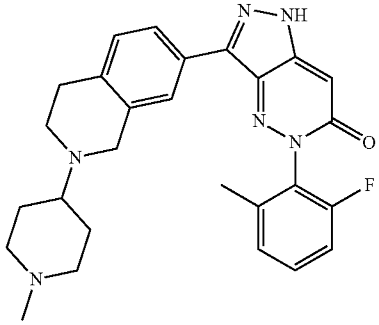 [SMILES: Cc1cccc(F)c1-n1nc2c(-c3ccc4c(c3)CN(C3CCN(C)CC3)CC4)n[nH]c2cc1=O] | ESI-MS: 473.4 [M + H]+ $^1$H NMR (400 MHz, DMSO-$d_6$) δ 13.12 (br, 1H), 7.86 (dd, J = 7.6, 1.6 Hz, 1H), 7.76 (s, 1H), 7.52-7.47 (m, 1H), 7.32-7.28 (m, 2H), 7.20 (d, J = 8.0 Hz, 1H), 6.74 (s, 1H), 3.72 (s, 2H), 2.87 (d, J = 10.4 Hz, 2H), 2.82-2.72 (m, 4H), 2.42-2.36 (m, 1H), 2.21 (s, 1H), 2.10 (s, 1H), 2.04-1.94 (m. 2H), 1.79 (d, J = 11.6 Hz, 2H), 1.60-1.51 (m, 2H). | 2A |

-continued

| Example | Compound | Structural Formula | Spectrum Data | Synthetic Scheme |
|---|---|---|---|---|
| Example 137 | Compound 169 | 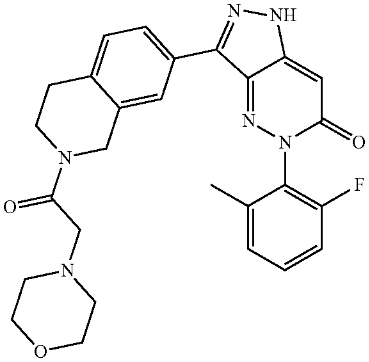 [SMILES: Cc1cccc(F)c1-n1nc2c(-c3ccc4c(c3)CN(C(=O)CN3CCOCC3)CC4)n[nH]c2cc1=O] | ESI-MS: 503.4 [M + H]+ $^1$H NMR (400 MHz, DMSO-$d_6$) δ 13.12 (s, 1H), 7.94-7.88 (m, 2H), 7.51-7.48 (m, 1H), 7.32-7.28 (m, 3H), 6.77 (s, 0.4H), 6.76 (s, 0.6H), 4.81 (s, 0.8H), 4.63 (s, 1.2H), 3.79-3.74 (m, 1.2H), 3.67 (t, J = 4.0 Hz, 0.8H), 3.58-3.54 (m, 2.4H), 3.40-3.36 (m, 1.6H), 3.25-3.23 (m, 1H), 2.92 (t, J = 3.6 Hz, 1.2H), 2.80 (t, J = 3.6 Hz, 0.8H), 2.4 (s, 2.4H), 2.34 (s, 1.6H), 2.11 (s, 3H). | 2A |
| Example 138 | Compound 170 | 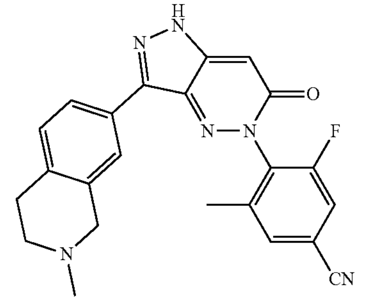 [SMILES: Cc1cc(C#N)cc(F)c1-n1nc2c(-c3ccc4c(c3)CN(C)CC4)n[nH]c2cc1=O] | ESI-MS: 415.3 [M + H]+ $^1$H NMR (400 MHz, DMSO-$d_6$) δ 13.12 (s, 1H), 8.02 (d, J = 8.8 Hz, 1H), 7.90 (s, 1H), 7.86 (d, J = 7.6 Hz, 1H), 7.76 (s, 1H), 7.23 (d, J = 7.6 Hz, 1H), 6.79 (s, 1H), 3.54 (s, 2H), 2.85 (t, J = 5.2 Hz, 2H), 2.63 (t, J = 5.2 Hz, 2H), 2.36 (s, 3H), 2.17 (s, 3H). | 2A |
| Example 139 | Compound 171 | 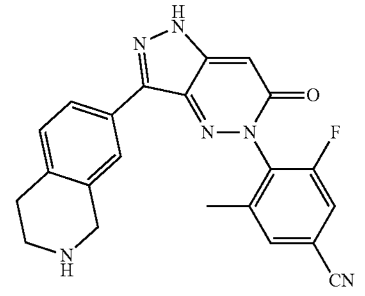 [SMILES: Cc1cc(C#N)cc(F)c1-n1nc2c(-c3ccc4c(c3)CNCC4)n[nH]c2cc1=O] | ESI-MS: 401.3 [M + H]+ $^1$H NMR (400 MHz, DMSO-$d_6$) δ 8.01 (d, J = 8.8 Hz, 1H), 7.89 (s, 1H), 7.85 (d, J = 7.6 Hz, 1H), 7.75 (s, 1H), 7.19 (d, J = 8.0 Hz, 1H), 6.78 (s, 1H), 3.92 (s, 2H), 3.00 (t, J = 5.6 Hz, 2H), 2.75 (t, J = 5.6 Hz, 2H), 2.17 (s, 3H). | 2A |
| Example 140 | Compound 172 | 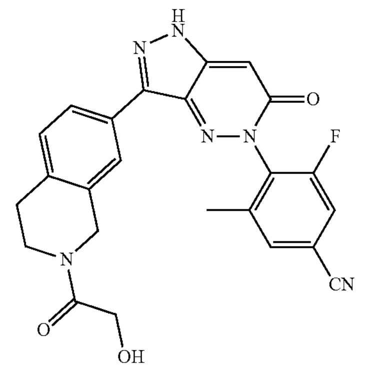 [SMILES: Cc1cc(C#N)cc(F)c1-n1nc2c(-c3ccc4c(c3)CN(C(=O)CO)CC4)n[nH]c2cc1=O] | ESI-MS: 459.3 [M + H]+ $^1$H NMR (400 MHz, DMSO-$d_6$) δ 13.15 (s, 1H), 8.01 (d, J = 9.2 Hz, 1H), 7.92-7.87 (m, 3H), 7.30 (d, J = 8.0 Hz, 1H), 6.80 (s, 1H), 4.68-4.55 (m, 3H), 4.19-4.16 (m, 2H), 3.74-3.66 (m, 0.8H), 3.62-3.58 (m, 1.2H), 2.90-2.81 (m, 2H), 2.18 (s, 3H). | 2B |

-continued

| Example | Compound | Structural Formula | Spectrum Data | Synthetic Scheme |
|---|---|---|---|---|
| Example 141 | Compound 173 | 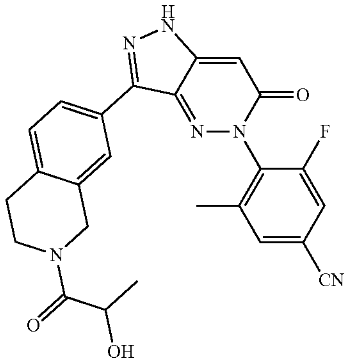 [SMILES: Cc1cc(C#N)cc(F)c1-n1nc2c(-c3ccc4c(c3)CN(C(=O)C(C)O)CC4)n[nH]c2cc1=O] | ESI-MS: 473.3 $[M + H]^+$ $^1H$ NMR (400 MHz, DMSO-$d_6$) δ 13.14 (s, 1H), 8.01 (d, J = 9.5 Hz, 1H), 7.93-7.89 (m, 3H), 7.30 (d, J = 7.9 Hz, 1H), 6.80 (s, 1H), 5.00-4.90 (m, 1H), 4.88-4.58 (m, 3H), 4.56-4.46 (m, 1H), 3.82-3.61 (m, 2H), 2.90-2.80 (m, 2H), 2.18 (s, 3H), 1.23-1.16 (m, 3H). | 2B |
| Example 142 | Compound 174 | 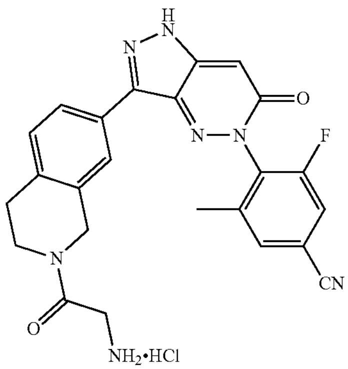 | ESI-MS: 458.3 $[M + H - HCl]^+$ $^1H$ NMR (400 MHz, DMSO-$d_6$) δ 13.19 (br, 1H), 8.10 (br, 3H), 8.02 (d, J = 9.2 Hz, 1H), 7.96-7.91 (m, 3H), 7.36-7.31 (m, 1H), 6.82-6.79 (m, 1H),4.71-4.68 (m, 2H), 3.98-3.95 (m, 2H), 3.74 (t, J = 6.0 Hz, 0.9H), 3.64 (t, J = 6.0 Hz, 1.1H), 2.94 (t, J = 6.0 Hz, 1.1H), 2.84 (t, J = 6.0 Hz, 0.9H), 2.18 (s, 3H). | 2B |
| Example 143 | Compound 175 | 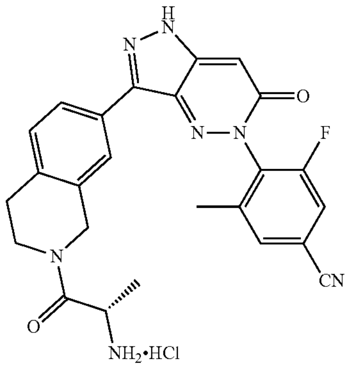 | ESI-MS: 472.3 $[M + H - HCl]^+$ $^1H$ NMR (400 MHz, DMSO-$d_6$) δ 13.22 (br, 1H), 8.19 (br, 3H), 8.02 (d, J = 9.2 Hz, 1H), 7.96-7.90 (m, 3H), 7.34-7.31 (m, 1H), 6.82-6.79 (m, 1H), 4.89-4.38 (m, 3H), 3.92-3.76 (m, 1H), 3.74-3.58 (m, 1H), 2.96-2.90 (m, 1H), 2.88-2.83 (m, 1H), 2.18 (s, 3H), 1.38-1.30 (m, 3H). | 2B |
| Example 144 | Compound 176 | 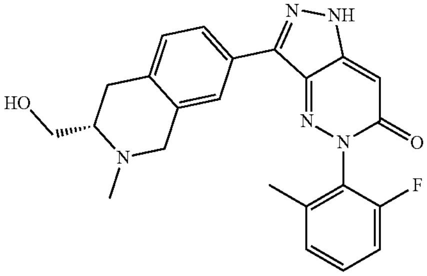 [SMILES: Cc1cccc(F)c1-n1nc2c(-c3ccc4c(c3)CN(C)[C@H](CO)C4)n[nH]c2cc1=O] | ESI-MS: 420.2 $[M + H]^+$ $^1H$ NMR (400 MHz, DMSO-$d_6$) δ 13.07 (s, 1H), 7.89 (d, J = 8.0 Hz, 1H), 7.77 (s, 1H), 7.50(td, J = 8.1,5.6 Hz, 1H), 7.34-7.27 (m, 2H), 7.24 (d, J = 8.0 Hz, 1H), 6.74 (s, 1H), 4.64 (br, 1H), 3.83 (d, J = 15.8 Hz, 1H), 3.66-3.54 (m, 2H), 3.48-3.38 (m, 1H), 2.88-2.69 (m, 2H), 2.68-2.56 (m, 1H), 2.40 (s, 3H), 2.10 (s, 3H). | 2A |

-continued

| Example | Compound | Structural Formula | Spectrum Data | Synthetic Scheme |
|---|---|---|---|---|
| Example 145 | Compound 177 | 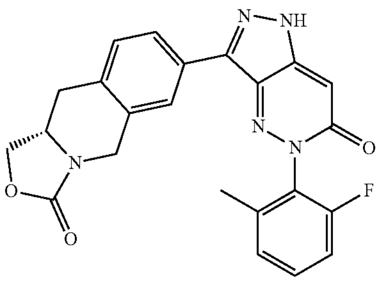 [SMILES: Cc1cccc(F)c1-n1nc2c(-c3ccc4c(c3)CN3C(=O)OC[C@@H]3C4)n[nH]c2cc1=O] | ESI-MS: 432.2 $[M+H]^+$ $^1$H NMR (400 MHz, DMSO-$d_6$) δ 13.09 (br, 1H), 8.00-7.88 (m, 2H), 7.53-7.46 (m, 1H), 7.38-7.23 (m, 3H), 6.76 (s, 1H), 4.67 (d, J = 17.0 Hz, 1H), 4.54( t, J = 8.2 Hz, 1H), 4.40 (d, J = 17.0 Hz, 1H), 4.14 (dd, J = 8.6, 5.2 Hz, 1H), 4.08-3.92 (m, 1H), 2.99 (dd, J = 16.0, 4.0 Hz, 1H), 2.81 (dd, J = 15.9, 10.9 Hz, 1H), 2.12-2.10 (m, 3H). | 2A |
| Example 146 | Compound 178 | 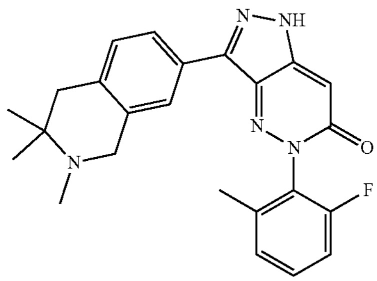 [SMILES: Cc1cccc(F)c1-n1nc2c(-c3ccc4c(c3)CN(C)C(C)(C)C4)n[nH]c2cc1=O] | ESI-MS: 418.2 $[M+H]^+$ $^1$HNMR (400 MHz, DMSO-$d_6$) δ 13.07 (s, 1H), 7.88 (d, J = 7.7 Hz, 1H), 7.78 (s, 1H), 7.53-7.46 (m, 1H), 7.33-7.26 (m, 2H), 7.19 (d, J = 8.0 Hz, 1H), 6.74 (s, 1H), 3.67 (br, 2H), 2.67 (br, 2H), 2.27 (br, 3H), 1.02 (s, 6H). | 2A |
| Example 147 | Compound 179 | 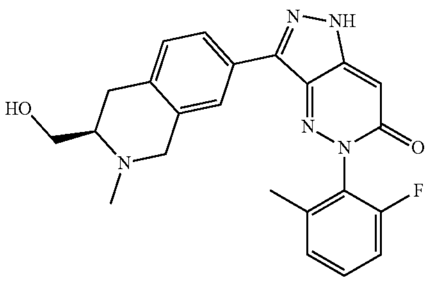 [SMILES: Cc1cccc(F)c1-n1nc2c(-c3ccc4c(c3)CN(C)[C@@H](CO)C4)n[nH]c2cc1=O] | ESI-MS: 420.2 $[M+H]^+$ $^1$HNMR (400 MHz, DMSO-$d_6$) δ 13.03 (s, 1H), 7.88 (d, J = 8.0 Hz, 1H), 7.76 (s, 1H), 7.53-7.45 (m, 1H), 7.34-7.26 (m, 2H), 7.23 (d, J = 8.1 Hz, 1H), 6.74 (s,1H), 4.60-4.52 (m, 1H), 3.78 (d, J = 15.7 Hz, 1H), 3.64-3.48 (m, 2H), 3.44-3.35 (m, 1H), 2.85-2.67 (m, 2H), 2.60-2.50 (m, 1H), 2.36 (s, 3H), 2.10 (s, 3H). | 2A |
| Example 148 | Compound 180 | 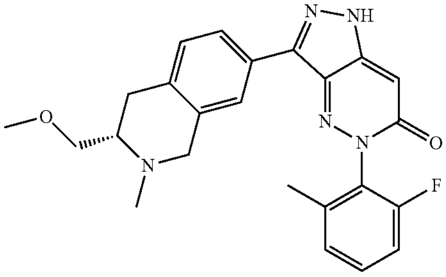 [SMILES: COC[C@@H]1Cc2ccc(-c3n[nH]c4cc(=O)n(-c5c(C)cccc5F)nc34)cc2CN1C] | ESI-MS: 434.2 $[M+H]^+$ | 2A |
| Example 149 | Compound 181 | 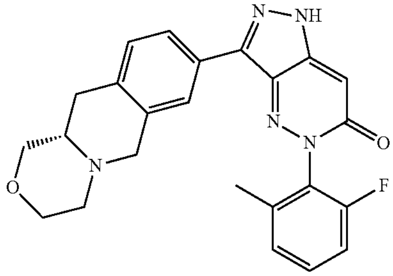 [SMILES: Cc1cccc(F)c1-n1nc2c(-c3ccc4c(c3)CN3CCOC[C@@H]3C4)n[nH]c2cc1=O] | ESI-MS: 432.2 $[M+H]^+$ $^1$H NMR (400 MHz, DMSO-$d_6$) δ 13.03 (s, 1H), 7.90-7.86 (m, 1H), 7.78 (s, 1H), 7.52-7.46 (m, 1H), 7.32-7.26 (m, 2H), 7.21 (d, J = 8.0 Hz, 1H), 6.74 (s, 1H), 3.88-3.77 (m, 3H), 3.61-3.53 (m, 1H), 3.36-3.30 (m, 1H), 3.21-3.15 (m, 1H), 2.85 (d, J = 11.6 Hz, 1H), 2.66 (d, J = 12.7 Hz, 1H), 2.46- | 2A |

-continued

| Example | Compound | Structural Formula | Spectrum Data | Synthetic Scheme |
|---|---|---|---|---|
| | | | 2.40 (m, 2H), 2.32-2.24 (m, 1H), 2.11-2.09 (m, 3H). | |
| Example 150 | Compound 182 | 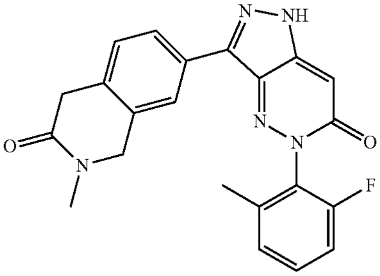 [SMILES: Cc1cccc(F)c1-n1nc2c(-c3ccc4c(c3)CN(C)C(=O)C4)n[nH]c2cc1=O] | ESI-MS: 404.2 $[M + H]^+$ $^1H$ NMR (400 MHz, DMSO-$d_6$) δ 13.12 (s, 1H), 8.01-7.96 (m, 2H),7.53-7.46 (m, 1H), 7.36-7.26 (m, 2H), 6.77 (s, 1H), 4.56 (s, 2H), 3.56 (s, 2H), 2.96 (s, 3H), 2.11 (s, 3H). | 2A |
| Example 151 | Compound 183 | 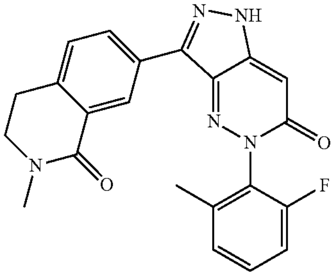 [SMILES: Cc1cccc(F)c1-n1nc2c(-c3ccc4c(c3)C(=O)N(C)CC4)n[nH]c2cc1=O] | ESI-MS: 404.2 $[M + H]^+$ $^1H$ NMR (400 MHz, DMSO-$d_6$) δ 13.15 (s, 1H), 8.64 (d, J = 1.9 Hz, 1H), 8.17 (dd, J = 7.9, 1.8 Hz, 1H), 7.55-7.46 (m, 1H), 7.42 (d, J = 8.0 Hz, 1H), 7.36-7.26 (m, 2H), 6.78 (s, 1H), 3.56 (t, J = 6.6 Hz, 2H), 3.07-2.98 (m, 5H), 2.12 (s, 3H). | 2A |
| Example 152 | Compound 184 | 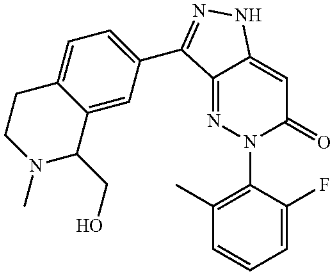 [SMILES: Cc1cccc(F)c1-n1nc2c(-c3ccc4c(c3)C(CO)N(C)CC4)n[nH]c2cc1=O] | ESI-MS: 420.2 $[M + H]^+$ $^1H$ NMR (400 MHz, DMSO-$d_6$) δ 13.04 (s, 1H), 7.98 (d, J = 11.2 Hz, 1H), 7.86 (d, J = 7.9 Hz, 1H), 7.49 (q, J = 7.6 Hz, 1H), 7.34-7.26 (m, 2H), 7.20 (d, J = 8.0 Hz, 1H), 6.74 (s, 1H), 4.47 (br, 1H), 3.68-3.60 (m, 1H), 3.58-3.46 (m, 2H), 3.10-3.00 (m, 1H), 2.85-2.75 (m, 1H), 2.74-2.64 (m, 1H), 2.64-2.55 (m, 1H), 2.45 (s, 3H), 2.11-2.09 (m, 3H). | 2A |
| Example 153 | Compound 185 | 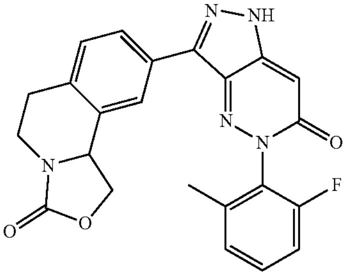 [SMILES: Cc1cccc(F)c1-n1nc2c(-c3ccc4c(c3)C3COC(=O)N3CC4)n[nH]c2cc1=O] | ESI-MS: 432.2 $[M + H]^+$ $^1H$ NMR (400 MHz, DMSO-$d_6$) δ 13.38 (s, 1H), 7.97 (d, J = 8.0 Hz, 1H), 7.88 (s, 1H), 7.54-7.46 (m,1H), 7.35-7.25 (m, 3H), 6.77 (s, 1H), 5.20-5.06 (m, 1H), 4.85 (td, J = 8.5, 3.4 Hz, 1H), 4.20-4.16 (m, 1H), 3.89-3.71 (m, 1H), 3.31-3.21 (m, 1H), 2.96-2.86 (m, 1H), 2.82-2.72 (m, 1H), 2.12-2.08 (m, 3H). | 2A |

-continued

| Example | Compound | Structural Formula | Spectrum Data | Synthetic Scheme |
| --- | --- | --- | --- | --- |
| Example 154 | Compound 186 | 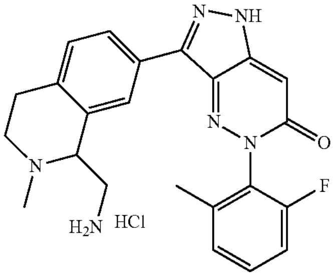 [SMILES: Cc1cccc(F)c1-n1nc2c(-c3ccc4c(c3)C(CN)N(C)CC4)n[nH]c2cc1=O ; Cl] | ESI-MS: 419.2 $[M + H - HCl]^+$ 1H NMR (700 MHz, DMSO-$d_6$) δ 13.29 (s, 1H), 11.76 (br, 1H), 8.58 (br, 3H), 8.15-7.95 (m, 2H), 7.53-7.38 (m, 2H), 7.33-7.23 (m, 2H), 6.79 (s, 1H), 3.90-3.60 (m, 3H), 3.30-3.00 (m, 4H), 3.00-2.70 (m, 3H), 2.13-2.08 (m, 3H). | 2A |
| Example 155 | Compound 187 | 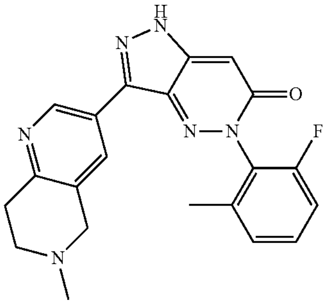 [SMILES: Cc1cccc(F)c1-n1nc2c(-c3cnc4c(c3)CN(C)CC4)n[nH]c2cc1=O] | ESI-MS: 391.2 $[M + H]^+$ $^1$H NMR (700 MHz, DMSO-$d_6$) δ 13.22 (s, 1H), 9.04 (s, 1H), 8.05 (s, 1H), 7.52-7.48 (m, 1H), 7.32-7.28 (m, 2H), 6.80 (s, 1H), 3.57 (s, 2H), 2.93 (t, J = 5.5 Hz, 2H), 2.71 (t, J = 5.6 Hz, 2H), 2.36 (s, 3H), 2.11 (s, 3H). | 2A |
| Example 156 | Compound 188 | 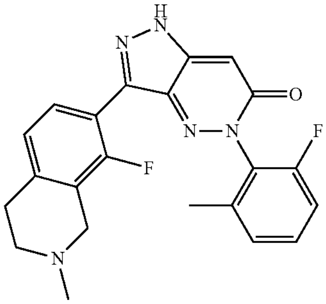 [SMILES: Cc1cccc(F)c1-n1nc2c(-c3ccc4c(c3F)CN(C)CC4)n[nH]c2cc1=O] | ESI-MS: 408.1[M + H]+ $^1$H NMR (400 MHz, DMSO-$d_6$) δ 13.20 (s, 1H), 7.66 (t, J = 7.6 Hz, 1H), 7.50-7.44 (m, 1H), 7.29-7.25 (m, 1H), 7.10 (d, J = 8.0 Hz, 1H), 6.77 (s, 1H), 3.53 (s, 2H), 2.86 (t, J = 5.6 Hz, 2H), 2.60 (t, J = 5.6 Hz, 2H), 2.38 (s, 3H), 2.07 (s, 3H). | 2A |
| Example 157 | Compound 189 | 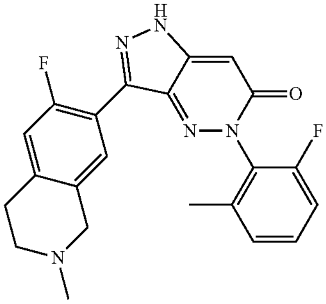 [SMILES: Cc1cccc(F)c1-n1nc2c(-c3cc4c(cc3F)CCN(C)C4)n[nH]c2cc1=O] | ESI-MS: 408.1 $[M + H]^+$ $^1$H NMR (400 MHz, DMSO-$d_6$) δ 13.24 (s, 1H), 7.56 (d, J = 7.1 Hz, 1H), 7.51-7.43 (m, 1H), 7.31-7.23 (m, 2H), 7.18 (d, J = 11.1 Hz, 1H), 6.78 (s,1H), 3.76 (s, 2H), 3.00-2.80 (m, 4H), 2.51 (s, 3H), 2.07 (s, 3H). | 2A |
| Example 158 | Compound 190 | 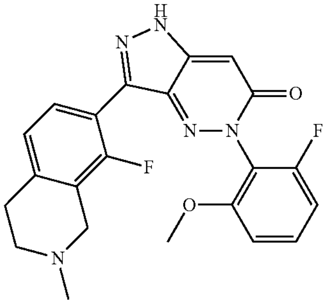 [SMILES: COc1cccc(F)c1-n1nc2c(-c3ccc4c(c3F)CN(C)CC4)n[nH]c2cc1=O] | ESI-MS: 424.2 $[M + H]^+$ $^1$H NMR (400 MHz, DMSO-$d_6$) δ 13.15 (s, 1H), 7.65 (t, J = 7.6 Hz, 1H), 7.57-7.51 (m, 1H), 7.11-7.08 (m, 2H), 7.04 (t, J = 8.4 Hz, 1H), 6.71 (s, 1H), 3.76 (s, 3H), 3.52 (s, 2H), 2.86 (t, J = 5.6 Hz, 2H), 2.60 (t, J = 5.6 Hz, 2H), 2.38 (s, 3H). | 2A |

-continued

| Example | Compound | Structural Formula | Spectrum Data | Synthetic Scheme |
|---|---|---|---|---|
| Example 159 | Compound 191 | 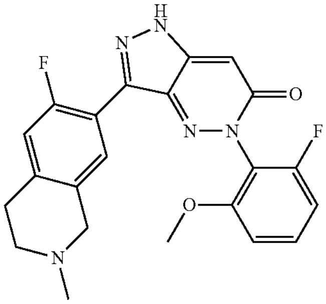 | ESI-MS: 410.1[M + H]+ $^1$H NMR (400 MHz, DMSO-$d_6$) δ 13.14 (s, 1H), 7.60-7.46 (m, 2H), 7.15-7.07 (m, 2H), 7.03 (t, J = 8.8 Hz, 1H), 6.71 (s, 1H), 3.77 (s, 3H), 3.46 (s, 2H), 2.85 (t, J = 5.7 Hz, 2H), 2.58 (t, J = 5.9 Hz, 2H), 2.32 (s, 3H). | 2A |
| Example 160 | Compound 193 | 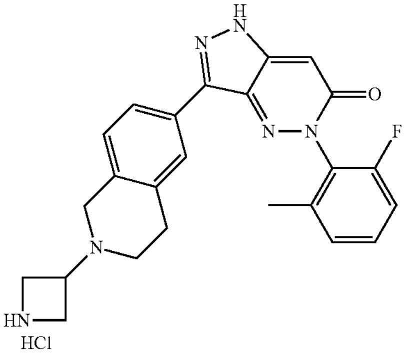 [SMILES: Cc1cccc(F)c1-n1nc2c(-c3ccc4c(c3)CCN(C3CNC3)C4)n[nH]c2cc1=O ; Cl] | ESI-MS: 431.3 [M + H]+ $^1$H NMR (400 MHz, DMSO-$d_6$) δ 13.22 (s, 1H), 12.92 (br, 1H), 9.71 (s, 1H), 9.19 (s, 1H), 8.02-7.97 (m, 1H), 7.95 (s, 1H), 7.53-7.46 (m, 1H), 7.34-7.26 (m, 3H), 6.77 (s, 1H), 4.76 -3.98 (m, 8H), 3.17 (br, 3H), 2.11 (s, 3H). | 2A |
| Example 161 | Compound 194 | 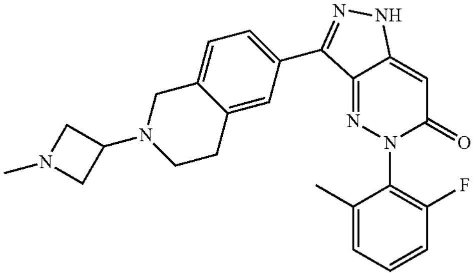 [SMILES: Cc1cccc(F)c1-n1nc2c(-c3ccc4c(c3)CCN(C3CN(C)C3)C4)n[nH]c2cc1=O] | ESI-MS: 445.3[M + H]+ $^1$H NMR (700 MHz, DMSO-$d_6$) δ 13.06 (br, 1H), 7.86 (d, J = 8.0 Hz, 1H), 7.83 (s, 1H), 7.53-7.45(m, 1H), 7.34-7.27 (m, 2H), 7.17 (d, J = 8.0 Hz, 1H), 6.74 (s, 1H), 3.46 (t, J = 6.4 Hz, 2H), 3.43 (s, 2H), 3.02-2.97 (m, 1H), 2.86-2.79 (m, 4H), 2.50-2.48 (m, 2H), 2.23 (s, 3H), 2.10 (s, 3H). | 2A |
| Example 162 | Compound 195 | 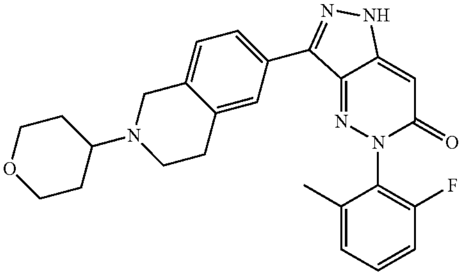 [SMILES: Cc1cccc(F)c1-n1nc2c(-c3ccc4c(c3)CCN(C3CCOCC3)C4)n[nH]c2cc1=O] | ESI-MS: 460.3 [M + H]+ $^1$H NMR (400 MHz, DMSO-$d_6$) δ 13.04 (s, 1H), 7.86 (dd, J = 8.0, 1.4 Hz, 1H), 7.83-7.80 (m, 1H), 7.52-7.46 (m, 1H), 7.34-7.26 (m, 2H), 7.18 (d, J = 8.1 Hz, 1H), 6.74 (s, 1H), 3.91 (dd, J = 11.2, 2.9 Hz, 2H), 3.72 (s, 2H), 3.31-3.26 (m, 2H), 2.85-2.71 (m 4H), 2.64-2.54 (m, 1H), 2.10 (s, 3H), 1.81-1.72 (m, 2H), 1.57-1.43 (m, 2H). | 2A |

-continued

| Example | Compound | Structural Formula | Spectrum Data | Synthetic Scheme |
|---|---|---|---|---|
| Example 163 | Compound 196 | 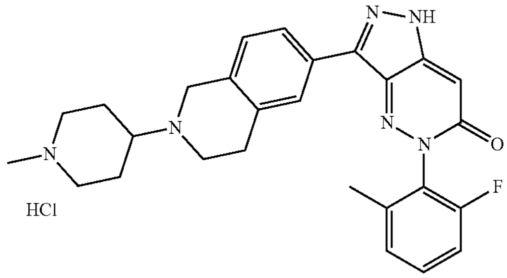 [SMILES: Cc1cccc(F)c1-n1nc2c(-c3ccc4c(c3)CCN(C3CCN(C)CC3)C4)n[nH]c2cc1=O ; Cl] HCl | ESI-MS: 473.3[M + H]+ $^{1}$H NMR (700 MHz, DMSO-d6) δ 13.08 (s, 1H),10.01 (s, 1H), 7.92-7.79 (m, 2H), 7.55-7.44 (m, 1H), 7.34-7.25 (m, 2H), 7.22-7.14 (m, 1H), 6.74 (s, 1H), 3.73 (br, 2H), 3.46-3.34 (m, 4H), 2.89-2.76 (m, 4H), 2.61-2.57 (m, 1H), 2.49 (s, 3H), 2.10 (s, 3H), 2.01 - 1.90 (m, 2H), 1.85-1.62 (m, 2H). | 2A |
| Example 164 | Compound 197 | 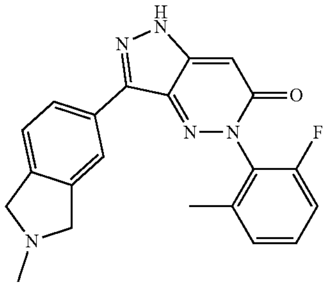 [SMILES: Cc1cccc(F)c1-n1nc2c(-c3ccc4c(c3)CN(C)C4)n[nH]c2cc1=O] | ESI-MS: 376.1 [M + H]+ $^{1}$HNMR (400 MHz, DMSO-$d_6$) δ 13.08 (s, 1H), 8.00-7.96 (m, 1H), 7.95 (s, 1H), 7.52-7.46 (m, 1H), 7.36 (d, J = 8.0 Hz, 1H), 7.33-7.27 (m, 2H), 6.75 (s, 1H), 3.90 (s, 2H), 3.88 (s, 2H), 2.51 (s, 3H), 2.10 (s, 3H). | 2A |
| Example 165 | Compound 198 | 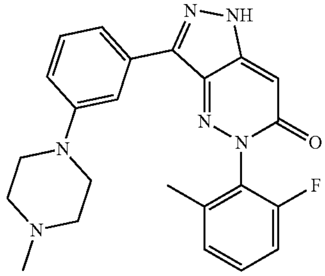 [SMILES: Cc1cccc(F)c1-n1nc2c(-c3cccc(N4CCN(C)CC4)c3)n[nH]c2cc1=O] | ESI-MS: 419.3 [M + H]+ $^{1}$H NMR (700 MHz, DMSO-$d_6$) δ 7.65-7.64 (m, 1H),7.54 (d, J = 7.7 Hz, 1H), 7.51-7.47 (m, 1H), 7.29-7.32 (m, 3H), 7.04 (dd, J = 8.4, 2.1 Hz,1H), 6.74 (s, 1H), 3.16-3.14 (m, 4H), 2.44-2.42 (m, 4H), 2.21 (s, 3H), 2.11 (s, 3H). | 2A |
| Example 166 | Compound 199 | 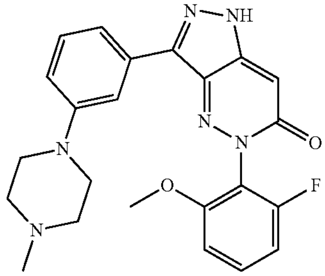 [SMILES: COc1cccc(F)c1-n1nc2c(-c3cccc(N4CCN(C)CC4)c3)n[nH]c2cc1=O] | ESI-MS: 435.2 [M + H]+ $^{1}$H NMR (400 MHz, DMSO-$d_6$) δ 7.66-7.63 (m, 1H), 7.59-7.51 (m, 2H), 7.31 (t, J = 8.0 Hz, 1H), 7.12 (d, J = 8.0 Hz, 1H), 7.08-7.01 (m, 2H), 6.68 (s, 1H), 3.79 (s, 3H), 3.15 (t, J = 4.8 Hz, 4H), 2.44 (t, J = 4.8 Hz, 4H), 2.21 (s, 3H). | 2A |
| Example 167 | Compound 200 | 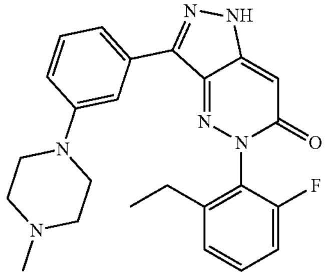 [SMILES: CCc1cccc(F)c1-n1nc2c(-c3cccc(N4CCN(C)CC4)c3)n[nH]c2cc1=O] | ESI-MS: 433.4 [M + H]+ $^{1}$H NMR (400 MHz, DMSO-$d_6$) δ 13.05 (s, 1H),7.65-7.63 (m, 1H), 7.57-7.50 (m, 2H), 7.33-7.28 (m, 3H), 7.04 (dd, J = 8.4, 2.0 Hz, 1H), 6.74 (s, 1H), 3.16-3.11 (m, 4H), 2.47-2.36 (m, 6H), 2.21 (s, 3H), 1.06 (t, J = 7.6 Hz, 3H). | 2A |

-continued

| Example | Compound | Structural Formula | Spectrum Data | Synthetic Scheme |
|---|---|---|---|---|
| Example 168 | Compound 201 | 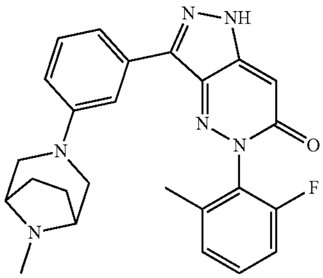 [SMILES: Cc1cccc(F)c1-n1nc2c(-c3cccc(N4CC5CCC(C4)N5C)c3)n[nH]c2cc1=O] | ESI-MS: 445.3 [M + H]$^+$ $^1$H NMR (700 MHz, DMSO-$d_6$) δ 13.06 (br, 1H), 7.52-7.46 (m, 3H), 7.32-7.26 (m, 3H), 6.91 (dd, J = 8.4, 2.1 Hz, 1H), 6.75 (s, 1H), 3.38-3.34 (m, 2H), 3.19 (s, 2H), 2.85 (d, J = 10.5 Hz, 2H), 2.22 (s, 3H), 2.11 (s, 3H), 1.97-1.92 (m, 2H), 1.62-1.59 (m, 2H). | 2A |
| Example 169 | Compound 202 | 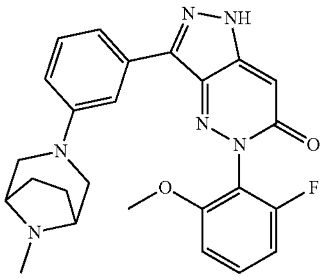 [SMILES: COc1cccc(F)c1-n1nc2c(-c3cccc(N4CC5CCC(C4)N5C)c3)n[nH]c2cc1=O] | ESI-MS: 461.2 [M + H]$^+$ $^1$H NMR (400 MHz, DMSO-$d_6$) δ 13.00 (s, 1H), 7.59-7.50 (m, 2H), 7.47 (d, J = 7.6 Hz, 1H), 7.28 (t, J = 8.0 Hz, 1H), 7.13 (d, J = 8.4 Hz, 1H), 7.06 (t, J = 8.8 Hz, 1H), 6.92 (dd, J = 8.4, 2.1 Hz, 1H), 6.68 (s, 1H), 3.79 (s, 3H), 3.38 (d, J = 10.4 Hz, 2H), 2.90 (d, J = 10.4 Hz, 2H), 2.28 (s, 3H), 2.03 - 1.93 (m, 2H), 1.65-1.63 (m, 2H). | 2A |
| Example 170 | Compound 203 | 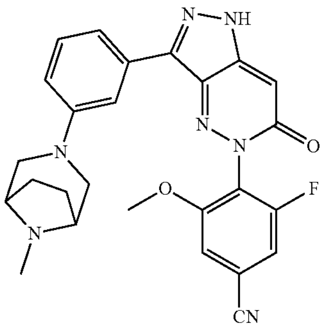 [SMILES: COc1cc(C#N)cc(F)c1-n1nc2c(-c3cccc(N4CC5CCC(C4)N5C)c3)n[nH]c2cc1=O] | ESI-MS: 486.2 [M + H]$^+$ | 2B |
| Example 171 | Compound 204 | 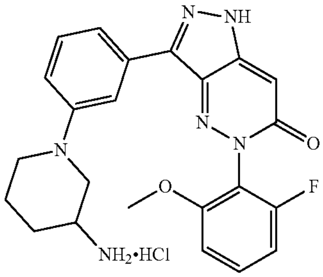 | ESI-MS: 435.2 [M + H]$^+$ $^1$H NMR (400 MHz, DMSO-$d_6$) δ 13.15 (s, 1H), 8.26 (s, 3H), 7.67 (s, 1H), 7.64 - 7.51 (m, 2H), 7.36 (t, J = 8.0 Hz, 1H), 7.15 - 7.03 (m, 3H), 6.71 (s, 1H), 3.79 (s, 3H), 3.71-3.62 (m, 1H), 3.43-3.27 (m, 2H), 3.12-3.02 (m, 1H), 3.00-2.90 (m, 1H), 2.02-1.92 (m, 1H), 1.88-1.78 (m, 1H), 1.70-1.54 (m, 2H). | 2A |

-continued

| Example | Compound | Structural Formula | Spectrum Data | Synthetic Scheme |
|---|---|---|---|---|
| Example 172 | Compound 205 | 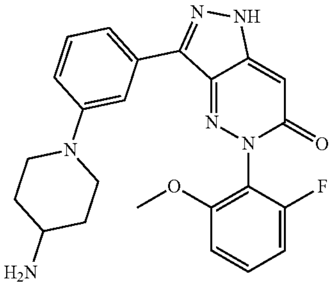 [SMILES: COc1cccc(F)c1-n1nc2c(-c3cccc(N4CCC(N)CC4)c3)n[nH]c2cc1=O] | ESI-MS: 435.2 [M + H]+ $^1$H NMR (400 MHz, DMSO-$d_6$) δ 7.68-7.65 (m, 1H), 7.59-7.53 (m, 1H), 7.49 (d, J = 8.0 Hz, 1H), 7.31 (t, J = 8.0 Hz, 1H), 7.12 (d, J = 8.8 Hz, 1H), 7.09-7.02 (m, 2H), 6.69 (s, 1H), 3.79 (s, 3H), 3.72-3.65 (m, 2H), 2.98-2.89 (m, 1H), 2.83-2.74 (m, 2H), 1.86-1.76 (m, 2H), 1.48-1.36 (m, 2H). | 2A |
| Example 173 | Compound 206 | 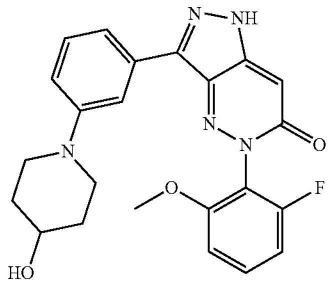 [SMILES: COc1cccc(F)c1-n1nc2c(-c3cccc(N4CCC(O)CC4)c3)n[nH]c2cc1=O] | ESI-MS: 436.2 [M + H]+ $^1$H NMR (400 MHz, DMSO-$d_6$) δ 12.99 (s, 1H), 7.68-7.66 (m, 1H), 7.59-7.53 (m, 1H), 7.47 (d, J = 8.0 Hz, 1H), 7.29 (t, J = 8.0 Hz, 1H), 7.13 (d, J = 8.8 Hz, 1H), 7.09-7.01 (m, 2H), 6.69 (s, 1H), 4.66 (d, J = 4.0 Hz, 1H), 3.79 (s, 3H), 3.67-3.59 (m, 1H), 3.57-3.50 (m, 2H), 2.92-2.85 (m, 2H), 1.78-1.74 (m, 2H), 1.49-1.39 (m, 2H). | 2A |
| Example 174 | Compound 207 | 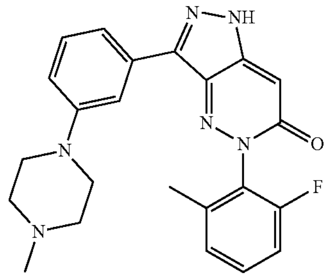 | ESI-MS: 437.2 [M + H]+ $^1$H NMR (400 MHz, DMSO-$d_6$) δ 13.22 (br, 1H),7.50-7.40 (m, 2H), 7.31-7.14 (m, 4H), 6.78 (s, 1H), 3.05-3.00 (m, 4H), 2.49-2.44 (m, 4H), 2.22 (s, 3H), 2.08 (s, 3H). | 2A |
| Example 175 | Compound 208 | 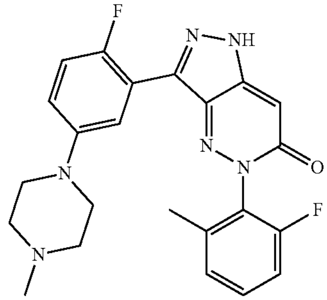 [SMILES: Cc1cccc(F)c1-n1nc2c(-c3cc(N4CCN(C)CC4)ccc3F)n[nH]c2cc1=O] | ESI-MS: 437.2 [M + H]+ $^1$H NMR (400 MHz, DMSO-$d_6$) δ 13.17 (br, 1H),7.50-7.43 (m, 1H), 7.39-7.34 (m, 1H), 7.30-7.27 (m, 2H), 7.19 (t, J = 9.5 Hz, 1H), 7.10-7.05 (m, 1H), 6.78 (s, 1H), 3.10-3.06 (m, 4H), 2.42-2.39 (m, 4H), 2.19 (s, 3H), 2.09 (s, 3H). | 2A |
| Example 176 | Compound 209 | 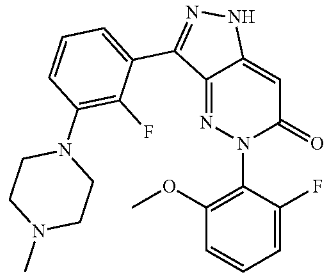 [SMILES: COc1cccc(F)c1-n1nc2c(-c3cccc(N4CCN(C)CC4)c3F)n[nH]c2cc1=O] | ESI-MS: 453.2 [M + H]+ $^1$H NMR (400 MHz, DMSO-$d_6$) δ 13.13 (br, 1H), 7.57-7.49 (m, 1H), 7.43-7.38 (m, 1H), 7.21 (t, J = 7.9 Hz, 1H), 7.17-7.07 (m, 2H), 7.03 (t, J = 8.8 Hz, 1H), 6.70 (s, 1H), 3.76 (s, 3H), 3.05-3.00 (m, 4H), 2.50-2.44 (m, 4H), 2.22 (s, 3H). | 2A |

-continued

| Example | Compound | Structural Formula | Spectrum Data | Synthetic Scheme |
|---|---|---|---|---|
| Example 177 | Compound 210 | 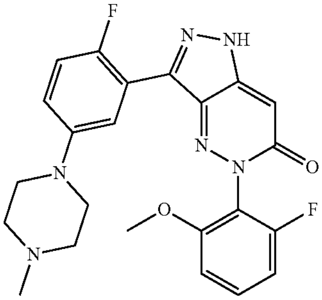 [SMILES: COc1cccc(F)c1-n1nc2c(-c3cc(N4CCN(C)CC4)ccc3F)n[nH]c2cc1=O] | ESI-MS: 453.2 $[M+H]^+$ $^1H$ NMR (400 MHz, DMSO-$d_6$) δ 13.13 (br, 1H), 7.57-7.50 (m, 1H), 7.40-7.36 (m, 1H), 7.19 (t, J = 9.5 Hz, 1H), 7.13-7.00 (m, 3H), 6.71 (s, 1H), 3.77 (s, 3H), 3.10-3.04 (m, 4H), 2.43-2.38 (m, 4H), 2.19 (s, 3H). | 2A |

Biological Activity Test and Results:

1. HPK1 Kinase Activity Inhibition Test

The kinase activity of HPK1 is manifested as activity of autophosphorylation and phosphorylation of downstream substrates. In the process of autophosphorylation, additional substrates are not required, and ATP is consumed to generate ADP. The amount of the product was measured by ADP-Glo reagent and luminescence method to reflect kinase activity.

Test compounds: compounds prepared in the examples of this application.

Prepare compound stock solution: dissolve the compound to be tested in 100% DMSO to make a 10 mM stock solution;

Prepare 4 × Kinase Reaction Buffer:

| Material | Concentration of Stock Solution | Volume | Final Concentration |
|---|---|---|---|
| Tris | 1M (25×) | 240 μL | 40 mM |
| $MgCl_2$ | 1M (50×) | 120 μL | 20 mM |
| BSA | 7.5% (75×) | 80 μL | 0.1% |
| DTT | 1M (500×) | 3 μL | 0.5 mM |
| $ddH_2O$ | | 5557 μL | |

Prepare 2 × HPK1 Kinase Solution:

| Material | Concentration of Stock Solution | Volume | 2 × Final Concentration | Final Concentration |
|---|---|---|---|---|
| HPK1 | 4878 nM | 1 μL | 10 nM | 5 nM |
| 1 × kinase reaction buffer solution | | 487 μL | | |

Prepare 4 × ATP mixture:

| Material | ATP Km | Concentration of Stock Solution | Volume | 4 × Final Concentration | Final Concentration |
|---|---|---|---|---|---|
| ATP | 1.669 μM | 1 mM (125×) | 3 μL | 8 μM | 2 μM |
| 4 × kinase reaction buffer solution | | | 372 μL | | |

Procedures:

Dilute the stock solution of the compound to be tested by 5 times with 100% DMSO, make a 4-fold equal dilution in a 96-well dilution plate, add 1 μL of the compound to 49 μL of kinase reaction buffer, and shake on a microplate shaker for 20 minutes. Transfer 2 μL of 2×HPK1 kinase solution to 384 reaction plate, add 1 μL of the test compound to the 384 reaction plate (Greiner, 784075), centrifuge for 1 minute (1000 rpm/min), incubate at 25° C. for 10 minutes. Transfer 1 μL of the 4×ATP mixture to a 384 reaction plate, centrifuge for 1 minute (1000 rpm/min), and incubate at 25° C. for 60 minutes. In the reaction system, the final concentration of DMSO was 0.5%. Transfer 4 μL of ADP-Glo to a 384 reaction plate, centrifuge for 1 minute (1000 rpm/min), and incubate at 25° C. for 40 minutes. Transfer 8 μL detection solution to a 384 reaction plate, centrifuge for 1 minute (1000 rpm/min), and incubate at 25° C. for 40 minutes. The fluorescence signal was read using a Biotek multi-function plate reader, and the IC50 (half inhibitory concentration) of the compound was obtained using a four-coefficient nonlinear fitting formula.

Compounds as shown in the Examples exhibited IC50 values in the following ranges: +++=IC50≤50 nM, ++=50 nM<IC50≤500 nM, +=500 nM<IC50<2000 nM.

TABLE 1

Inhibitory effects of compounds on HPK1 kinase activity

| Compound | IC50 |
|---|---|
| Compound 1 | +++ |
| Compound 2 | ++ |
| Compound 3 | +++ |
| Compound 4 | +++ |
| Compound 5 | ++ |
| Compound 6 | +++ |
| Compound 7 | ++ |
| Compound 8 | +++ |
| Compound 9 | +++ |
| Compound 10 | +++ |
| Compound 11 | ++ |
| Compound 12 | + |
| Compound 13 | ++ |
| Compound 14 | ++ |
| Compound 15 | + |
| Compound 16 | + |
| Compound 17 | + |
| Compound 19 | + |
| Compound 20 | ++ |
| Compound 21 | ++ |
| Compound 23 | +++ |

TABLE 1-continued

| Inhibitory effects of compounds on HPK1 kinase activity | |
|---|---|
| Compound | IC50 |
| Compound 24 | +++ |
| Compound 25 | ++ |
| Compound 26 | + |
| Compound 27 | +++ |
| Compound 28 | +++ |
| Compound 29 | +++ |
| Compound 32 | ++ |
| Compound 33 | +++ |
| Compound 34 | +++ |
| Compound 42 | +++ |
| Compound 47 | + |
| Compound 48 | ++ |
| Compound 55 | ++ |
| Compound 58 | ++ |
| Compound 61 | +++ |
| Compound 72 | ++ |
| Compound 73 | +++ |
| Compound 74 | +++ |
| Compound 75 | + |
| Compound 76 | +++ |
| Compound 77 | +++ |
| Compound 78 | ++ |
| Compound 79 | +++ |
| Compound 80 | +++ |
| Compound 81 | +++ |
| Compound 82 | +++ |
| Compound 83 | +++ |
| Compound 84 | ++ |
| Compound 85 | +++ |
| Compound 86 | +++ |
| Compound 87 | +++ |
| Compound 88 | ++ |
| Compound 89 | +++ |
| Compound 90 | +++ |
| Compound 91 | +++ |
| Compound 92 | +++ |
| Compound 93 | +++ |
| Compound 94 | +++ |
| Compound 95 | ++ |
| Compound 96 | ++ |
| Compound 97 | ++ |
| Compound 98 | +++ |
| Compound 99 | ++ |
| Compound 100 | ++ |
| Compound 101 | +++ |
| Compound 102 | ++ |
| Compound 103 | +++ |
| Compound 104 | ++ |
| Compound 105 | +++ |
| Compound 106 | +++ |
| Compound 107 | +++ |
| Compound 108 | ++ |
| Compound 109 | +++ |
| Compound 110 | ++ |
| Compound 111 | +++ |
| Compound 112 | +++ |
| Compound 113 | +++ |
| Compound 114 | +++ |
| Compound 115 | +++ |
| Compound 116 | +++ |
| Compound 117 | +++ |
| Compound 118 | +++ |
| Compound 119 | +++ |
| Compound 120 | +++ |
| Compound 121 | +++ |
| Compound 122 | +++ |
| Compound 123 | +++ |
| Compound 124 | +++ |
| Compound 125 | +++ |
| Compound 126 | +++ |
| Compound 127 | +++ |
| Compound 128 | +++ |
| Compound 129 | +++ |
| Compound 130 | +++ |
| Compound 131 | ++ |

TABLE 1-continued

| Inhibitory effects of compounds on HPK1 kinase activity | |
|---|---|
| Compound | IC50 |
| Compound 132 | +++ |
| Compound 133 | +++ |
| Compound 134 | +++ |
| Compound 135 | +++ |
| Compound 136 | +++ |
| Compound 137 | +++ |
| Compound 138 | +++ |
| Compound 139 | +++ |
| Compound 140 | +++ |
| Compound 141 | +++ |
| Compound 142 | +++ |
| Compound 143 | +++ |
| Compound 144 | +++ |
| Compound 145 | +++ |
| Compound 146 | +++ |
| Compound 147 | +++ |
| Compound 148 | +++ |
| Compound 149 | + |
| Compound 150 | + |
| Compound 151 | ++ |
| Compound 152 | ++ |
| Compound 153 | ++ |
| Compound 154 | ++ |
| Compound 155 | ++ |
| Compound 156 | +++ |
| Compound 157 | +++ |
| Compound 158 | ++ |
| Compound 159 | +++ |
| Compound 160 | +++ |
| Compound 161 | +++ |
| Compound 162 | +++ |
| Compound 163 | ++ |
| Compound 164 | ++ |
| Compound 165 | ++ |
| Compound 166 | ++ |
| Compound 167 | ++ |
| Compound 168 | ++ |
| Compound 169 | ++ |
| Compound 170 | +++ |
| Compound 171 | ++ |
| Compound 172 | ++ |
| Compound 173 | ++ |
| Compound 174 | ++ |
| Compound 175 | ++ |
| Compound 176 | +++ |
| Compound 177 | +++ |
| Compound 178 | ++ |
| Compound 179 | ++ |
| Compound 180 | +++ |
| Compound 181 | ++ |
| Compound 182 | ++ |
| Compound 183 | + |
| Compound 184 | ++ |
| Compound 185 | + |
| Compound 186 | + |
| Compound 187 | ++ |
| Compound 188 | ++ |
| Compound 189 | ++ |
| Compound 190 | ++ |
| Compound 191 | ++ |
| Compound 193 | +++ |
| Compound 194 | +++ |
| Compound 195 | ++ |
| Compound 196 | ++ |
| Compound 197 | +++ |
| Compound 198 | +++ |
| Compound 199 | +++ |
| Compound 200 | +++ |
| Compound 201 | +++ |
| Compound 202 | +++ |
| Compound 203 | +++ |
| Compound 204 | +++ |
| Compound 205 | +++ |
| Compound 206 | ++ |
| Compound 207 | + |

TABLE 1-continued

| Inhibitory effects of compounds on HPK1 kinase activity | |
|---|---|
| Compound | IC50 |
| Compound 208 | +++ |
| Compound 209 | ++ |
| Compound 210 | +++ |

The data in Table 1 show that the compounds of the examples of the present application have inhibitory effect on HPK1 kinase activity.

2. Measurement of IL-2 Secretion of Jurkat Cells by ELISA Procedures:

Human Jurkat-E6-1 cells were incubated with various concentrations of test compounds for 30 minutes in a humidified incubator at 37° C. and 5% CO2. Cells were transferred to cell culture plates pre-coated with anti-human CD3 antibody, then soluble anti-human CD28 antibody was added, and cells were stimulated for 24 hours at 37° C. and 5% $CO_2$ in a humidified incubator. The cell culture medium was collected by centrifugation, and was then transferred to a 96-well transparent microtiter plate (Thermo) pre-coated with anti-human IL-2 antibody, incubated at room temperature for 2 hours, and gently shaken, washed with washing buffer for 4 times, and then followed the ELISA MAX Deluxe Set Human IL-2 (BioLegend) kit procedure, used a microplate reader (Molecular Device, i3X) to read the OD value. The best standard curve was selected by the microplate reader application software, and the corresponding concentration was calculated according to the OD value of the standard. Results are expressed as a percentage of the amount of IL-2 secreted from compound-treated/DMSO-treated cells.

TABLE 2

| Effects of compounds on secretion of IL-2 from human Jurkat cells. | | |
|---|---|---|
| Compound | Percentage of the amount of IL-2 secreted from compound treated/DMSO-treated cells | Concentration of the Test Compound (μM) |
| Compound 1 | 277% | 1.0 |
| Compound 2 | 238% | 3.0 |
| Compound 3 | 211% | 1.0 |
| Compound 5 | 162% | 1.0 |
| Compound 6 | 185% | 1.0 |
| Compound 7 | 314% | 1.0 |
| Compound 8 | 306% | 0.33 |
| Compound 9 | 188% | 3.0 |
| Compound 11 | 296% | 1.0 |
| Compound 13 | 315% | 3.0 |
| Compound 14 | 255% | 3.0 |
| Compound 16 | 156% | 1.0 |
| Compound 20 | 329% | 1.0 |
| Compound 21 | 258% | 3.0 |
| Compound 23 | 379% | 0.33 |
| Compound 25 | 187% | 1.0 |
| Compound 27 | 302% | 0.33 |
| Compound 28 | 302% | 1.0 |
| Compound 29 | 291% | 1.0 |
| Compound 33 | 631% | 1.0 |
| Compound 34 | 284% | 1.0 |
| Compound 42 | 365% | 3.0 |
| Compound 58 | 233% | 3.0 |
| Compound 61 | 635% | 3.0 |
| Compound 73 | 926% | 3.0 |
| Compound 74 | 411% | 3.0 |
| Compound 76 | 561% | 3.0 |
| Compound 77 | 233% | 1.0 |

TABLE 2-continued

| Effects of compounds on secretion of IL-2 from human Jurkat cells. | | |
|---|---|---|
| Compound | Percentage of the amount of IL-2 secreted from compound treated/DMSO-treated cells | Concentration of the Test Compound (μM) |
| Compound 79 | 361% | 3.0 |
| Compound 80 | 191% | 3.0 |
| Compound 81 | 679% | 3.0 |
| Compound 82 | 195% | 3.0 |
| Compound 83 | 252% | 3.0 |
| Compound 85 | 239% | 3.0 |
| Compound 86 | 334% | 3.0 |
| Compound 87 | 584% | 3.0 |
| Compound 88 | 550% | 3.0 |
| Compound 89 | 689% | 3.0 |
| Compound 90 | 667% | 3.0 |
| Compound 92 | 1101% | 3.0 |
| Compound 93 | 210% | 3.0 |
| Compound 94 | 414% | 3.0 |
| Compound 98 | 850% | 3.0 |
| Compound 99 | 237% | 3.0 |
| Compound 100 | 284% | 3.0 |
| Compound 103 | 716% | 3.0 |
| Compound 105 | 623% | 3.0 |
| Compound 106 | 833% | 3.0 |
| Compound 107 | 599% | 3.0 |
| Compound 108 | 312% | 3.0 |
| Compound 109 | 491% | 3.0 |
| Compound 111 | 522% | 3.0 |
| Compound 112 | 703% | 3.0 |
| Compound 113 | 368% | 3.0 |
| Compound 114 | 309% | 3.0 |
| Compound 115 | 542% | 3.0 |
| Compound 116 | 193% | 1.0 |
| Compound 117 | 566% | 3.0 |
| Compound 118 | 550% | 3.0 |
| Compound 119 | 531% | 3.0 |
| Compound 120 | 482% | 3.0 |
| Compound 121 | 459% | 3.0 |
| Compound 122 | 1008% | 3.0 |
| Compound 123 | 1117% | 3.0 |
| Compound 124 | 570% | 3.0 |
| Compound 125 | 216% | 3.0 |
| Compound 126 | 428% | 3.0 |
| Compound 127 | 758% | 3.0 |
| Compound 128 | 472% | 3.0 |
| Compound 129 | 807% | 3.0 |
| Compound 130 | 454% | 3.0 |
| Compound 133 | 800% | 3.0 |
| Compound 134 | 527% | 3.0 |
| Compound 135 | 964% | 3.0 |
| Compound 136 | 702% | 3.0 |
| Compound 137 | 291% | 3.0 |
| Compound 138 | 873% | 3.0 |
| Compound 139 | 315% | 3.0 |
| Compound 140 | 436% | 3.0 |
| Compound 141 | 390% | 3.0 |
| Compound 142 | 708% | 3.0 |
| Compound 143 | 786% | 3.0 |
| Compound 144 | 716% | 3.0 |
| Compound 145 | 776% | 3.0 |
| Compound 146 | 537% | 3.0 |
| Compound 147 | 616% | 3.0 |
| Compound 148 | 531% | 1.0 |
| Compound 151 | 230% | 3.0 |
| Compound 154 | 382% | 1.0 |
| Compound 155 | 435% | 3.0 |
| Compound 156 | 849% | 3.0 |
| Compound 157 | 935% | 3.0 |
| Compound 159 | 454% | 3.0 |
| Compound 160 | 354% | 3.0 |
| Compound 161 | 393% | 3.0 |
| Compound 162 | 586% | 3.0 |
| Compound 163 | 117% | 3.0 |
| Compound 164 | 159% | 3.0 |
| Compound 165 | 181% | 1.0 |
| Compound 170 | 279% | 1.0 |
| Compound 171 | 220% | 3.0 |

TABLE 2-continued

Effects of compounds on secretion of IL-2 from human Jurkat cells.

| Compound | Percentage of the amount of IL-2 secreted from compound treated/DMSO-treated cells | Concentration of the Test Compound (μM) |
|---|---|---|
| Compound 177 | 481% | 3.0 |
| Compound 193 | 169% | 3.0 |
| Compound 198 | 280% | 3.0 |
| Compound 199 | 328% | 1.0 |
| Compound 200 | 286% | 3.0 |
| Compound 202 | 539% | 1.0 |
| Compound 204 | 260% | 3.0 |
| Compound 210 | 298% | 1.0 |

The data in Table 2 shows that, compared with Jurkat cells treated with DMSO as a blank control group, the compounds of the examples of the present application have a significant promoting effect on the secretion of cytokine IL-2 by Jurkat cells.

Unless otherwise defined, the terms used in this application are the meanings commonly understood by those skilled in the art.

The embodiments described in this application are only for exemplary purposes and are not intended to limit the protection scope of this application. Those skilled in the art can make various other substitutions, changes and improvements within the scope of this application. Therefore, this application is not limited to the above-described embodiments, but only by the claims.

The invention claimed is:

1. A compound of formula (I) or a pharmaceutically acceptable salt, hydrate, solvate, active metabolite, polymorph, isotope labeled compound, stereoisomer or prodrug thereof,

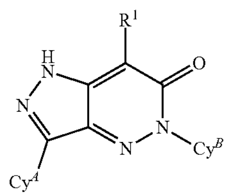

(I)

wherein, $R^1$ is selected from the group consisting of:

1) hydrogen, halogen, cyano, —C(=O)$NR^aR^b$, —$OR^a$ and —$NR^aR^b$;
2) $C_{1-6}$ alkyl, $C_{2-4}$ alkenyl, $C_{2-4}$ alkynyl, $C_{3-8}$ cycloalkyl and 3- to 8-membered aliphatic heterocyclyl, unsubstituted or optionally substituted with 1, 2, 3 or 4 substituents independently selected from $R^{11}$;

$R^a$ and $R^b$ are each independently selected from the group consisting of:

1) hydrogen;
2) $C_{1-6}$ alkyl, $C_{2-4}$ alkenyl, $C_{2-4}$ alkynyl, $C_{3-6}$ monocyclic cycloalkyl, and 3- to 6-membered aliphatic monocyclic heterocyclyl, unsubstituted or optionally substituted with 1, 2, or 3 substituents independently selected from $R^{11}$; or $R^a$ and $R^b$ attached to the same nitrogen atom, together with the nitrogen atom, form a 3-6 membered aliphatic monocyclic heterocyclyl, unsubstituted or optionally substituted with 1, 2 or 3 substituents independently selected from $R^{11}$;

$R^{11}$ is selected from the group consisting of fluorine, chlorine, cyano, $C_{1-3}$ alkyl and hydroxyl;

$Cy^A$ is selected from 6- to 10-membered aryl or 5- to 10-membered heteroaryl, unsubstituted or optionally substituted with 1, 2, 3, 4 or 5 substituents independently selected from $R^{12}$;

$R^{12}$ is selected from the group consisting of:

1) oxo, halogen, cyano, —C(=O)$R^{a2}$, —C(=O)$OR^{a2}$, —C(=O)$NR^{a2}R^{b2}$, —C(=$NR^{d2}$)NR $^{a2}R^{b2}$, —$OR^{a2}$, —OC(=O)$R^{a2}$, —OC(=O)$OR^{c2}$, —OC(=O)$NR^{a2}R^{b2}$, —$SR^{a2}$, —S(=O)$R^{c2}$, —S(=O)$_2R^{c2}$, sulfonic acid group, —S(=O)$NR^{a2}R^{b2}$, —S(=O)$_2NR^{a2}R^{b2}$, —S(=O)(=$NR^{d2}$)$R^{c2}$, —$NR^{a2}R^{b2}$, —$NR^{a2}$C(=O)$R^{b2}$, —$NR^{a2}$C(=O)$OR^{c2}$, —$NR^{c2}$C(=O)$NR^{a2}R^{b2}$, —$NR^{e2}$C(=$NR^{d2}$)$NR^{a2}R^{b2}$, —$NR^{a2}$S(=O)$_2R^{c2}$, —$NR^{e2}$S(=O)$_2NR^{a2}R^{b2}$, nitro, —$PR^{c2}R^{f2}$, —P(=O)$R^{c2}R^{f2}$ and phosphonic acid group;
2) $C_{1-6}$ alkyl, $C_{2-6}$ alkenyl, $C_{2-6}$ alkynyl, 6- to 10-membered aryl, 5- to 10-membered heteroaryl, $C_{3-12}$ cycloalkyl and 3- to 12-membered aliphatic heterocyclyl, unsubstituted or optionally substituted with 1, 2, 3, 4, 5 or 6 substituents independently selected from $R^{22}$;
3) The two $R^{12}$ substituents attached to two adjacent ring-forming atoms on the aryl or heteroaryl group of $Cy^A$, respectively, together with the two said ring-forming atoms, form a $C_{5-12}$ alicyclic or a 5- to 12-membered aliphatic heterocyclyl, unsubstituted or optionally substituted by 1, 2, 3, 4, 5 or 6 substituents independently selected from $R^{22}$;

$R^{a2}$, $R^{b2}$ and $R^{e2}$ are each independently selected from the group consisting of:

1) hydrogen;
2) $C_{1-4}$ alkyl, $C_{2-4}$ alkenyl, $C_{2-4}$ alkynyl, phenyl, 5-6 membered heteroaryl, $C_{3-12}$ cycloalkyl and 3-12 membered aliphatic heterocyclyl, unsubstituted or optionally substituted with 1, 2, 3, 4, 5 or 6 substituents independently selected from $R^{22}$;

or, $R^{a2}$ and $R^{b2}$ attached to the same nitrogen atom, together with the nitrogen, form a 3-12 membered aliphatic heterocyclyl, unsubstituted or optionally substituted with 1, 2, 3, 4 or 5 substituents independently selected from $R^{22}$;

$R^{c2}$ and $R^{f2}$ are each independently selected from the group consisting of $C_{1-4}$ alkyl, $C_{2-4}$ alkenyl, $C_{2-4}$ alkynyl, phenyl, 5-6 membered heteroaryl, $C_{3-12}$ cycloalkyl and 3-12 membered aliphatic heterocyclyl, unsubstituted or optionally substituted with 1, 2, 3, 4 or 5 substituents independently selected from $R^{22}$;

or, $R^{c2}$ and $R^{f2}$ attached to the same phosphorous atom, together with the phosphorous, form a 3-12 membered aliphatic heterocyclyl, unsubstituted or optionally substituted with 1, 2, 3, 4 or 5 substituents independently selected from $R^{22}$;

$R^{d2}$ is selected from the group consisting of:

1) hydrogen, cyano, nitro and —S(=O)$_2R^G$;
2) $C_{1-4}$ alkyl, $C_{2-4}$ alkenyl, $C_{2-4}$ alkynyl, phenyl, 5-6 membered heteroaryl, $C_{3-12}$ cycloalkyl and 3-12 membered aliphatic heterocyclyl, unsubstituted or optionally substituted with 1, 2, 3, 4 or 5 substituents independently selected from $R^{22}$;

$R^{22}$ is selected from the group consisting of:

1) oxo, halogen, cyano, —C(=O)$R^{a4}$, —C(=O)$OR^{a4}$, —C(=O)$NR^{a4}R^{b4}$, —C(=$NR^{d4}$)$NR^{a4}R^{b4}$, —$OR^{a4}$, —OC(=O)$R^{a4}$, —OC(=O)$OR^{c4}$, —OC(=O)$NR^{a4}R^{b4}$, —$SR^{a4}$, —S(=O)$R^{c4}$, —S(=O)$_2R^{c4}$, sulphonic acid group, —S(═O)NR$^{a4}$R$^{b4}$, —S(═O)$_2$NR$^{a4}$R$^{b4}$, —S(═O)(═NR$^{d4}$)R$^{c4}$, —NR$^{a4}$R$^{b4}$, —NR$^{a4}$C(═O)R$^{b4}$, —NR$^{a4}$C(═O)OR$^{c4}$, —NR$^{e4}$C(═O)NR$^{a4}$R$^{b4}$, —NR$^{e4}$C(═NR$^{d4}$)NR$^{a4}$R$^{b4}$, —NR$^{a4}$S(═O)$_2$R$^{c4}$, —NR$^{e4}$S(═O)$_2$NR$^{a4}$R$^{b4}$, nitro, —PR$^{c4}$R$^{f4}$, —P(═O)R$^{c4}$R$^{f4}$, phosphonic acid group, and ═N—R$^{d4}$;

2) $C_{1-6}$ alkyl, $C_{1-6}$ alkylene, $C_{2-6}$ alkenyl, $C_{2-6}$ alkynyl, phenyl, 5-6 membered heteroaryl, $C_{3-10}$ cycloalkyl and 3-10 membered aliphatic heterocyclyl, unsubstituted or optionally substituted with 1, 2, 3, 4 or 5 substituents independently selected from R$^{32}$;

R$^{a4}$, R$^{b4}$ and R$^{c4}$ are each independently selected from the group consisting of:

1) hydrogen;

2) $C_{1-4}$ alkyl, $C_{2-4}$ alkenyl, $C_{2-4}$ alkynyl, phenyl, 5-6 membered heteroaryl, $C_{3-10}$ cycloalkyl and 3-10 membered aliphatic heterocyclyl, unsubstituted or optionally substituted with 1, 2, 3, 4 or 5 substituents independently selected from R$^{32}$;

or,

R$^{a4}$ and R$^{b4}$ attached to the same nitrogen atom, together with the nitrogen, form a 3-10 membered aliphatic heterocyclyl, unsubstituted or optionally substituted with 1, 2, 3, 4 or 5 substituents independently selected from R$^{32}$;

R$^{c4}$ and R$^{f4}$ are each independently selected from the group consisting of $C_{1-4}$ alkyl, $C_{2-4}$ alkenyl, $C_{2-4}$ alkynyl, phenyl, 5-6 membered heteroaryl, $C_{3-10}$ cycloalkyl and 3-10 membered aliphatic heterocyclyl, unsubstituted or optionally substituted with 1, 2, 3, 4 or 5 substituents independently selected from R$^{32}$;

or,

R$^{c4}$ and R$^{f4}$ attached to the same phosphorous atom, together with the phosphorous, form a 3-10 membered aliphatic heterocyclyl, unsubstituted or optionally substituted with 1, 2, 3, 4 or 5 substituents independently selected from R$^{32}$;

R$^{d4}$ is selected from the group consisting of:

1) hydrogen, cyano, nitro, and —S(═O)$_2$R$^G$;

2) $C_{1-4}$ alkyl, $C_{2-4}$ alkenyl, $C_{2-4}$ alkynyl, phenyl, 5-6 membered heteroaryl, $C_{3-10}$ cycloalkyl and 3-10 membered aliphatic heterocyclyl, unsubstituted or optionally substituted with 1, 2, 3, 4 or 5 substituents independently selected from R$^{32}$;

R$^{32}$ is selected from the group consisting of:

1) oxo, halogen, cyano, —C(═O)R$^{a6}$, —C(═O)OR$^{a6}$, —C(═O)NR$^{a6}$R$^{b6}$, —C(═NR$^{d6}$)NR$^{a6}$R$^{b6}$, —OR$^{a6}$, —OC(═O)R$^{a6}$, —OC(═O)OR$^{c6}$, —OC(═O)NR$^{a6}$R$^{b6}$, —SR$^{a6}$, —S(═O)R$^{c6}$, —S(═O)$_2$R$^{c6}$, sulphonic acid group, —S(═O)NR$^{a6}$R$^{b6}$, —S(═O)$_2$NR$^{a6}$R$^{b6}$, —S(═O)(═NR$^{d6}$)R$^{c6}$, —NR$^{a6}$R$^{b6}$, —NR$^{a6}$C(═O)R$^{b6}$, —NR$^{a6}$C(═O)OR$^{c6}$, —NR$^{e6}$C(═O)NR$^{a6}$R$^{b6}$, —NR$^{e6}$C(═NR$^{d6}$)NR$^{a6}$R$^{b6}$, —NR$^{a6}$S(═O)$_2$R$^{c6}$, —NR$^{e6}$S(═O)$_2$NR$^{a6}$R$^{b6}$, nitro, —PR$^{c6}$R$^{f6}$, —P(═O)R$^{c6}$R$^{f6}$, phosphonic acid group, and ═N—R$^{d6}$;

2) $C_{1-4}$ alkyl, $C_{1-4}$ alkylene, $C_{2-4}$ alkenyl, $C_{2-4}$ alkynyl, phenyl, 5-6 membered heteroaryl, $C_{3-8}$ cycloalkyl, and 3-8 membered aliphatic heterocyclyl, unsubstituted or optionally substituted with 1, 2, 3 or 4 substituents independently selected from R$^G$;

R$^{a6}$, R$^{b6}$ and R$^{e6}$ are each independently selected from the group consisting of:

1) hydrogen;

2) $C_{1-4}$ alkyl, $C_{2-4}$ alkenyl, $C_{2-4}$ alkynyl, phenyl, 5-6 membered heteroaryl, $C_{3-8}$ cycloalkyl, and 3-8 membered aliphatic heterocyclyl, unsubstituted or optionally substituted with 1, 2, 3 or 4 substituents independently selected from R$^G$;

or,

R$^{a6}$ and R$^{b6}$ attached to the same nitrogen atom, together with the nitrogen, form a 3-8 membered aliphatic heterocyclyl, unsubstituted or optionally substituted with 1, 2, 3 or 4 substituents independently selected from R$^G$;

R$^{c6}$ and R$^{f6}$ are each independently selected from the group consisting of $C_{1-4}$ alkyl, $C_{2-4}$ alkenyl, $C_{2-4}$ alkynyl, phenyl, 5-6 membered heteroaryl, $C_{3-8}$ cycloalkyl, and 3-8 membered aliphatic heterocyclyl, unsubstituted or optionally substituted with 1, 2, 3 or 4 substituents independently selected from R$^G$;

or,

R$^{c6}$ and R$^{f6}$ attached to the same phosphorous atom, together with the phosphorous, form a 3-8 membered aliphatic heterocyclyl, unsubstituted or optionally substituted with 1, 2, 3 or 4 substituents independently selected from R$^G$;

R$^{d6}$ is selected from the group consisting of:

1) hydrogen, cyano, nitro, and —S(═O)$_2$R$^G$;

2) $C_{1-4}$ alkyl, $C_{2-4}$ alkenyl, $C_{2-4}$ alkynyl, phenyl, 5-6 membered heteroaryl, $C_{3-8}$ cycloalkyl, and 3-8 membered aliphatic heterocyclyl, unsubstituted or optionally substituted with 1, 2, 3 or 4 substituents independently selected from R$^G$;

Cy$^B$ is selected from the group consisting of 6-10 membered aryl and 5-10 membered heteroaryl, unsubstituted or optionally substituted with 1, 2, 3, 4 or 5 substituents independently selected from R$^{13}$;

R$^{13}$ is selected from the group consisting of:

1) oxo, halogen, cyano, —C(═O)R$^{a3}$, —C(═O)OR$^{a3}$, —C(═O)NR$^{a3}$R$^{b3}$, —C(═NR$^{d3}$)NR$^{a3}$R$^{b3}$, —OR$^{a3}$, —OC(═O)R$^{a3}$, —OC(═O)OR$^{c3}$, —OC(═O)NR$^{a3}$R$^{b3}$, —SR$^{a3}$, —S(═O)R$^{c3}$, —S(═O)$_2$R$^{c3}$, sulphonic acid group, —S(═O)NR$^{a3}$R$^{b3}$, —S(═O)$_2$NR$^{a3}$R$^{b3}$, —S(═O)(═NR$^{d3}$)R$^{c3}$, —NR$^{a3}$R$^{b3}$, —NR$^{a3}$C(═O)R$^{b3}$, —NR$^{a3}$C(═O)OR$^{c3}$, —NR$^{c3}$C(═O)NR$^{a3}$R$^{b3}$, —NR$^{c3}$C(═NR$^{c3}$)NR$^{a3}$R$^{b3}$, —NR$^{a3}$S(═O)$_2$R$^{c3}$, —NR$^{c3}$S(═O)$_2$NR$^{a3}$R$^{b3}$, nitro, —PR$^{c3}$R$^{f3}$, —P(═O)R$^{c3}$R$^{f3}$, and phosphonic acid group;

2) $C_{1-6}$ alkyl, $C_{2-6}$ alkenyl, $C_{2-6}$ alkynyl, 6-10 membered aryl, 5-10 membered heteroaryl, $C_{3-12}$ cycloalkyl, and 3-12 membered aliphatic heterocyclyl, unsubstituted or optionally substituted with 1, 2, 3, 4, 5 or 6 substituents independently selected from R$^{23}$;

3) Two R$^{13}$ substituents attached to two adjacent ring-forming atoms of the aryl or heteroaryl of Cy$^B$ respectively, together with the two said ring-forming atoms, form a $C_{5-12}$ aliphatic cyclyl or a 5-12 membered aliphatic heterocyclyl, unsubstituted or optionally substituted with 1, 2, 3, 4 or 5 substituents independently selected from R$^{23}$;

R$^{a3}$, R$^{b3}$ and R$^{e3}$ are each independently selected from the group consisting of:

1) hydrogen;

2) $C_{1-4}$ alkyl, $C_{2-4}$ alkenyl, $C_{2-4}$ alkynyl, phenyl, 5-6 membered heteroaryl, $C_{3-12}$ cycloalkyl, and 3-12 membered aliphatic heterocyclyl, unsubstituted or optionally substituted with 1, 2, 3, 4, 5 or 6 substituents independently selected from R$^{23}$;

or,

R$^{a3}$ and R$^{b3}$ attached to the same nitrogen atom, together with the nitrogen, form a 3-12 membered aliphatic heterocyclyl, unsubstituted or optionally substituted with 1, 2, 3, 4 or 5 substituents independently selected from $R^{23}$;

$R^{c3}$ and $R^{f3}$ are each independently selected from the group consisting of $C_{1-4}$ alkyl, $C_{2-4}$ alkenyl, $C_{2-4}$ alkynyl, phenyl, 5-6 membered heteroaryl, $C_{3-12}$ cycloalkyl, and 3-12 membered aliphatic heterocyclyl, unsubstituted or optionally substituted with 1, 2, 3, 4 or 5 substituents independently selected from $R^{23}$;

or, $R^{c3}$ and $R^{f3}$ attached to the same phosphorous atom, together with the phosphorous atom, form a 3-12 membered aliphatic heterocyclyl, unsubstituted or optionally substituted with 1, 2, 3, 4 or 5 substituents independently selected from $R^{23}$;

$R^{d3}$ is selected from the group consisting of:

1) hydrogen, cyano, nitro, and $S(=O)_2R^G$;

2) $C_{1-4}$ alkyl, $C_{2-4}$ alkenyl, $C_{2-4}$ alkynyl, phenyl, 5-6 membered heteroaryl, $C_{3-12}$ cycloalkyl, and 3-12 membered aliphatic heterocyclyl, unsubstituted or optionally substituted with 1, 2, 3, 4 or 5 substituents independently selected from $R^{23}$;

$R^{23}$ is selected from the group consisting of:

1) oxo, halogen, cyano, $-C(=O)R^{a5}$, $-C(=O)OR^{a5}$, $-C(=O)NR^{a5}R^{b5}$, $-C(=NR^{d5})NR^{a5}R^{b5}$, $-OR^{a5}$, $-OC(=O)R^{a5}$, $-OC(=O)OR^{c5}$, $-OC(=O)NR^{a5}R^{b5}$, $-SR^{a5}$, $-S(=O)R^{c5}$, $-S(=O)_2R^{c5}$, sulphonic acid group, $-S(=O)NR^{a5}R^{b5}$, $-S(=O)_2NR^{a5}R^{b5}$, $-S(=O)(=NR^{d5})R^{c5}$, $-NR^{a5}R^{b5}$, $-NR^{a5}C(=O)R^{b5}$, $-NR^{a5}C(=O)OR^{c5}$, $-NR^{e5}C(=O)NR^{a5}R^{b5}$, $-NR^{e5}C(=NR^{d5})NR^{a5}R^{b5}$, $-NR^{a5}S(=O)_2R^{c5}$, $-NR^{e5}S(=O)_2NR^{a5}R^{b5}$, nitro, $-PR^{c5}R^{f5}$, $-P(=O)R^{c5}R^{f5}$, phosphonic acid group, and $=N-R^{d5}$;

2) $C_{1-6}$ alkyl, $C_{1-6}$ alkylene, $C_{2-6}$ alkenyl, $C_{2-6}$ alkynyl, phenyl, 5-6 membered heteroaryl, $C_{3-10}$ cycloalkyl, and 3-10 membered aliphatic heterocyclyl, unsubstituted or optionally substituted with 1, 2, 3, 4 or 5 substituents independently selected from $R^{33}$;

$R^{a5}$, $R^{b5}$ and $R^{e5}$ are each independently selected from the group consisting of:

1) hydrogen;

2) $C_{1-4}$ alkyl, $C_{2-4}$ alkenyl, $C_{2-4}$ alkynyl, phenyl, 5-6 membered heteroaryl, $C_{3-10}$ cycloalkyl, and 3-10 membered aliphatic heterocyclyl, unsubstituted or optionally substituted with 1, 2, 3, 4 or 5 substituents independently selected from $R^{33}$, or, $R^{a5}$ and $R^{b5}$ attached to the same nitrogen atom, together with the nitrogen atom, form a 3-10 membered aliphatic heterocyclyl, unsubstituted or optionally substituted with 1, 2, 3, 4 or 5 substituents independently selected from $R^{33}$;

$R^{c5}$ and $R^{f5}$ are each independently selected from the group consisting of $C_{1-4}$ alkyl, $C_{2-4}$ alkenyl, $C_{2-4}$ alkynyl, phenyl, 5-6 membered heteroaryl, $C_{3-10}$ cycloalkyl, and 3-10 membered aliphatic heterocyclyl, unsubstituted or optionally substituted with 1, 2, 3, 4 or 5 substituents independently selected from $R^{33}$;

or, $R^{c5}$ and $R^{f5}$ attached to the same phosphorous atom, together with the phosphorous atom, form a 3-10 membered aliphatic heterocyclyl, unsubstituted or optionally substituted with 1, 2, 3, 4 or 5 substituents independently selected from $R^{33}$;

$R^{d5}$ is selected from the group consisting of:

1) hydrogen, cyano, nitro, and $-S(=O)_2R^G$;

2) $C_{1-4}$ alkyl, $C_{2-4}$ alkenyl, $C_{2-4}$ alkynyl, phenyl, 5-6 membered heteroaryl, $C_{3-10}$ cycloalkyl, and 3-10 membered aliphatic heterocyclyl, unsubstituted or optionally substituted with 1, 2, 3, 4 or 5 substituents independently selected from $R^{33}$;

$R^{33}$ is selected from the group consisting of:

1) oxo, halogen, cyano, $-C(=O)R^{a7}$, $-C(=O)OR^{a7}$, $-C(=O)NR^{a7}R^{b7}$, $-C(=NR^{d7})NR^{a7}R^{b7}$, $-OR^{a7}$, $-OC(=O)R^{a7}$, $-OC(=O)OR^{c7}$, $-OC(=O)NR^{a7}R^{b7}$, $-SR^{a7}$, $-S(=O)R^{c7}$, $-S(=O)_2R^{c7}$, sulphonic acid group, $-S(=O)NR^{a7}R^{b7}$, $-S(=O)_2NR^{a7}R^{b7}$, $-S(=O)(=NR^{d7})R^{c7}$, $-NR^{a7}R^{b7}$, $-NR^{a7}C(=O)R^{b7}$, $-NR^{a7}C(=O)OR^{c7}$, $-NR^{c7}C(=O)NR^{a7}R^{b7}$, $-NR^{e7}C(=NR^{d7})NR^{a7}R^{b7}$, $-NR^{a7}S(=O)_2R^{c7}$, $-NR^{e7}S(=O)_2NR^{a7}R^{b7}$, nitro, $-PR^{c7}R^{f7}$, $-P(=O)R^{c7}R^{f7}$, phosphonic acid group, and $=N-R^{d7}$;

2) $C_{1-4}$ alkyl, $C_{1-4}$ alkylene, $C_{2-4}$ alkenyl, $C_{2-4}$ alkynyl, phenyl, 5-6 membered heteroaryl, $C_{3-8}$ cycloalkyl, and 3-8 membered aliphatic heterocyclyl, unsubstituted or optionally substituted with 1, 2, 3 or 4 substituents independently selected from $R^G$;

$R^{a7}$, $R^{b7}$ and $R^{e7}$ are each independently selected from the group consisting of:

1) hydrogen;

2) $C_{1-4}$ alkyl, $C_{2-4}$ alkenyl, $C_{2-4}$ alkynyl, phenyl, 5-6 membered heteroaryl, $C_{3-8}$ cycloalkyl, and 3-8 membered aliphatic heterocyclyl, unsubstituted or optionally substituted with 1, 2, 3 or 4 substituents independently selected from $R^G$;

or, $R^{a7}$ and $R^{b7}$ attached to the same nitrogen atom, together with the nitrogen atom, form a 3-8 membered aliphatic heterocyclyl, unsubstituted or optionally substituted with 1, 2, 3 or 4 substituents independently selected from $R^G$;

$R^{c7}$ and $R^{f7}$ are each independently selected from the group consisting of $C_{1-4}$ alkyl, $C_{2-4}$ alkenyl, $C_{2-4}$ alkynyl, phenyl, 5-6 membered heteroaryl, $C_{3-8}$ cycloalkyl, and 3-8 membered aliphatic heterocyclyl, unsubstituted or optionally substituted with 1, 2, 3 or 4 substituents independently selected from $R^G$;

or, $R^{c7}$ and $R^{f7}$ attached to the same phosphorous atom, together with the phosphorous atom, form a 3-8 membered aliphatic heterocyclyl, unsubstituted or optionally substituted with 1, 2, 3 or 4 substituents independently selected from $R^G$;

$R^{d7}$ is selected from the group consisting of:

1) hydrogen, cyano, nitro, and $-S(=O)_2R^G$;

2) $C_{1-4}$ alkyl, $C_{2-4}$ alkenyl, $C_{2-4}$ alkynyl, phenyl, 5-6 membered heteroaryl, $C_{3-8}$ cycloalkyl, and 3-8 membered aliphatic heterocyclyl, unsubstituted or optionally substituted with 1, 2, 3 or 4 substituents independently selected from $R^G$;

$R^G$ is selected from the group consisting of:

1) Halogen, oxo, cyano, carboxyl, hydroxyl, $C_{1-4}$ alkoxy, amino, $C_{1-4}$ alkylamino, nitro, $C_{1-4}$ alkylthio, sulphonic acid group, $C_{1-4}$ alkyl sulfinyl, $C_{1-4}$ alkyl sulfonyl, $C_{1-4}$ alkylaminosulfinyl, and $C_{1-4}$ alkylaminosulfonyl;

2) $C_{1-4}$ alkyl, $C_{1-4}$ alkylene, $C_{2-4}$ alkenyl, $C_{2-4}$ alkynyl, $C_{3-6}$ cycloalkyl and 3-8 membered aliphatic heterocyclyl, unsubstituted or optionally substituted with 1, 2, 3 or 4 substituents independently selected from the group consisting of oxo, halogen, hydroxyl, hydroxymethyl, carboxyl, cyano, $C_{1-3}$ alkoxy, amino, $C_{1-4}$ alkylamino, nitro, and sulphonic acid group.

2. The compound according to claim 1, wherein, $R^1$ is selected from the group consisting of hydrogen, fluorine, cyano, methyl, ethyl, 1-propyl, isopropyl, cyclopropyl, methoxy, ethoxy and cyclopropyloxy;

$Cy^A$ is selected from the group consisting of phenyl, naphthyl and 5-10 membered heteroaryl, unsubstituted or optionally substituted with 1, 2, 3 or 4 substituents independently selected from $R^{12}$; wherein 5-10 membered heteroaryl contains at least two ring-forming carbon atoms and 1, 2, or 3 ring-forming heteroatoms independently selected from the group consisting of N, O and S;

$R^{12}$ is selected from the group consisting of:

1) oxo, halogen, cyano, $—C(═O)R^{a2}$, $—C(═O)OR^{a2}$, $—C(═O)NR^{a2}R^{b2}$, $—C(═NR^{d2})NR^{a2}R^{b2}$, $—OR^{a2}$, $—NR^{a2}R^{b2}$, $—NR^{a2}C(═O)R^{b2}$, $—NR^{a2}C(═O)OR^{c2}$, $—NR^{e2}C(═O)NR^{a2}R^{b2}$, $—NR^{e2}C(═NR^{d2})NR^{a2}R^{b2}$, $—NR^{a2}S(═O)_2R^{c2}$ and $—NR^{e2}S(═O)_2NR^{a2}R^{b2}$;

2) $C_{1-6}$ alkyl, $C_{2-6}$ alkenyl, $C_{2-6}$ alkynyl, 6-10 membered aryl, 5-10 membered heteroaryl, $C_{3-10}$ cycloalkyl, 3-10 membered aliphatic heterocyclyl, unsubstituted or optionally substituted with 1, 2, 3 or 4 substituents independently selected from $R^{22}$;

3) Two $R^{12}$, together with two adjacent ring-forming atoms of the aryl or heteroaryl in $Cy^A$ to which they are attached respectively, form a $C_{5-8}$ aliphatic cyclyl or 5-8 membered aliphatic heterocyclyl, unsubstituted or optionally substituted with 1, 2 or 3 substituents independently selected from $R^{22}$;

$R^{a2}$, $R^{b2}$ and $R^{e2}$ are each independently selected from the group consisting of:

1) hydrogen;

2) $C_{1-4}$ alkyl, $C_{2-4}$ alkenyl, $C_{2-4}$ alkynyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^{22}$;

or, $R^{a2}$ and $R^{b2}$, together with the same N atom to which they are attached, form a 3-8 membered aliphatic heterocyclyl, unsubstituted or optionally substituted with 1, 2 or 3 substituents independently selected from $R^{22}$;

$R^{c2}$ is selected from the group consisting of $C_{1-4}$ alkyl, $C_{2-4}$ alkenyl, $C_{2-4}$ alkynyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^{22}$;

$R^{d2}$ is selected from the group consisting of:

1) hydrogen, cyano, nitro, and $—S(═O)_2R^G$;

2) $C_{1-4}$ alkyl, $C_{2-4}$ alkenyl, $C_{2-4}$ alkynyl, phenyl, 5-6 membered heteroaryl, $C_{3-6}$ cycloalkyl, and 3-6 membered aliphatic heterocyclyl, unsubstituted or optionally substituted with 1, 2 or 3 substituents independently selected from $R^{22}$;

$R^{22}$ is selected from the group consisting of:

1) oxo, halogen, cyano, carboxyl, $—C(═O)R^{a4}$, $—C(═O)OR^{a4}$, $—C(═O)NR^{a4}R^{b4}$, $—C(═NR^{d4})NR^{a4}R^{b4}$, $—OR^{a4}$, $—S(═O)_2R^{c4}$, sulphonic acid group, $—S(═O)_2NR^{a4}R^{b4}$, $—S(═O)(═NR^{d4})R^{c4}$, $—NR^{a4}R^{b4}$, $—NR^{a4}C(═O)R^{b4}$, $—NR^{e4}C(═O)NR^{a4}R^{b4}$, $—NR^{e4}C(═NR^{d4})NR^{a4}R^{b4}$, $—NR^{a4}S(═O)_2R^{c4}$, $—NR^{c4}S(═O)_2NR^{a4}R^{b4}$ and $═N—R^{d4}$;

2) $C_{1-4}$ alkyl, $C_{1-4}$ alkylene, phenyl, 5-6 membered heteroaryl, $C_{3-7}$ cycloalkyl and 3-7 membered aliphatic heterocyclyl, unsubstituted or optionally substituted with 1, 2 or 3 substituents independently selected from $R^{32}$;

$R^{a4}$, $R^{b4}$ and $R^{e4}$ are each independently selected from the group consisting of:

1) hydrogen;

2) $C_{1-4}$ alkyl, phenyl, 5-6 membered heteroaryl, $C_{3-6}$ cycloalkyl, and 3-6 membered aliphatic heterocyclyl, unsubstituted or optionally substituted with 1, 2 or 3 substituents independently selected from $R^{32}$;

or, $R^{a4}$ and $R^{b4}$, together with the same N atom to which they are attached, form a 3-6 membered aliphatic heterocyclyl, unsubstituted or optionally substituted with 1, 2 or 3 substituents independently selected from $R^{32}$;

$R^{c4}$ is selected from the group consisting of $C_{1-4}$ alkyl, phenyl, 5-6 membered heteroaryl, $C_{3-6}$ cycloalkyl, and 3-6 membered aliphatic heterocyclyl, unsubstituted or optionally substituted with 1, 2 or 3 substituents independently selected from $R^{32}$;

$R^{d4}$ is selected from the group consisting of:

1) hydrogen, cyano, nitro, and $—S(═O)_2R^G$;

2) $C_{1-4}$ alkyl, phenyl, 5-6 membered heteroaryl, $C_{3-6}$ cycloalkyl, and 3-6 membered aliphatic heterocyclyl, unsubstituted or optionally substituted with 1, 2 or 3 substituents independently selected from $R^{32}$;

$R^{32}$ is selected from the group consisting of:

1) oxo, halogen, cyano, $—C(═O)R^{a6}$, $—C(═O)OR^{a6}$, $C(═O)NR^{a6}R^{b6}$, $—C(═NR^{d6})NR^{a6}R^{b6}$, $—OR^{a6}$, $—S(═O)_2R^{c6}$, $—S(═O)_2NR^{a6}R^{b6}$, $—S(═O)(═NR^{d6})R^{c6}$, $—NR^{a6}R^{b6}$, $—NR^{a6}C(═O)R^{b6}$, $—NR^{e6}C(═O)NR^{a6}R^{b6}$, $NR^{e6}C(═NR^{d6})NR^{a6}R^{b6}$, $—NR^{a6}S(═O)_2R^{c6}$, $—NR^{e6}$ $(═O)_2NR^{a6}R^{b6}$, and $=N—R^{d6}$;

2) $C_{1-4}$ alkyl, $C_{1-4}$ alkylene, phenyl, 5-6 membered heteroaryl, $C_{3-6}$ cycloalkyl, and 3-6 membered aliphatic heterocyclyl, unsubstituted or optionally substituted with 1, 2, 3 or 4 substituents independently selected from $R^G$;

$R^{a6}$, $R^{b6}$ and $R^{e6}$ are each independently selected from the group consisting of:

1) hydrogen;

2) $C_{1-4}$ alkyl, phenyl, 5-6 membered heteroaryl, $C_{3-6}$ cycloalkyl, and 3-6 membered aliphatic heterocyclyl, unsubstituted or optionally substituted with 1, 2, or 3 substituents independently selected from $R^G$;

or, $R^{a6}$ and $R^{b6}$ attached to the same nitrogen atom, together with the nitrogen, form a 3-6 membered aliphatic heterocyclyl, unsubstituted or optionally substituted with 1, 2, or 3 substituents independently selected from $R^G$;

$R^{c6}$ is independently selected from the group consisting of $C_{1-4}$ alkyl, phenyl, 5-6 membered heteroaryl, $C_{3-6}$ cycloalkyl and 3-6 membered aliphatic heterocyclyl, unsubstituted or optionally substituted with 1, 2, or 3 substituents independently selected from $R^G$;

$R^{d6}$ is selected from the group consisting of:

1) hydrogen, cyano, nitro, and $—S(═O)_2R^G$;

2) $C_{1-4}$ alkyl, phenyl, 5-6 membered heteroaryl, $C_{3-6}$ cycloalkyl, and 3-6 membered aliphatic heterocyclyl, unsubstituted or optionally substituted with 1, 2 or 3 substituents independently selected from $R^G$;

$Cy^B$ is selected from the group consisting of phenyl, naphthyl and 5-10 membered heteroaryl, unsubstituted or optionally substituted with 1, 2, 3 or 4 substituents independently selected from $R^{13}$; wherein the 5-10 membered heteroaryl contains at least one ring-forming carbon atom and 1, 2, or 3 ring-forming heteroatoms independently selected from the group consisting of N, O and S;

$R^{13}$ is selected from the group consisting of:

1) oxo, halogen, cyano, —C(═O)$R^{a3}$, —C(═O)O$R^{a3}$, —C(═O)N$R^{a3}R^{b3}$, —C(═N$R^{d3}$)N$R^{a3}R^{b3}$, —O$R^{a3}$, —N$R^{a3}R^{b3}$, —N$R^{a3}$C(═O)$R^{b3}$, —N$R^{c3}$C(═O)N$R^{a3}R^{b3}$, —N$R^{c3}$C(═N$R^{d3}$)N$R^{a3}R^{b3}$, —N$R^{a3}$S(═O)$_2$ $R^{c3}$ and —N$R^{c3}$S(═O)$_2$N$R^{a3}R^{b3}$;

2) $C_{1-6}$ alkyl, $C_{2-6}$ alkenyl, $C_{2-6}$ alkynyl, 6-10 membered aryl, 5-10 membered heteroaryl, $C_{3-10}$ cycloalkyl, and 3-10 membered aliphatic heterocyclyl;

3) Two $R^{13}$, together with two adjacent ring-forming atoms of the aryl or heteroaryl of $Cy^B$ to which they are attached respectively, form a $C_{4-8}$ aliphatic cyclyl or 4-8 membered aliphatic heterocyclyl, unsubstituted or optionally substituted with 1, 2 or 3 substituents independently selected from $R^{23}$;

$R^{a3}$, $R^{b3}$ and $R^{e3}$ are each independently selected from the group consisting of:

1) hydrogen;

2) $C_{1-4}$ alkyl, $C_{2-4}$ alkenyl, $C_{2-4}$ alkynyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^{23}$;

or, $R^{a3}$ and $R^{b3}$ together with the same N atom to which they are attached form a 3-8 membered aliphatic heterocyclyl, unsubstituted or optionally substituted with 1, 2 or 3 substituents independently selected from $R^{23}$;

$R^{c3}$ is selected from the group consisting of $C_{1-4}$ alkyl, $C_{2-4}$ alkenyl, $C_{2-4}$ alkynyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^{23}$;

$R^{d3}$ is selected from the group consisting of:

1) hydrogen, cyano, nitro and —S(═O)$_2R^G$;

2) $C_{1-4}$ alkyl, $C_{2-4}$ alkenyl, $C_{2-4}$ alkynyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^{23}$;

$R^{23}$ is selected from the group consisting of:

1) oxo, halogen, cyano, carboxyl, —C(═O)$R^{a5}$, —C(═O)O$R^{a5}$, —C(═O)N$R^{a5}R^{b5}$, —C(═N$R^{d5}$)N$R^{a5}R^{b5}$, —O$R^{a5}$, —S(═O)$_2R^{c5}$, sulphonic acid group, —S(═O)$_2$N$R^{a5}R^{b5}$, —S(═O)(═N$R^{d5}$)$R^{c5}$, —N$R^{a5}R^{b5}$, —N$R^{a5}$C(═O)$R^{b5}$, —N$R^{e5}$C(═O)N$R^{a5}R^{b5}$, —N$R^{e5}$C(═N$R^{d5}$)N$R^{a5}R^{b5}$, —N$R^{a5}$S(═O)$_2$ $R^{c5}$, —N$R^{e5}$S(═O)$_2$N$R^{a5}R^{b5}$ and =N—$R^{d5}$;

2) $C_{1-6}$ alkyl, $C_{1-6}$ alkylene, phenyl, 5-6 membered heteroaryl, $C_{3-7}$ cycloalkyl and 3-7 membered aliphatic heterocyclyl, unsubstituted or optionally substituted with 1, 2 or 3 substituents substituents independently selected from $R^{33}$;

$R^{a5}$, $R^{b5}$ and $R^{e5}$ are each independently selected from the group consisting of:

1) hydrogen;

2) $C_{1-4}$ alkyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^{33}$;

or, $R^{a5}$ and $R^{b5}$ together with the same N atom to which they are linked form a 3-6 membered aliphatic heterocyclyl, unsubstituted or optionally substituted with 1, 2 or 3 substituents independently selected from $R^{33}$;

$R^{c5}$ is selected from the group consisting of $C_{1-4}$ alkyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^{33}$;

$R^{d5}$ is selected from the group consisting of:

1) hydrogen, cyano, nitro and —S(═O)$_2R^G$;

2) $C_{1-4}$ alkyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^{33}$;

$R^{33}$ is selected from the group consisting of:

1) oxo, halogen, cyano, —C(═O)$R^{a7}$, —C(═O)O$R^{a7}$, —C(═O)N$R^{a7}R^{b7}$, —C(═N$R^{d7}$)N$R^{a7}R^{b7}$, —O$R^{a7}$, —S(═O)$_2R^{c7}$, —S(═O)$_2$N$R^{a7}R^{b7}$, —S(═O)(═N$R^{d7}$)$R^{e7}$, —N$R^{a7}R^{b7}$, —N$R^{a7}$C(═O)$R^{b7}$, —N$R^{c7}$C(═O)N$R^{a7}R^{b7}$, —N$R^{c7}$C(═N$R^{d7}$)N$R^{a7}R^{b7}$, —N$R^{a7}$S(═O)$_2R^{c7}$, —N$R^{e7}$S(═O)$_2$N$R^{a7}R^{b7}$ and —N—$R^{d7}$;

2) $C_{1-4}$ alkyl, $C_{1-4}$ alkylene, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^G$;

$R^{a7}$, $R^{b7}$ and $R^{e7}$ are each independently selected from the group consisting of:

1) hydrogen;

2) $C_{1-4}$ alkyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^G$;

or, $R^{a7}$ and $R^{b7}$ together with the same N atom to which they are attached form a 3-6 membered aliphatic heterocyclyl, unsubstituted or optionally substituted with 1, 2 or 3 substituents independently selected from $R^G$;

$R^{c7}$ is selected from the group consisting of $C_{1-4}$ alkyl, $C_{2-4}$ alkenyl, $C_{2-4}$ alkynyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^G$;

$R^{d7}$ is selected from the group consisting of:

1) hydrogen, cyano, nitro and —S(═O)$_2R^G$;

2) $C_{1-4}$ alkyl, phenyl, 5-6 membered heteroaryl, $C_{3-6}$ cycloalkyl and 3-6 membered aliphatic heterocyclyl, unsubstituted or optionally substituted with 1, 2 or 3 substituents independently selected from $R^G$;

$R^G$ is selected from the group consisting of:

1) Halogen, oxo, cyano, carboxyl, hydroxyl, $C_{1-4}$ alkoxy, amino, $C_{1-4}$ alkylamino, sulfonic acid group, $C_{1-4}$ alkylsulfonyl and $C_{1-4}$ alkylaminosulfonyl;

2) $C_{1-4}$ alkyl, $C_{1-4}$ alkylene, $C_{2-4}$ alkenyl, $C_{2-4}$ alkynyl, $C_{3-6}$ cycloalkyl and 3-8 membered aliphatic heterocyclyl, unsubstituted or optionally substituted with 1, 2, or 3 substituents independently selected from the group consisting of oxo, halogen, hydroxyl, hydroxymethyl, carboxyl, cyano, $C_{1-3}$ alkoxy, amino, and $C_{1-3}$ alkylamino;

or a pharmaceutically acceptable salt, hydrate, solvate, active metabolite, polymorph, isotope labeled compound, stereoisomer or prodrug thereof.

3. The compound according to claim 2, wherein, $R^1$ is selected from the group consisting of hydrogen, fluorine, cyano, methyl and methoxy;

$Cy^A$ is selected from phenyl and 5 or 6 membered heteroaryl, unsubstituted or optionally substituted with 1 or 2, or 3 substituents independently selected from $R^{12}$; wherein 5 or 6 membered heteroaryl contains 1 or 2 heteroatom(s) independently selected from the group consisting of N and S;

$Cy^B$ is selected from phenyl and 5 or 6 membered heteroaryl, unsubstituted or optionally substituted with 1, 2, 3 or 4 substituents independently selected from $R^{13}$; wherein the 5 or 6 membered heteroaryl contains 1, 2, or 3 ring-forming heteroatoms independently selected from the group consisting of N and S;

$R^{12}$ is selected from the group consisting of:

1) oxo, halogen, cyano, $—C(=O)R^{a2}$, $—C(=O)NR^{a2}R^{b2}$, $—C(=NR^{d2})NR^{a2}R^{b2}$, $—OR^{a2}$, $—NR^{a2}R^{b2}$, $—NR^{a2}C(=O)R^{b2}$, $—NR^{a2}C(=O)OR^{c2}$, $—NR^{e2}C(=O)NR^{a2}R^{b2}$, $—NR^{e2}C(=NR^{d2})NR^{a2}R^{b2}$, $—NR^{a2}S(=O)_2R^{c2}$, and $—NR^{e2}S(=O)_2NR^{a2}R^{b2}$;
2) $C_{1-6}$ alkyl, phenyl, 5-6 membered heteroaryl, $C_{3-10}$ cycloalkyl and 3-10 membered aliphatic heterocyclyl, unsubstituted or optionally substituted with 1, 2, 3 or 4 substituents independently selected from $R^{22}$;
3) Two $R^{12}$, together with two adjacent ring-forming atoms of the aryl or heteroaryl of $Cy^A$ to which they are connected respectively, form a $C_5$, $C_6$, $C_7$ aliphatic monocyclyl or 5-, 6-, 7-membered aliphatic monoheterocyclyl, unsubstituted or optionally substituted with 1, 2 or 3 substituents independently selected from $R^{22}$;

$R^{13}$ is selected from the group consisting of:

1) oxo, halogen, cyano, $—C(=O)R^{a3}$, $—C(=O)NR^{a3}R^{b3}$, $—C(=NR^{d3})NR^{a3}R^{b3}$, $—OR^{a3}$, $—NR^{a3}R^{b3}$, $—NR^{a3}C(=O)R^{b3}$, $—NR^{c3}C(=O)NR^{a3}R^{b3}$, $—NR^{c3}C(=NR^{c3})NR^{a3}R^{b3}$, $—NR^{a3}S(=O)_2 R^{c3}$, and $—NR^{c3}S(=O)_2NR^{a3}R^{b3}$;
2) $C_{1-6}$ alkyl, phenyl, 5-6 membered heteroaryl, $C_{3-10}$ cycloalkyl and 3-10 membered aliphatic heterocyclyl, unsubstituted or optionally substituted with 1, 2, 3 or 4 substituents independently selected from $R^{23}$;
3) Two $R^{13}$, together with two adjacent ring-forming atoms of the aryl or heteroaryl of $Cy^B$ to which they are connected respectively, form a $C_5$, $C_6$, $C_7$ aliphatic monocyclyl or 5-, 6-, 7-membered aliphatic monoheterocyclyl, unsubstituted or optionally substituted with 1, 2 or 3 substituents independently selected from $R^{23}$;

or a pharmaceutically acceptable salt, hydrate, solvate, active metabolite, polymorph, isotope labeled compound, stereoisomer or prodrug thereof.

4. A compound of formula (I), (I)

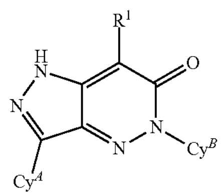

$R^1$ is selected from the group consisting of hydrogen, fluorine, cyano, methyl and methoxy;

$Cy^A$ is phenyl, pyridyl, pyrimidyl, pyrazolyl, imidazolyl, thiazolyl, isothiazolyl or a bicyclyl represented by

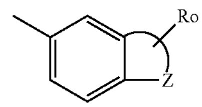

where a phenyl is fused with a 5-7 membered saturated aliphatic heterocyclyl, or a bicyclyl represented by

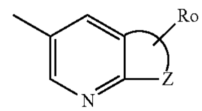

where a pyridyl is fused with a 5-7 membered saturated aliphatic heterocyclyl; wherein Z represents 1-3 heteroatoms selected from the group consisting of nitrogen and oxygen; when Z═N, Nis optionally linked to Ry; Ro is selected from the group consisting of oxo, F, amino, and optionally substituted $C_{1-3}$ alkyl; wherein said aliphatic heterocyclyl may be fused with another 5-6 membered nitrogen-containing saturated aliphatic heterocyclyl to form a fused ring;

1) when $Cy^A$ is substituted with one $R^{12}$, the $R^{12}$ is selected from one of the followings:

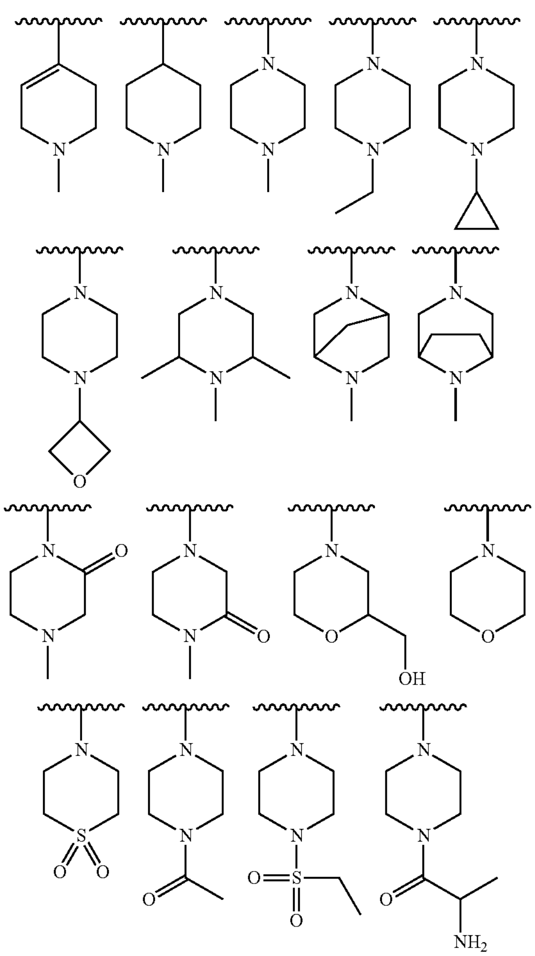

-continued

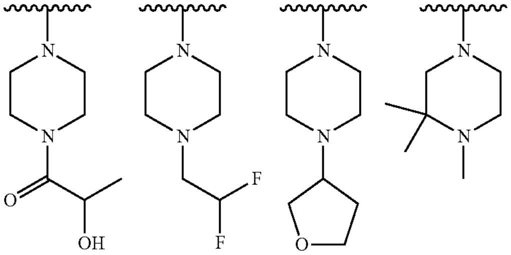

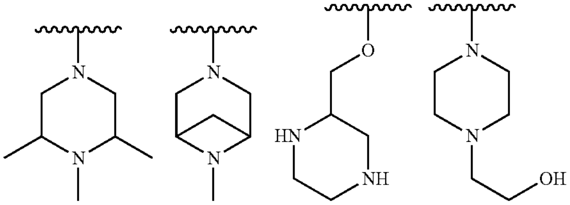

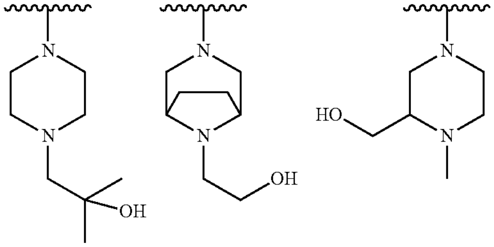

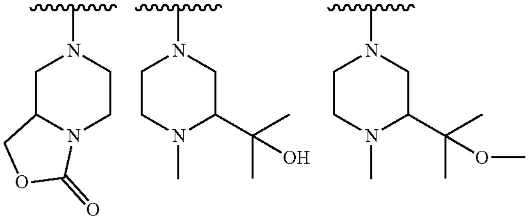

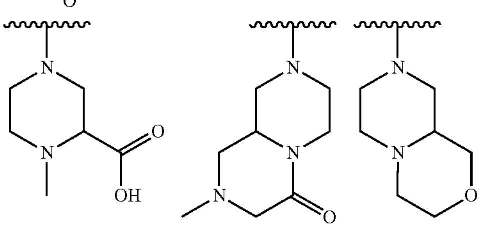

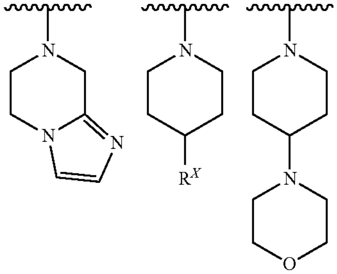

and

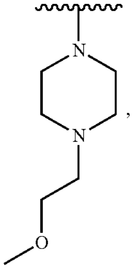

, wherein $R^x$ is selected from the group consisting of —OH, $C_{1-6}$ alkyl, $C_{1-6}$ alkoxy, —$NH_2$, $C_{1-6}$ alkylamino,

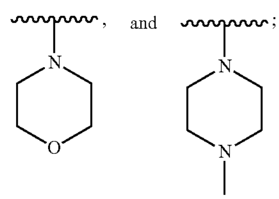

, and ;

2) When $Cy^A$ is substituted with more than one $R^{12}$, the others of $R^{12}$ are each independently selected from the group consisting of fluorine, $C_{1-6}$ alkyl, $C_{1-6}$ alkoxy, and ($C_{1-6}$ alkylamino)methyl;

$Cy^B$ is selected from one of the following structures:

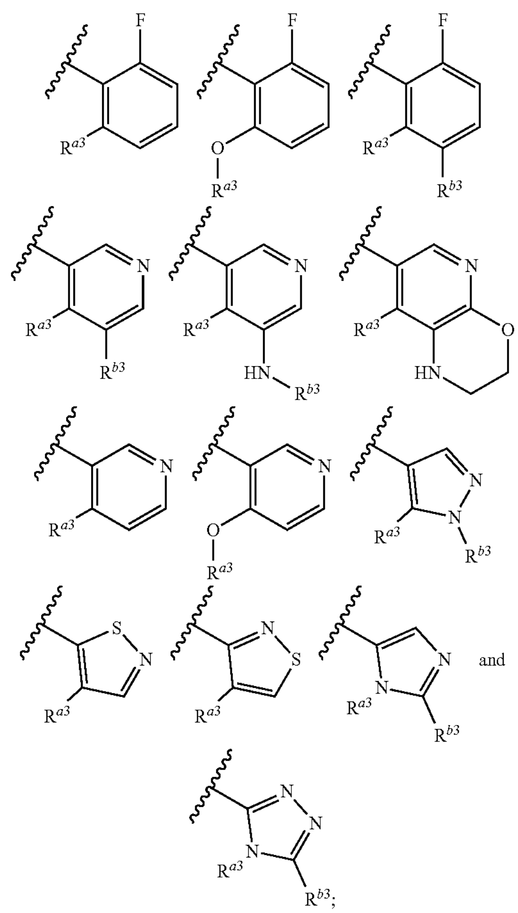

and

;

$R^{a3}$ and $R^{b3}$ are each independently selected from the group consisting of hydrogen, $C_{1-4}$ alkyl and $C_{3-6}$ cycloalkyl, or $R^{a3}$ and $R^{b3}$ together with N atom to which they are attached form a 4-6 membered saturated aliphatic heterocyclyl; said $C_{1-6}$ alkyl, $C_{3-6}$ cycloalkyl, and 4-6 membered saturated aliphatic heterocyclyl is unsubstituted or optionally substituted with substituent(s) selected from the group consisting of fluorine, hydroxyl, $C_{1-6}$ alkyl, and fluoro-substituted $C_{1-6}$ alkyl;

$R^y$ is selected from the group consisting of H, $C_{1-6}$ alkyl, $C_{1-6}$ alkyl substituted with a substituent selected from the group consisting of hydroxyl and halogen, $C_{3-6}$ cycloalkyl, nitrogen-containing 4-6 membered saturated aliphatic heterocyclyl, oxygen-containing 5-6 membered saturated aliphatic heterocyclyl, and —C(═O)Rs; Rs is selected from $C_{1-6}$ alkyl optionally substituted with substituents selected from the group consisting of hydroxyl, amino, and nitrogen-containing aliphatic heterocyclyl;

or a pharmaceutically acceptable salt, hydrate, solvate, active metabolite, polymorph, isotope labeled compound, stereoisomer or prodrug thereof.

5. A compound of formula (I), (I)

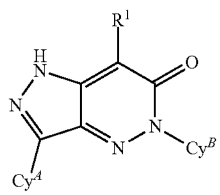

wherein, $Cy^A$ is phenyl, pyridyl, pyrimidyl, thiazolyl or a bicyclyl represented by

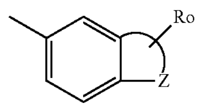

where a phenyl is fused with a 5-7 membered saturated aliphatic heterocyclyl, or a bicyclyl represented by

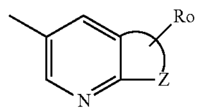

where a pyridyl is fused with a 5-7 membered saturated aliphatic heterocyclyl, wherein Z represents 1-3 heteroatoms selected from the group consisting of nitrogen and oxygen; when Z═N, N is optionally linked to Ry; Ro is selected from the group consisting of oxo, F, amino, optionally substituted $C_{1-3}$ alkyl; wherein said saturated aliphatic heterocyclyl may be fused with another 5-6 membered nitrogen-containing saturated aliphatic heterocyclyl form a fused ring, wherein, $R^y$ is selected from the group consisting of H, $C_{1-6}$ alkyl, $C_{1-6}$ alkyl substituted with the substituent consisting of hydroxyl and halogen, $C_{3-6}$ cycloalkyl, 4-6 membered N-containing saturated aliphatic heterocyclyl, 5-6 membered O-containing saturated aliphatic heterocyclyl, and —C(═O)Rs, Rs is selected from $C_{1-6}$ alkyl optionally substituted with the group consisting of hydroxyl, amino, and N-containing aliphatic heterocyclyl;

when $Cy^A$ is selected from the group consisting of phenyl, pyridyl, pyrimidyl, and thiazolyl, said phenyl, pyridyl, pyrimidyl, and thiazolyl is unsubstituted or optionally substituted with 1, 2 or 3 substituents independently selected from $R^{12}$, wherein, $R^{12}$ is selected from the group consisting of

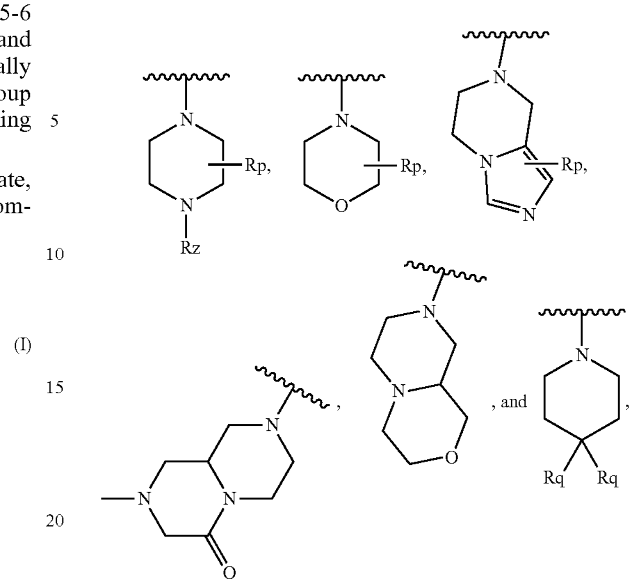

wherein Rz is selected from the group consisting of hydrogen, optionally substituted $C_{1-6}$ alkyl, 4-6 membered O-containing aliphatic heterocyclyl, and —S(═O)$_2$—$C_{1-6}$ alkyl; Rp, single or multiple substituent(s), are each optionally selected from the group consisting of hydrogen, and optionally substituted $C_{1-6}$ alkyl; Rq is selected from the group consisting of hydroxyl, amino, optionally substituted $C_{1-3}$ alkyl, spiro heterocyclyl composed of two 4-5 membered nitrogen- and/or oxygen-containing rings, and 5-6 membered aliphatic heterocyclyl containing one or two heteroatoms selected from the group consisting of nitrogen and oxygen, said aliphatic heterocyclyl is optionally substituted with F, and $C_{1-3}$ alkyl; and $R^1$ and $Cy^B$ are defined independently as those in claim 1;

or a pharmaceutically acceptable salt, hydrate, solvate, active metabolite, polymorph, isotope labeled compound, stereoisomer or prodrug thereof.

6. The compound according to claim 5, wherein, $Cy^A$ is selected from phenyl, $R^{12}$ is selected from the group consisting of

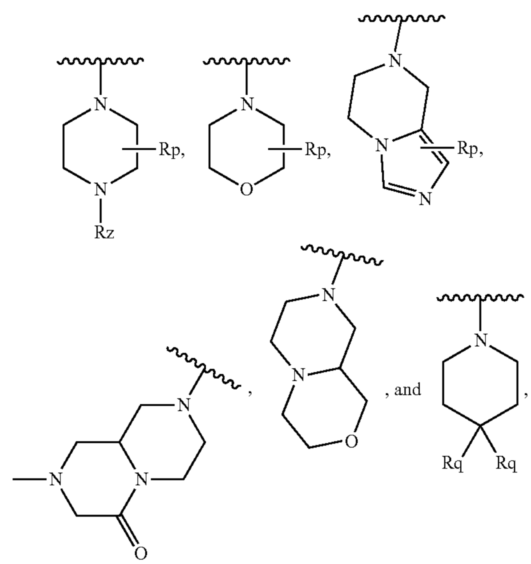

wherein Rz is selected from the group consisting of hydrogen, optionally substituted $C_{1-6}$ alkyl, 4-6 membered O-containing aliphatic heterocyclyl, and —S(═O)$_2$—$C_{1-6}$ alkyl; Rp, single or multiple substituent(s), are each optionally selected from the group consisting of hydrogen, and optionally substituted $C_{1-6}$ alkyl; Rq is selected from the group consisting of hydroxyl, amino, optionally substituted $C_{1-3}$ alkyl, spiro heterocyclyl composed of two 4-5 membered nitrogen and/or oxygen containing rings, and 5-6 membered aliphatic heterocyclyl containing one or two heteroatoms selected from the group consisting of nitrogen and oxygen, said aliphatic heterocyclyl is optionally substituted with F, and $C_{1-3}$ alkyl;

or a pharmaceutically acceptable salt, hydrate, solvate, active metabolite, polymorph, isotope labeled compound, stereoisomer or prodrug thereof.

7. A compound of formula (I), (I)

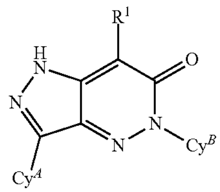

wherein, $Cy^A$ is selected from the group consisting of:

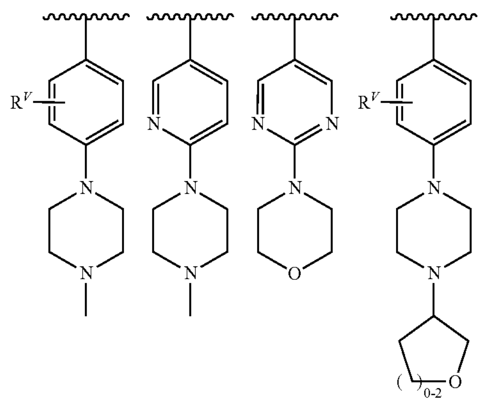

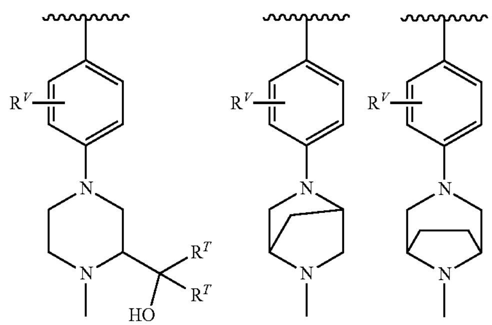

-continued

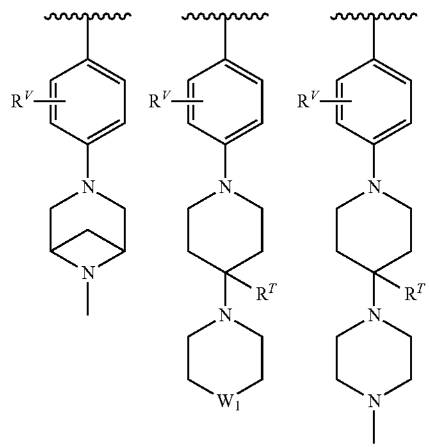

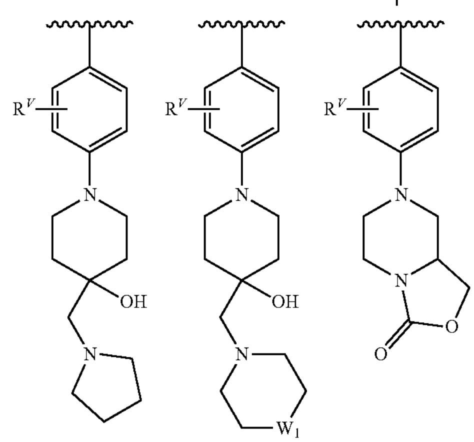

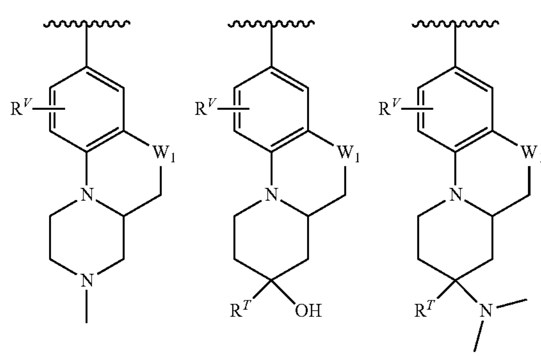

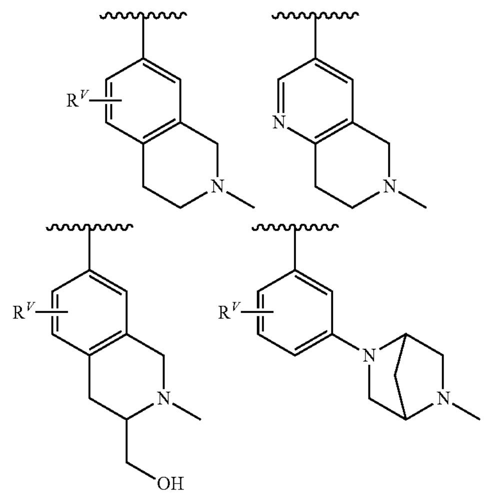

-continued

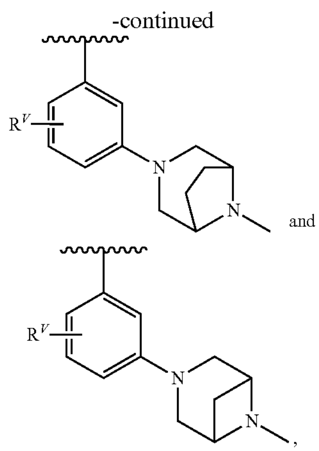

wherein, $W_1$ is selected from $CH_2$ or oxygen;

$R^T$ is selected from hydrogen or methyl;

$R^V$ is selected from fluorine or methyl, the number of $R^V$ is 0, 1 or 2;

$R^1$ and $Cy^B$ are defined independently as those in claim 1;

or a pharmaceutically acceptable salt, hydrate, solvate, active metabolite, polymorph, isotope labeled compound, stereoisomer or prodrug thereof.

8. The compound according to claim 1, wherein, $Cy^B$ is selected from phenyl optionally substituted with a group selected from the group consisting of H, F, —CN, optionally substituted $C_{1-3}$ alkyl, optionally substituted $C_{1-3}$ alkoxy, optionally substituted $C_{3-6}$ cycloalkoxy and $C(=O)NR^{a3}R^{b3}$, wherein $R^{a3}$ and $R^{b3}$ are each independently selected from the group consisting of hydrogen, $C_{1-4}$ alkyl and optionally substituted $C_{3-6}$ cycloalkyl, or $R^{a3}$ and $R^{b3}$ together with the N atom to which they attached form an optionally substituted 4-5 membered alicyclic heterocyclyl;

or a pharmaceutically acceptable salt, hydrate, solvate, active metabolite, polymorph, isotope labeled compound, stereoisomer or prodrug thereof.

9. The compound according to claim 8, wherein, $Cy^B$ is selected from the group consisting of:

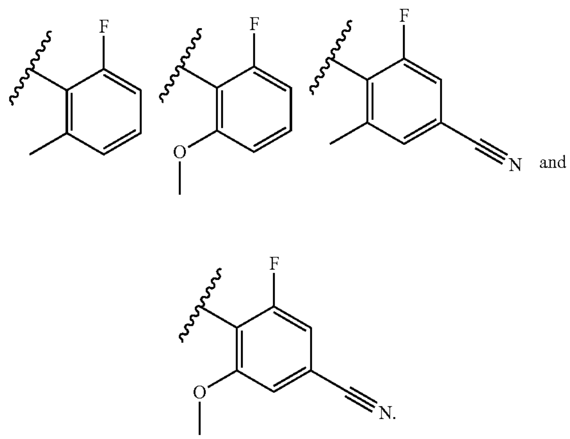

10. A compound of formula (I), (I)

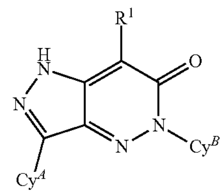

wherein, $R^1$ is H;

$Cy^A$ is selected from the group consisting of:

1) Phenyl, pyridyl, and pyrimidyl, unsubstituted or optionally substituted with 1, 2 or 3 substituents independently selected from $R^{12}$; each $R^{12}$ is independently selected from the group consisting of fluorine, chlorine, non-hydrogen $R^{G1}$, and $OR^{G1}$;

2) Phenyl, pyridyl, and pyrimidyl, optionally substituted with 1, 2 or 3 substituents independently selected from $R^{12}$; one of $R^{12}$ is selected from the group consisting of:

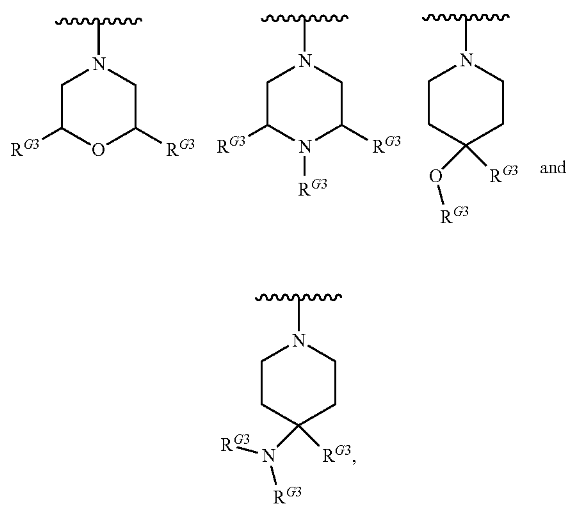

and other $R^{12}$ are each independently selected from the group consisting of: fluorine, chlorine; non-hydrogen $R^{G1}$, and $OR^{G1}$;

3) The following structure:

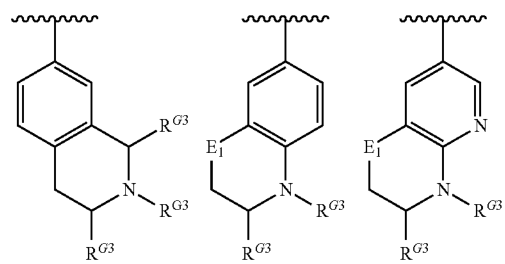

-continued

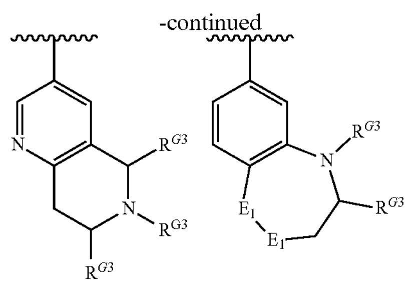

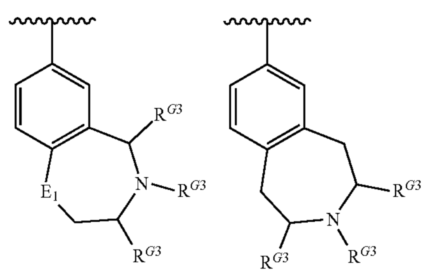

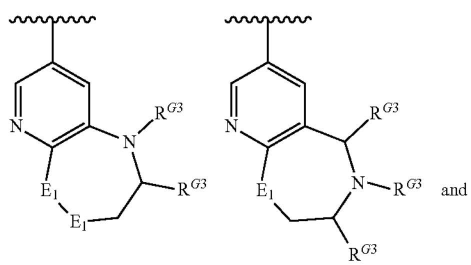

and

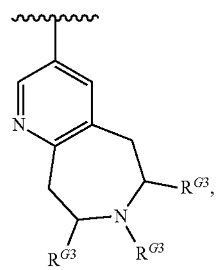

wherein the phenyl or pyridyl is unsubstituted or optionally substituted with 1 or 2 substituents independently selected from $R^{12}$;

$Cy^B$ is selected from

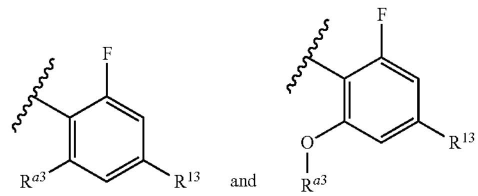

wherein $R^{a3}$ is selected from the group consisting of methyl, ethyl, difluoromethyl, trifluoromethyl, isopropyl and cyclopropyl;

$E^1$ is independently selected from the group consisting of —$CH_2$— and oxygen;

$R^{G1}$ is selected from the group consisting of hydrogen, oxo, methyl, ethyl, isopropyl, cyclopropyl, 3-oxetanyl and 3-methyl-3-azetidinyl;

$R^{13}$ is selected from the group consisting of hydrogen, fluorine, cyano and —C(═O)—N($R^{G3}$)$_2$;

each $R^{G3}$ is independently selected from the group consisting of:

1) hydrogen, methyl, ethyl, isopropyl, cyclopropyl, oxetanyl, oxacyclopentyl, azetidinyl, and azacyclopentyl;

2) Two $R^{G3}$ connected to the same atom, together with said atom, form a $C_{3-6}$ monocyclyl or a 3-6 membered aliphatic monoheterocyclyl;

3) Two $R^{G3}$ respectively connected to two different ring-forming atoms on the same single ring are connected to form a ring structure together with part of the ring-forming atoms of said single ring, and the two connected $R^{G3}$ form a $C_2$, $C_3$ or $C_4$ alkylene, or a 2-, 3- or 4-membered oxaalkylene, or a 2-, 3- or 4-membered azaalkylene;

and, when $R^{G3}$ is not hydrogen, $R^{G3}$ is unsubstituted or independently substituted with 1, 2 or 3 substituents optionally selected from the group consisting of oxo, fluorine, hydroxyl, methoxy, amino, methylamino, dimethylamino, methyl, ethyl, and cyano;

or a pharmaceutically acceptable salt, hydrate, solvate, active metabolite, polymorph, isotope labeled compound, stereoisomer or prodrug thereof.

11. The compound according to claim 10, wherein, when $Cy^A$ is phenyl, and $R^{12}$ is heterocyclyl, $R^{12}$ is attached to para- or meta-position of the phenyl; or a pharmaceutically acceptable salt, hydrate, solvate, active metabolite, polymorph, isotope labeled compound, stereoisomer or prodrug thereof.

12. The compound according to claim 1, wherein the compound is selected from:

| Compound | Structural Formula | Name of Compound |
|---|---|---|
| Compound 1 | 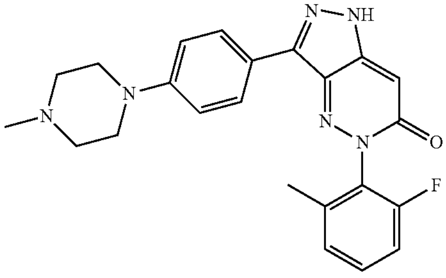 [SMILES: Cc1cccc(F)c1-n1nc2c(-c3ccc(N4CCN(C)CC4)cc3)n[nH]c2cc1=O] | 5-(2-fluoro-6-methylphenyl)-3-(4-(4-methylpiperazin-1-yl)phenyl)-1H-pyrazolo[4,3-c]pyridazin-6(5H)-one |
| Compound 2 | 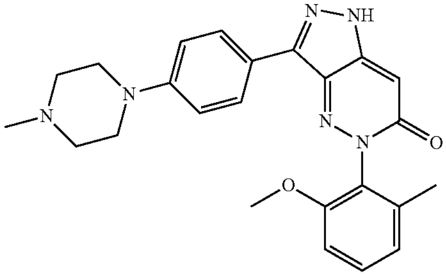 | 5-(2-methoxy-6-methylphenyl)-3-(4-(4-methylpiperazin-1-yl)phenyl)-1H-pyrazolo[4,3-c]pyridazin-6(5H)-one |
| Compound 3 | 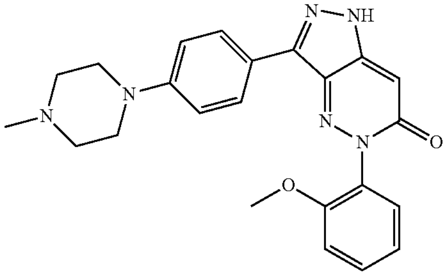 [SMILES: COc1ccccc1-n1nc2c(-c3ccc(N4CCN(C)CC4)cc3)n[nH]c2cc1=O] | 5-(2-methoxyphenyl)-3-(4-(4-methylpiperazin-1-yl)phenyl)-1H-pyrazolo[4,3-c]pyridazin-6(5H)-one |
| Compound 4 | 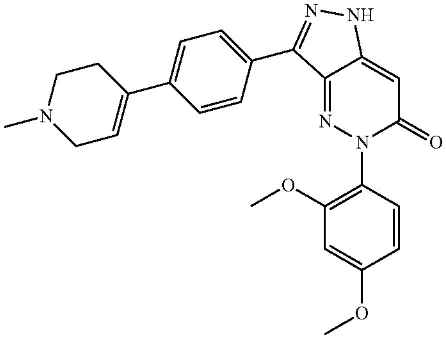 [SMILES: COc1ccc(-n2nc3c(-c4ccc(C5=CCN(C)CC5)cc4)n[nH]c3cc2=O)c(OC)c1] | 5-(2,4-dimethoxyphenyl)-3-(4-(1-methyl-1,2,3,6-tetrahydropyridin-4-yl)phenyl)-1H-pyrazolo[4,3-c]pyridazin-6(5H)-one |
| Compound 5 | 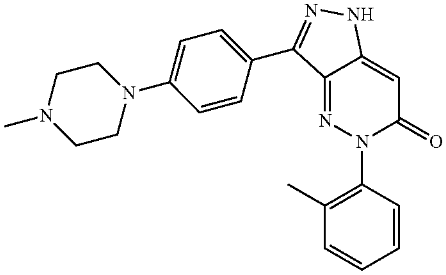 [SMILES: Cc1ccccc1-n1nc2c(-c3ccc(N4CCN(C)CC4)cc3)n[nH]c2cc1=O] | 5-(2-methylphenyl)-3-(4-(4-methylpiperazin-1-yl)phenyl)-1H-pyrazolo[4,3-c]pyridazin-6(5H)-one |

-continued

| Compound | Structural Formula | Name of Compound |
|---|---|---|
| Compound 6 | 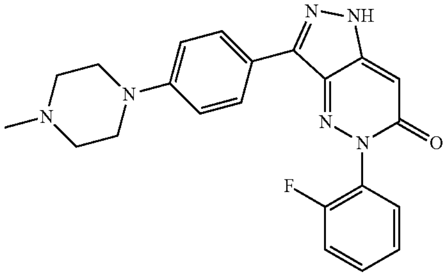 [SMILES: CN1CCN(c2ccc(-c3n[nH]c4cc(=O)n(-c5ccccc5F)nc34)cc2)CC1] | 5-(2-fluorophenyl)-3-(4-(4-methylpiperazin-1-yl)phenyl)-1H-pyrazolo[4,3-c]pyridazin-6(5H)-one |
| Compound 7 | 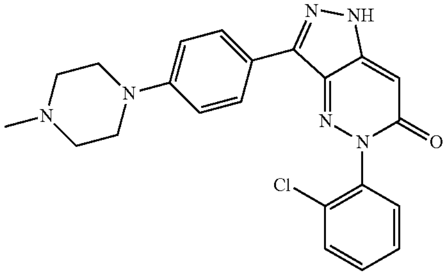 [SMILES: CN1CCN(c2ccc(-c3n[nH]c4cc(=O)n(-c5ccccc5Cl)nc34)cc2)CC1] | 5-(2-chlorophenyl)-3-(4-(4-methylpiperazin-1-yl)phenyl)-1H-pyrazolo[4,3-c]pyridazin-6(5H)-one |
| Compound 8 | 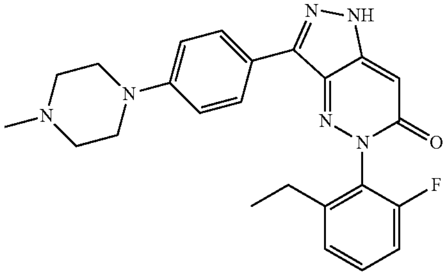 [SMILES: CCc1cccc(F)c1-n1nc2c(-c3ccc(N4CCN(C)CC4)cc3)n[nH]c2cc1=O] | 5-(2-ethyl-6-fluorophenyl)-3-(4-(4-methylpiperazin-1-yl)phenyl)-1H-pyrazolo[4,3-c]pyridazin-6(5H)-one |
| Compound 9 | 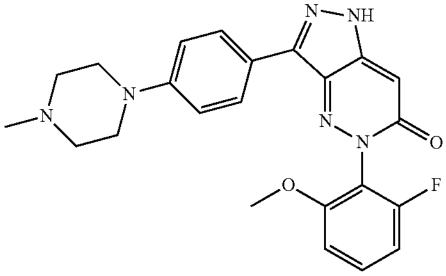 [SMILES: COc1cccc(F)c1-n1nc2c(-c3ccc(N4CCN(C)CC4)cc3)n[nH]c2cc1=O] | 5-(2-fluoro-6-methoxyphenyl)-3-(4-(4-methylpiperazin-1-yl)phenyl)-1H-pyrazolo[4,3-c]pyridazin-6(5H)-one |
| Compound 10 | 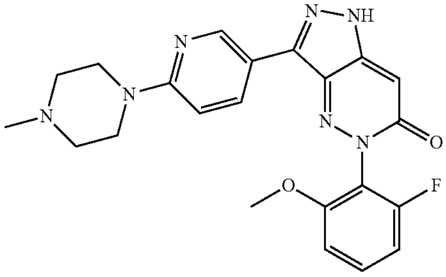 [SMILES: COc1cccc(F)c1-n1nc2c(-c3ccc(N4CCN(C)CC4)nc3)n[nH]c2cc1=O] | 5-(2-fluoro-6-methoxyphenyl)-3-(6-(4-methylpiperazin-1-yl)pyrid-3-y1)-1H-pyrazolo[4,3-c]pyridazin-6(5H)-one |

-continued

| Compound | Structural Formula | Name of Compound |
| --- | --- | --- |
| Compound 11 | 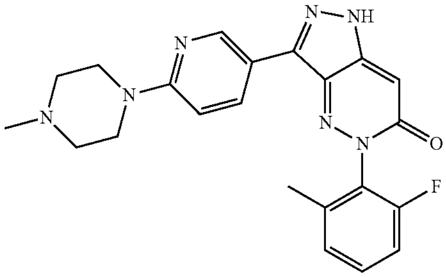 | 5-(2-fluoro-6-methylphenyl)-3-(6-(4-methylpiperazin-1-yl)pyrid-3-yl)-1H-pyrazolo[4,3-c]pyridazin-6(5H)-one |
| Compound 12 | 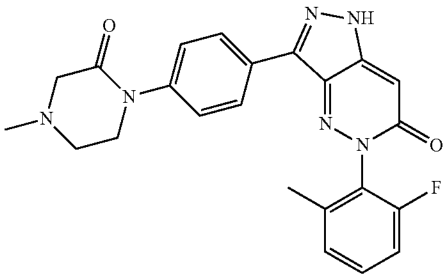 [SMILES: Cc1cccc(F)c1-n1nc2c(-c3ccc(N4CCN(C)CC4=O)cc3)n[nH]c2cc1=O] | 5-(2-fluoro-6-methylphenyl)-3-(4-(4-methyl-2-oxopiperazin-1-yl)phenyl)-1H-pyrazolo[4,3-c]pyridazin-6(5H)-one |
| Compound 13 | 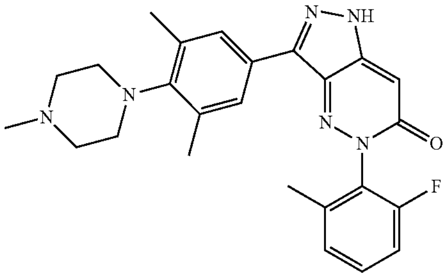 [SMILES: Cc1cc(-c2n[nH]c3cc(=O)n(-c4c(C)cccc4F)nc23)cc(C)c1N1CCN(C)CC1] | 3-(3,5-dimethyl-4-(4-methylpiperazin-1-yl)phenyl)-5-(2-fluoro-6-methylphenyl)-1H-pyrazolo[4,3-c]pyridazin-6(5H)-one |
| Compound 14 | 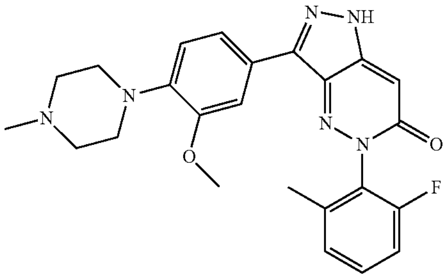 [SMILES: COc1cc(-c2n[nH]c3cc(=O)n(-c4c(C)cccc4F)nc23)ccc1N1CCN(C)CC1] | 5-(2-fluoro-6-methylphenyl)-3-(3-methoxy-4-(4-methylpiperazin-1-yl)phenyl)-1H-pyrazolo[4,3-c]pyridazin-6(5H)-one |
| Compound 15 | 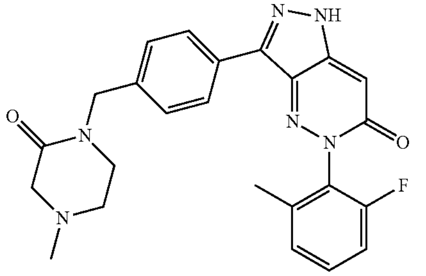 [SMILES: Cc1cccc(F)c1-n1nc2c(-c3ccc(CN4CCN(C)CC4=O)cc3)n[nH]c2cc1=O] | 5-(2-fluoro-6-methylphenyl)-3-(4-((4-methyl-2-oxo-piperazin-1-yl)methyl)phenyl)-1H-pyrazolo[4,3-c]pyridazin-6(5H)-one |

-continued

| Compound | Structural Formula | Name of Compound |
|---|---|---|
| Compound 16 | 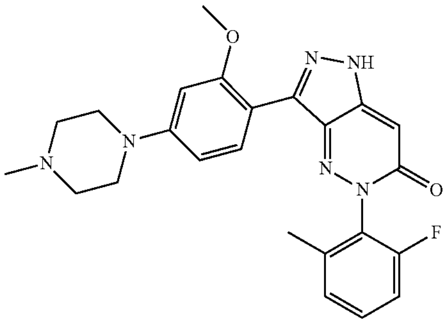 [SMILES: COc1cc(N2CCN(C)CC2)ccc1-c1n[nH]c2cc(=O)n(-c3c(C)cccc3F)nc12] | 5-(2-fluoro-6-methylphenyl)-3-(2-methoxy-4-(4-methylpiperazin-1-yl)phenyl)-1H-pyrazolo[4,3-c]pyridazin-6(5H)-one |
| Compound 17 | 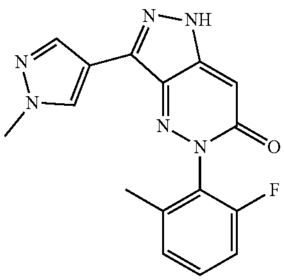 [SMILES: Cc1cccc(F)c1-n1nc2c(-c3cnn(C)c3)n[nH]c2cc1=O] | 5-(2-fluoro-6-methylphenyl)-3-(1-methyl-1H-pyrazol-4-yl)-1H-pyrazolo[4,3-c]pyridazin-6(5H)-one |
| Compound 18 | 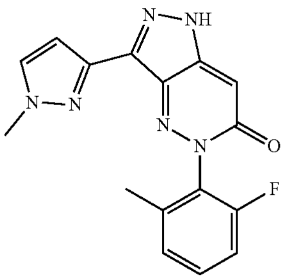 [SMILES: Cc1cccc(F)c1-n1nc2c(-c3ccn(C)n3)n[nH]c2cc1=O] | 5-(2-fluoro-6-methylphenyl)-3-(1-methyl-1H-pyrazol-3-yl)-1H-pyrazolo[4,3-c]pyridazin-6(5H)-one |
| Compound 19 | 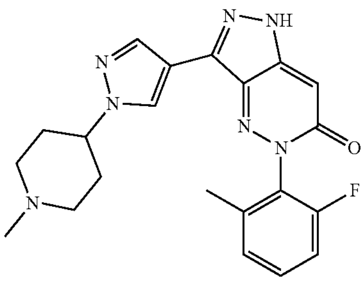 [SMILES: Cc1cccc(F)c1-n1nc2c(-c3cnn(C4CCN(C)CC4)c3)n[nH]c2cc1=O] | 5-(2-fluoro-6-methylphenyl)-3-(1-(1-methylpiperidin-4-yl)-1H-pyrazol-4-yl)-1H-pyrazolo[4,3-c]pyridazin-6(5H)-one |
| Compound 20 | 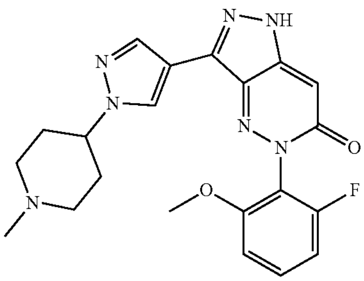 [SMILES: COc1cccc(F)c1-n1nc2c(-c3cnn(C4CCN(C)CC4)c3)n[nH]c2cc1=O] | 5-(2-fluoro-6-methoxyphenyl)-3-(1-(1-methylpiperidin-4-yl)-1H-pyrazol-4-y1)-1H-pyrazolo[4,3-c]pyridazin-6(5H)-one |

-continued

| Compound | Structural Formula | Name of Compound |
|---|---|---|
| Compound 21 | 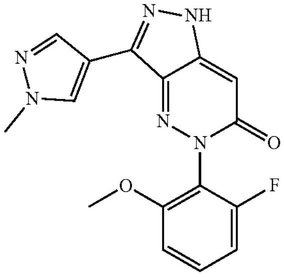 [SMILES: COc1cccc(F)c1-n1nc2c(-c3cnn(C)c3)n[nH]c2cc1=O] | 5-(2-fluoro-6-methoxyphenyl)-3-(1-methyl-1H-pyrazol-4-yl)-1H-pyrazolo[4,3-c]pyridazin-6(5H)-one |
| Compound 22 | 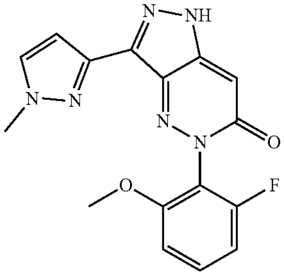 [SMILES: COc1cccc(F)c1-n1nc2c(-c3ccn(C)n3)n[nH]c2cc1=O] | 5-(2-fluoro-6-methoxyphenyl)-3-(1-methyl-1H-pyrazol-3-yl)-1H-pyrazolo[4,3-c]pyridazin-6(5H)-one |
| Compound 23 | 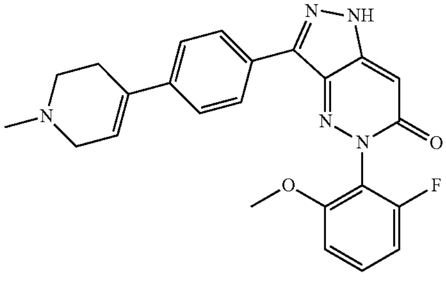 [SMILES: COc1cccc(F)c1-n1nc2c(-c3ccc(C4=CCN(C)CC4)cc3)n[nH]c2cc1=O] | 5-(2-fluoro-6-methoxyphenyl)-3-(4-(1-methyl-1,2,3,6-tetrahydropyridin-4-yl)phenyl)-1H-pyrazolo[4,3-c]pyridazin-6(5H)-one |
| Compound 24 | 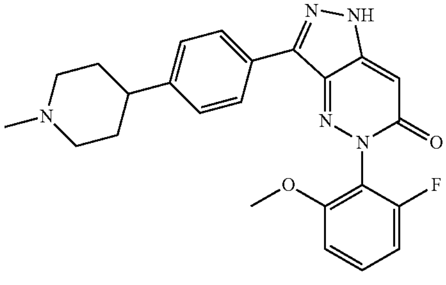 [SMILES: COc1cccc(F)c1-n1nc2c(-c3ccc(C4CCN(C)CC4)cc3)n[nH]c2cc1=O] | 5-(2-fluoro-6-methoxyphenyl)-3-(4-(1-methylpiperidin-4-yl)phenyl)-1H-pyrazolo[4,3-c]pyridazin-6(5H)-one |
| Compound 25 | 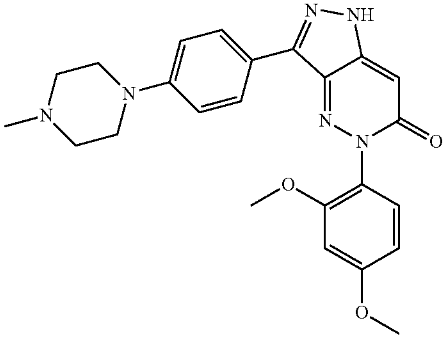 [SMILES: COc1ccc(-n2nc3c(-c4ccc(N5CCN(C)CC5)cc4)n[nH]c3cc2=O)c(OC)c1] | 5-(2,4-dimethoxyphenyl)-3-(4-(4-methylpiperazin-1-yl)phenyl)-1H-pyrazolo[4,3-c]pyridazin-6(5H)-one |

-continued

| Compound | Structural Formula | Name of Compound |
|---|---|---|
| Compound 26 | 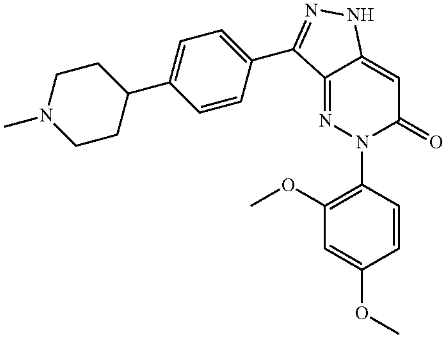 [SMILES: COc1ccc(-n2nc3c(-c4ccc(C5CCN(C)CC5)cc4)n[nH]c3cc2=O)c(OC)c1] | 5-(2,4-dimethoxyphenyl)-3-(4-(1-methylpiperidin-4-yl)phenyl)-1H-pyrazolo[4,3-c]pyridazin-6(5H)-one |
| Compound 27 | 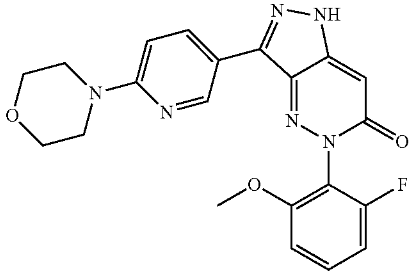 [SMILES: COc1cccc(F)c1-n1nc2c(-c3ccc(N4CCOCC4)nc3)n[nH]c2cc1=O] | 5-(2-fluoro-6-methoxyphenyl)-3-(6-morpholinopyrid-3-yl)-1H-pyrazolo[4,3-c]pyridazin-6(5H)-one |
| Compound 28 | 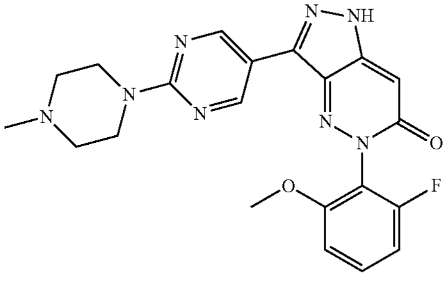 [SMILES: COc1cccc(F)c1-n1nc2c(-c3cnc(N4CCN(C)CC4)nc3)n[nH]c2cc1=O] | 5-(2-fluoro-6-methoxyphenyl)-3-(2-(4-methylpiperazin-1-yl)pyrimidin-5-yl)-1H-pyrazolo[4,3-c]pyridazin-6(5H)-one |
| Compound 29 | 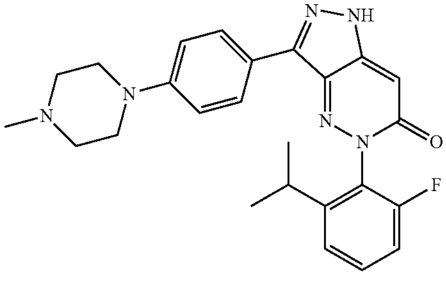 [SMILES: CC(C)c1cccc(F)c1-n1nc2c(-c3ccc(N4CCN(C)CC4)cc3)n[nH]c2cc1=O] | 5-(2-fluoro-6-isopropylphenyl)-3-(4-(4-methylpiperazin-1-yl)phenyl)-1H-pyrazolo[4,3-c]pyridazin-6(5H)-one |
| Compound 30 | 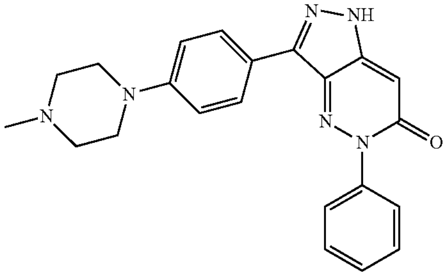 [SMILES: CN1CCN(c2ccc(-c3n[nH]c4cc(=O)n(-c5ccccc5)nc34)cc2)CC1] | 3-(4-(4-methylpiperazin-1-yl)phenyl)-5-phenyl-1H-pyrazolo[4,3-c]pyridazin-6(5H)-one |

-continued

| Compound | Structural Formula | Name of Compound |
| --- | --- | --- |
| Compound 31 | 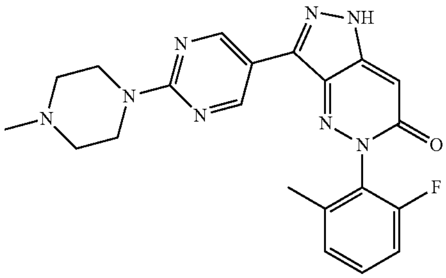 [SMILES: Cc1cccc(F)c1-n1nc2c(-c3cnc(N4CCN(C)CC4)nc3)n[nH]c2cc1=O] | 5-(2-fluoro-6-methylpheny])-3-(2-(4-methylpiperazin-1-yl)pyrimidin-5-yl)-1H-pyrazolo[4,3-c]pyridazin-6(5H)-one |
| Compound 32 | 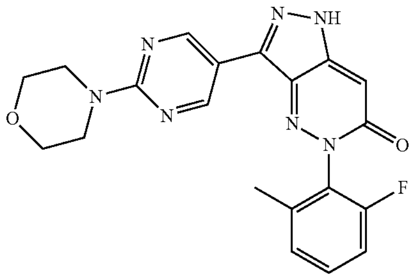 [SMILES: Cc1cccc(F)c1-n1nc2c(-c3cnc(N4CCOCC4)nc3)n[nH]c2cc1=O] | 5-(2-fluoro-6-methylphenyl)-3-(2-morpholinyl pyrimidin-5-yl)-1H-pyrazolo[4,3-c]pyridazin-6(5H)-one |
| Compound 33 | 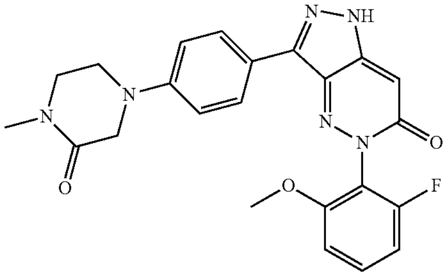 [SMILES: COc1cccc(F)c1-n1nc2c(-c3ccc(N4CCN(C)C(=O)C4)cc3)n[nH]c2cc1=O] | 5-(2-fluoro-6-methoxyphenyl)-3-(4-(4-methyl-3-oxopiperazin-1-yl)phenyl)-1H-pyrazolo[4,3-c]pyridazin-6(5H)-one |
| Compound 34 | 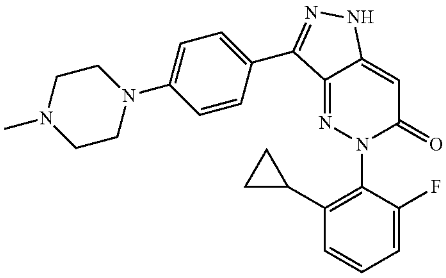 [SMILES: CN1CCN(c2ccc(-c3n[nH]c4cc(=O)n(-c5c(F)cccc5C5CC5)nc34)cc2)CC1] | 5-(2-cyclopropyl-6-fluorophenyl)-3-(4-(4-methylpiperazin-1-yl)phenyl)-1H-pyrazolo[4,3-c]pyridazin-6(5H)-one |
| Compound 35 | 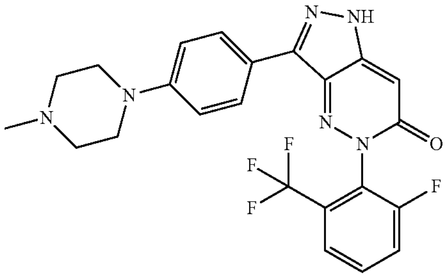 [SMILES: CN1CCN(c2ccc(-c3n[nH]c4cc(=O)n(-c5c(F)cccc5C(F)(F)F)nc34)cc2)CC1] | 5-(2-fluoro-6-(trifluoromethyl)phenyl)-3-(4-(4-methylpiperazin-1-yl)phenyl)-1H-pyrazolo[4,3-c]pyridazin-6(5H)-one |

-continued

| Compound | Structural Formula | Name of Compound |
|---|---|---|
| Compound 36 | 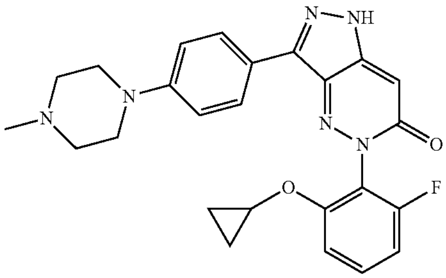 [SMILES: CN1CCN(c2ccc(-c3n[nH]c4cc(=O)n(-c5c(F)cccc5OC5CC5)nc34)cc2)CC1] | 5-(2-cyclopropoxy-6-fluorophenyl)-3-(4-(4-methylpiperazin-1-yl)phenyl)-1H-pyrazolo[4,3-c]pyridazin-6(5H)-one |
| Compound 37 | 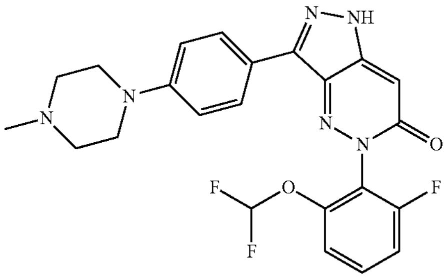 [SMILES: CN1CCN(c2ccc(-c3n[nH]c4cc(=O)n(-c5c(F)cccc5OC(F)F)nc34)cc2)CC1] | 5-(2-(difluoromethoxy)-6-fluorophenyl)-3-(4-(4-methylpiperazin-1-yl)phenyl)-1H-pyrazolo[4,3-c]pyridazin-6(5H)-one |
| Compound 38 | 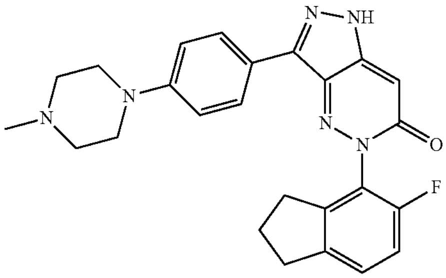 [SMILES: CN1CCN(c2ccc(-c3n[nH]c4cc(=O)n(-c5c(F)ccc6c5CCC6)nc34)cc2)CC1] | 5-(5-fluoro-2,3-dihydro-1H-indan-4-yl)-3-(4-(4-methylpiperazin-1-yl)phenyl)-1H-pyrazolo[4,3-c]pyridazin-6(5H)-one |
| Compound 39 | 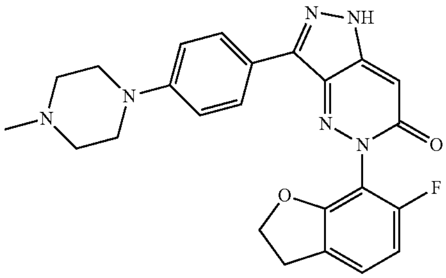 | 5-(6-fluoro-2,3-dihydrobenzofuran-7-yl)-3-(4-(4-methylpiperazin-1-yl)phenyl)-1H-pyrazolo[4,3-c]pyridazin-6(5H)-one |
| Compound 40 | 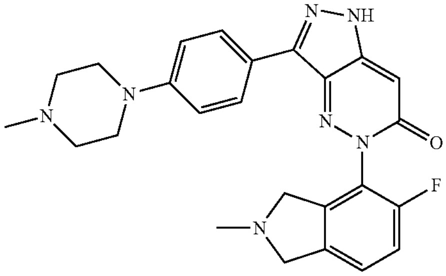 [SMILES: CN1CCN(c2ccc(-c3n[nH]c4cc(=O)n(-c5c(F)ccc6c5CN(C)C6)nc34)cc2)CC1] | 5-(5-fluoro-2-methylisoindolin-4-yl)-3-(4-(4-methylpiperazin-1-yl)phenyl)-1H-pyrazolo[4,3-c]pyridazin-6(5H)-one |

-continued

| Compound | Structural Formula | Name of Compound |
|---|---|---|
| Compound 41 | 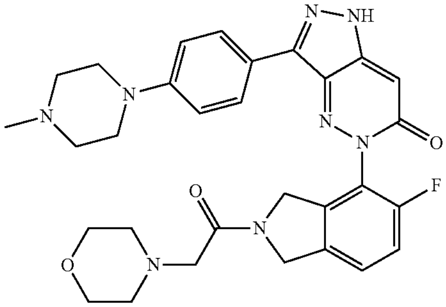 [SMILES: CN1CCN(c2ccc(-c3n[nH]c4cc(=O)n(-c5c(F)ccc6c5CN(C(=O)CN5CCOCC5)C6)nc34)cc2)CC1] | 5-(5-fluoro-2-(2-morpholinoacetyl)isoindolin-4-yl)-3-(4-(4-methylpiperazin-1-yl)phenyl)-1H-pyrazolo[4,3-c]pyridazin-6(5H)-one |
| Compound 42 | 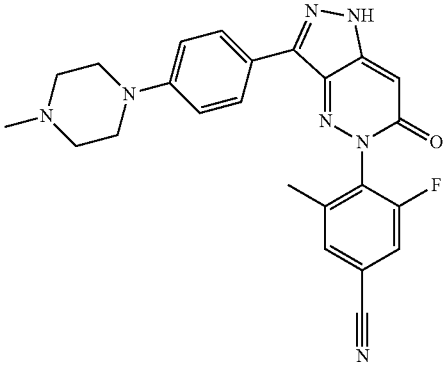 [SMILES: Cc1cc(C#N)cc(F)c1-n1nc2c(-c3ccc(N4CCN(C)CC4)cc3)n[nH]c2cc1=O] | 3-fluoro-5-methyl-4-(3-(4-(4-methylpiperazin-1-yl)phenyl)-6-oxo-1H-pyrazolo[4,3-c]pyridazin-5(6H)-yl)benzonitrile |
| Compound 43 | 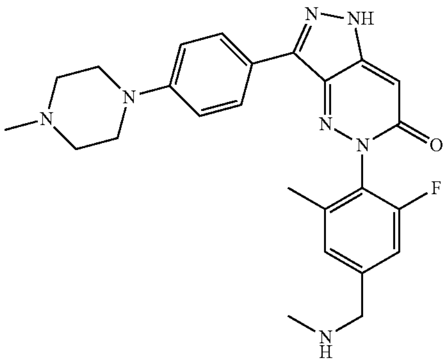 [SMILES: CNCc1cc(C)c(-n2nc3c(-c4ccc(N5CCN(C)CC5)cc4)n[nH]c3cc2=O)c(F)c1] | 5-(2-fluoro-6-methyl-4-((methylamino)methyl)phenyl)-3-(4-(4-methylpiperazin-1-yl)phenyl)-1H-pyrazolo[4,3-c]pyridazin-6(5H)-one |
| Compound 44 | 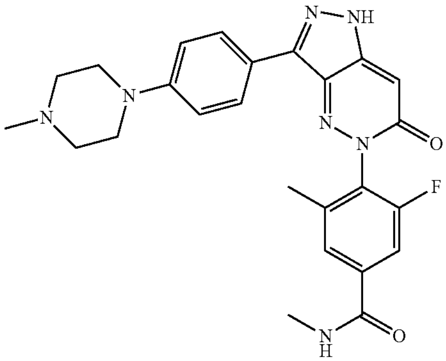 [SMILES: CNC(=O)c1cc(C)c(-n2nc3c(-c4ccc(N5CCN(C)CC5)cc4)n[nH]c3cc2=O)c(F)c1] | 3-fluoro-N,5-dimethyl-4-(3-(4-(4-methylpiperazin-1-yl)phenyl)-6-oxo-1H-pyrazolo[4,3-c]pyridazin-5(6H)-yl)benzamide |

-continued

| Compound | Structural Formula | Name of Compound |
|---|---|---|
| Compound 45 | 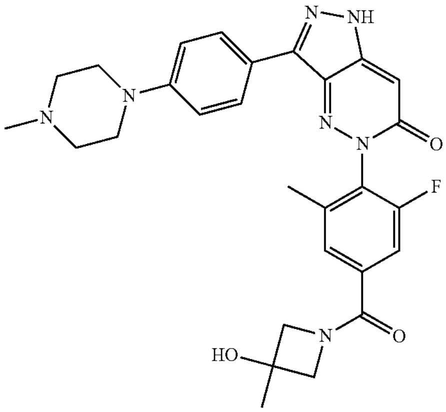 [SMILES: Cc1cc(C(=O)N2CC(C)(O)C2)cc(F)c1-n1nc2c(-c3ccc(N4CCN(C)CC4)cc3)n[nH]c2cc1=O] | 5-(2-fluoro-4-(3-hydroxyl-3-methylazetidine-1-carbonyl)-6-methylphenyl)-3-(4-(4-methylpiperazin-1-yl)phenyl)-1H-pyrazolo[4,3-c]pyridazin-6(5H)-one |
| Compound 46 | 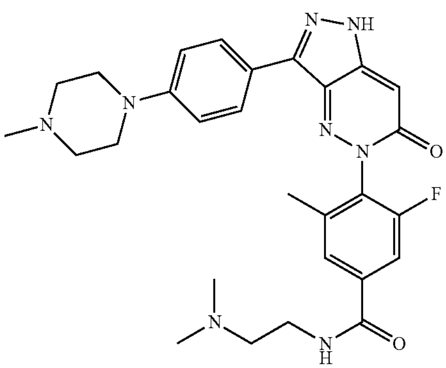 [SMILES: Cc1cc(C(=O)NCCN(C)C)cc(F)c1-n1nc2c(-c3ccc(N4CCN(C)CC4)cc3)n[nH]c2cc1=O] | N-(2-(dimethylamino)ethyl)-3-fluoro-5-methyl-4-(3-(4-(4-methylpiperazin-1-yl)phenyl)-6-oxo-1H-pyrazolo[4,3-c]pyridazin-5(6H)-yl)benzamide |
| Compound 47 | 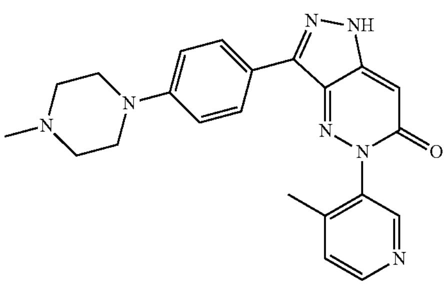 [SMILES: Cc1ccncc1-n1nc2c(-c3ccc(N4CCN(C)CC4)cc3)n[nH]c2cc1=O] | 3-(4-(4-methylpiperazin-1-yl)phenyl)-5-(4-methylpyrid-3-yl)-1H-pyrazolo[4,3-c]pyridazin-6(5H)-one |
| Compound 48 | 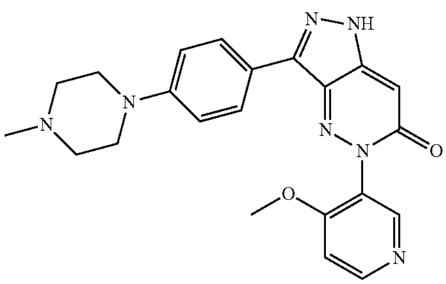 [SMILES: COc1ccncc1-n1nc2c(-c3ccc(N4CCN(C)CC4)cc3)n[nH]c2cc1=O] | 5-(4-methoxypyrid-3-yl)-3-(4-(4-methylpiperazin-1-yl)phenyl)-1H-pyrazolo[4,3-c]pyridazin-6(5H)-one |

-continued

| Compound | Structural Formula | Name of Compound |
| --- | --- | --- |
| Compound 49 | 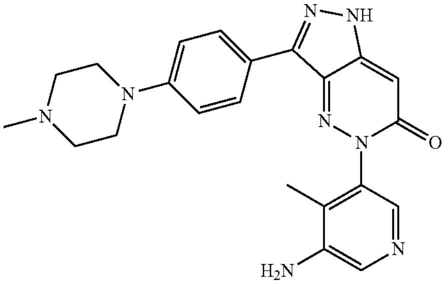 [SMILES: Cc1c(N)cncc1-n1nc2c(-c3ccc(N4CCN(C)CC4)cc3)n[nH]c2cc1=O] | 5-(5-amino-4-methylpyrid-3-yl)-3-(4-(4-methylpiperazin-1-yl)phenyl)-1H-pyrazolo[4,3-c]pyridazin-6(5H)-one |
| Compound 50 | 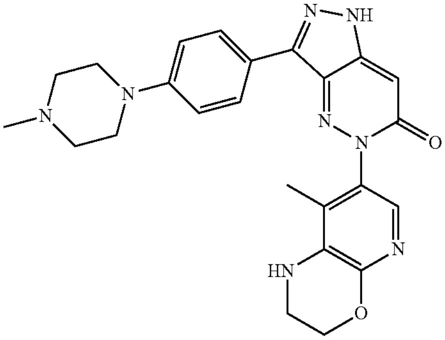 [SMILES: Cc1c(-n2nc3c(-c4ccc(N5CCN(C)CC5)cc4)n[nH]c3cc2=O)cnc2c1NCCO2] | 5-(8-methyl-2,3-dihydro-1H-pyrido[2,3-b][1,4]oxazin-7-yl)-3-(4-(4-methylpiperazin-1-yl)phenyl)-1H-pyrazolo[4,3-c]pyridazin-6(5H)-one |
| Compound 51 | 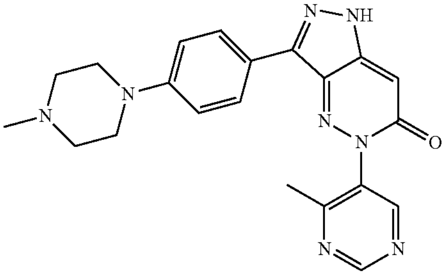 [SMILES: Cc1ncncc1-n1nc2c(-c3ccc(N4CCN(C)CC4)cc3)n[nH]c2cc1=O] | 3-(4-(4-methylpiperazin-1-yl)phenyl)-5-(4-methylpyrimidin-5-yl)-1H-pyrazolo[4,3-c]pyridazin-6(5H)-one |
| Compound 52 | 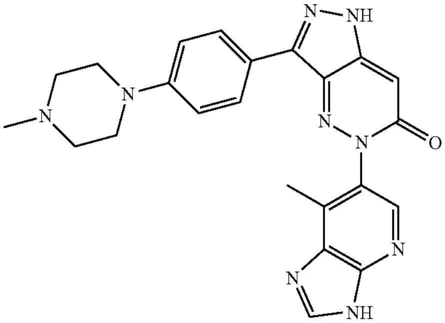 [SMILES: Cc1c(-n2nc3c(-c4ccc(N5CCN(C)CC5)cc4)n[nH]c3cc2=O)cnc2[nH]cnc12] | 5-(7-methyl-3H-imidazolo[4,5-b]pyrid-6-yl)-3-(4-(4-methylpiperazin-1-yl)phenyl)-1H-pyrazolo[4,3-c]pyridazin-6(5H)-one |
| Compound 53 | 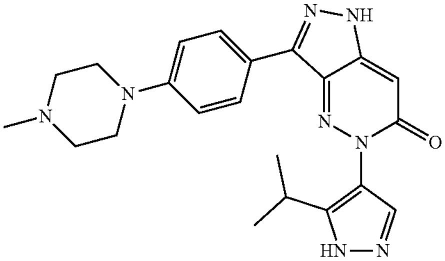 [SMILES: CC(C)c1[nH]ncc1-n1nc2c(-c3ccc(N4CCN(C)CC4)cc3)n[nH]c2cc1=O] | 5-(5-isopropyl-1H-pyrazol-4-yl)-3-(4-(4-methylpiperazin-1-yl)phenyl)-1H-pyrazolo[4,3-c]pyridazin-6(5H)-one |

-continued

| Compound | Structural Formula | Name of Compound |
|---|---|---|
| Compound 54 | 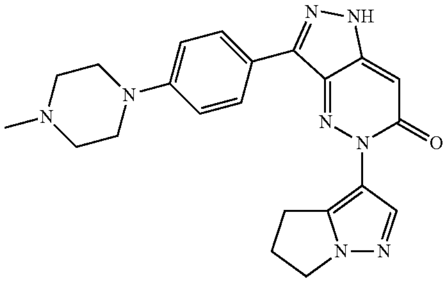 [SMILES: CN1CCN(c2ccc(-c3n[nH]c4cc(=O)n(-c5cnn6c5CCC6)nc34)cc2)CC1] | 5-(5,6-dihydro-4H-pyrrolo[1,2-b]pyrazol-3-yl)-3-(4-(4-methylpiperazin-1-yl)phenyl)-1H-pyrazolo[4,3-c]pyridazin-6(5H)-one |
| Compound 55 | 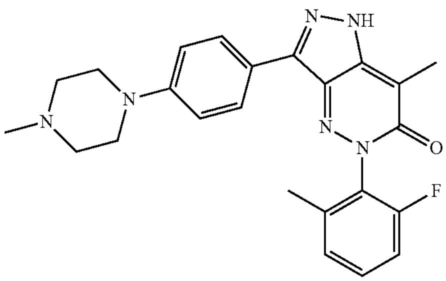 [SMILES: Cc1cccc(F)c1-n1nc2c(-c3ccc(N4CCN(C)CC4)cc3)n[nH]c2c(C)c1=O] | 5-(2-fluoro-6-methylphenyl)-7-methyl-3-(4-(4-methylpiperazin-1-yl)phenyl)-1H-pyrazolo[4,3-c]pyridazin-6(5H)-one |
| Compound 56 | 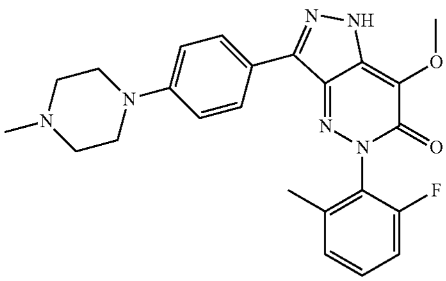 | 5-(2-fluoro-6-methylphenyl)-7-methoxy-3-(4-(4-methylpiperazin-1-yl)phenyl)-1H-pyrazolo[4,3-c]pyridazin-6(5H)-one |
| Compound 57 | 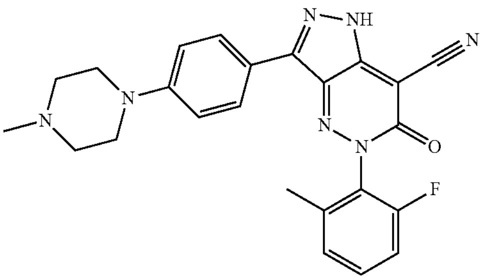 [SMILES: Cc1cccc(F)c1-n1nc2c(-c3ccc(N4CCN(C)CC4)cc3)n[nH]c2c(C#N)c1=O] | 5-(2-fluoro-6-methylphenyl)-3-(4-(4-methylpiperazin-1-yl)phenyl)-6-oxo-5,6-dihydro-1H-pyrazolo[4,3-c]pyridazin-7-carbonitrile |
| Compound 58 | 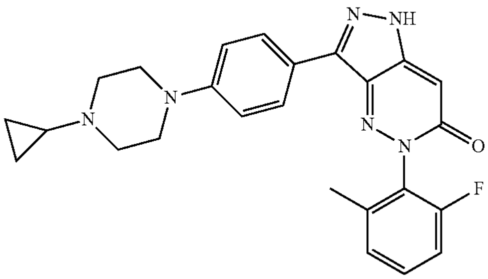 [SMILES: Cc1cccc(F)c1-n1nc2c(-c3ccc(N4CCN(C5CC5)CC4)cc3)n[nH]c2cc1=O] | 3-(4-(4-cyclopropylpiperazin-1-yl)phenyl)-5-(2-fluoro-6-methylphenyl)-1H-pyrazolo[4,3-c]pyridazin-6(5H)-one |

-continued

| Compound | Structural Formula | Name of Compound |
|---|---|---|
| Compound 59 | 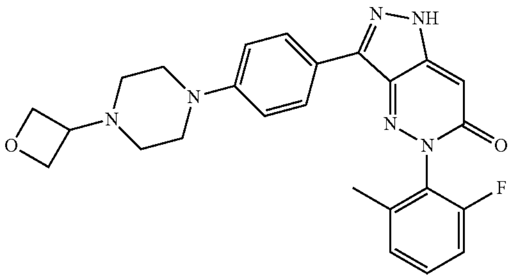 [SMILES: Cc1cccc(F)c1-n1nc2c(-c3ccc(N4CCN(C5COC5)CC4)cc3)n[nH]c2cc1=O] | 5-(2-fluoro-6-methylphenyl)-3-(4-(4-(oxetan-3-yl)piperazin-1-yl)phenyl)-1H-pyrazolo[4,3-c]pyridazin-6(5H)-one |
| Compound 60 | 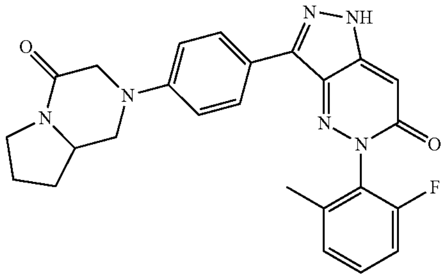 [SMILES: Cc1cccc(F)c1-n1nc2c(-c3ccc(N4CC(=O)N5CCCC5C4)cc3)n[nH]c2cc1=O] | 5-(2-fluoro-6-methylphenyl)-3-(4-(4-oxohexahydropyrrolo[1,2-a]pyrazin-2(1H)-yl)phenyl)-1H-pyrazolo[4,3-c]pyridazin-6(5H)-one |
| Compound 61 | 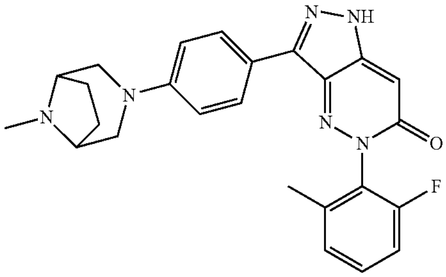 [SMILES: Cc1cccc(F)c1-n1nc2c(-c3ccc(N4CC5CCC(C4)N5C)cc3)n[nH]c2cc1=O] | 5-(2-fluoro-6-methylphenyl)-3-(4-(8-methyl-3,8-diazabicyclo[3.2.1]octan-3-yl)phenyl)-1H-pyrazolo[4,3-c]pyridazin-6(5H)-one |
| Compound 62 | 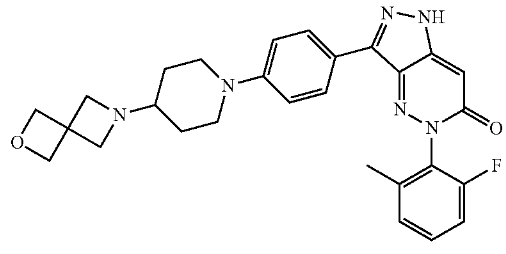 [SMILES: Cc1cccc(F)c1-n1nc2c(-c3ccc(N4CCC(N5CC6(COC6)C5)CC4)cc3)n[nH]c2cc1=O] | 3-(4-(4-(2-oxa-6-azaspiro[3.3]heptan-6-yl)piperidin-1-yl)phenyl)-5-(2-fluoro-6-methylphenyl)-1H-pyrazolo[4,3-c]pyridazin-6(5H)-one |
| Compound 63 | 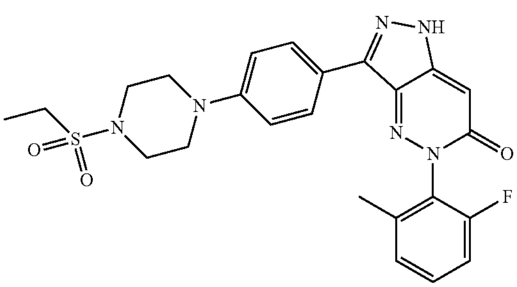 [SMILES: CCS(=O)(=O)N1CCN(c2ccc(-c3n[nH]c4cc(=O)n(-c5c(C)cccc5F)nc34)cc2)CC1] | 3-(4-(4-(ethylsulfonyl)piperazin-1-yl)phenyl)-5-(2-fluoro-6-methylphenyl)-1H-pyrazolo[4,3-c]pyridazin-6(5H)-one |

-continued

| Compound | Structural Formula | Name of Compound |
|---|---|---|
| Compound 64 | 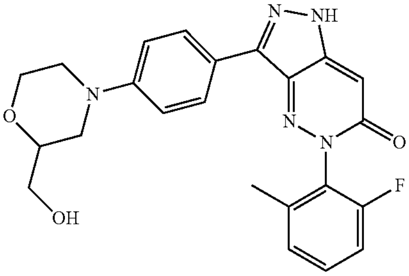 [SMILES: Cc1cccc(F)c1-n1nc2c(-c3ccc(N4CCOC(CO)C4)cc3)n[nH]c2cc1=O] | 5-(2-fluoro-6-methylphenyl)-3-(4-(2-(hydroxymethyl)morpholino)phenyl)-1H-pyrazolo[4,3-c]pyridazin-6(5H)-one |
| Compound 65 | 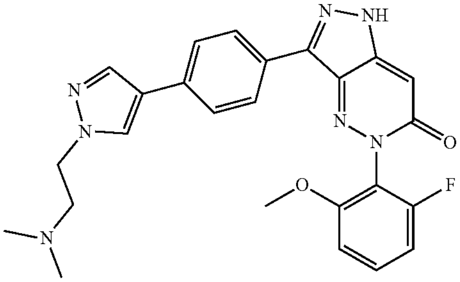 [SMILES: COc1cccc(F)c1-n1nc2c(-c3ccc(-c4cnn(CCN(C)C)c4)cc3)n[nH]c2cc1=O] | 3-(4-(1-(2-(dimethylamino)ethyl)-1H-pyrazol-4-yl)phenyl)-5-(2-fluoro-6-methoxyphenyl)-1H-pyrazolo[4,3-c]pyridazin-6(5H)-one |
| Compound 66 | 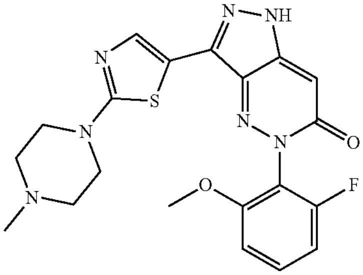 [SMILES: COc1cccc(F)c1-n1nc2c(-c3cnc(N4CCN(C)CC4)s3)n[nH]c2cc1=O] | 5-(2-fluoro-6-methoxyphenyl)-3-(2-(4-methylpiperazin-1-yl)thiazol-5-yl)-1H-pyrazolo[4,3-c]pyridazin-6(5H)-one |
| Compound 67 | 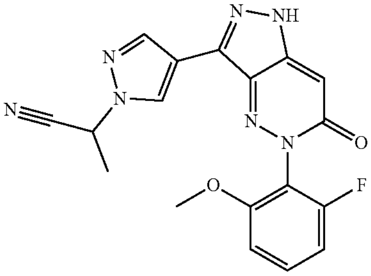 [SMILES: COc1cccc(F)c1-n1nc2c(-c3cnn(C(C)C#N)c3)n[nH]c2cc1=O] | 2-(4-(5-(2-fluoro-6-methoxyphenyl)-6-oxo-5,6-dihydro-1H-pyrazolo[4,3-c]pyridazin-3-yl)-1H-pyrazol-1-yl)propionitrile |
| Compound 68 | 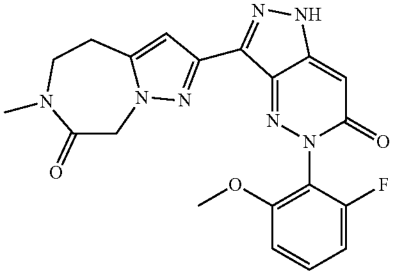 [SMILES: COc1cccc(F)c1-n1nc2c(-c3cc4n(n3)CC(=O)N(C)CC4)n[nH]c2cc1=O] | 2-(5-(2-fluoro-6-methoxyphenyl)-6-oxo-5,6-dihydro-1H-pyrazolo[4,3-c]pyridazin-3-yl)-6-methyl-5,6-dihydro-4H-pyrazolo[1,5-d][1,4]diazepin-7(8H)-one |

-continued

| Compound | Structural Formula | Name of Compound |
|---|---|---|
| Compound 69 | 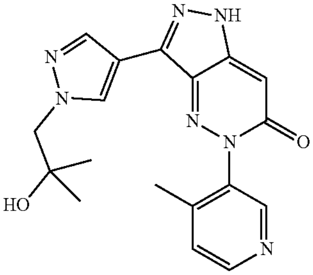 [SMILES: Cc1ccncc1-n1nc2c(-c3cnn(CC(C)(C)O)c3)n[nH]c2cc1=O] | 3-(1-(2-hydroxyl-2-methylpropyl)-1H-pyrazol-4-yl)-5-(4-methylpyrid-3-yl)-1H-pyrazolo[4,3-c]pyridazin-6(5H)-one |
| Compound 70 | 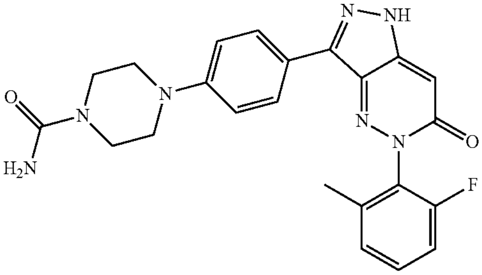 [SMILES: Cc1cccc(F)c1-n1nc2c(-c3ccc(N4CCN(C(N)=O)CC4)cc3)n[nH]c2cc1=O] | 4-(4-(5-(2-fluoro-6-methylphenyl)-6-oxo-5,6-dihydro-1H-pyrazolo[4,3-c]pyridazin-3-yl)phenyl)piperazinyl-1-carbonamide |
| Compound 71 | 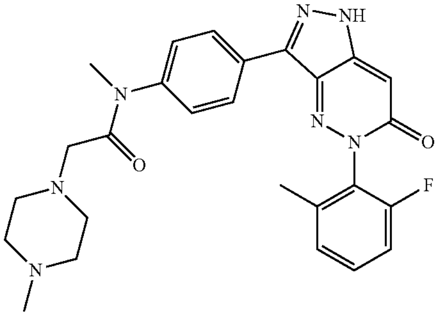 [SMILES: Cc1cccc(F)c1-n1nc2c(-c3ccc(N(C)C(=O)CN4CCN(C)CC4)cc3)n[nH]c2cc1=O] | N-(4-(5-(2-fluoro-6-methylphenyl)-6-oxo-5,6-dihydro-1H-pyrazolo[4,3-c]pyridazin-3-yl)phenyl)-N-methyl-2-(4-methylpiperazin-1-yl)acetamide |
| Compound 72 | 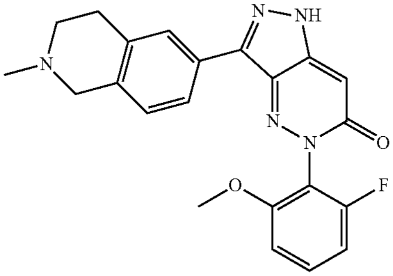 [SMILES: COc1cccc(F)c1-n1nc2c(-c3ccc4c(c3)CCN(C)C4)n[nH]c2cc1=O] | 5-(2-fluoro-6-methoxyphenyl)-3-(2-methyl-1,2,3,4-tetrahydroisoquinolin-6-yl)-1H-pyrazolo[4,3-c]pyridazin-6(5H)-one |
| Compound 73 | 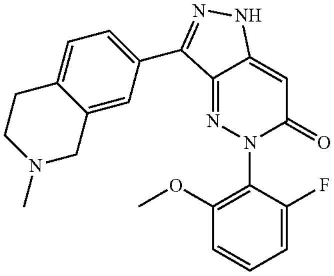 [SMILES: COc1cccc(F)c1-n1nc2c(-c3ccc4c(c3)CN(C)CC4)n[nH]c2cc1=O] | 5-(2-fluoro-6-methoxyphenyl)-3-(2-methyl-1,2,3,4-tetrahydroisoquinolin-7-yl)-1H-pyrazolo[4,3-c]pyridazin-6(5H)-one |

-continued

| Compound | Structural Formula | Name of Compound |
| --- | --- | --- |
| Compound 74 | 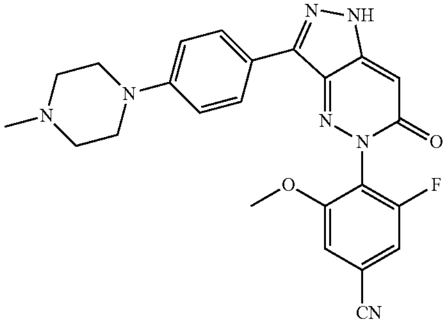 [SMILES: COc1cc(C#N)cc(F)c1-n1nc2c(-c3ccc(N4CCN(C)CC4)cc3)n[nH]c2cc1=O] | 3-fluoro-5-methoxy-4-(3-(4-(4-methylpiperazin-1-yl)phenyl)-6-oxo-1H-pyrazolo[4,3-c]pyridazin-5(6H)-yl)benzonitrile |
| Compound 75 | 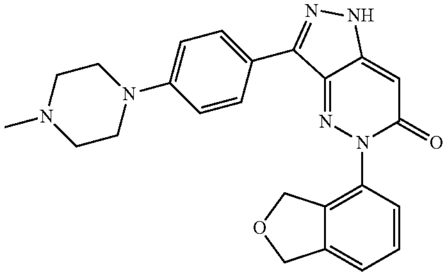 [SMILES: CN1CCN(c2ccc(-c3n[nH]c4cc(=O)n(-c5cccc6c5COC6)nc34)cc2)CC1] | 5-(1,3-dihydroisobenzofuran-4-yl)-3-(4-(4-methylpiperazin-1-yl)phenyl)-1H-pyrazolo[4,3-c]pyridazin-6(5H)-one |
| Compound 76 | 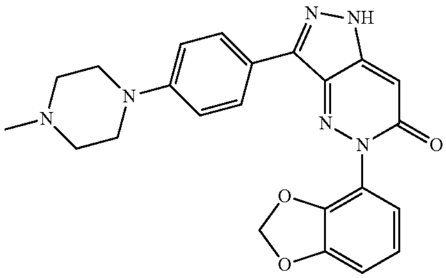 [SMILES: CN1CCN(c2ccc(-c3n[nH]c4cc(=O)n(-c5cccc6c5OCO6)nc34)cc2)CC1] | 5-(benzo[d][1,3]dioxacyclopent-4-yl)-3-(4-(4-methylpiperazin-1-yl)phenyl)-1H-pyrazolo[4,3-c]pyridazin-6(5H)-one |
| Compound 77 | 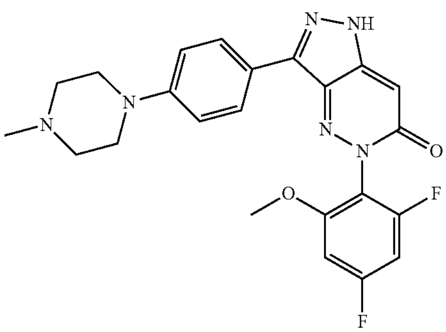 [SMILES: COc1cc(F)cc(F)c1-n1nc2c(-c3ccc(N4CCN(C)CC4)cc3)n[nH]c2cc1=O] | 5-(2,4-difluoro-6-methoxyphenyl)-3-(4-(4-methylpiperazin-1-yl)phenyl)-1H-pyrazolo[4,3-c]pyridazin-6(5H)-one |
| Compound 78 | 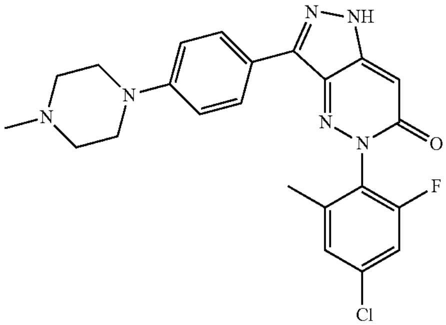 [SMILES: Cc1cc(Cl)cc(F)c1-n1nc2c(-c3ccc(N4CCN(C)CC4)cc3)n[nH]c2cc1=O] | 5-(4-chloro-2-fluoro-6-methylphenyl)-3-(4-(4-methylpiperazin-1-yl)phenyl)-1H-pyrazolo[4,3-c]pyridazin-6(5H)-one |

-continued

| Compound | Structural Formula | Name of Compound |
|---|---|---|
| Compound 79 | 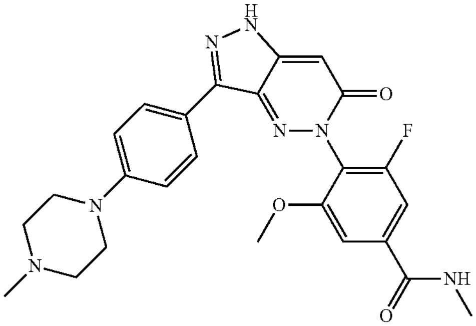 | 3-fluoro-5-methoxy-N-methyl-4-(3-(4-(4-methylpiperazin-1-yl)phenyl)-6-oxo-1H-pyrazolo[4,3-c]pyridazin-5(6H)-yl)benzamide |
| Compound 80 | 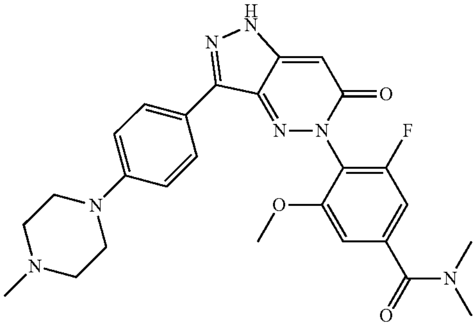 | 3-fluoro-5-methoxy-N,N-dimethyl-4-(3-(4-(4-methylpiperazin-1-yl)phenyl)-6-oxo-1H-pyrazolo[4,3-c]pyridazin-5(6H)-yl)benzamide |
| Compound 81 | 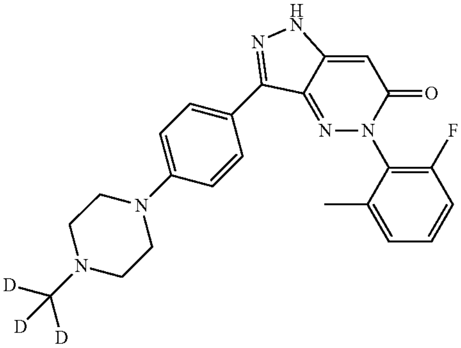 [SMILES: [2H]C([2H])([2H])N1CCN(c2ccc(-c3n[nH]c4cc(=O)n(-c5c(C)cccc5F)nc34)cc2)CC1] | 5-(2-fluoro-6-methylphenyl)-3-(4-(4-(methyl-$d_3$)piperazin-1-yl)phenyl)-1H-pyrazolo[4,3-c]pyridazin-6(5H)-one |
| Compound 82 | 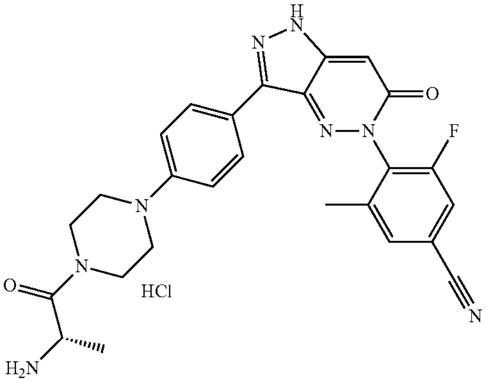 [SMILES: Cc1cc(C#N)cc(F)c1-n1nc2c(-c3ccc(N4CCN(C(=O)[C@H](C)N)CC4)cc3)n[nH]c2cc1=O ; Cl] | (S)-4-(3-(4-(4-(2-aminopropionyl)piperazin-1-yl)phenyl)-6-oxo-1H-pyrazolo[4,3-c]pyridazin-5(6H)-yl)-3-fluoro-5-methylbenzonitrile hydrochloride |

-continued

| Compound | Structural Formula | Name of Compound |
| --- | --- | --- |
| Compound 83 | 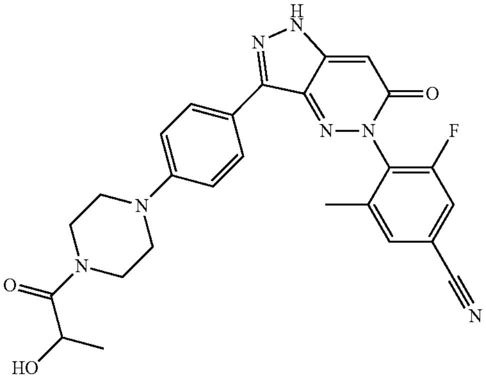 [SMILES: Cc1cc(C#N)cc(F)c1-n1nc2c(-c3ccc(N4CCN(C(=O)C(C)O)CC4)cc3)n[nH]c2cc1=O] | 4-(3-(4-(4-(2-hydroxylpropionyl)piperazin-1-yl)phenyl)-6-oxo-1H-pyrazolo[4,3-c]pyridazin-5(6H)-y1)-3-fluoro-5-methylbenzonitrile |
| Compound 84 | 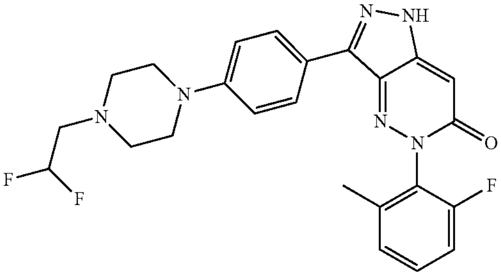 [SMILES: Cc1cccc(F)c1-n1nc2c(-c3ccc(N4CCN(CC(F)F)CC4)cc3)n[nH]c2cc1=O] | 3-(4-(4-(2,2-difluoroethyl)piperazin-1-yl)phenyl)-5-(2-fluoro-6-methylphenyl)-1H-pyrazolo[4,3-c]pyridazin-6(5H)-one |
| Compound 85 | 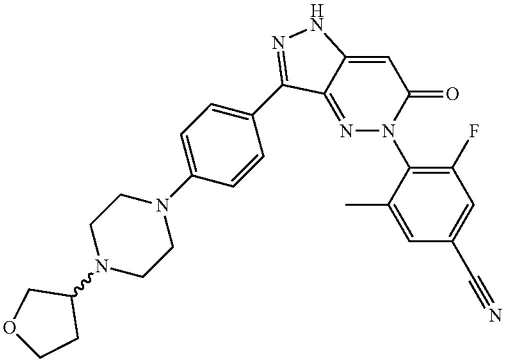 [SMILES: Cc1cc(C#N)cc(F)c1-n1nc2c(-c3ccc(N4CCN(C5CCOC5)CC4)cc3)n[nH]c2cc1=O] | 3-fluoro-5-methyl-4-(6-oxo-3-(4-(4-(tetrahydrofuran-3-yl)piperazin-1-yl)phenyl)-1H-pyrazolo[4,3-c]pyridazin-5(6H)-yl)benzonitrile |
| Compound 86 | 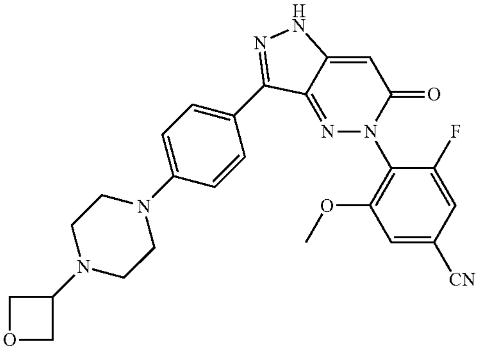 [SMILES: COc1cc(C#N)cc(F)c1-n1nc2c(-c3ccc(N4CCN(C5COC5)CC4)cc3)n[nH]c2cc1=O] | 3-fluoro-5-methoxy-4-(3-(4-(4-(oxetan-3-yl)piperazin-1-yl)phenyl)-6-oxo-1H-pyrazolo[4,3-c]pyridazin-5(6H)-yl)benzonitrile |

-continued

| Compound | Structural Formula | Name of Compound |
| --- | --- | --- |
| Compound 87 | 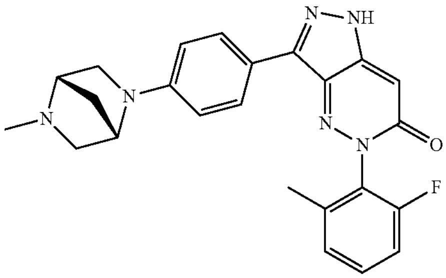 [SMILES: Cc1cccc(F)c1-n1nc2c(-c3ccc(N4C[C@@H]5C[C@H]4CN5C)cc3)n[nH]c2cc1=O] | 5-(2-fluoro-6-methylphenyl)-3-(4-((1S,4S)-5-methyl-2,5-diazabicyclo[2.2.1]heptan-2-yl)phenyl)-1H-pyrazolo[4,3-c]pyridazin-6(5H)-one |
| Compound 88 | 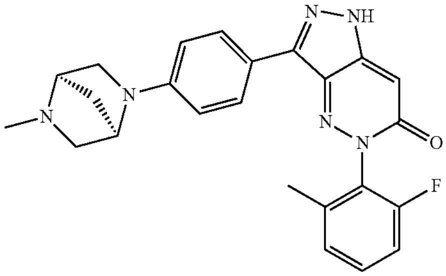 [SMILES: Cc1cccc(F)c1-n1nc2c(-c3ccc(N4C[C@H]5C[C@@H]4CN5C)cc3)n[nH]c2cc1=O] | 5-(2-fluoro-6-methylphenyl)-3-(4-((1R,4R)-5-methyl-2,5-diazabicyclo[2.2.1]heptan-2-yl)phenyl)-1H-pyrazolo[4,3-c]pyridazin-6(5H)-one |
| Compound 89 | 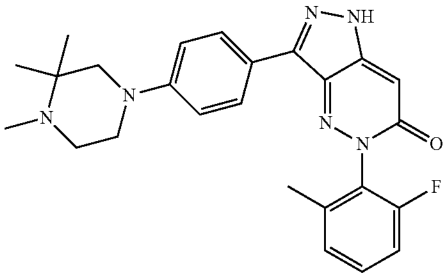 [SMILES: Cc1cccc(F)c1-n1nc2c(-c3ccc(N4CCN(C)C(C)(C)C4)cc3)n[nH]c2cc1=O] | 5-(2-fluoro-6-methylphenyl)-3-(4-(3,3,4-trimethylpiperazin-1-yl)phenyl)-1H-pyrazolo[4,3-c]pyridazin-6(5H)-one |
| Compound 90 | 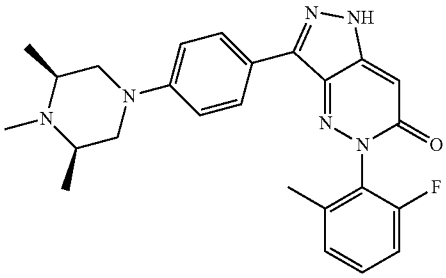 [SMILES: Cc1cccc(F)c1-n1nc2c(-c3ccc(N4C[C@@H](C)N(C)[C@@H](C)C4)cc3)n[nH]c2cc1=O] | 5-(2-fluoro-6-methylphenyl)-3-(4-((3S,5R)-3,4,5-trimethylpiperazin-1-yl)phenyl)-1H-pyrazolo[4,3-c]pyridazin-6(5H)-one |
| Compound 91 | 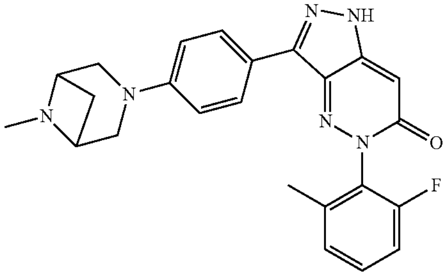 [SMILES: Cc1cccc(F)c1-n1nc2c(-c3ccc(N4CC5CC(C4)N5C)cc3)n[nH]c2cc1=O] | 5-(2-fluoro-6-methylphenyl)-3-(4-(6-methyl-3,6-diazabicyclo[3.1.1]heptan-3-yl)phenyl)-1H-pyrazolo[4,3-c]pyridazin-6(5H)-one |

-continued

| Compound | Structural Formula | Name of Compound |
|---|---|---|
| Compound 92 | 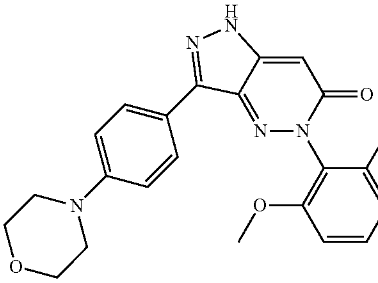 | 5-(2-fluoro-6-methoxyphenyl)-3-(4-morpholinophenyl)-1H-pyrazolo[4,3-c]pyridazin-6(5H)-one |
| Compound 93 | 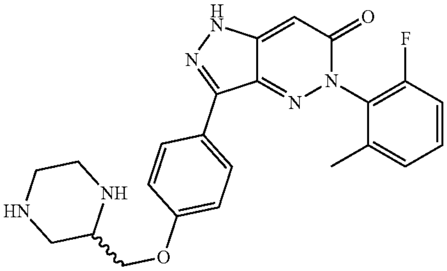 [SMILES: Cc1cccc(F)c1-n1nc2c(-c3ccc(OCC4CNCCN4)cc3)n[nH]c2cc1=O] | 5-(2-fluoro-6-methylphenyl)-3-(4-(piperazin-2-ylmethoxy)phenyl)-1H-pyrazolo[4,3-c]pyridazin-6(5H)-one |
| Compound 94 | 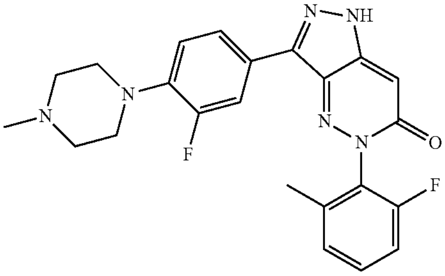 [SMILES: Cc1cccc(F)c1-n1nc2c(-c3ccc(N4CCN(C)CC4)c(F)c3)n[nH]c2cc1=O] | 3-(3-fluoro-4-(4-methylpiperazin-1-yl)phenyl)-5-(2-fluoro-6-methylphenyl)-1H-pyrazolo[4,3-c]pyridazin-6(5H)-one |
| Compound 95 | 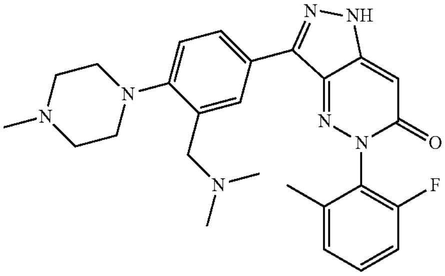 [SMILES: Cc1cccc(F)c1-n1nc2c(-c3ccc(N4CCN(C)CC4)c(CN(C)C)c3)n[nH]c2cc1=O] | 3-(3-((dimethylamino)methyl)-4-(4-methylpiperazin-1-yl)phenyl)-5-(2-fluoro-6-methylphenyl)-1H-pyrazolo[4,3-c]pyridazin-6(5H)-one |
| Compound 96 | 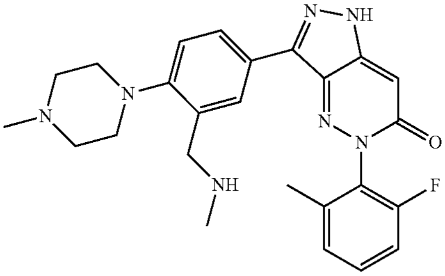 [SMILES: CNCc1cc(-c2n[nH]c3cc(=O)n(-c4c(C)cccc4F)nc23)ccc1N1CCN(C)CC1] | 3-(3-((methylamino)methyl)-4-(4-methylpiperazin-1-yl)phenyl)-5-(2-fluoro-6-methylphenyl)-1H-pyrazolo[4,3-c]pyridazin-6(5H)-one |

-continued

| Compound | Structural Formula | Name of Compound |
|---|---|---|
| Compound 97 | 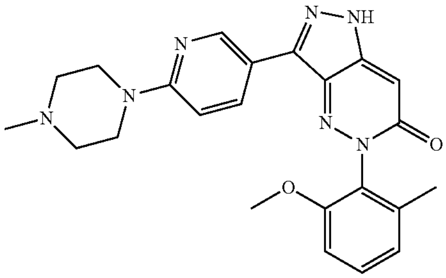 | 5-(2-methoxy-6-methylphenyl)-3-(6-(4-methylpiperazin-1-yl)pyrid-3-yl)-1H-pyrazolo[4,3-c]pyridazin-6(5H)-one |
| Compound 98 | 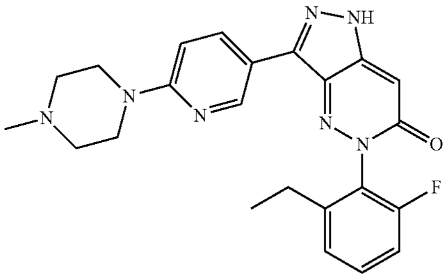 [SMILES: CCc1cccc(F)c1-n1nc2c(-c3ccc(N4CCN(C)CC4)nc3)n[nH]c2cc1=O] | 5-(2-ethyl-6-fluorophenyl)-3-(6-(4-methylpiperazin-1-yl)pyrid-3-yl)-1H-pyrazolo[4,3-c]pyridazin-6(5H)-one |
| Compound 99 | 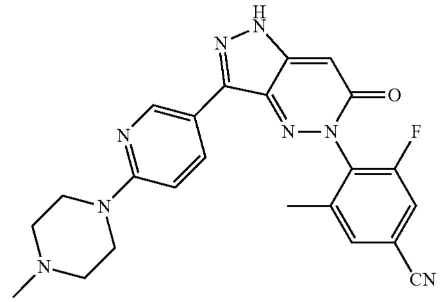 [SMILES: Cc1cc(C#N)cc(F)c1-n1nc2c(-c3ccc(N4CCN(C)CC4)nc3)n[nH]c2cc1=O] | 3-fluoro-5-methyl-4-(3-(6-(4-methylpiperazin-1-yl)pyrid-3-yl)-6-oxo-1H-pyrazolo[4,3-c]pyridazin-5(6H)-yl)benzonitrile |
| Compound 100 | 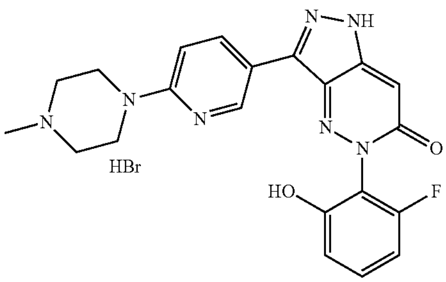 [SMILES: CN1CCN(c2ccc(-c3n[nH]c4cc(=O)n(-c5c(O)cccc5F)nc34)cn2)CC1 ; Br] | 5-(2-fluoro-6-hydroxylphenyl)-3-(6-(4-methylpiperazin-1-yl)pyrid-3-yl)-1H-pyrazolo[4,3-c]pyridazin-6(5H)-one hydrobromide |
| Compound 101 | 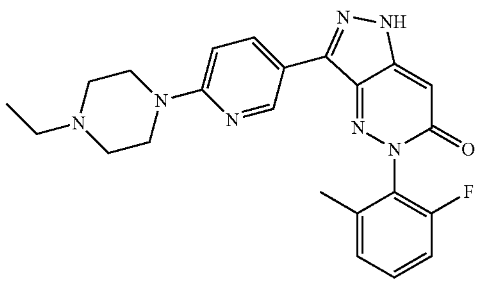 [SMILES: CCN1CCN(c2ccc(-c3n[nH]c4cc(=O)n(-c5c(C)cccc5F)nc34)cn2)CC1] | 3-(6-(4-ethylpiperazin-1-yl)pyrid-3-yl)-5-(2-fluoro-6-methylphenyl)-1H-pyrazolo[4,3-c]pyridazin-6(5H)-one |

-continued

| Compound | Structural Formula | Name of Compound |
|---|---|---|
| Compound 102 | 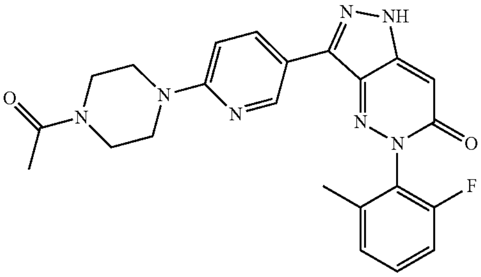 [SMILES: CC(=O)N1CCN(c2ccc(-c3n[nH]c4cc(=O)n(-c5c(C)cccc5F)nc34)cn2)CC1] | 3-(6-(4-acetylpiperazin-1-yl)pyrid-3-yl)-5-(2-fluoro-6-methylphenyl)-1H-pyrazolo[4,3-c]pyridazin-6(5H)-one |
| Compound 103 | 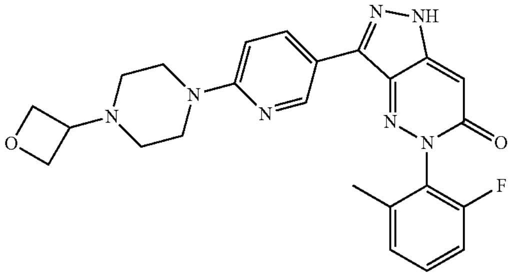 [SMILES: Cc1cccc(F)c1-n1nc2c(-c3ccc(N4CCN(C5COC5)CC4)nc3)n[nH]c2cc1=O] | 5-(2-fluoro-6-methylphenyl)-3-(6-(4-(oxetan-3-yl))piperazin-1-yl)pyrid-3-yl)-1H-pyrazolo[4,3-c]pyridazin-6(5H)-one |
| Compound 104 | 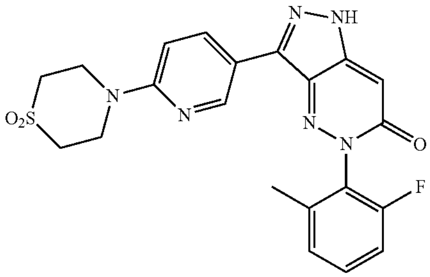 [SMILES: Cc1cccc(F)c1-n1nc2c(-c3ccc(N4CCS(=O)(=O)CC4)nc3)n[nH]c2cc1=O] | 3-(6-(1,1-dioxidothiomorpholino)pyrid-3-yl)-5-(2-fluoro-6-methylphenyl)-1H-pyrazolo[4,3-c]pyridazin-6(5H)-one |
| Compound 105 | 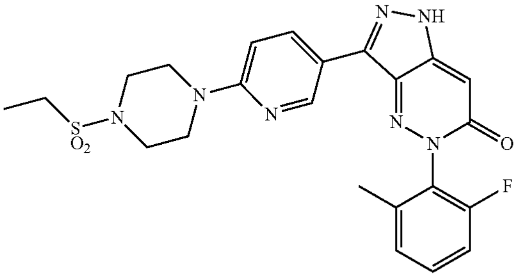 [SMILES: CCS(=O)(=O)N1CCN(c2ccc(-c3n[nH]c4cc(=O)n(-c5c(C)cccc5F)nc34)cn2)CC1] | 3-(6-(4-(ethylsulfonyl)piperazin-1-yl)pyrid-3-yl)-5-(2-fluoro-6-methylphenyl)-1H-pyrazolo[4,3-c]pyridazin-6(5H)-one |
| Compound 106 | 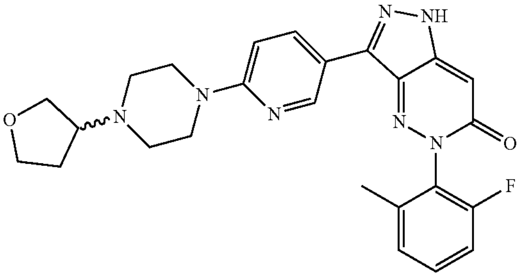 [SMILES: Cc1cccc(F)c1-n1nc2c(-c3ccc(N4CCN(C5CCOC5)CC4)nc3)n[nH]c2cc1=O] | 5-(2-fluoro-6-methylphenyl)-3-(6-(4-(tetrahydrofuran-3-yl)piperazin-1-yl)pyrid-3-yl)-1H-pyrazolo[4,3-c]pyridazin-6(5H)-one |

-continued

| Compound | Structural Formula | Name of Compound |
|---|---|---|
| Compound 107 | 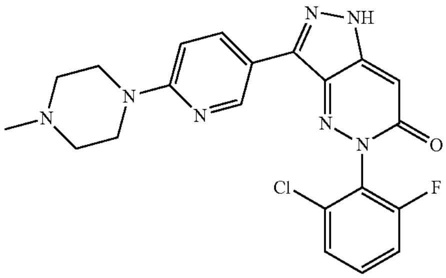 [SMILES: CN1CCN(c2ccc(-c3n[nH]c4cc(=O)n(-c5c(F)cccc5Cl)nc34)cn2)CC1] | 5-(2-chloro-6-fluorophenyl)-3-(6-(4-methylpiperazin-1-yl)pyrid-3-y1)-1H-pyrazolo[4,3-c]pyridazin-6(5H)-one |
| Compound 108 | 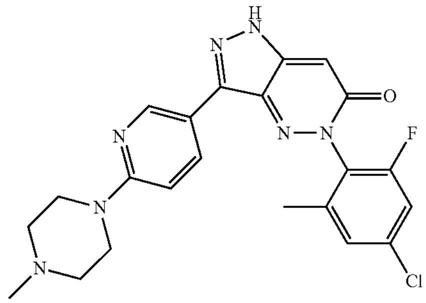 [SMILES: Cc1cc(Cl)cc(F)c1-n1nc2c(-c3ccc(N4CCN(C)CC4)nc3)n[nH]c2cc1=O] | 5-(4-chloro-2-fluoro-6-methylphenyl)-3-(4-(4-methylpiperazin-1-yl)pyrid-3-y1)-1H-pyrazolo[4,3-c]pyridazin-6(5H)-one |
| Compound 109 | 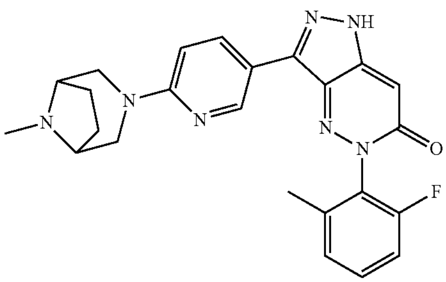 [SMILES: Cc1cccc(F)c1-n1nc2c(-c3ccc(N4CC5CCC(C4)N5C)nc3)n[nH]c2cc1=O] | 5-(2-fluoro-6-methylphenyl)-3-(6-(8-methyl-3,8-diazabicyclo[3.2.1]octan-3-yl)pyrid-3-yl)-1H-pyrazolo[4,3-c]pyridazin-6(5H)-one |
| Compound 110 | 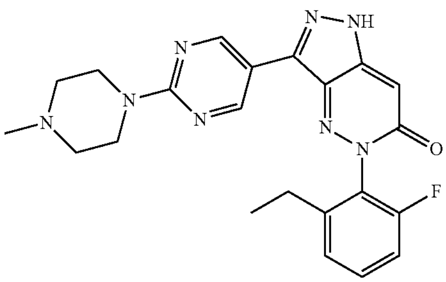 [SMILES: CCc1cccc(F)c1-n1nc2c(-c3cnc(N4CCN(C)CC4)nc3)n[nH]c2cc1=O] | 5-(2-ethyl-6-fluorophenyl)-3-(2-(4-methylpiperazin-1-yl)pyrimidin-5-yl)-1H-pyrazolo[4,3-c]pyridazin-6(5H)-one |
| Compound 111 | 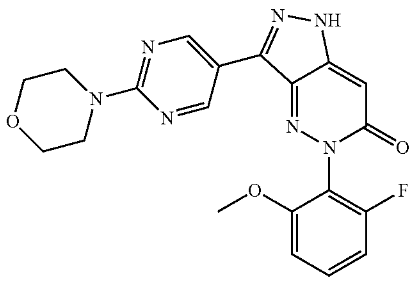 [SMILES: COc1cccc(F)c1-n1nc2c(-c3cnc(N4CCOCC4)nc3)n[nH]c2cc1=O] | 5-(2-fluoro-6-methoxyphenyl)-3-(2-morpholinyl-pyrimidin-5-yl)-1H-pyrazolo[4,3-c]pyridazin-6(5H)-one |

-continued

| Compound | Structural Formula | Name of Compound |
|---|---|---|
| Compound 112 | 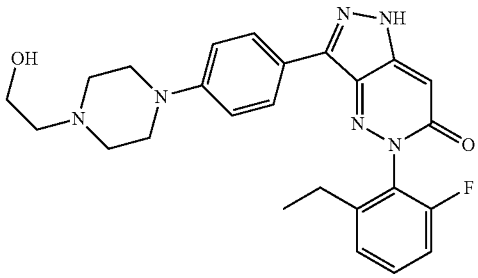 [SMILES: CCc1cccc(F)c1-n1nc2c(-c3ccc(N4CCN(CCO)CC4)cc3)n[nH]c2cc1=O] | 5-(2-ethyl-6-fluorophenyl)-3-(4-(4-(2-hydroxyethyl)piperazin-1-yl)phenyl)-1H-pyrazolo[4,3-c]pyridazin-6(5H)-one |
| Compound 113 | 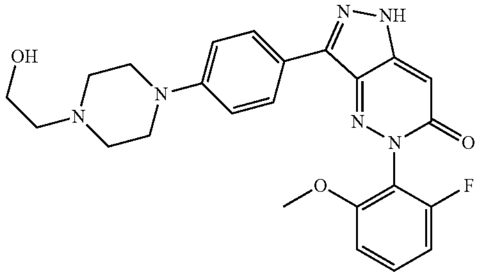 | 5-(2-fluoro-6-methoxyphenyl)-3-(4-(4-(2-hydroxyethyl)piperazin-1-yl)phenyl)-1H-pyrazolo[4,3-c]pyridazin-6(5H)-one |
| Compound 114 | 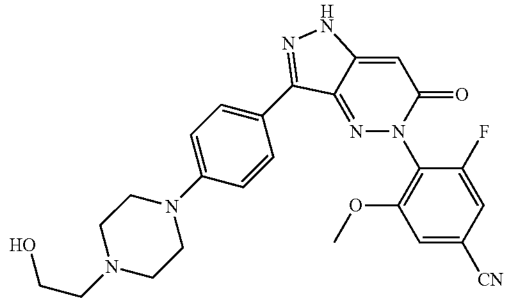 [SMILES: COc1cc(C#N)cc(F)c1-n1nc2c(-c3ccc(N4CCN(CCO)CC4)cc3)n[nH]c2cc1=O] | 3-fluoro-4-(3-(4-(4-(2-hydroxyethyl)piperazin-1-yl)phenyl)-6-oxo-1H-pyrazolo[4,3-c]pyridazin-5(6H)-yl)-5-methoxybenzonitrile |
| Compound 115 | 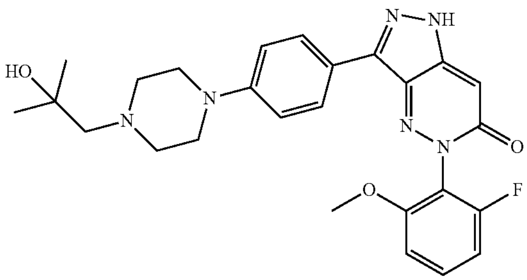 [SMILES: COc1cccc(F)c1-n1nc2c(-c3ccc(N4CCN(CC(C)(C)O)CC4)cc3)n[nH]c2cc1=O] | 5-(2-fluoro-6-methoxyphenyl)-3-(4-(4-(2-hydroxyl-2-methylpropyl)piperazin-1-yl)phenyl)-1H-pyrazolo[4,3-c]pyridazin-6(5H)-one |
| Compound 116 | 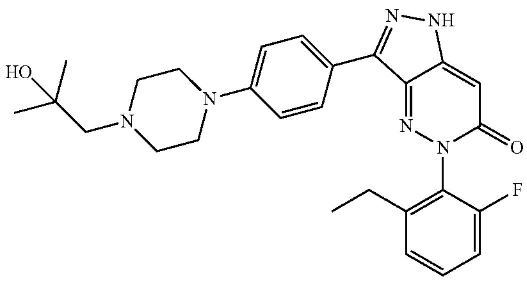 [SMILES: CCc1cccc(F)c1-n1nc2c(-c3ccc(N4CCN(CC(C)(C)O)CC4)cc3)n[nH]c2cc1=O] | 5-(2-ethyl-6-fluorophenyl)-3-(4-(4-(2-hydroxyl-2-methylpropyl)piperazin-1-yl)phenyl)-1H-pyrazolo[4,3-c]pyridazin-6(5H)-one |

-continued

| Compound | Structural Formula | Name of Compound |
|---|---|---|
| Compound 117 | 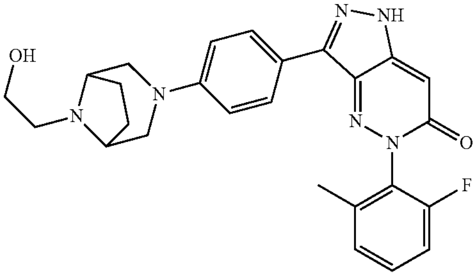 [SMILES: Cc1cccc(F)c1-n1nc2c(-c3ccc(N4CC5CCC(C4)N5CCO)cc3)n[nH]c2cc1=O] | 5-(2-fluoro-6-methylphenyl)-3-(4-(8-(2-hydroxyethyl)-3,8-diazabicyclo[3.2.1]octan-3-yl)phenyl)-1H-pyrazolo[4,3-c]pyridazin-6(5H)-one |
| Compound 118 | 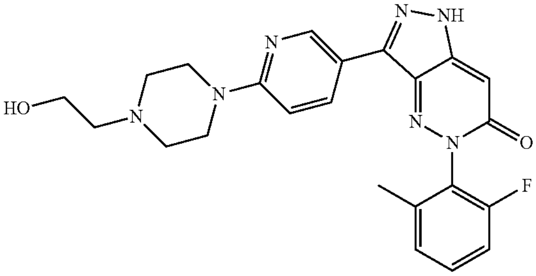 [SMILES: Cc1cccc(F)c1-n1nc2c(-c3ccc(N4CCN(CCO)CC4)nc3)n[nH]c2cc1=O] | 5-(2-fluoro-6-methylphenyl)-3-(6-(4-(2-hydroxyethyl)piperazin-1-yl)pyrid-3-yl)-1H-pyrazolo[4,3-c]pyridazin-6(5H)-one |
| Compound 119 | 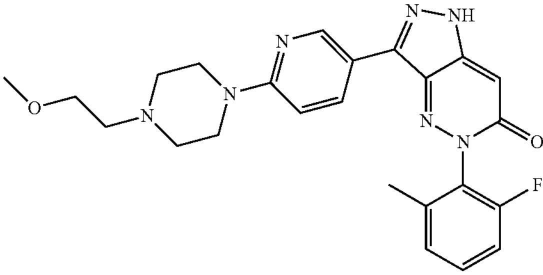 [SMILES: COCCN1CCN(c2ccc(-c3n[nH]c4cc(=O)n(-c5c(C)cccc5F)nc34)cn2)CC1] | 5-(2-fluoro-6-methylphenyl)-3-(6-(4-(2-methoxyethyl)piperazin-1-yl)pyrid-3-yl)-1H-pyrazolo[4,3-c]pyridazin-6(5H)-one |
| Compound 120 | 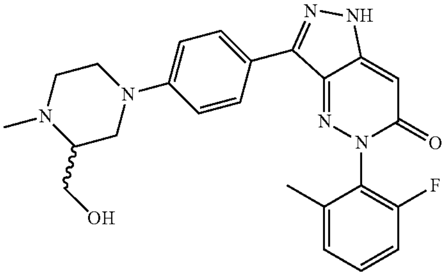 [SMILES: Cc1cccc(F)c1-n1nc2c(-c3ccc(N4CCN(C)C(CO)C4)cc3)n[nH]c2cc1=O] | 5-(2-fluoro-6-methylphenyl)-3-(4-(3-(hydroxymethyl)-4-methylpiperazin-1-yl)phenyl)-1H-pyrazolo[4,3-c]pyridazin-6(5H)-one |
| Compound 121 | 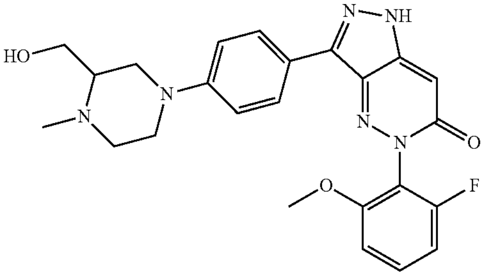 | 5-(2-fluoro-6-methoxyphenyl)-3-(4-(3-(hydroxymethyl)-4-methylpiperazin-1-yl)phenyl)-1H-pyrazolo[4,3-c]pyridazin-6(5H)-one |

-continued

| Compound | Structural Formula | Name of Compound |
|---|---|---|
| Compound 122 | 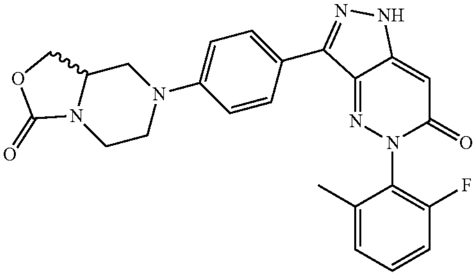 [SMILES: Cc1cccc(F)c1-n1nc2c(-c3ccc(N4CCN5C(=O)OCC5C4)cc3)n[nH]c2cc1=O] | 7-(4-(5-(2-fluoro-6-methylphenyl)-6-oxo-5,6-dihydro-1H-pyrazolo[4,3-c]pyridazin-3-yl)phenyl)tetrahydro-1H-oxazolo[3,4-a]pyrazin-3(5H)-one |
| Compound 123 | 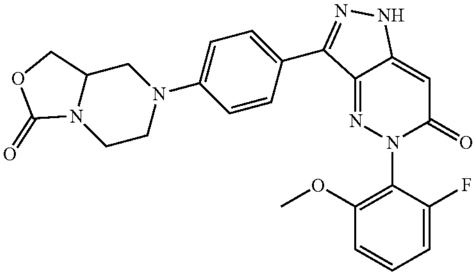 [SMILES: COc1cccc(F)c1-n1nc2c(-c3ccc(N4CCN5C(=O)OCC5C4)cc3)n[nH]c2cc1=O] | 7-(4-(5-(2-fluoro-6-methoxyphenyl)-6-oxo-5,6-dihydro-1H-pyrazolo[4,3-c]pyridazin-3-yl)phenyl)tetrahydro-1H-oxazolo[3,4-a]pyrazin-3(5H)-one |
| Compound 124 | 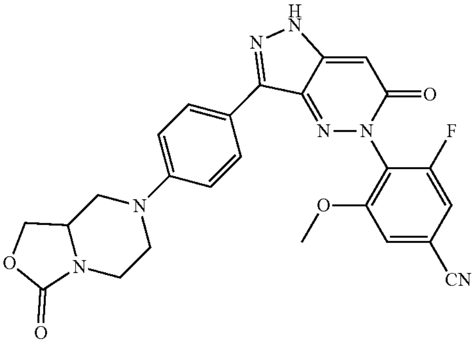 [SMILES: COc1cc(C#N)cc(F)c1-n1nc2c(-c3ccc(N4CCN5C(=O)OCC5C4)cc3)n[nH]c2cc1=O] | 3-fluoro-5-methoxy-4-(6-oxo-3-(4-(3-oxotetrahydro-1H-oxazolo[3,4-a]pyrazin-7(3H)-yl)phenyl)-1H-pyrazolo[4,3-c]pyridazin-5(6H)-yl)benzonitrile |
| Compound 125 | 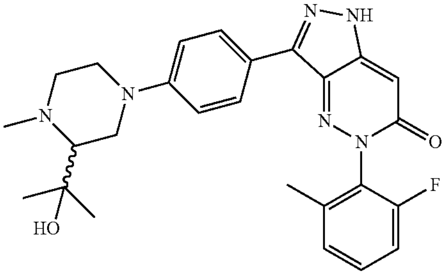 [SMILES: Cc1cccc(F)c1-n1nc2c(-c3ccc(N4CCN(C)C(C(C)(C)O)C4)cc3)n[nH]c2cc1=O] | 5-(2-fluoro-6-methylphenyl)-3-(4-(3-(2-hydroxylprop-2-yl)-4-methylpiperazin-1-yl)phenyl)-1H-pyrazolo[4,3-c]pyridazin-6(5H)-one |
| Compound 126 | 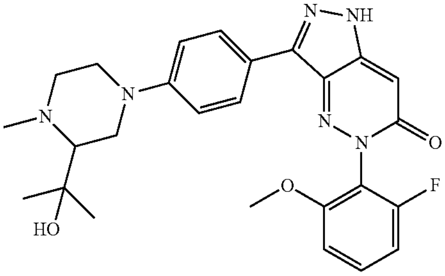 [SMILES: COc1cccc(F)c1-n1nc2c(-c3ccc(N4CCN(C)C(C(C)(C)O)C4)cc3)n[nH]c2cc1=O] | 5-(2-fluoro-6-methoxyphenyl)-3-(4-(3-(2-hydroxylprop-2-yl)-4-methylpiperazin-1-y1)phenyl)-1H-pyrazolo[4,3-c]pyridazin-6(5H)-one |

-continued

| Compound | Structural Formula | Name of Compound |
|---|---|---|
| Compound 127 | 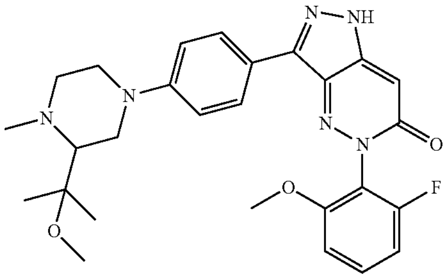 [SMILES: COc1cccc(F)c1-n1nc2c(-c3ccc(N4CCN(C)C(C(C)(C)OC)C4)cc3)n[nH]c2cc1=O] | 5-(2-fluoro-6-methoxyphenyl)-3-(4-(3-(2-methoxyprop-2-yl)-4-methylpiperazin-1-yl)phenyl)-1H-pyrazolo[4,3-c]pyridazin-6(5H)-one |
| Compound 128 | 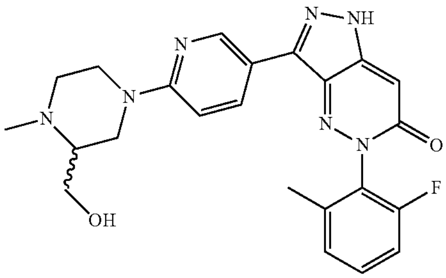 [SMILES: Cc1cccc(F)c1-n1nc2c(-c3ccc(N4CCN(C)C(CO)C4)nc3)n[nH]c2cc1=O] | 5-(2-fluoro-6-methylphenyl)-3-(6-(3-(hydroxymethyl)-4-methylpiperazin-1-yl)pyrid-3-yl)-1H-pyrazolo[4,3-c]pyridazin-6(5H)-one |
| Compound 129 | 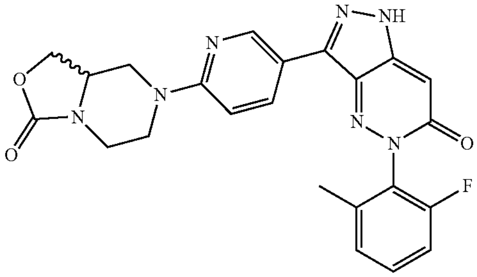 [SMILES: Cc1cccc(F)c1-n1nc2c(-c3ccc(N4CCN5C(=O)OCC5C4)nc3)n[nH]c2cc1=O] | 7-(5-(5-(2-fluoro-6-methylphenyl)-6-oxo-5,6-dihydro-1H-pyrazolo[4,3-c]pyridazin-3-yl)pyridin-2-yl)tetrahydro-1H-oxazolo[3,4-a]pyrazin-3(5H)-one |
| Compound 130 | 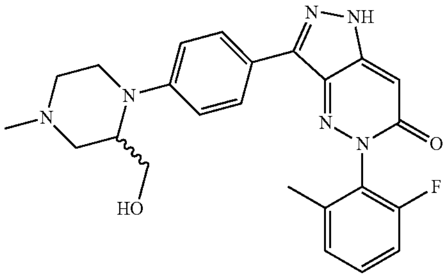 [SMILES: Cc1cccc(F)c1-n1nc2c(-c3ccc(N4CCN(C)CC4CO)cc3)n[nH]c2cc1=O] | 5-(2-fluoro-6-methylphenyl)-3-(4-(2-(hydroxymethyl)-4-methylpiperazin-1-yl)phenyl)-1H-pyrazolo[4,3-c]pyridazin-6(5H)-one |
| Compound 131 | 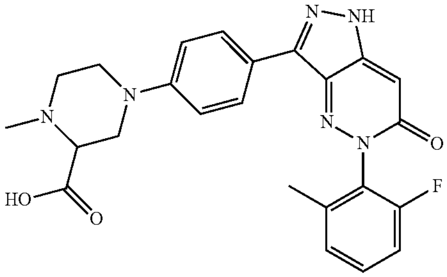 [SMILES: Cc1cccc(F)c1-n1nc2c(-c3ccc(N4CCN(C)C(C(=O)O)C4)cc3)n[nH]c2cc1=O] | 4-(4-(5-(2-fluoro-6-methylphenyl)-6-oxo-5,6-dihydro-1H-pyrazolo[4,3-c]pyridazin-3-yl)phenyl)-1-methylpiperazin-2-carboxylic acid |

-continued

| Compound | Structural Formula | Name of Compound |
|---|---|---|
| Compound 132 | 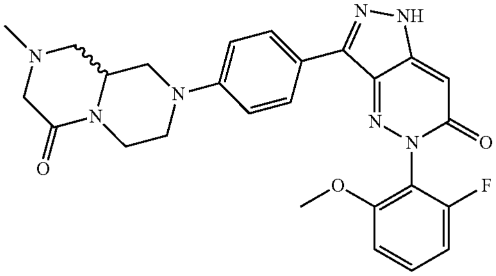 [SMILES: COc1cccc(F)c1-n1nc2c(-c3ccc(N4CCN5C(=O)CN(C)CC5C4)cc3)n[nH]c2cc1=O] | 8-(4-(5-(2-fluoro-6-methoxyphenyl)-6-oxo-5,6-dihydro-1H-pyrazolo[4,3-c]pyridazin-3-yl)phenyl)-2-methylhexahydro-1H-pyrazino[1,2-a]pyrazin-4(6H)-one |
| Compound 133 | 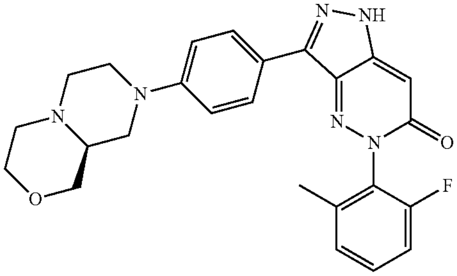 [SMILES: Cc1cccc(F)c1-n1nc2c(-c3ccc(N4CCN5CCOC[C@@H]5C4)cc3)n[nH]c2cc1=O] | (S)-5-(2-fluoro-6-methylphenyl)-3-(4-(hexahydropyrazino[2,1-c][1,4]oxazin-8(1H)-yl)phenyl)-1H-pyrazolo[4,3-c]pyridazin-6(5H)-one |
| Compound 134 | 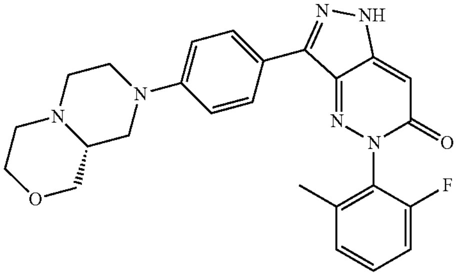 [SMILES: Cc1cccc(F)c1-n1nc2c(-c3ccc(N4CCN5CCOC[C@H]5C4)cc3)n[nH]c2cc1=O] | (R)-5-(2-fluoro-6-methylphenyl)-3-(4-(hexahydropyrazino[2,1-c][1,4]oxazin-8(1H)-yl)phenyl)-1H-pyrazolo[4,3-c]pyridazin-6(5H)-one |
| Compound 135 | 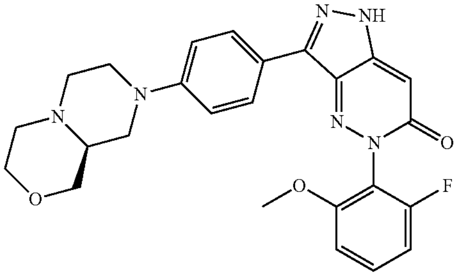 | (S)-5-(2-fluoro-6-methoxyphenyl)-3-(4-(hexahydropyrazino[2,1-c][1,4]oxazin-8(1H)-yl)phenyl)-1H-pyrazolo[4,3-c]pyridazin-6(5H)-one |
| Compound 136 | 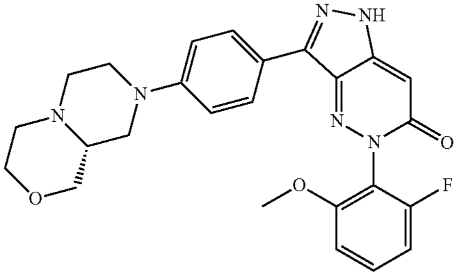 | (R)-5-(2-fluoro-6-methoxyphenyl)-3-(4-(hexahydropyrazino[2,1-c][1,4]oxazin-8(1H)-yl)phenyl)-1H-pyrazolo[4,3-c]pyridazin-6(5H)-one |

-continued

| Compound | Structural Formula | Name of Compound |
|---|---|---|
| Compound 137 | 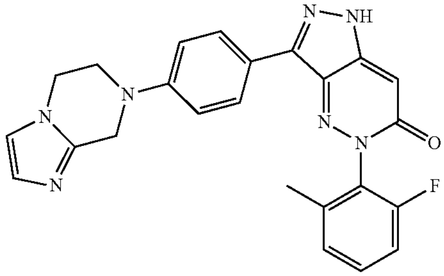 [SMILES: Cc1cccc(F)c1-n1nc2c(-c3ccc(N4CCn5ccnc5C4)cc3)n[nH]c2cc1=O] | 3-(4-(5,6-dihydroimidazolo[1,2-a]pyrazin-7(8H)-yl)phenyl)-5-(2-fluoro-6-methylphenyl)-1H-pyrazolo[4,3-c]pyridazin-6(5H)-one |
| Compound 138 | 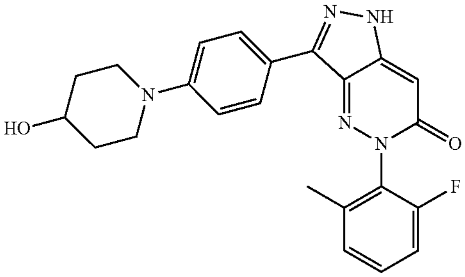 [SMILES: Cc1cccc(F)c1-n1nc2c(-c3ccc(N4CCC(O)CC4)cc3)n[nH]c2cc1=O] | 5-(2-fluoro-6-methylphenyl)-3-(4-(4-hydroxylpiperidin-1-yl)phenyl)-1H-pyrazolo[4,3-c]pyridazin-6(5H)-one |
| Compound 139 | 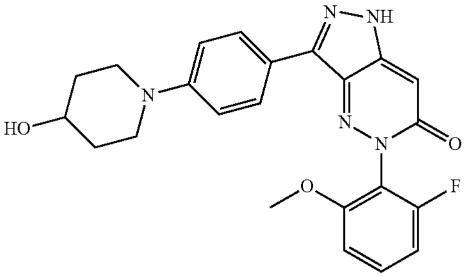 [SMILES: COc1cccc(F)c1-n1nc2c(-c3ccc(N4CCC(O)CC4)cc3)n[nH]c2cc1=O] | 5-(2-fluoro-6-methoxyphenyl)-3-(4-(4-hydroxylpiperidin-1-yl)phenyl)-1H-pyrazolo[4,3-c]pyridazin-6(5H)-one |
| Compound 140 | 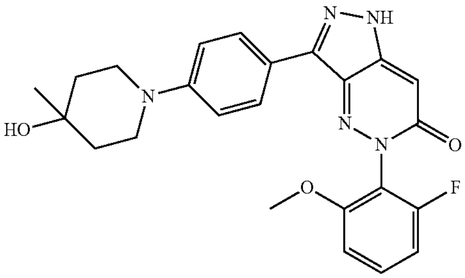 [SMILES: COc1cccc(F)c1-n1nc2c(-c3ccc(N4CCC(C)(O)CC4)cc3)n[nH]c2cc1=O] | 5-(2-fluoro-6-methoxyphenyl)-3-(4-(4-hydroxyl-4-methylpiperidin-1-yl)phenyl)-1H-pyrazolo[4,3-c]pyridazin-6(5H)-one |
| Compound 141 | 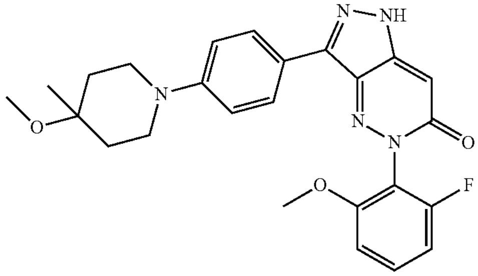 [SMILES: COc1cccc(F)c1-n1nc2c(-c3ccc(N4CCC(C)(OC)CC4)cc3)n[nH]c2cc1=O] | 5-(2-fluoro-6-methoxyphenyl)-3-(4-(4-methoxy-4-methylpiperidin-1-yl)phenyl)-1H-pyrazolo[4,3-c]pyridazin-6(5H)-one |

-continued

| Compound | Structural Formula | Name of Compound |
|---|---|---|
| Compound 142 | 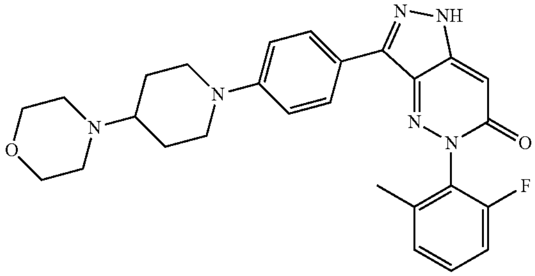 [SMILES: Cc1cccc(F)c1-n1nc2c(-c3ccc(N4CCC(N5CCOCC5)CC4)cc3)n[nH]c2cc1=O] | 5-(2-fluoro-6-methylphenyl)-3-(4-(4-morpholinopiperidin-1-yl)phenyl)-1H-pyrazolo[4,3-c]pyridazin-6(5H)-one |
| Compound 143 | 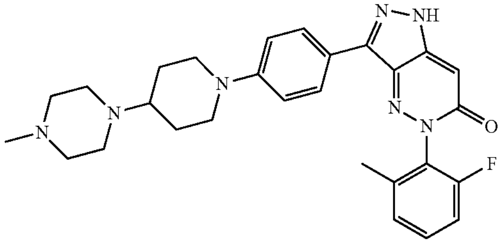 [SMILES: Cc1cccc(F)c1-n1nc2c(-c3ccc(N4CCC(N5CCN(C)CC5)CC4)cc3)n[nH]c2cc1=O] | 5-(2-fluoro-6-methylphenyl)-3-(4-(4-(4-methylpiperazin-1-yl)piperidin-1-yl)phenyl)-1H-pyrazolo[4,3-c]pyridazin-6(5H)-one |
| Compound 144 | 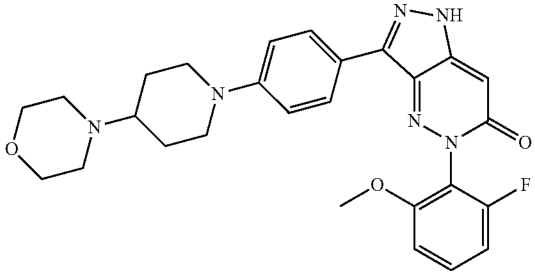 [SMILES: COc1cccc(F)c1-n1nc2c(-c3ccc(N4CCC(N5CCOCC5)CC4)cc3)n[nH]c2cc1=O] | 5-(2-fluoro-6-methoxyphenyl)-3-(4-(4-morpholinopiperidin-1-yl)phenyl)-1H-pyrazolo[4,3-c]pyridazin-6(5H)-one |
| Compound 145 | 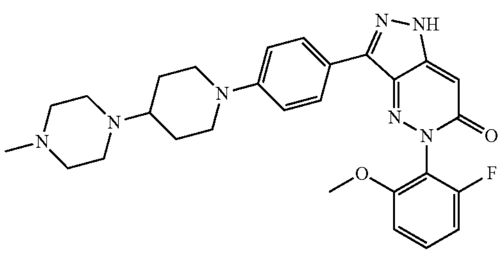 [SMILES: COc1cccc(F)c1-n1nc2c(-c3ccc(N4CCC(N5CCN(C)CC5)CC4)cc3)n[nH]c2cc1=O] | 5-(2-fluoro-6-methoxyphenyl)-3-(4-(4-(4-methylpiperazin-1-yl)piperidin-1-yl)phenyl)-1H-pyrazolo[4,3-c]pyridazin-6(5H)-one |
| Compound 146 | 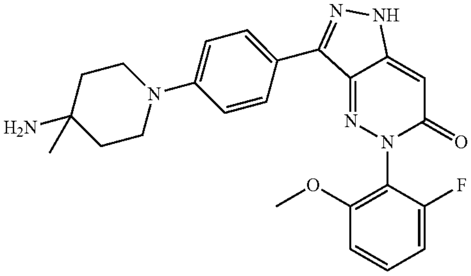 [SMILES: COc1cccc(F)c1-n1nc2c(-c3ccc(N4CCC(C)(N)CC4)cc3)n[nH]c2cc1=O] | 3-(4-(4-amino-4-methylpiperidin-1-yl)phenyl)-5-(2-fluoro-6-methoxyphenyl)-1H-pyrazolo[4,3-c]pyridazin-6(5H)-one |

-continued

| Compound | Structural Formula | Name of Compound |
|---|---|---|
| Compound 147 | 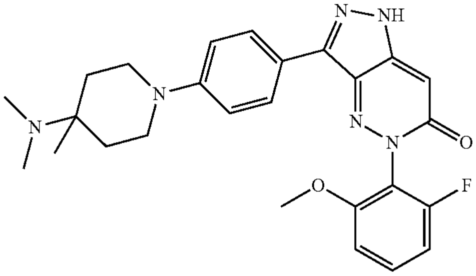 [SMILES: COc1cccc(F)c1-n1nc2c(-c3ccc(N4CCC(C)(N(C)C)CC4)cc3)n[nH]c2cc1=O] | 3-(4-(4-(dimethylamino)-4-methylpiperidin-1-yl)phenyl)-5-(2-fluoro-6-methoxyphenyl)-1H-pyrazolo[4,3-c]pyridazin-6(5H)-one |
| Compound 148 | 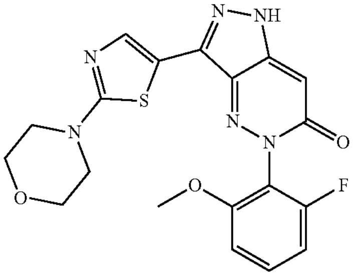 [SMILES: COc1cccc(F)c1-n1nc2c(-c3cnc(N4CCOCC4)s3)n[nH]c2cc1=O] | 5-(2-fluoro-6-methoxyphenyl)-3-(2-morpholinothiazol-5-y1)-1H-pyrazolo[4,3-c]pyridazin-6(5H)-one |
| Compound 149 | 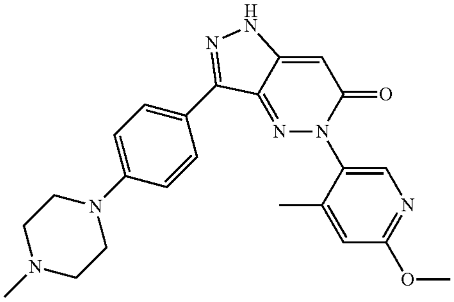 | 5-(6-methoxy-4-methylpyrid-3-yl)-3-(4-(4-methylpiperazin-1-yl)phenyl)-1H-pyrazolo[4,3-c]pyridazin-6(5H)-one |
| Compound 150 | 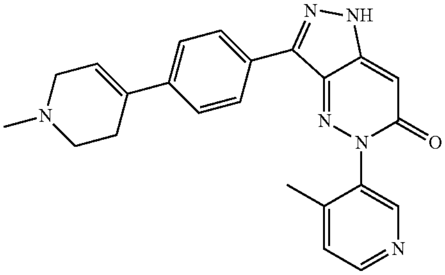 [SMILES: Cc1ccncc1-n1nc2c(-c3ccc(C4=CCN(C)CC4)cc3)n[nH]c2cc1=O] | 3-(4-(1-methyl-1,2,3,6-tetrahydropyridin-4-yl)phenyl)-5-(4-methylpyrid-3-yl)-1H-pyrazolo[4,3-c]pyridazin-6(5H)-one |
| Compound 151 | 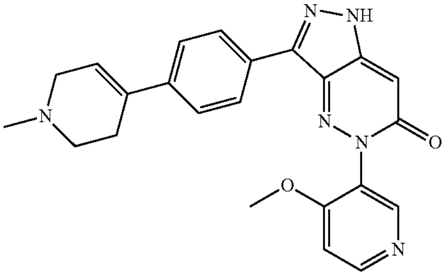 [SMILES: COc1ccncc1-n1nc2c(-c3ccc(C4=CCN(C)CC4)cc3)n[nH]c2cc1=O] | 5-(4-methoxypyrid-3-yl)-3-(4-(1-methyl-1,2,3,6-tetrahydropyridin-4-yl)phenyl)-1H-pyrazolo[4,3-c]pyridazin-6(5H)-one |

-continued

| Compound | Structural Formula | Name of Compound |
| --- | --- | --- |
| Compound 152 | 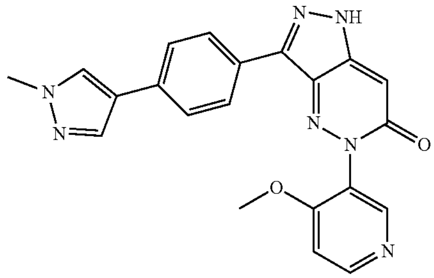 [SMILES: COc1ccncc1-n1nc2c(-c3ccc(-c4cnn(C)c4)cc3)n[nH]c2cc1=O] | 5-(4-methoxypyrid-3-yl)-3-(4-(1-methyl-1H-pyrazol-4-yl)phenyl)-1H-pyrazolo[4,3-c]pyridazin-6(5H)-one |
| Compound 153 | 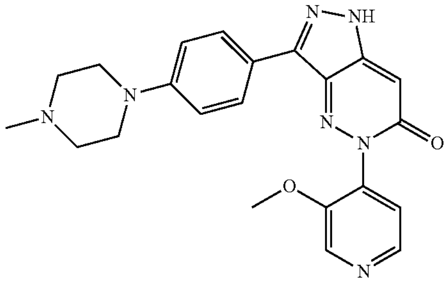 [SMILES: COc1cnccc1-n1nc2c(-c3ccc(N4CCN(C)CC4)cc3)n[nH]c2cc1=O] | 5-(3-methoxypyrid-4-yl)-3-(4-(4-methylpiperazin-1-yl)phenyl)-1H-pyrazolo[4,3-c]pyridazin-6(5H)-one |
| Compound 154 | 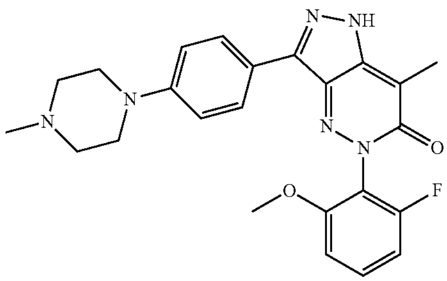 | 5-(2-fluoro-6-methoxyphenyl)-7-methyl-3-(4-(4-methylpiperazin-1-yl)phenyl)-1H-pyrazolo[4,3-c]pyridazin-6(5H)-one |
| Compound 155 | 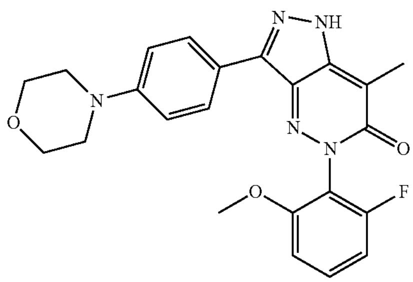 [SMILES: COc1cccc(F)c1-n1nc2c(-c3ccc(N4CCOCC4)cc3)n[nH]c2c(C)c1=O] | 5-(2-fluoro-6-methoxyphenyl)-7-methyl-3-(4-morpholinophenyl)-1H-pyrazolo[4,3-c]pyridazin-6(5H)-one |
| Compound 156 | 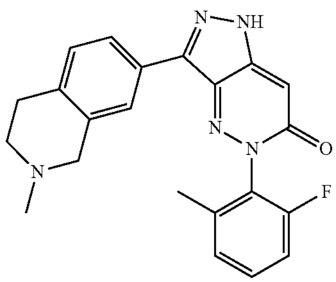 [SMILES: Cc1cccc(F)c1-n1nc2c(-c3ccc4c(c3)CN(C)CC4)n[nH]c2cc1=O] | 5-(2-fluoro-6-methylphenyl)-3-(2-methyl-1,2,3,4-tetrahydroisoquinolin-7-yl)-1H-pyrazolo[4,3-c]pyridazin-6(5H)-one |

-continued

| Compound | Structural Formula | Name of Compound |
| --- | --- | --- |
| Compound 157 | 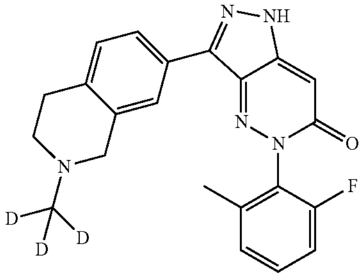 [SMILES: [2H]C([2H])([2H])N1CCc2ccc(-c3n[nH]c4cc(=O)n(-c5c(C)cccc5F)nc34)cc2C1] | 5-(2-fluoro-6-methylphenyl)-3-(2-(methyl-$d_3$)-1,2,3,4-tetrahydroisoquinolin-7-yl)-1H-pyrazolo[4,3-c]pyridazin-6(5H)-one |
| Compound 158 | 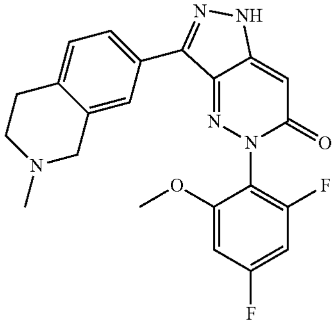 [SMILES: COc1cc(F)cc(F)c1-n1nc2c(-c3ccc4c(c3)CN(C)CC4)n[nH]c2cc1=O] | 5-(2,4-difluoro-6-methoxyphenyl)-3-(2-methyl-1,2,3,4-tetrahydroisoquinolin-7-yl)-1H-pyrazolo[4,3-c]pyridazin-6(5H)-one |
| Compound 159 | 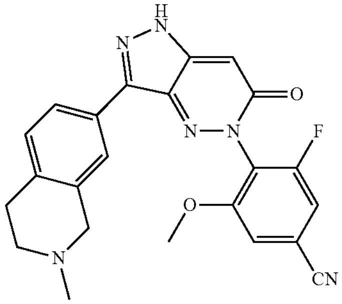 [SMILES: COc1cc(C#N)cc(F)c1-n1nc2c(-c3ccc4c(c3)CN(C)CC4)n[nH]c2cc1=O] | 3-fluoro-5-methoxy-4-(3-(2-methyl-1,2,3,4-tetrahydroisoquinolin-7-yl)-6-oxo-1H-pyrazolo[4,3-c]pyridazin-5(6H)-yl)benzonitrile |
| Compound 160 | 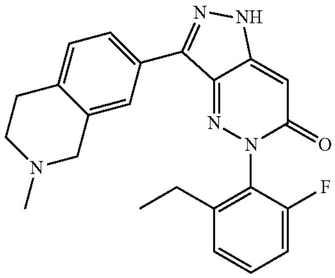 [SMILES: CCc1cccc(F)c1-n1nc2c(-c3ccc4c(c3)CN(C)CC4)n[nH]c2cc1=O] | 5-(2-ethyl-6-fluorophenyl)-3-(2-methyl-1,2,3,4-tetrahydroisoquinolin-7-yl)-1H-pyrazolo[4,3-c]pyridazin-6(5H)-one |
| Compound 161 | 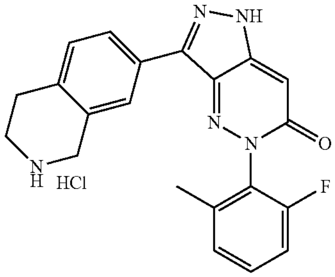 [SMILES: Cc1cccc(F)c1-n1nc2c(-c3ccc4c(c3)CNCC4)n[nH]c2cc1=O ; Cl] | 5-(2-fluoro-6-methylphenyl)-3-(1,2,3,4-tetrahydroisoquinolin-7-yl)-1H-pyrazolo[4,3-c]pyridazin-6(5H)-one hydrochloride |

-continued

| Compound | Structural Formula | Name of Compound |
| --- | --- | --- |
| Compound 162 | 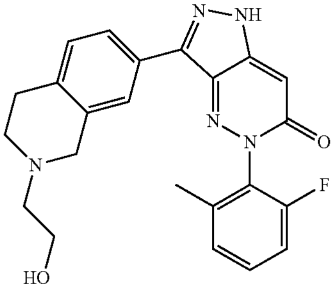 [SMILES: Cc1cccc(F)c1-n1nc2c(-c3ccc4c(c3)CN(CCO)CC4)n[nH]c2cc1=O] | 5-(2-fluoro-6-methylphenyl)-3-(2-(2-hydroxyethyl)-1,2,3,4-tetrahydroisoquinolin-7-yl)-1H-pyrazolo[4,3-c]pyridazin-6(5H)-one |
| Compound 163 | 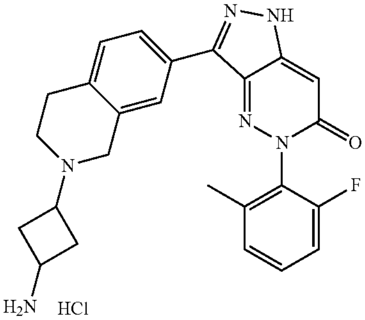 [SMILES: Cc1cccc(F)c1-n1nc2c(-c3ccc4c(c3)CN(C3CC(N)C3)CC4)n[nH]c2cc1=O ; Cl] | 3-(2-(3-aminocyclobutyl)-1,2,3,4-tetrahydroisoquinolin-7-yl)-5-(2-fluoro-6-methylpheny1)-1H-pyrazolo[4,3-c]pyridazin-6(5H)-one hydrochloride |
| Compound 164 | 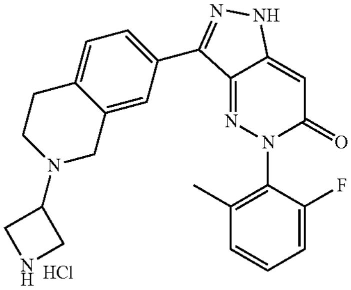 [SMILES: Cc1cccc(F)c1-n1nc2c(-c3ccc4c(c3)CN(C3CNC3)CC4)n[nH]c2cc1=O ; Cl] | 3-(2-(azetidin-3-yl)-1,2,3,4-tetrahydroisoquinolin-7-yl)-5-(2-fluoro-6-methylphenyl)-1H-pyrazolo[4,3-c]pyridazin-6(5H)-one hydrochloride |
| Compound 165 | 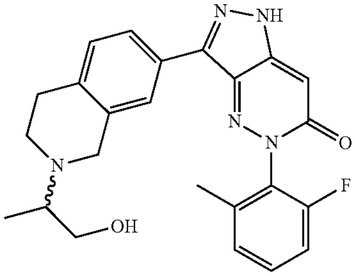 [SMILES: Cc1cccc(F)c1-n1nc2c(-c3ccc4c(c3)CN(C(C)CO)CC4)n[nH]c2cc1=O] | 5-(2-fluoro-6-methylphenyl)-3-(2-(1-hydroxylprop-2-yl)-1,2,3,4-tetrahydroisoquinolin-7-yl)-1H-pyrazolo[4,3-c]pyridazin-6(5H)-one |
| Compound 166 | 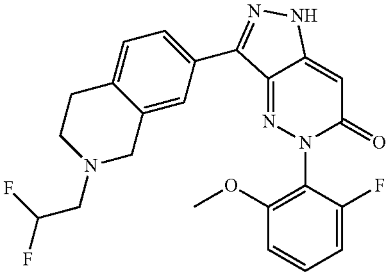 [SMILES: COc1cccc(F)c1-n1nc2c(-c3ccc4c(c3)CN(CC(F)F)CC4)n[nH]c2cc1=O] | 3-(2-(2,2-difluoroethyl)-1,2,3,4-tetrahydroisoquinolin-7-yl)-5-(2-fluoro-6-methoxyphenyl)-1H-pyrazolo[4,3-c]pyridazin-6(5H)-one |

-continued

| Compound | Structural Formula | Name of Compound |
|---|---|---|
| Compound 167 | 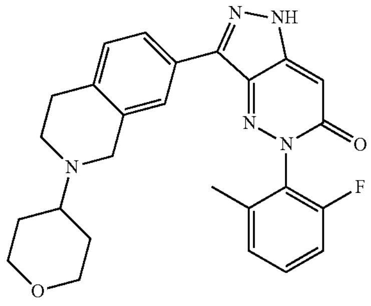 [SMILES: Cc1cccc(F)c1-n1nc2c(-c3ccc4c(c3)CN(C3CCOCC3)CC4)n[nH]c2cc1=O] | 5-(2-fluoro-6-methylphenyl)-3-(2-(tetrahydro-2H-pyran-4-yl)-1,2,3,4-tetrahydroisoquinolin-7-yl)-1H-pyrazolo[4,3-c]pyridazin-6(5H)-one |
| Compound 168 | 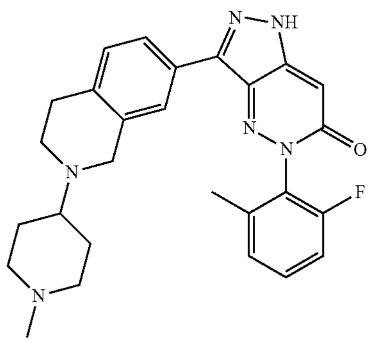 [SMILES: Cc1cccc(F)c1-n1nc2c(-c3ccc4c(c3)CN(C3CCN(C)CC3)CC4)n[nH]c2cc1=O] | 5-(2-fluoro-6-methylphenyl)-3-(2-(1-methylpiperidin-4-yl)-1,2,3,4-tetrahydroisoquinolin-7-yl)-1H-pyrazolo[4,3-c]pyridazin-6(5H)-one |
| Compound 169 | 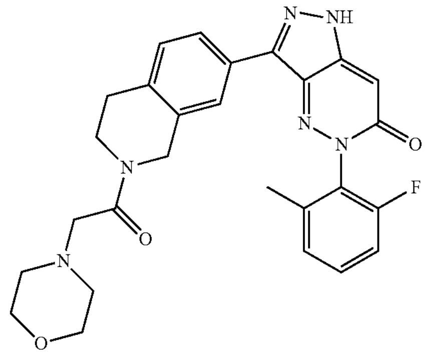 [SMILES: Cc1cccc(F)c1-n1nc2c(-c3ccc4c(c3)CN(C(=O)CN3CCOCC3)CC4)n[nH]c2cc1=O] | 5-(2-fluoro-6-methylphenyl)-3-(2-(2-morpholinoacetyl)-1,2,3,4-tetrahydroisoquinolin-7-yl)-1H-pyrazolo[4,3-c]pyridazin-6(5H)-one |
| Compound 170 | 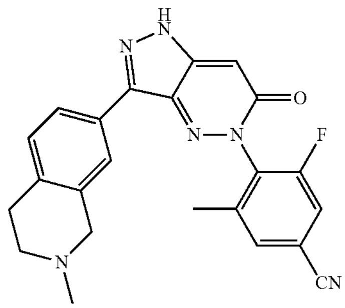 [SMILES: Cc1cc(C#N)cc(F)c1-n1nc2c(-c3ccc4c(c3)CN(C)CC4)n[nH]c2cc1=O] | 3-fluoro-5-methyl-4-(3-(2-methyl-1,2,3,4-tetrahydroisoquinolin-7-yl)-6-oxo-1H-pyrazolo[4,3-c]pyridazin-5(6H)-yl)benzonitrile |
| Compound 171 | 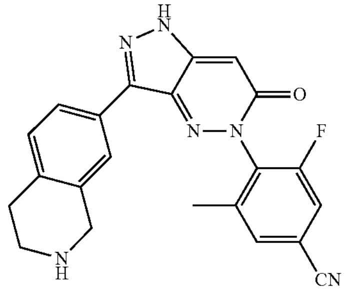 [SMILES: Cc1cc(C#N)cc(F)c1-n1nc2c(-c3ccc4c(c3)CNCC4)n[nH]c2cc1=O] | 3-fluoro-5-methyl-4-(3-(1,2,3,4-tetrahydroisoquinolin-7-yl)-6-oxo-1H-pyrazolo[4,3-c]pyridazin-5(6H)-yl)benzonitrile |

-continued

| Compound | Structural Formula | Name of Compound |
| --- | --- | --- |
| Compound 172 | 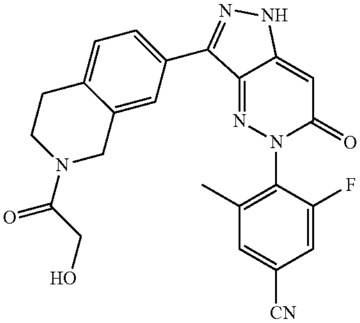 [SMILES: Cc1cc(C#N)cc(F)c1-n1nc2c(-c3ccc4c(c3)CN(C(=O)CO)CC4)n[nH]c2cc1=O] | 3-fluoro-4-(3-(2-(2-hydroxylacetyl)-1,2,3,4-tetrahydroisoquinolin-7-yl)-6-oxo-1H-pyrazolo[4,3-c]pyridazin-5(6H)-yl)-5-methylbenzonitrile |
| Compound 173 | 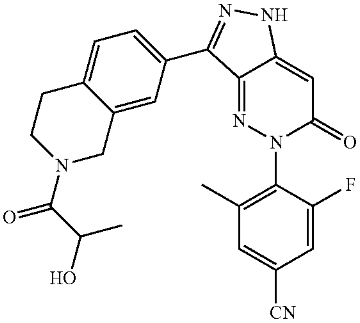 [SMILES: Cc1cc(C#N)cc(F)c1-n1nc2c(-c3ccc4c(c3)CN(C(=O)C(C)O)CC4)n[nH]c2cc1=O] | 3-fluoro-4-(3-(2-(2-hydroxylpropionyl)-1,2,3,4-tetrahydroisoquinolin-7-yl)-6-oxo-1H-pyrazolo[4,3-c]pyridazin-5(6H)-yl)-5-methylbenzonitrile |
| Compound 174 | 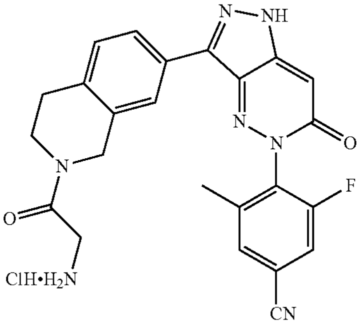 | 3-fluoro-4-(3-(2-(2-aminoacetyl)-1,2,3,4-tetrahydroisoquinolin-7-yl)-6-oxo-1H-pyrazolo[4,3-c]pyridazin-5(6H)-yl)-5-methylbenzonitrile hydrochloride |
| Compound 175 | 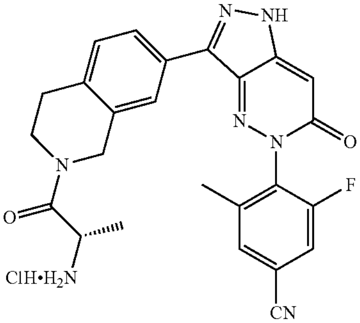 | (S)-3-fluoro-4-(3-(2-(2-aminopropionyl)-1,2,3,4-tetrahydroisoquinolin-7-yl)-6-oxo-1H-pyrazolo[4,3-c]pyridazin-5(6H)-yl)-5-methylbenzonitrile hydrochloride |

-continued

| Compound | Structural Formula | Name of Compound |
|---|---|---|
| Compound 176 | 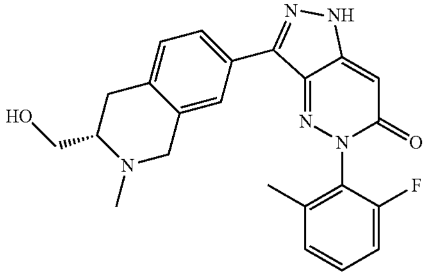 [SMILES: Cc1cccc(F)c1-n1nc2c(-c3ccc4c(c3)CN(C)[C@H](CO)C4)n[nH]c2cc1=O] | (S)-5-(2-fluoro-6-methylphenyl)-3-(3-(hydroxymethyl)-2-methyl-1,2,3,4-tetrahydroisoquinolin-7-yl)-1H-pyrazolo[4,3-c]pyridazin-6(5H)-one |
| Compound 177 | 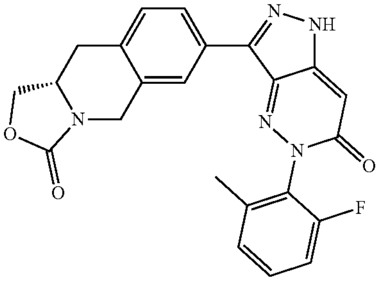 [SMILES: Cc1cccc(F)c1-n1nc2c(-c3ccc4c(c3)CN3C(=O)OC[C@@H]3C4)n[nH]c2cc1=O] | (S)-7-(5-(2-fluoro-6-methylphenyl)-6-oxo-5,6-dihydro-1H-pyrazolo[4,3-c]pyridazin-3-yl)-10,10a-dihydro-1H-oxazolo[3,4-b]isoquinolin-3(5H)-one |
| Compound 178 | 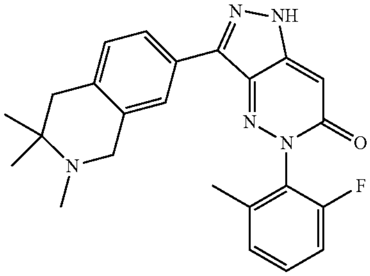 [SMILES: Cc1cccc(F)c1-n1nc2c(-c3ccc4c(c3)CN(C)C(C)(C)C4)n[nH]c2cc1=O] | 5-(2-fluoro-6-methylphenyl)-3-(2,3,3-trimethyl-1,2,3,4-tetrahydroisoquinolin-7-yl)-1H-pyrazolo[4,3-c]pyridazin-6(5H)-one |
| Compound 179 | 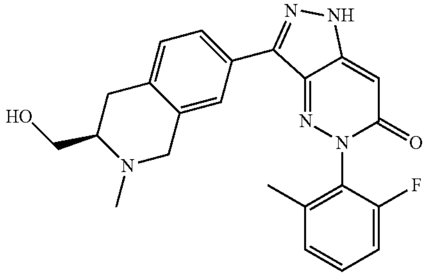 [SMILES: Cc1cccc(F)c1-n1nc2c(-c3ccc4c(c3)CN(C)[C@@H](CO)C4)n[nH]c2cc1=O] | (R)-5-(2-fluoro-6-methylphenyl)-3-(3-(hydroxymethyl)-2-methyl-1,2,3,4-tetrahydroisoquinolin-7-yl)-1H-pyrazolo[4,3-c]pyridazin-6(5H)-one |
| Compound 180 | 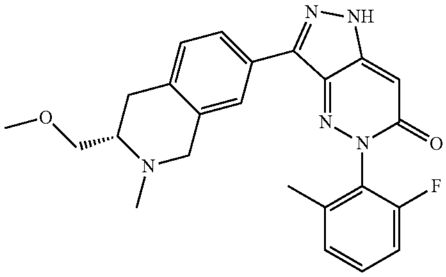 [SMILES: COC[C@@H]1Cc2ccc(-c3n[nH]c4cc(=O)n(-c5c(C)cccc5F)nc34)cc2CN1C] | (S)-5-(2-fluoro-6-methylphenyl)-3-(3-(methoxymethyl)-2-methyl-1,2,3,4-tetrahydroisoquinolin-7-yl)-1H-pyrazolo[4,3-c]pyridazin-6(5H)-one |

-continued

| Compound | Structural Formula | Name of Compound |
|---|---|---|
| Compound 181 | 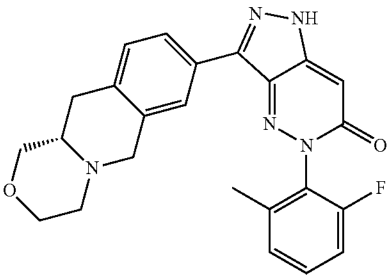 [SMILES: Cc1cccc(F)c1-n1nc2c(-c3ccc4c(c3)CN3CCOC[C@@H]3C4)n[nH]c2cc1=O] | (S)-5-(2-fluoro-6-methylphenyl)-3-(1,3,4,6,11,11a-hexahydro-[1,4]oxazino[4,3-b]isoquinolin-8-yl)-1H-pyrazolo[4,3-c]pyridazin-6(5H)-one |
| Compound 182 | 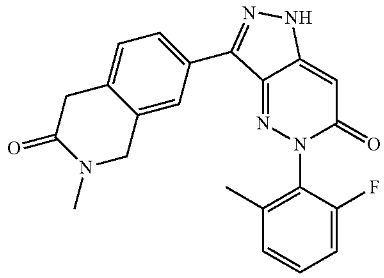 [SMILES: Cc1cccc(F)c1-n1nc2c(-c3ccc4c(c3)CN(C)C(=O)C4)n[nH]c2cc1=O] | 7-(5-(2-fluoro-6-methylphenyl)-6-oxo-5,6-dihydro-1H-pyrazolo[4,3-c]pyridazin-3-yl)-2-methyl-1,2-dihydroisoquinolin-3(4H)-one |
| Compound 183 | 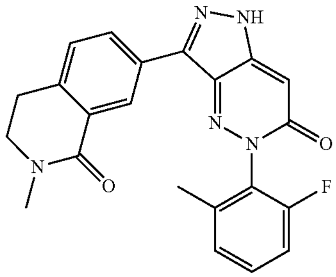 [SMILES: Cc1cccc(F)c1-n1nc2c(-c3ccc4c(c3)C(=O)N(C)CC4)n[nH]c2cc1=O] | 7-(5-(2-fluoro-6-methylphenyl)-6-oxo-5,6-dihydro-1H-pyrazolo[4,3-c]pyridazin-3-yl)-2-methyl-3,4-dihydroisoquinolin-1(2H)-one |
| Compound 184 | 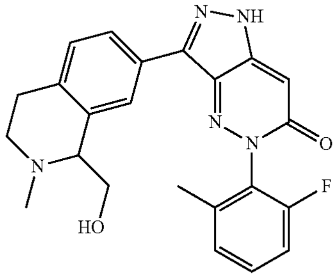 [SMILES: Cc1cccc(F)c1-n1nc2c(-c3ccc4c(c3)C(CO)N(C)CC4)n[nH]c2cc1=O] | 5-(2-fluoro-6-methylphenyl)-3-(1-(hydroxymethyl)-2-methyl-1,2,3,4-tetrahydroisoquinolin-7-yl)-1H-pyrazolo[4,3-c]pyridazin-6(5H)-one |
| Compound 185 | 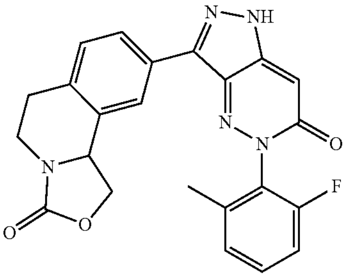 [SMILES: Cc1cccc(F)c1-n1nc2c(-c3ccc4c(c3)C3COC(=O)N3CC4)n[nH]c2cc1=O] | 9-(5-(2-fluoro-6-methylphenyl)-6-oxo-5,6-dihydro-1H-pyrazolo[4,3-c]pyridazin-3-yl)-5,6-dihydro-1H-oxazolo[4,3-a]isoquinolin-3(10bH)-one |

-continued

| Compound | Structural Formula | Name of Compound |
| --- | --- | --- |
| Compound 186 | 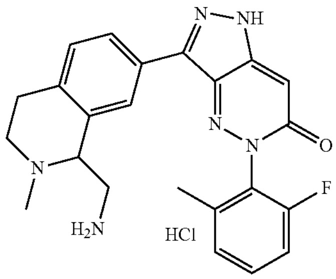 [SMILES: Cc1cccc(F)c1-n1nc2c(-c3ccc4c(c3)C(CN)N(C)CC4)n[nH]c2cc1=O ; Cl] | 3-(1-(aminomethyl)-2-methyl-1,2,3,4-tetrahydroisoquinolin-7-yl)-5-(2-fluoro-6-methylphenyl)-1H-pyrazolo[4,3-c]pyridazin-6(5H)-one hydrochloride |
| Compound 187 | 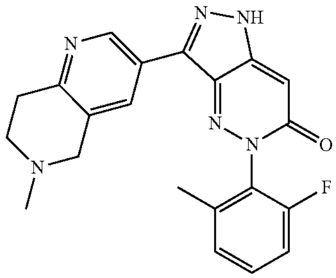 [SMILES: Cc1cccc(F)c1-n1nc2c(-c3cnc4c(c3)CN(C)CC4)n[nH]c2cc1=O] | 5-(2-fluoro-6-methylphenyl)-3-(6-methyl-5,6,7,8-tetrahydro-1,6-naphthyridin-3-yl)-1H-pyrazolo[4,3-c]pyridazin-6(5H)-one |
| Compound 188 | 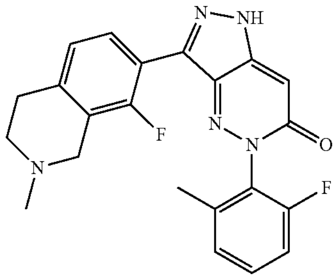 [SMILES: Cc1cccc(F)c1-n1nc2c(-c3ccc4c(c3F)CN(C)CC4)n[nH]c2cc1=O] | 3-(8-fluoro-2-methyl-1,2,3,4-tetrahydroisoquinolin-7-yl)-5-(2-fluoro-6-methylphenyl)-1H-pyrazolo[4,3-c]pyridazin-6(5H)-one |
| Compound 189 | 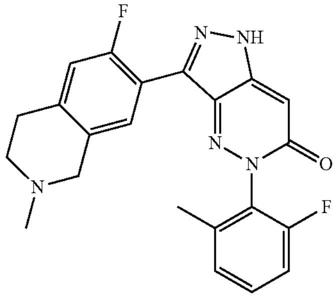 [SMILES: Cc1cccc(F)c1-n1nc2c(-c3cc4c(cc3F)CCN(C)C4)n[nH]c2cc1=O] | 3-(6-fluoro-2-methyl-1,2,3,4-tetrahydroisoquinolin-7-yl)-5-(2-fluoro-6-methylphenyl)-1H-pyrazolo[4,3-c]pyridazin-6(5H)-one |
| Compound 190 | 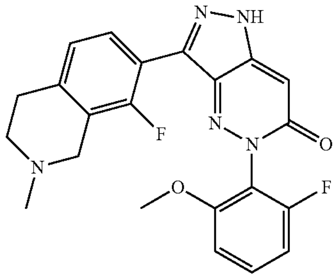 [SMILES: COc1cccc(F)c1-n1nc2c(-c3ccc4c(c3F)CN(C)CC4)n[nH]c2cc1=O] | 3-(8-fluoro-2-methyl-1,2,3,4-tetrahydroisoquinolin-7-yl)-5-(2-fluoro-6-methoxyphenyl)-1H-pyrazolo[4,3-c]pyridazin-6(5H)-one |

-continued

| Compound | Structural Formula | Name of Compound |
|---|---|---|
| Compound 191 | 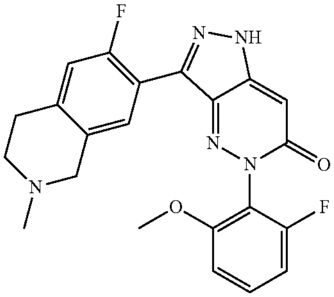 [SMILES: COc1cccc(F)c1-n1nc2c(-c3cc4c(cc3F)CCN(C)C4)n[nH]c2cc1=O] | 3-(6-fluoro-2-methyl-1,2,3,4-tetrahydroisoquinolin-7-yl)-5-(2-fluoro-6-methoxyphenyl)-1H-pyrazolo[4,3-c]pyridazin-6(5H)-one |
| Compound 193 | 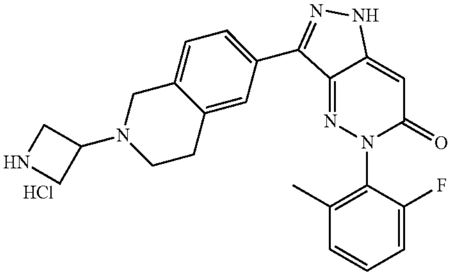 [SMILES: Cc1cccc(F)c1-n1nc2c(-c3ccc4c(c3)CCN(C3CNC3)C4)n[nH]c2cc1=O ; Cl] | 3-(2-(azetidin-3-yl)-1,2,3,4-tetrahydroisoquinolin-6-y1)-5-(2-fluoro-6-methylphenyl)-1H-pyrazolo[4,3-c]pyridazin-6(5H)-one hydrochloride |
| Compound 194 | 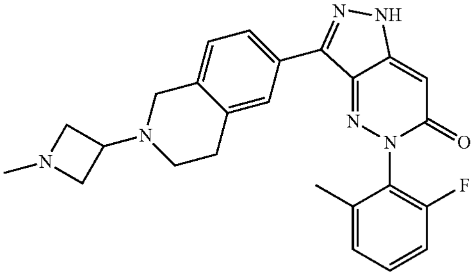 [SMILES: Cc1cccc(F)c1-n1nc2c(-c3ccc4c(c3)CCN(C3CN(C)C3)C4)n[nH]c2cc1=O] | 5-(2-fluoro-6-methylphenyl)-3-(2-(1-methylazetidin-3-yl)-1,2,3,4-tetrahydroisoquinolin-6-yl)-1H-pyrazolo[4,3-c]pyridazin-6(5H)-one |
| Compound 195 | 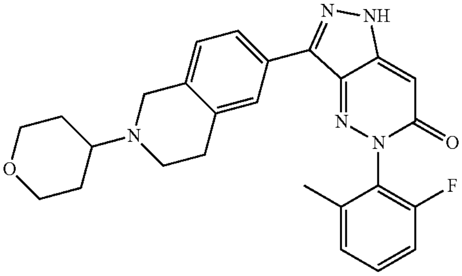 [SMILES: Cc1cccc(F)c1-n1nc2c(-c3ccc4c(c3)CCN(C3CCOCC3)C4)n[nH]c2cc1=O] | 5-(2-fluoro-6-methylphenyl)-3-(2-(tetrahydro-2H-pyran-4-yl)-1,2,3,4-tetrahydroisoquinolin-6-yl)-1H-pyrazolo[4,3-c]pyridazin-6(5H)-one |
| Compound 196 | 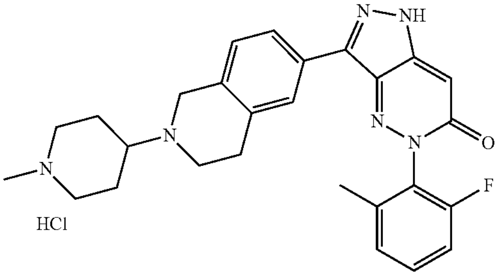 [SMILES: Cc1cccc(F)c1-n1nc2c(-c3ccc4c(c3)CCN(C3CCN(C)CC3)C4)n[nH]c2cc1=O ; Cl] | 5-(2-fluoro-6-methylphenyl)-3-(2-(1-methylpiperidin-4-yl)-1,2,3,4-tetrahydroisoquinolin-6-yl)-1H-pyrazolo[4,3-c]pyridazin-6(5H)-one hydrochloride |

-continued

| Compound | Structural Formula | Name of Compound |
| --- | --- | --- |
| Compound 197 | 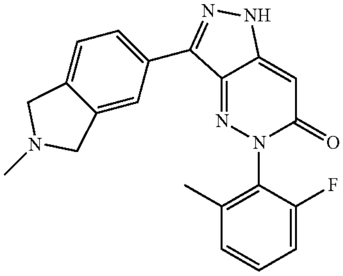 [SMILES: Cc1cccc(F)c1-n1nc2c(-c3ccc4c(c3)CN(C)C4)n[nH]c2cc1=O] | 5-(2-fluoro-6-methylphenyl)-3-(2-methylisoindolin-5-yl)-1H-pyrazolo[4,3-c]pyridazin-6(5H)-one |
| Compound 198 | 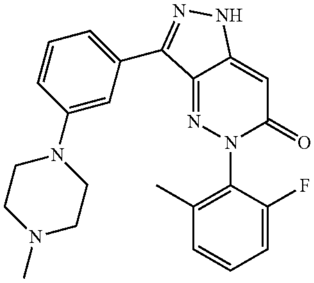 [SMILES: Cc1cccc(F)c1-n1nc2c(-c3cccc(N4CCN(C)CC4)c3)n[nH]c2cc1=O] | 5-(2-fluoro-6-methylphenyl)-3-(3-(4-methylpiperazin-1-yl)phenyl)-1H-pyrazolo[4,3-c]pyridazin-6(5H)-one |
| Compound 199 | 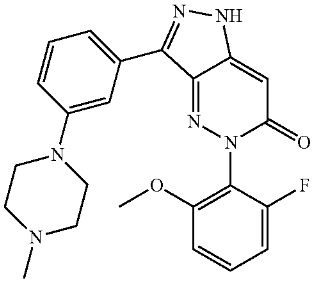 [SMILES: COc1cccc(F)c1-n1nc2c(-c3cccc(N4CCN(C)CC4)c3)n[nH]c2cc1=O] | 5-(2-fluoro-6-methoxyphenyl)-3-(3-(4-methylpiperazin-1-yl)phenyl)-1H-pyrazolo[4,3-c]pyridazin-6(5H)-one |
| Compound 200 | 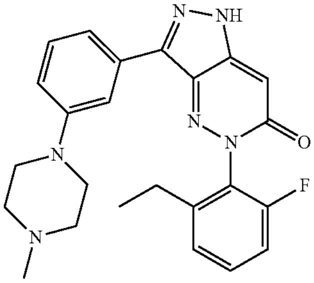 [SMILES: CCc1cccc(F)c1-n1nc2c(-c3cccc(N4CCN(C)CC4)c3)n[nH]c2cc1=O] | 5-(2-ethyl-6-fluorophenyl)-3-(3-(4-methylpiperazin-1-yl)phenyl)-1H-pyrazolo[4,3-c]pyridazin-6(5H)-one |
| Compound 201 | 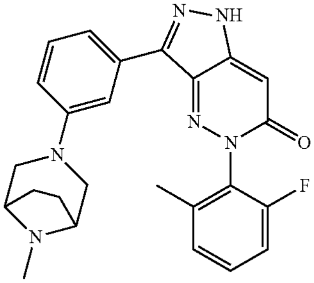 [SMILES: Cc1cccc(F)c1-n1nc2c(-c3cccc(N4CC5CCC(C4)N5C)c3)n[nH]c2cc1=O] | 5-(2-fluoro-6-methylphenyl)-3-(3-(8-methyl-3,8-diazabicyclo[3.2.1]octan-3-yl)phenyl)-1H-pyrazolo[4,3-c]pyridazin-6(5H)-one |

-continued

| Compound | Structural Formula | Name of Compound |
|---|---|---|
| Compound 202 | 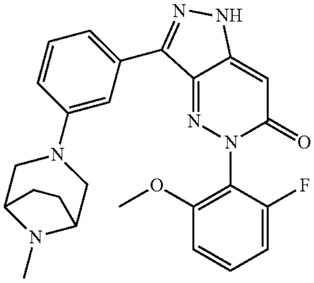 [SMILES: COc1cccc(F)c1-n1nc2c(-c3cccc(N4CC5CCC(C4)N5C)c3)n[nH]c2cc1=O] | 5-(2-fluoro-6-methoxyphenyl)-3-(3-(8-methyl-3,8-diazabicyclo[3.2.1]octan-3-yl)phenyl)-1H-pyrazolo[4,3-c]pyridazin-6(5H)-one |
| Compound 203 | 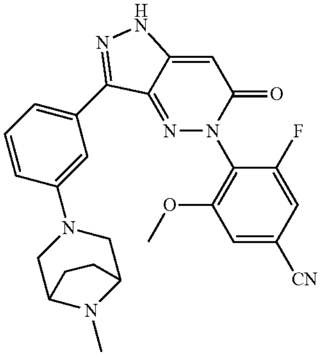 [SMILES: COc1cc(C#N)cc(F)c1-n1nc2c(-c3cccc(N4CC5CCC(C4)N5C)c3)n[nH]c2cc1=O] | 3-fluoro-5-methoxy-4-(3-(3-(8-methyl-3,8-diazabicyclo[3.2.1]octan-3-yl)phenyl)-6-oxo-1H-pyrazolo[4,3-c]pyridazin-5(6H)-yl)benzonitrile |
| Compound 204 | 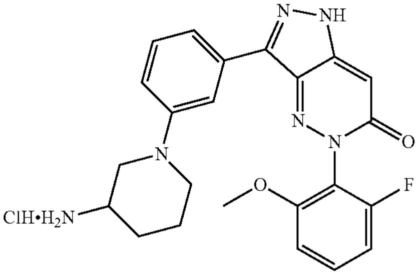 | 3-(3-(3-aminopiperidin-1-yl)phenyl)-5-(2-fluoro-6-methoxyphenyl)-1H-pyrazolo[4,3-c]pyridazin-6(5H)-one hydrochloride |
| Compound 205 | 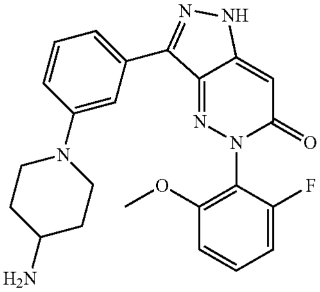 [SMILES: COc1cccc(F)c1-n1nc2c(-c3cccc(N4CCC(N)CC4)c3)n[nH]c2cc1=O] | 3-(3-(4-aminopiperidin-1-yl)phenyl)-5-(2-fluoro-6-methoxyphenyl)-1H-pyrazolo[4,3-c]pyridazin-6(5H)-one |
| Compound 206 | 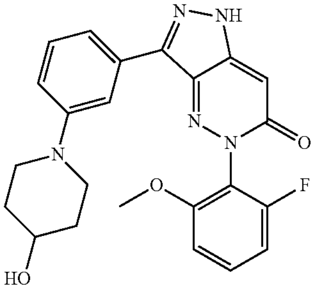 [SMILES: COc1cccc(F)c1-n1nc2c(-c3cccc(N4CCC(O)CC4)c3)n[nH]c2cc1=O] | 3-(3-(4-hydroxylpiperidin-1-yl)phenyl)-5-(2-fluoro-6-methoxyphenyl)-1H-pyrazolo[4,3-c]pyridazin-6(5H)-one |

-continued

| Compound | Structural Formula | Name of Compound |
| --- | --- | --- |
| Compound 207 | 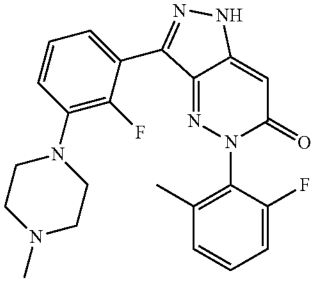 [SMILES: Cc1cccc(F)c1-n1nc2c(-c3cccc(N4CCN(C)CC4)c3F)n[nH]c2cc1=O] | 3-(2-fluoro-3-(4-methylpiperazin-1-yl)phenyl)-5-(2-fluoro-6-methylphenyl)-1H-pyrazolo[4,3-c]pyridazin-6(5H)-one |
| Compound 208 | 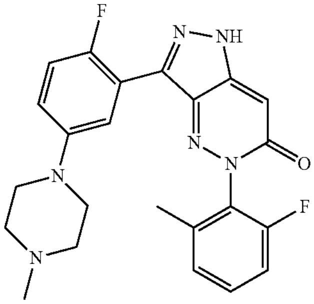 [SMILES: Cc1cccc(F)c1-n1nc2c(-c3cc(N4CCN(C)CC4)ccc3F)n[nH]c2cc1=O] | 3-(2-fluoro-5-(4-methylpiperazin-1-yl)phenyl)-5-(2-fluoro-6-methylphenyl)-1H-pyrazolo[4,3-c]pyridazin-6(5H)-one |
| Compound 209 | 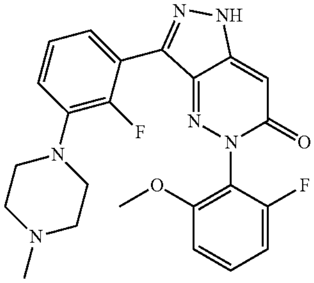 [SMILES: COc1cccc(F)c1-n1nc2c(-c3cccc(N4CCN(C)CC4)c3F)n[nH]c2cc1=O] | 3-(2-fluoro-3-(4-methylpiperazin-1-yl)phenyl)-5-(2-fluoro-6-methoxyphenyl)-1H-pyrazolo[4,3-c]pyridazin-6(5H)-one; and |
| Compound 210 | 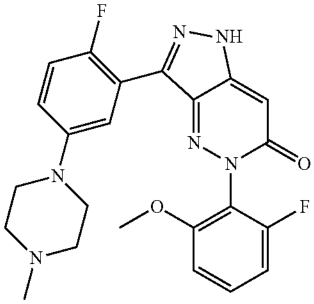 [SMILES: COc1cccc(F)c1-n1nc2c(-c3cc(N4CCN(C)CC4)ccc3F)n[nH]c2cc1=O] | 3-(2-fluoro-5-(4-methylpiperazin-1-yl)phenyl)-5-(2-fluoro-6-methoxyphenyl)-1H-pyrazolo[4,3-c]pyridazin-6(5H)-one. |

13. A pharmaceutical composition comprising the compound or a pharmaceutically acceptable salt, hydrate, solvate, active metabolite, polymorph, isotope labeled compound, stereoisomer or prodrug thereof according to claim 1 and a pharmaceutically acceptable carrier.

14. A method of treating a disease or disorder mediated with HPK1 in a patient, comprising administering therapeutically effective amount of the compound of formula (I) or a pharmaceutically acceptable salt, hydrate, solvate, active metabolite, polymorph, isotope labeled compound, stereoisomer or prodrug thereof according to claim 1 to the patient.

15. A method of preventing or treating benign or malignant tumors, myelodysplastic syndromes and diseases caused by viruses in a subject comprising administering the compound or a pharmaceutically acceptable salt, hydrate, solvate, active metabolite, polymorph, isotope labeled compound, stereoisomer or prodrug thereof according to claim 1 to the subject.

16. The method according to claim 15, wherein the benign or malignant tumor is selected from the group consisting of leukemia, lymphoma, multiple myeloma, lung cancer, hepatocellular carcinoma, cholangiocarcinoma, gallbladder cancer, gastric cancer, colorectal cancer, intestinal leiomyosarcoma, breast cancer, ovarian cancer, cervical cancer, endometrial cancer, vaginal cancer, malignant teratoma, pancreatic cancer, pancreatic ductal adenocarcinoma, nasopharyngeal cancer, oral cancer, laryngeal cancer, esophageal squamous cell carcinoma, thyroid cancer, kidney cancer, bladder cancer, malignant brain tumor, rhabdomyosarcoma, osteosarcoma, chondrosarcoma, osteofibrosarcoma, malignant thymoma, malignant peripheral nerve sheath tumor, prostate cancer, testicular cancer, penile cancer and other malignant tumors, as well as benign and malignant tumors of the skin.

17. The method according to claim 15, wherein the virus is selected from the group consisting of hepatitis virus, human immunodeficiency virus, human papillomavirus, herpes simplex virus, measles virus, norovirus, Boca virus, Coxsackie virus, Ebola virus, enterovirus, lymphocytic meningitis virus, influenza virus, SARS virus and COVID-19 virus.

* * * * *